(12) United States Patent
Virsik et al.

(10) Patent No.: US 12,109,179 B2
(45) Date of Patent: Oct. 8, 2024

(54) PHARMACEUTICAL COMPOSITIONS AND COMBINATIONS COMPRISING INHIBITORS OF THE ANDROGEN RECEPTOR AND USES THEREOF

(71) Applicants: ESSA Pharma Inc., Vancouver (CA); The University of British Columbia, Vancouver (CA); Provincial Health Services Authority, Vancouver (CA)

(72) Inventors: Peter Virsik, Portola Valley, CA (US); Han-Jie Zhou, Foster City, CA (US); Marianne Dorothy Sadar, West Vancouver (CA); Raymond John Andersen, Vancouver (CA); Kunzhong Jian, Surrey (CA); Daniel Andrew Golec, Vancouver (CA)

(73) Assignees: ESSA PHARMA INC., Vancouver (CA); THE UNIVERSITY OF BRITISH COLUMBIA, Vancouver (CA); PROVINCIAL HEALTH SERVICES AUTHORITY, Vancouver (CA)

( * ) Notice: Subject to any disclaimer, the term of this patent is extended or adjusted under 35 U.S.C. 154(b) by 18 days.

(21) Appl. No.: 17/599,329

(22) PCT Filed: Mar. 27, 2020

(86) PCT No.: PCT/US2020/025545
§ 371 (c)(1),
(2) Date: Sep. 28, 2021

(87) PCT Pub. No.: WO2020/198712
PCT Pub. Date: Oct. 1, 2020

(65) Prior Publication Data
US 2022/0218632 A1     Jul. 14, 2022

Related U.S. Application Data

(60) Provisional application No. 62/857,519, filed on Jun. 5, 2019, provisional application No. 62/842,980, filed on May 3, 2019, provisional application No. 62/825,450, filed on Mar. 28, 2019, provisional application No. 62/825,440, filed on Mar. 28, 2019.

(51) Int. Cl.
*A61K 31/145*     (2006.01)
*A61K 31/203*     (2006.01)
*A61K 31/519*     (2006.01)

(52) U.S. Cl.
CPC .......... *A61K 31/145* (2013.01); *A61K 31/203* (2013.01); *A61K 31/519* (2013.01)

(58) Field of Classification Search
CPC .. A61K 31/145; A61K 31/203; A61K 31/519; A61K 31/09
See application file for complete search history.

(56) References Cited

U.S. PATENT DOCUMENTS

| | | | |
|---|---|---|---|
| 2,571,217 | A | 10/1951 | Davis et al. |
| 2,890,189 | A | 6/1959 | Greenlee |
| 3,074,974 | A | 1/1963 | Gebura |
| 3,162,615 | A | 12/1964 | Bremmer |
| 4,284,574 | A | 8/1981 | Bagga |
| 4,369,298 | A | 1/1983 | Kida et al. |
| 4,855,184 | A | 8/1989 | Klun et al. |
| 4,904,760 | A | 2/1990 | Gaku et al. |
| 5,043,375 | A | 8/1991 | Henning et al. |
| 5,155,196 | A | 10/1992 | Kolb et al. |
| 5,362,615 | A | 11/1994 | Hagemann et al. |
| 5,403,697 | A | 4/1995 | Doessel et al. |
| 5,753,730 | A | 5/1998 | Nagata et al. |
| 5,807,899 | A | 9/1998 | Bohlmann et al. |
| 5,998,674 | A | 12/1999 | Taketani et al. |
| 6,218,430 | B1 | 4/2001 | Allegretto et al. |
| 6,245,117 | B1 | 6/2001 | Nishikawa et al. |
| 7,183,323 | B2 | 2/2007 | Chinn et al. |
| 7,273,867 | B2 | 9/2007 | Dorsch et al. |
| 7,595,345 | B2 | 9/2009 | Bunel et al. |
| 7,666,868 | B2 | 2/2010 | Maier et al. |

(Continued)

FOREIGN PATENT DOCUMENTS

| CA | 2206422 A1 | 6/1996 |
|---|---|---|
| CA | 2226469 A1 | 1/1997 |

(Continued)

OTHER PUBLICATIONS

Comstock et al. Oncogene, 2013, vol. 32, p. 5481-5491 (Year: 2013).*
Gucalp et al. Curr. Probl. Cancer, 2016, vol. 40, p. 141-150 (Year: 2016).*
Ji et al. Int. J. Biol. Sci., 2019, vol. 15, p. 522-532 (Published Online Jan. 1, 2019) (Year: 2019).*
Alabi, A. et al., "Quick and simple sample treatment for multiresidue analysis of bisphenols, bisphenol diglycidyl ethers and their derivatives in canned food prior to liquid chromatography and fluorescence detection," J. of Chromatography A, 2014, 1336, 23-33.

(Continued)

*Primary Examiner* — James D. Anderson
(74) *Attorney, Agent, or Firm* — COOLEY LLP

(57) ABSTRACT

The present disclosure generally relates to pharmaceutical compositions and combinations comprising an androgen receptor N-terminal domain inhibitor or an inhibitor and a second therapeutically active agent, such as an CDK4/6 inhibitor, a Pin1 inhibitor (inhibitor of peptidyl-prolyl cis/trans isomerases), or an antiandrogen. In particular, the present disclosure relates to pharmaceutical compositions and combinations useful for treatment of various cancers, for example breast cancer and prostate cancer. Further, the present disclosure relates administering an androgen receptor N-terminal domain inhibitor in combination with radiation therapy for treatment of various cancers.

23 Claims, 29 Drawing Sheets
Specification includes a Sequence Listing.

(56) References Cited

U.S. PATENT DOCUMENTS

| | | |
|---|---|---|
| 7,674,795 B2 | 3/2010 | Mailliet et al. |
| 8,048,888 B2 | 11/2011 | Wosikowski-Buters et al. |
| 8,445,507 B2 | 5/2013 | Jung et al. |
| 8,455,477 B2 | 6/2013 | Katz et al. |
| 8,686,050 B2 | 4/2014 | Sadar et al. |
| 9,173,939 B2 | 11/2015 | Andersen et al. |
| 9,365,510 B2 | 6/2016 | Andersen et al. |
| 9,375,496 B2 | 6/2016 | Andersen et al. |
| 9,388,112 B2 | 7/2016 | Sadar et al. |
| 9,862,667 B2 | 1/2018 | Sadar et al. |
| 10,471,023 B2 | 11/2019 | Andersen et al. |
| 10,654,811 B2 | 5/2020 | Andersen et al. |
| 11,059,795 B2 | 7/2021 | Zhou et al. |
| 11,142,508 B2 * | 10/2021 | Andersen ............... A61P 17/14 |
| 11,242,324 B2 | 2/2022 | Zhou et al. |
| 11,345,670 B2 | 5/2022 | Andersen et al. |
| 11,358,938 B2 | 6/2022 | Zhou et al. |
| 11,485,713 B2 | 11/2022 | Zhou et al. |
| 11,518,747 B2 | 12/2022 | Zhou et al. |
| 2003/0092724 A1 | 5/2003 | Kao et al. |
| 2003/0105268 A1 | 6/2003 | Boriack et al. |
| 2004/0049004 A1 | 3/2004 | Boriak et al. |
| 2004/0243316 A1 | 12/2004 | Weinmann et al. |
| 2008/0153837 A1 | 6/2008 | Mailliet et al. |
| 2008/0193380 A1 | 8/2008 | Dalton et al. |
| 2008/0255395 A1 | 10/2008 | Dai et al. |
| 2009/0105349 A1 | 4/2009 | Barvian et al. |
| 2009/0246158 A1 | 10/2009 | Rudolph et al. |
| 2011/0230556 A1 | 9/2011 | Sadar et al. |
| 2013/0045204 A1 | 2/2013 | Andersen et al. |
| 2013/0109758 A1 | 5/2013 | Sadar et al. |
| 2013/0131167 A1 | 5/2013 | Sadar et al. |
| 2013/0245129 A1 | 9/2013 | Sadar et al. |
| 2013/0336962 A1 | 12/2013 | Andersen et al. |
| 2014/0248263 A1 | 9/2014 | Andersen et al. |
| 2014/0335080 A1 | 11/2014 | Andersen et al. |
| 2015/0010469 A1 | 1/2015 | Andersen et al. |
| 2015/0125389 A1 | 5/2015 | Andersen et al. |
| 2015/0210681 A1 | 7/2015 | Bourque et al. |
| 2016/0068466 A1 | 3/2016 | Andersen et al. |
| 2016/0367707 A1 | 12/2016 | Andersen et al. |
| 2017/0056336 A1 | 3/2017 | Sadar et al. |
| 2017/0081192 A1 | 3/2017 | Schwab et al. |
| 2017/0121261 A1 | 5/2017 | Sadar et al. |
| 2017/0298033 A1 | 10/2017 | Andersen et al. |
| 2017/0368036 A1 | 12/2017 | Hattersley et al. |
| 2018/0064657 A1 | 3/2018 | Andersen et al. |
| 2018/0235925 A1 | 8/2018 | Andersen et al. |
| 2018/0327368 A1 | 11/2018 | Andersen et al. |
| 2019/0022093 A1 | 1/2019 | Wipf et al. |
| 2019/0202800 A1 | 7/2019 | Freeman et al. |
| 2020/0123117 A1 | 4/2020 | Zhou et al. |
| 2020/0247763 A1 | 8/2020 | Zhou et al. |
| 2020/0281949 A1 | 9/2020 | Warner et al. |
| 2020/0325106 A1 | 10/2020 | Andersen et al. |
| 2021/0198213 A1 | 7/2021 | Essa |
| 2021/0323931 A1 | 10/2021 | Zhou et al. |
| 2021/0332016 A1 | 10/2021 | Zhou et al. |
| 2021/0387957 A1 | 12/2021 | Andersen et al. |
| 2022/0073472 A1 | 3/2022 | Zhou et al. |
| 2022/0105093 A1 | 4/2022 | Virsik et al. |
| 2022/0202780 A1 | 6/2022 | Virsik et al. |
| 2023/0078913 A1 | 3/2023 | Zhou et al. |

FOREIGN PATENT DOCUMENTS

| | | |
|---|---|---|
| CA | 2339775 A1 | 3/2000 |
| CA | 2606262 A1 | 11/2006 |
| CA | 2728219 A1 | 1/2010 |
| CA | 2786319 A1 | 7/2011 |
| CN | 102083780 A | 6/2011 |
| CN | 103342892 A | 10/2013 |
| EA | 009199 B1 | 12/2007 |
| EP | 0056175 A1 | 7/1982 |
| EP | 0155238 A2 | 9/1985 |
| EP | 0293768 A1 | 12/1988 |
| EP | 0515128 A1 | 11/1992 |
| FR | 1389005 A | 2/1965 |
| JP | BS45008432 | 3/1970 |
| JP | S565472 A | 1/1981 |
| JP | S63196675 A | 8/1988 |
| JP | S63317539 A | 12/1988 |
| JP | H01503541 | 11/1989 |
| JP | H024815 A | 1/1990 |
| JP | 6049473 A | 2/1994 |
| JP | 7117349 A | 5/1995 |
| JP | H09176240 A | 7/1997 |
| JP | H10133427 A | 5/1998 |
| JP | H10316803 A | 12/1998 |
| JP | H11166087 A | 6/1999 |
| JP | 2000072705 A | 3/2000 |
| JP | 2001511170 A | 8/2001 |
| JP | 2005325301 A | 11/2005 |
| JP | 2006208607 A | 8/2006 |
| JP | 2006265351 A | 10/2006 |
| JP | 2007513089 A | 5/2007 |
| JP | 2007290980 A | 11/2007 |
| KR | 20110044216 A | 4/2011 |
| PL | 141793 B1 | 8/1987 |
| RU | 2454394 C2 | 6/2012 |
| SU | 638596 A1 | 12/1978 |
| SU | 929630 A1 | 5/1982 |
| WO | WO-1988009782 A1 | 12/1988 |
| WO | WO-9616646 A1 | 6/1996 |
| WO | WO-1998034930 A1 | 8/1998 |
| WO | WO-2000001813 A2 | 1/2000 |
| WO | WO-2000010958 A1 | 3/2000 |
| WO | WO-2001088013 A2 | 11/2001 |
| WO | WO-2002005813 A2 | 1/2002 |
| WO | WO-2003004481 A1 | 1/2003 |
| WO | WO-03106401 A1 | 12/2003 |
| WO | WO-2005042464 A1 | 5/2005 |
| WO | WO-2005077967 A1 | 8/2005 |
| WO | WO-2007079078 A1 | 7/2007 |
| WO | WO-2008101806 A2 | 8/2008 |
| WO | WO-2010000066 A1 | 1/2010 |
| WO | WO-2011082487 A1 | 7/2011 |
| WO | WO-2011082488 A1 | 7/2011 |
| WO | WO-2011103202 A2 | 8/2011 |
| WO | WO-2012139039 A2 | 10/2012 |
| WO | WO-2012145328 A1 | 10/2012 |
| WO | WO-2012145330 A1 | 10/2012 |
| WO | WO-2013028572 A1 | 2/2013 |
| WO | WO-2013028791 A1 | 2/2013 |
| WO | WO-2014011220 A2 | 1/2014 |
| WO | WO-2014179867 A1 | 11/2014 |
| WO | WO-2015031984 A1 | 3/2015 |
| WO | WO-2016058080 A1 | 4/2016 |
| WO | WO-2016058082 A1 | 4/2016 |
| WO | WO-2016112455 A1 | 7/2016 |
| WO | WO-2016141458 A1 | 9/2016 |
| WO | WO-2017177307 A1 | 10/2017 |
| WO | WO-2017210771 A1 | 12/2017 |
| WO | WO-2018045450 A1 | 3/2018 |
| WO | WO-2018157232 A1 | 9/2018 |
| WO | WO-2019226991 A1 | 11/2019 |
| WO | WO-2020081999 A1 | 4/2020 |
| WO | WO-2020198710 A1 | 10/2020 |
| WO | WO-2020198711 A1 | 10/2020 |
| WO | WO-2020198712 A1 | 10/2020 |

OTHER PUBLICATIONS

Alvarez, C. et al., "Conformational and Experimental Studies on the Dipole Moments of Models of Comblike Polymers", Macromolecules, 30(20): 6369-6375 (1997).

Anderson, R. et al., "Regression of Castrate-Recurrent Prostate Cancer by a Small-Molecule Inhibitor of the Amino-Terminus Domain of the Androgen Receptor", Cancer Cell, 17:535-546 (2010).

Anton, R. et al., Opinion of the scientific panel on food additives, flavourings, processing aids and materials in contact with food (AFC) on a request from the commission related to 2,2-bis(4-hydroxyphenyl)propane bis(2,3-epoxypropyl)ether (bisphenol A

(56) References Cited

OTHER PUBLICATIONS diglycidyl ether, Badge), Ref. No. 13510 and 39700 (EFSA-Q-2003-178), The EFSA Journal, 86:1-40 (2004).
Antonarakis et al., "Androgen receptor variant-driven prostate cancer: clinical implications and therapeutic targeting," Prostate Cancer and Prostatic Diseases (2016), 1-11.
Antonarakis et al., "Targeting the N-Terminal Domain of the Androgen Receptor: A New Approach for the Treatment of Advanced Prostate Cancer," The Oncologist 2016;21:1-9.
Auzou et al., European Journal of Medicinal Chemistry, 9(5):548-554 (1974) (with English Abstract).
Balbay, M.D. et al., "Highly Metastatic Human Prostate Cancer Growing within the Prostate of Athymic Mice Overexpresses Vascular Endothelial Growth Factor", Clinical Cancer Research, 5:783-789 (1999).
Banker (ed.) et al., Modern Pharmaceutics, Third Edition, Revised and Expanded, Marcel Dekker, Inc., 1997, pp. 451 and 596.
Banuelos et al., "Sintokamide A is a novel antagonist of androgen receptor that uniquely binds activation function-1 in its amino-terminal domain," The Journal of Biological Chemistry, vol. 291, No. 42, pp. 22231-22243, Oct. 14, 2016.
Bao, B. et al., "Androgen signaling is required for the vitamin D-mediated growth inhibition in human prostate cancer cells", Oncogene, 23:3350-3360 (2004).
Berge, S. M., et al., "Pharmaceutical Salts," Journal of Pharmaceutical Sciences, Jan. 1977, vol. 66, No. 1, pp. 1-19.
Berger, U. et al., "Identification of Derivatives of Bisphenol A Diglycidyl Ether and Novolac Glycidyl Ether in Can Coatings by Liquid Chromatography/Ion Trap Mass Spectrometry," Journal of AOAC International, Food Chemical Contaminants, 83(6):1367-1376 (2000).
Biles, J.E. et al., "Determination of the Diglycidyl Ether of Bisphenol A and its Derivatives in Canned Foods", J. Agric. Food Chem., 47:1965-1969 (1999).
Bisson, W.H. et al., "Discovery of antiandrogen activity of nonsteroidal scaffolds of marketed drugs", PNAS, 104(29):11927-11932 (2007).
Blaszczyk, N. et al., "Osteoblast-Derived factors Induce Androgen-Independent Proliferation and Expression of Prostate-Specific Antigen in Human Prostate Cancer Cells", Clin. Cancer Res., 10:1860-1869 (2004).
Bodei, et al., "Radionuclide Therapy with Iodine-125 and Other Auger-Electron-Emitting Radionuclides: Experimental Models and Clinical Applications." Cancer Biother. & Radiopharm. (2003); 18(6): 861-877.
Bohler, Paul et al., "Identification of Migrants from Coatings of Food Cans and Tubes: Reaction Products of Bisphenol-A-Diglycidyl Ether (BADGE) with Phenols and Solvents", Mitt. Gebiete Lebensm. Hyg., 89:529-547 (1998).
Brand et al., "EPI-001 is a selective peroxisome proliferator-activated receptor-gamma modulator with inhibitory effects on androgen receptor expression and activity in prostate cancer." Oncotarget (2015); 6(6): 3811-3824.
Bruckheimer, E.M. et al., "Apoptosis in prostate carcinogenesisA growth regulator and a therapeutic target", Cell Tissue Res, 301:153-162 (2000).
Brzozowski, Z. et al., "Precursors for bisphenolic resins", CAPLUS Database Accession No. 1990:36690, Document No. 112:33690, (1987), 1 page (Abstract).
Cascini, et al., "124Iodine: A Longer-Life Positron Emitter Isotope—New Opportunities in Molecular Imaging." Hindawi Publishing Corp.Biomed. Res. Int. (2014); vol. 2014, Article ID 672094, 7 pages.
Chang, C. et al., "Development of Peptide Antagonists for the Androgen Receptor Using Combinatorial Peptide Phage Display", Molecular Endocrinology, 19(10):2478-2490 (2005).
Choi, K. M. et al., "New Families of Photocurable Oligomeric Fluoromonomers for Use in Dental Composites", Chemistry of Materials, 8(12):2704-2707 (1996).
Clinton, G.M. et al., "Estrogen action in human ovarian cancer", Critical Reviews in Oncology/Hematology, 25:1-9 (1997).
Cook, W. D., "Fracture and Structure of Highly Crosslinked Polymer Composites", Journal of Applied Polymer Science, 42:1259-1269 (1991).
Crivello, J. V. et al., "Synthesis and photopolymerization of multifunctional propenyl ether monomers," Database CAPLUS [online], Chemical Abstracts Service, Columbus, Ohio, US, XP002729292, retrieved from STN CA Caesar Accession No. 1994-606067 (1994), 3 pages.
Crivello, J. V. et al., "Synthesis and photopolymerization of multifunctional propenyl ether monomers", Journal of Macromolecular Science, Pure and Applied Chemistry,A31(9):1105-1119 (1994).
Culig, Zoran et al., "Androgen Receptor Activation in Prostatic Tumor Cell Lines by Insulin-like Growth Factor-I, Keratinocyte Growth Factor, and Epidermal Growth Factor", Cancer Research, 54:5474-5478 (1994).
Danquah, M. et al., "Micellar Delivery of Bicalutamide and Embelin for Treating Prostate Cancer", Pharmaceutical Research, 26:2081-2092 (2009).
Das, Debasish et al., "Sulfonic acid functionalized mesoporous MCM-41 silica as a convenient catalyst for Bisphenol-A synthesis", Chemical Communications, pp. 2178-2179 (2001).
De Mol et al., "EPI-001, a compound active against castration-resistant prostate cancer, targets transactivation unit 5 of the androgen receptor," ACS Chem. Biol., 2016, 11, 9, 2499-2505.
De Santis, M., et al., "Practical Guidance on the Role of Corticosteroids in the Treatment of Metastatic Castration-resistant Prostate Cancer," Urology, Oct. 2016, vol. 96, pp. 156-164.
Decision of Refusal for Japanese Application No. 2011-515039, mailed Dec. 2, 2014, 18 pages (English translation).
Dehm, S. et al., "Ligand-independent Androgen Receptor Activity is Activation Function-2-independent and Resistant to Antiandrogens in Androgen Refractory Prostate Cancer Cells", The Journal of Biological Chemistry, 281(38):27882-27893 (2006).
Dehm, S. et al., "Splicing of a Novel Androgen Receptor Exon Generates a Constitutively Active Androgen Receptor that Mediates Prostate Cancer Therapy Resistance", Cancer Research, 68:5469-5477 (2008).
Edmondson, R.J., et al., "The human ovarian surface epithelium is an androgen responsive tissue", British Journal of Cancer, 86:879-885 (2002).
Estebanez-Perpi, E. et al., "A surface on the androgen receptor that allosterically regulates coactivator binding," PNAS, 104 (41):16074-16079 (2007).
Estebanez-Perpi, E. et al., "The Molecular Mechanisms of Coactivator Utilization in Ligand-dependent Transactivation by the Androgen Receptor," The Journal of Biological Chemistry, 280(9):8060-8068 (2005).
Extended European Search Report for European Application No. 17781660.0 dated Oct. 31, 2019,8 pages.
Extended European Search Report in Application No. 16736999.0 dated May 24, 2018, 14 pages.
Extended European Search Report in Application No. 21212648.6 dated Feb. 21, 2022, 8 pages.
Extended European Search Report in Application No. EP 12768410.8 dated Sep. 22, 2014, 10 pages.
Extended European Search Report in Application No. EP 14793978.9 dated Sep. 1, 2016, 8 pages.
Extended European Search Report in Application No. EP 14843037.4 dated Mar. 8, 2017, 5 pages.
Extended European Search Report in Application No. EP 17177010.0 dated Oct. 20, 2017, 10 pages.
Fehlberg S. et al., "Bisphenol A diglycidyl ether induces apoptosis in tumor cells independently of peroxisome proliferator-activated receptor-γ, in caspase-dependent and -independent manners," Biochem. J., 362:573-578 (2002).
Gallart-Ayala, H. et al., "The analysis of bisphenol A-diglycidyl ether (BADGE), bisphenol F-diglycidyl ether (BFDGE) and their derivatives in canned food and beverages by LC-MS/MS", Thermo Fisher Scientific Inc., 4 pages (2011).
Garcia et al., "Determination of compounds from epoxy resins in food simulants by HPLC-fluorescence." Chromatographia, 58(5-6): 337-342 (2003).

(56) References Cited

OTHER PUBLICATIONS

Garuti, L., et al., "Irreversible Protein Kinase Inhibitors", Current Medicinal Chemistry, 18:2981-2994 (2011).
Gleave, Martin et al., "Acceleration of Human Prostate Cancer Growth in Vivo by Factors Produced by Prostate and Bone Fibroblasts", Cancer Research, 51:3753-3761 (1991).
Gregory, Christopher et al., "Epidermal Growth Factor Increases Coactivation of the Androgen Receptor in Recurrent Prostate Cancer", The Journal of Biological Chemistry, 279(8):7119-7130 (2004).
Guinan, P.D. et al., "Impotence Therapy and Cancer of the Prostate", The American Journal of Surgery, 131:599-600 (1976).
Guo, Zhiyong et al., "A Novel Androgen Receptor Splice Variant Is Up-regulated during Prostate Cancer Progression and Promotes Androgen Depletion—Resistant Growth", Cancer Research, 69:2305-13 (2009).
Haggstrom, Stina et al., "Testosterone Induces Vascular Endothelial Growth Factor Synthesis in the Ventral Prostate in Castrated Rats", The Journal of Urology, 161:1620-1625 (1999).
Harper et al., "Expression of Androgen Receptor and Growth Factors in Premalignant Lesions of the Prostate", Journal of Pathology, 186:169-177 (1998).
He, B. et al., "Activation Function 2 in the Human Androgen Receptor Ligand Binding Domain Mediates Interdomain Communication with the NH2-terminal Domain", The Journal of Biological Chemistry, 274(52):37219-37225 (1999).
He, B. et al., "Structural Basis for Androgen Receptor Interdomain and Coactivator Interactions Suggests a Transition in Nuclear Receptor Activation Function Dominance", Molecular Cell, 16:425-438 (2004).
Heinlein, Cynthia A., et al., "Androgen Receptor in Prostate Cancer", Endocrine Reviews, 25(2):276-308 (2004).
Helzlsouer, Kathy J., et al., "Serum Gonadotropins and Steroid Hormones and the Development of Ovarian Cancer", JAMA, 274(24):1926-1930 (1995).
Henke, H., "Selektive prparative gelchromatographische Trennung niedermolekularer Verbindungen an Sephadex LH-20", Journal of Chromatography, 254: 296-308 (1983).
Horoszewicz, J.S. et al., "LNCaP Model of Human Prostatic Carcinoma", Cancer Research, 43:1809-1818 (1983).
Hu, R. et al., "Ligand-Independent Androgen Receptor Variants Derived fromSplicing of Cryptic Exons Signify Hormone-Refractory Prostate Cancer", Cancer Research, 69:16-22 (2009).
Huber, P.R. et al., "Prostate Specific Antigen. Experimental and Clinical Observations", Scand. J. Urol Nephrol., 104:33-39 (1987).
Hur, E. et al., "Recognition and Accommodation at the Androgen Receptor Coactivator Binding Interface", PLoS Biology, 2(9)(e274):1303-1312 (2004).
Imamura et al., "An imaging agent to detect androgen receptor and its active splice variants in prostate cancer," JCI Insight. 2016;1(11):e87850 15 pages.
Imamura et al., "Androgen receptor targeted therapies in castration-resistant prostate cancer: Bench to clinic," International Journal of Urology (2016), 23(8):654-65.
International Search Report and Written Opinion for International Application No. PCT/US2021/027771 mailed Jul. 9, 2020, 8 pages.
International Preliminary Report on Patentability for International Application No. PCT/CA2009/000902 issued Jan. 5, 2011, 7 pages.
International Preliminary Report on Patentability for International Application No. PCT/CA2011/000019 dated Jul. 10, 2012, 8 pages.
International Preliminary Report on Patentability for International Application No. PCT/CA2011/000021 dated Jul. 10, 2012, 8 pages.
International Preliminary Report on Patentability for International Application No. PCT/CA2014/000414 mailed Nov. 10, 2015, 7 pages.
International Preliminary Report on Patentability for International Application No. PCT/CA2014/000685 mailed Mar. 15, 2016, 7 pages.
International Preliminary Report on Patentability for International Application No. PCT/CA2015/000533 dated Apr. 18, 2017, 7 pages.
International Preliminary Report on Patentability for International Application No. PCT/CA2015/000535 dated Apr. 18, 2017, 6 pages.
International Preliminary Report on Patentability for International Application No. PCT/CA2016/000008 dated Jul. 18, 2017, 7 pages.
International Preliminary Report on Patentability for International Application No. PCT/CA2016/000070 dated Sep. 12, 2017, 6 pages.
International Preliminary Report on Patentability for International Application No. PCT/US2012/033957 dated Oct. 22, 2013, 6 pages.
International Preliminary Report on Patentability for International Application No. PCT/US2012/033959 dated Oct. 22, 2013, 8 pages.
International Preliminary Report on Patentability for International Application No. PCT/US2012/051481 dated Feb. 25, 2014, 8 pages.
International Preliminary Report on Patentability for International Application No. PCT/US2012/051923 dated Feb. 25, 2014, 9 pages.
International Preliminary Report on Patentability for PCT/US2012/032584 issued Oct. 8, 2013, 6 pages.
International Search Report and Written Opinion for International Application No. PCT/US2020/025542 mailed Aug. 14, 2020,10 pages.
International Search Report and Written Opinion for International Application No. PCT/US2020/025545 mailed Jul. 9, 2020,11 pages.
International Search Report and Written Opinion for International Application No. PCT/CA2014/000414 mailed Aug. 5, 2014, 6 pages.
International Search Report and Written Opinion for International Application No. PCT/CA2014/000685 mailed Dec. 4, 2014, 13 pages.
International Search Report and Written Opinion for International Application No. PCT/CA2015/000533 mailed Dec. 18, 2015, 11 pages.
International Search Report and Written Opinion for International Application No. PCT/CA2015/000535 mailed Dec. 23, 2015, 9 pages.
International Search Report and Written Opinion for International Application No. PCT/CA2016/000008 mailed Mar. 15, 2016, 13 pages.
International Search Report and Written Opinion for International Application No. PCT/CA2016/000070 mailed Jun. 2, 2016, 10 pages.
International Search Report and Written Opinion for International Application No. PCT/CA2017/000083 mailed Aug. 3, 2017, 14 pages.
International Search Report and Written Opinion for International Application No. PCT/CA2017/000141 mailed Sep. 1, 2017, 11 pages.
International Search Report and Written Opinion for International Application No. PCT/CA2017/000201 mailed Dec. 8, 2017, 9 pages.
International Search Report and Written Opinion for International Application No. PCT/US2019/057034 mailed Feb. 6, 2020, 10 pages.
International Search Report and Written Opinion for International Application No. PCT/US2020/025539 mailed Aug. 18, 2020,11 pages.
International Search Report and Written Opinion for International Application No. PCT/US2021/050644 dated Feb. 3, 2022, 13 pages.
International Search Report for International Application No. PCT/CA2009/000902 mailed Sep. 1, 2009, 4 pages.
International Search Report for International Application No. PCT/CA2011/000019 mailed Mar. 21, 2011, 7 pages.
International Search Report for International Application No. PCT/CA2011/000021 mailed Apr. 18, 2011, 8 pages.
International Search Report for International Application No. PCT/US2012/032584 mailed Jul. 31, 2012, 3 pages.
International Search Report for International Application No. PCT/US2012/033957 mailed Jul. 18, 2012, 3 pages.
International Search Report for International Application No. PCT/US2012/033959 mailed Jul. 18, 2012, 3 pages.
International Search Report for International Application No. PCT/US2012/051481 mailed Nov. 26, 2012, 4 pages.
International Search Report for International Application No. PCT/US2012/051923 mailed Jan. 28, 2013, 4 pages.

(56) References Cited

OTHER PUBLICATIONS

Isaacs, J.T., "Antagonistic Effect of Androgen on Prostatic Cell Death", The Prostate, 5:545-557 (1984).
Isaacs, J.T., et al., "New Biochemical Methods to Determine Androgen Sensitivity of Prostatic Cancer: The Relative Enzymatic Index (REI)", Prostate Cancer and Hormone Receptors, pp. 133-144 (1979).
Jackson, J. A. et al., "Prostatic Complications of Testosterone Replacement Therapy", Arch Intern Med., 149:2365-2366 (1989).
Japanese Patent Application No. 2016-512175, Notice of Reasons for Rejection mailed Jun. 21, 2016 (and English translation), 12 pages.
Jenster, G. et al., "Domains of the Human Androgen Receptor Involved in Steroid Binding, Transcriptional Activation, and Subcellular Localization", Molecular Endocrinology, 5:1396-1404 (1991).
Jenster, G., et al. "Identification of two transcription activation units in the N-terminal domain of the human androgen receptor." Journal of Biological Chemistry (1995); 270.13: 7341-7346.
Jia, L. et al., "Androgen Receptor Signaling: Mechanism of Interleukin-6 Inhibition", Cancer Research, 64:2619-2626 (2004).
Jia, L. et al., "Androgen Receptor-Dependent PSA Expression in Androgen-Independent Prostate Cancer Cells Does Not Involve Androgen Receptor Occupancy of the PSA Locus", Cancer Research, 65:8003-8008 (2005).
Kaighn, M.E. et al., "Prostate Carcinoma: Tissue Culture Cell Lines", National Cancer Institute Monograph No. 49, pp. 17-21 (1978).
Kato, M. et al., "Cotargeting androgen receptor splice variants and mTOR signaling pathway for the treatment of castration-resistant prostate cancer," Clin Cancer Res, Jun. 2016, vol. 22, pp. 2744-2754.
Kemppainen, J. A. et al., "Distinguishing Androgen Receptor Agonists and Antagonists: Distinct Mechanisms of Activation by Medroxyprogesterone Acetate and Dihydrotestosterone", Mol. Endocrinol., 13:440-454 (1999).
Kim, D. et al., "Androgen Receptor Expression and Cellular Proliferation During Transition from Androgen-Dependent to Recurrent Growth after Castration inthe CWR22 Prostate Cancer Xenograft", American Journal of Pathology, 160(1):219-226 (2002).
Kolbel, M. et al., "Design of Liquid Crystalline Block Molecules with Nonconventional Mesophase Morphologies: Calamitic Bolaamphiphiles with Lateral Alkyl Chains", J. Am. Chem. Soc., 123:6809-6818 (2001).
Kumar, S. et al., "Synthesis of new crown analogs derived from bisphenol," Indian Journal Chemistry, 36B:656-661 (1997).
Langley, E. et al., "Evidence for an Anti-parallel Orientation of the Ligand-activated Human Androgen Receptor Dimer", The Journal of Biological Chemistry, 270(50):29983-29990 (1995).
Lannoye, G.S. et al., "N-Fluoroalkylated and N-alkylated analogs of the dopaminergic D-2 receptor antagonist raclopride", J. Med. Chem., 33(9):2430-2437 (1990).
Leepipatpiboon, N. et al., "Simultaneous determination of bisphenol-A-diglycidyl ether, bisphenol-F-diglycidyl ether, and their derivatives in oil-in-water and aqueous-based canned foods by high-performance liquid chromatography with fluorescence detection." Journal of Chromatography A (2005); 1073.1: 331-339.
Levoin et al., "Determination of the binding mode and interacting amino-acids for dibasic H3 receptor antagonists", Bioorganic & Medicinal Chemistry, 21 (2013) 4526-4529 and Levoin et al., "Supporting Information—Determination of the binding mode and interacting amino-acids for dibasic H3 receptor agonists", Bioorganic & Medicinal Chemistry, vol. 21, Jan. 2013, pp. S1-S3.
L'Heureux, A. et al., "Aminodifluorosulfinium Salts: Selective Fluorination Reagents with Enhanced Thermal Stability and Ease of Handling", J. Org. Chem, 75:3401-3411 (2010).
Lima, Lidia M., and Barreiro, Eliezer J. "Bioisosterism: a useful strategy for molecular modification and drug design." Current Medicinal Chemistry (2005); 12.1: 23-49.

Loren, J.C. et al., "Synthesis of achiral and racemic catenanes based on terpyridine and a directionalized terpyridine mimic, pyridyl-phenanthroline", Org. Biomol. Chem., 3(17):3105-3116 (2005).
Louie, M.C. et al., "Androgen-induced recruitment of RNA polymerase IIto a nuclear receptor-p160 coactivator complex", PNAS, 100(5):2226-2230 (2003).
Makary, P., "Principles of salt formation." UK Journal of Pharmaceutical and Biosciences (2014); 2(4): 01-04.
Marriott et al., "Pharmaceutical Compounding and Dispensing," Second Edition, Pharmaceutical Press, 305 pages (2005).
Martin, S.J. et al., "A new precursor for the radiosynthesis of [18F]FLT", Nuclear Medicine and Biology, 29:263-273 (2002).
Martin, S.K. et al., "N-terminal targeting of androgen receptor variant enhances response of castration resistant prostate cancer to taxane chemotherapy," Molecular Oncology, 2015, vol. 9, pp. 628-639.
Masiello, D. et al., "Bicalutamide Functions as an Androgen Receptor Antagonist by Assembly of a Transcriptionally Inactive Receptor", The Journal of Biological Chemistry, 277(29):26321-26326 (2002).
Mathur, A., et al., "Subverting ER-Stress towards Apoptosis by Nelfinavir and Curcumin Coexposure Augments Docetaxel Efficacy in Castration Resistant Prostate Cancer Cells," PLoS One, Aug. 2014, vol. 9(8), pp. 14.
Mawji et al., "Preparation of ester derivatives of bisphenol-related compounds as androgen receptor modulators", CAPLUS Database Accession No. 2014:1909735, Document No. 161:737220, Entered on Jan. 6, 2015, 7 pages (Abstract).
McClurg, U.L., et al., "The Novel Anti-Androgen Candidate Galeterone Targets Deubiquitinating Enzymes, USP12 and USP46, to Control Prostate Cancer Growth and Survival," Oncotarget, May 2018, vol. 9(38), pp. 24992-25007.
Melnyk, O. et al., "Neutralizing Anti-Vascular Endothelial Growth Factor Antibody Inhibits Further Growth of Established Prostate Cancer and Metastases in a Pre-Clinical Model", The Journal of Urology, 161:960-963 (1999).
Miller, J.I. et al., "The Clinical Usefulness of Serum Prostate Specific Antigen After Hormonal Therapy of Metastatic Prostate Cancer", The Journal of Urology, 147:956-961 (1992).
Mitsiades, C.S. et al., "Molecular biology and cellular physiology of refractoriness to androgen ablation therapy in advanced prostate cancer", Expert Opin. Investig. Drugs, 10(6):1099-1115 (2001).
Myung, J-K et al., "An androgen receptor N-terminal domain antagonist for treating prostate cancer", The Journal of Clinical Investigation, 123(7):2948-2960 (2013).
Nakazawa, H. et al., "In vitro assay of hydrolysis and chlorohydroxy derivatives of bisphenol A diglycidyl ether for estrogenic activity", Food and Chemical Toxicology, 40:1827-1832 (2002).
Nazareth, L.V. et al, "Activation of the Human Androgen Receptor through a Protein Kinase A Signaling Pathway." The Journal of Biological Chemistry, 271(33):19900-19907 (1996).
Nedolya, N. A. et al., Zhurnal Organicheskoi Khimii, 30(8):1163-1166 (1994) (non English document).
Nishikawa et al., "Epichlorohydrin derivative-based modifier of cellulose fibers and modification method of cellulose fibers," Accession No. 2000:98153 CAPLUS (2009).
Noble, R. L., "Sex steroids as a cause of adenocarcinoma of the dorsal prostate in Nb Rats, and their influence on the growth of transplants", Oncology, 34:138-141 (1977).
Noble, R. L., "The development of prostatic adenocarcinoma in Nb Rats following prolonged sex hormone administration", Cancer Research, 37:1929-1933 (1977).
Ogawa, Y. et al., "Estrogenic activities of chemicals related to food contact plastics and rubbers tested by the yeast two-hybrid assay," Food Additives and Contaminants, 23:4, 422-430 (2006).
Paris, F. et al., "Phenylphenols, biphenols, bisphenol-A and 4-tert-octyphenol exhibit and estrogen activities and antiandrogen activity in reporter cell lines," Molecular and Cellular Endocrinology, 193:43-49 (2002).
Patani, G. A. et al., "Bioisosterism: A Rational Approach in Drug Design," Chem. Rev., 96: 3147-3176 (1996).
Penczek, P. et al., "Synthesis and cyclotrimerization of dipropargyl derivatives of diepoxides," Database CAPLUS [Online] Chemical

(56) References Cited

OTHER PUBLICATIONS

Abstracts Service, Columbus, Ohio, retrieved from STN CA Caesar Accession No. 1995:741510 (1995), 2 pages.
Penczek, P. et al., "Synthesis and cyclotrimerization of dipropargyl derivatives of diepoxides," Polimery, (Warsaw), 40(5):274-277 (1995).
Petersen, H. et al., "Determination of bisphenol A diglycidyl ether (BADGE) and its derivatives in food: identification and quantification by internal Standard", Eur. Food Res. Technol., 216:355-364 (2003).
Poouthree, K. et al., "Comparison of resolution in microemulsion EKC and MEKC employing suppressed electroosmosis: Application to bisphenol-A-diglycidyl ether and its derivatives", Electrophoresis, 28(20):3705-3711 (2007).
Poustka, J. et al., "Determination and occurrence of bisphenol A, bisphenol A diglycidyl ether, and bisphenol F diglycidyl ether, including their derivatives, in canned foodstuffs' from the Czech retail market," Czech J. Food Sci., 25(4):221-229 (2006).
Poustkov et al., "Stability of bisphenol A diglycidyl ether and bisphenol F diglycidyl ether in water-based food simulants." European Food Research and Technology, 219(5): 534-539 (2004).
PubChem Compound Summary for CID 15305867, '4-Acetyl-4'-ethylbiphenyl', U.S. National Library of Medicine, Feb. 9, 2007, pp. 1-17; retrieved from https://pubchem.ncbi.nlm.nih.gov/compound/15305867.
PubChem Compound Summary for CID 18533308, '2-[4-[[4-(Aminomethoxy)phenyl]methyl]-2-methylphenoxy]acetic acid', U.S. National Library of Medicine, Dec. 4, 2007, pp. 1-15 retrieved from https://pubchem.ncbi.nlm.nih.gov/compound/18533308.
Qin. C., et al., "Discovery of QCA570 as an Exceptionally Potent and Efficacious Proteolysis Targeting Chimera (PROTAC) Degrader of the Bromodomain and Extra-Terminal (BET) Proteins Capable of Inducing Complete and Durable Tumor Regression", Journal of Medicinal Chemistry, Aug. 2018, vol. 61(15), pp. 6685-6704.
Quayle, S. et al., "Androgen receptor decoy molecules block the growth of prostate cancer", PNAS, 104(4):1331-1336 (2007).
Raina, K., et al., "PROTAC-Induced BET Protein Degradation as a Therapy for Castration-Resistant Prostate Cancer", Proceedings of the National Academy of Sciences, Jun. 2016, vol. 113(26), pp. 7124-7129.
Rao, B.R. et al., "Endocrine Factors in Common Epithelial Ovarian Cancer", Endocrine Reviews, 12(1):14-26 (1991).
Reader, C. E. L., "Epoxy Resin Derivatives for Stoving Systems", Surface Coatings Australia, 25(10):6-9 (1988).
Reid, J. et al., "Conformational Analysis of the Androgen Receptor Amino-terminal Domain Involved in Transactivation," The Journal of Biological Chemistry, 277:20079-20086 (2002).
Risch, H.A., "Hormonal Etiology of Epithelial Ovarian Cancer, With a Hypothesis Concerning the Role of Androgens and Progesterone", Journal of the National Cancer Institute, 90(23):1774-1786 (1998).
Riu, A. et al., "Characterization of Novel Ligands of ER, Er, and PPAR: The Case of Halogenated Bisphenol A and Their Conjugated Metabolites", Toxicology Sciences, 122(2): 372-382 (2011).
Roberts et al., "Emerging drugs for hepatocellular carcinoma," Expert Opin Emerg Drugs, 11(3):469-487 (2006).
Roberts, J. T. et al., "Adenocarcinoma of Prostate in 40-Year-Old Body-Builder", Lancet, 2:742 (1986).
Rokicki, G. et al., "Reactions of 4-chloromethyl-1,3-dioxolan-2-one with phenols as a new route to polyols and cyclic carbonates", Journal f. prakt. Chemie., 327:718-722 (1985).
Ross, R.K. et al., "Androgen Metabolism and Prostate Cancer: Establishing a Model of Genetic Susceptibility", European Urology, 35:355-361 (1999).
Roulin et al., "Targeting renal cell carcinoma with NVP-BEZ235, a dual PI3K/mTOR inhibitor, in combination with sorafenib," Mol Cancer, 10:90 (2011).
Rusu, E. et al.: "Photosensitive compounds with chloromethyl groups", Revue Roumaine de Chimie, 45(5):451-456 (2000).
Sadar, M., "Androgen-independent Induction of Prostate-specific Antigen Gene Expression via Cross-talk between the Androgen Receptor and Protein Kinase A signal Transduction Pathways," The Journal of Biological Chemistry, 274(12):7777-7783 (1999).
Sadar, M. et al., "Prostate cancer: molecular biology of early progression to androgen independence", Endocrine-Related Cancer, 6:487-502 (1999).
Sadar, M.D. et al., "Characterization of a New in Vivo Hollow Fiber Model for the Study of Progression of Prostate Cancer to Androgen Independence", Molecular Cancer Therapeutics, 1:629-637 (2002).
Sato, N. et al., "A Metastatic and Androgen-sensitive Human Prostate Cancer Model Using Intraprostatic Inoculation of LNCaP Cells in SCID Mice", Cancer Research, 57:1584-1589 (1997).
Sato, N. et al., "Intermittent Androgen Suppression Delays Progression to Androgen-independent Regulation of Prostate-specific Antigen Gene in the LNCaP Prostate Tumour Model", J. Steroid Biochem. Mol. Biol., 58:139-146 (1996).
Satoh, K. et al., "Study on Anti-Androgenic Effects of Bisphenol a Diglycidyl Ether (BADGE), Bisphenol F Diglycidyl Ether (BFDGE) and Their Derivatives Using Cells Stably Transfected with Human Androgen Receptor, AR-EcoScreen", Food and Chemical Toxicology, 42:983-993 (2004).
Schaefer, A. et al., "Migration from can coatings: Part 3. Synthesis, identification and quantification of migrating epoxy-based substances below 1000 Da", Food Additives and Contaminants, 21(4):390-405 (2004).
Schellhammer, "An evaluation of bicalutamide in the treatment of prostate cancer." Expert Opinion on Pharmacotherapy, 3(9): 1313-1328 (2002).
Sharp et al., "Targeting Androgen Receptor Aberrations in Castration-Resistant Prostate Cancer," Clin Cancer Res., Sep. 1, 2016;22(17):4280-4282.
Silverman, R. B., The Organic Chemistry of Drug Design and Drug Action, Academic Press, Inc., Harcourt Brace Jovanovich, pp. 15-20, 9 pages (1992).
Snoek, R. et al., "Induction of Cell-free, In Vitro Transcription by Recombinant Androgen Receptor Peptides", J. Steroid Biochem. Mol. Biol., 59:243-250 (1996).
Stanciuc et al., "Reaction of Pyrylium Salts with Nucleophiles. 23: Triarylethene Derivatives Containing an Oxyalkyleneamino or Oxyalkylene-N-pyridinium Side Chain", Journal of Pharmaceutical Sciences, vol. 82, No. 9, Sep. 1993, pp. 927-933.
Still, W. C. et al., "Rapid Chromatographic Technique for Preparative Separations with Moderate Resolution", J. Org. Chem., 43(14):2923-2925 (1978).
STN Structure Search, dated Oct. 30, 2014 citing PL 135932, 3 pages.
Strub and McKim, "Dimethyl Sulfoxide USP, PhEur in Approved Pharmaceutical Products and Medical Devices", PharmaTech.com, 6 pages (2008).http://www.pharmtech.com/print/224268 ?page=full &rel=canonical.
Sun, S. et al., "Castration resistance in human prostate cancer is conferred by a frequently occurring androgen receptor splice variant." The Journal of Clinical Investigation, 120(8):2715-2730 (2010).
Supplementary European Search Report in EP Application No. 09771876.1 dated Jun. 20, 2011, 5 pages.
Supplementary European Search Report in EP Application No. 11731645.5 dated mailed Jun. 20, 2013, 11 pages.
Tanji, N. et al., "Growth Factors: Roles in Andrology", Archives of Andrology, 47:1-7 (2001).
Taplin, M.E. et al., "Selection for Androgen Receptor Mutations in Prostate cancers Treated with Androgen Antagonist", Cancer Research, 59:2511-2515 (1999).
Taskeen, A. et al., "Analysis of bisphenol A in canned food: A mini review", Asian Journal of Chemistry, 22(5):4133-4135 (2010).
Thomson, A.A., "Role of androgens and fibroblast growth factors in prostatic development", Reproduction, 121:187-195 (2001).
Ueda, T. et al., "Activation of the Androgen Receptor N-terminal Domain by Interleukin-6 via MAPK and STAT3 Signal Transduction Pathways", The Journal of Biological Chemistry, 277(9):7076-7085 (2002).
Ueda, T. et al., "Ligand-independent Activation of the Androgen Receptor by Interleukin-6 and the Role of Steroid Receptor Coactivator-1 in Prostate cancer Cells", The Journal of Biological Chemistry, 277(41): 38087-38094 (2002).

(56) References Cited

OTHER PUBLICATIONS

Uematsu, Y. et al., "Chlorohydrins of bisphenol A diglycidyl ether (BADGE) and bisphenol F diglycidyl ether (BFDGE) in canned foods and ready-to-drink coffees from the Japanese market", Food Additives and Contaminants, 18(2):177-185 (2001).
Van Der Kwast, T.H. et al., "Androgen Receptors in Endocrine-Therapy-Resistant Human Prostate Cancer", Inter. J. Cancer, 48:189-193 (1991).
Van Scherpenzeel, M. et al., "Nanomolar affinity, iminosugar-based chemical probes for specific labeling of lysosomal glucocerebrosidase", Bioorganic & Medicinal Chemistry, 18:267-273 (2010).
Venkatesh, Srini, and Lipper, Robert A. "Role of the development scientist in compound lead selection and optimization." Journal of Pharmaceutical Sciences (2000); 89.2: 145-154.
Vippagunta, et al. Crystalline Solids, Advanced Drug Delivery Reviews 48:3-26 (2001).
Walfried et al., "Bisphenol F-Diglycidylether (BFDGE) und Folgeprodukte in Konservenfllgtern: Synthese und Analytik," Deutsche Lebensmittel-Rundschau, vol. 96, No. 11, 2000, pp. 417-422 (with English abstract).
Wang, G. et al., "Identification of genes targeted by the androgen and PKA signaling pathways in prostate cancer cells", Oncogene, 25:7311-7323 (2006).
Wang, Q. et al., "Spatial and Temporal Recruitment of Androgen Receptor and Its Coactivators Involves Chromosomal Looping and Polymerase Tracking", Molecular Cell, 19:631-642 (2005).
Wetherill, Y. B. et al., "In vitro molecular mechanisms of bisphenol A action," Reproductive Toxicology, 24:178-198 (2007).
Wiedmann and Naqwi, "Pharmaceutical salts: Theory, use in solid dosage forms and in situ preparation in an aerosol." Asian Journal of Pharmaceutical Sciences (2016); 11(6): 722-734.
Wilcox and Cowart, "New Approaches to Synthetic Receptors. Synthesis and Host Properties of a Water Soluble Macrocyclic Analog of Troger's Base", Tetrahedron Letters, 27(46): 5563-5566 (1986).
Wilding, G., "The Importance of Steroid Hormones in Prostate Cancer", Cancer Surveys, 14:113-130 (1992).
Wilson, J.D. et al., "Long-Term Consequences of Castration in Men: Lessonsfrom the Skoptzy and the Eunuchs of the Chinese and Ottoman Courts", The Journal of Clinical Endocrinology & Metabolism, 84:4324-4331 (1999).
Wolff, "Burger's Medicinal Chemistry and Drug Discovery," Fifth Edition, vol. 1: Principles and Practice, New York: John Wiley & Sons, 1994, 975-977.
Wong, C. et al., "Steroid Requirement for Androgen Receptor Dimerization and DNA Binding", J. Bioi. Chem., 268(25):19004-19012 (1993).
Written Opinion for International Application No. PCT/CA2009/000902 mailed Sep. 1, 2009, 6 pages.
Written Opinion for International Application No. PCT/CA2011/000019 mailed Mar. 21, 2011, 7 pages.
Written Opinion for International Application No. PCT/CA2011/000021 mailed Apr. 18, 2011, 7 pages.
Written Opinion for International Application No. PCT/US2012/032584 mailed Jul. 31, 2012, 5 pages.
Written Opinion for International Application No. PCT/US2012/033957 mailed Jul. 18, 2012, 5 pages.
Written Opinion for International Application No. PCT/US2012/033959 mailed Jul. 18, 2012, 7 pages.
Written Opinion for International Application No. PCT/US2012/051481 mailed Nov. 26, 2012, 7 pages.
Written Opinion for International Application No. PCT/US2012/051923 mailed Jan. 28, 2013, 8 pages.
Xu, X. et al., "Synthesis and Stability Study of Dental Monomers Containing Methacrylamidoethyl Phosphonic Acids", Journal of Polymer Science: Part A Polymer Chemistry, 45:99-110 (2007).
Yang et al., "Targeting Androgen Receptor Activation Function-1 with EPI to Overcome Resistance Mechanisms in Castration-Resistant Prostate Cancer," Clin Cancer Res; 22(17) Sep. 1, 2016, 4466-4477.
Ye, Deyong, "An Introduction to Computer-Aided Drug Design", 3 pages, Jan. 31, 2004 (non-English document).
Yonekubo, J. et al., "Concentrations of Bisphenol A, Bisphenol A Diglycidyl Ether, and Their Derivatives in Canned Foods in Japanese Markets," J. Agric. Food Chem., 2008, 56, 2041-2047.
Yong, Eu Leong, et al. "Molecular basis of androgen receptor diseases." Annals of Medicine (2000); 32.1: 15-22.
Zuhayra, M. et al., "New approach for the synthesis of [18F]fluoroethyltyrosine for cancer imaging: Simple, fast, and high yielding automated synthesis", Bioorganic & Medicinal Chemistry, 17:7441-7448 (2009).
Zurth, C., et al., "Drug-Drug Interaction Potential of Darolutamide: In Vitro and Clinical Studies," European Journal of Drug Metabolism and Pharmacokinetics, Dec. 2019, vol. 44(6), pp. 747-759.
Aitipamula, S. et al. "Polymorphs, Salts, and Cocrystals: What's in a Name?", Crystal Growth & Design, 2012, 12(5), p. 2147-2152.
Auberson et al., "Ligand Specific Efficiency (LSE) Index for PET Tracer Optimization," ChemMedChem, vol. 11, No. 13, Jul. 5, 2016, pp. 1415-1427.
Extended European Search Report for European Application No. 19873360.2 dated Jun. 15, 2022, 10 pages.
Extended European Search Report for European Application No. 20779267.2 dated Jun. 5, 2023, 10 pages.
International Search Report and Written Opinion for Application No. PCT/US2022/026010, mailed on Aug. 26, 2022, 10 pages.
International Search Report and Written Opinion for International Application No. PCT/US2022/025016, mailed Jun. 29, 2022, 9 pages.
Kant-Smits et al., "The RESISTANT study (Respiratory Muscle Training in Patients with Spinal Muscular Atrophy): study protocol fora randomized controlled trial," BMC Neurology (2023) 23:118, 11 pages.
Osuka et al., "Synthesis and Photoexcited-State Dynamics of Aromatic Group-Bridged Carotenoid-Porphyrin Dyads and Carotenoid-Porphyrin-Pyromellitimide Triads," J. Am. Chem. Soc. 1993, 115, 9439-9452.
PubChem Compound Summary for CID 145662858, 1-Cyclobutyl-3-cyclopropylcyclobutane, Dec. 12, 2019, 7 pages.
PubChem Compound Summary for CID 146484310, 'N-[4-[[4-[2-[3-chloro-4-(2-chloroethoxy)-5-cyanophenyl]propan-2-yl]phenoxy]methyl]pyrimidin-2yl]methanesulfonamide', U.S. National Library of Medicine, Jun. 27, 2020, 8 pages; retrieved from https://pubchem.ncbi.nlm.nih.gov/compound/146484310.
Reagan-Shaw S., et al. "Dose translation from animal to human studies revisited," The FASEB Journal, 2007, 22:659-661.

* cited by examiner

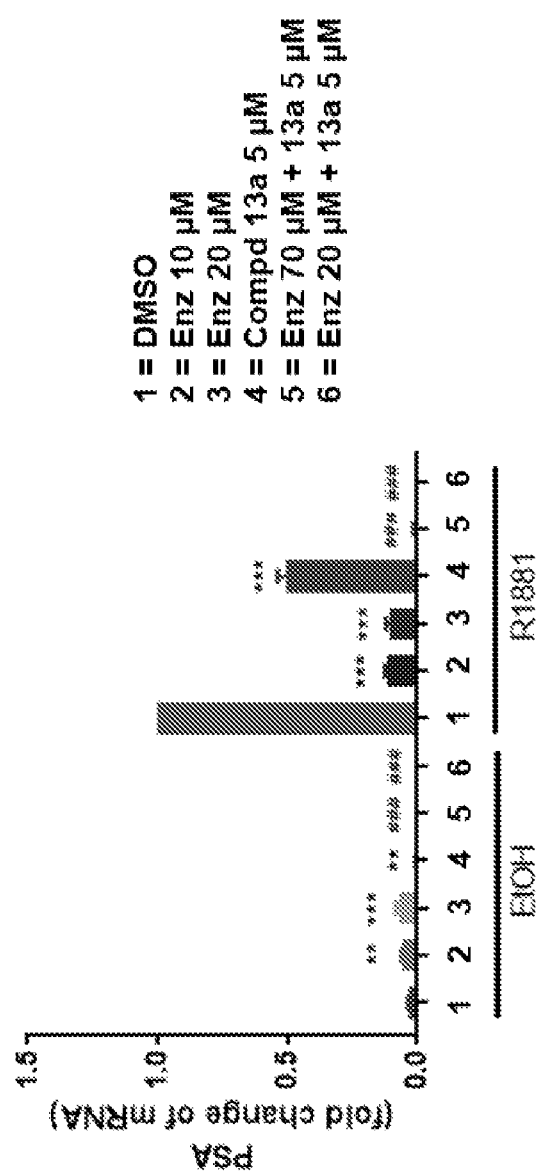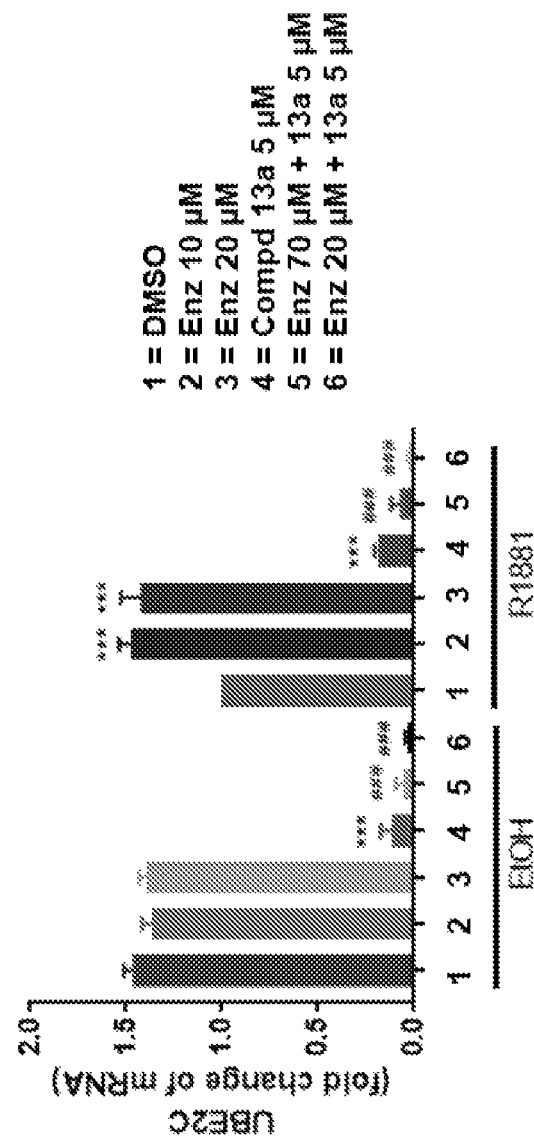
FIG. 7A
FIG. 7B

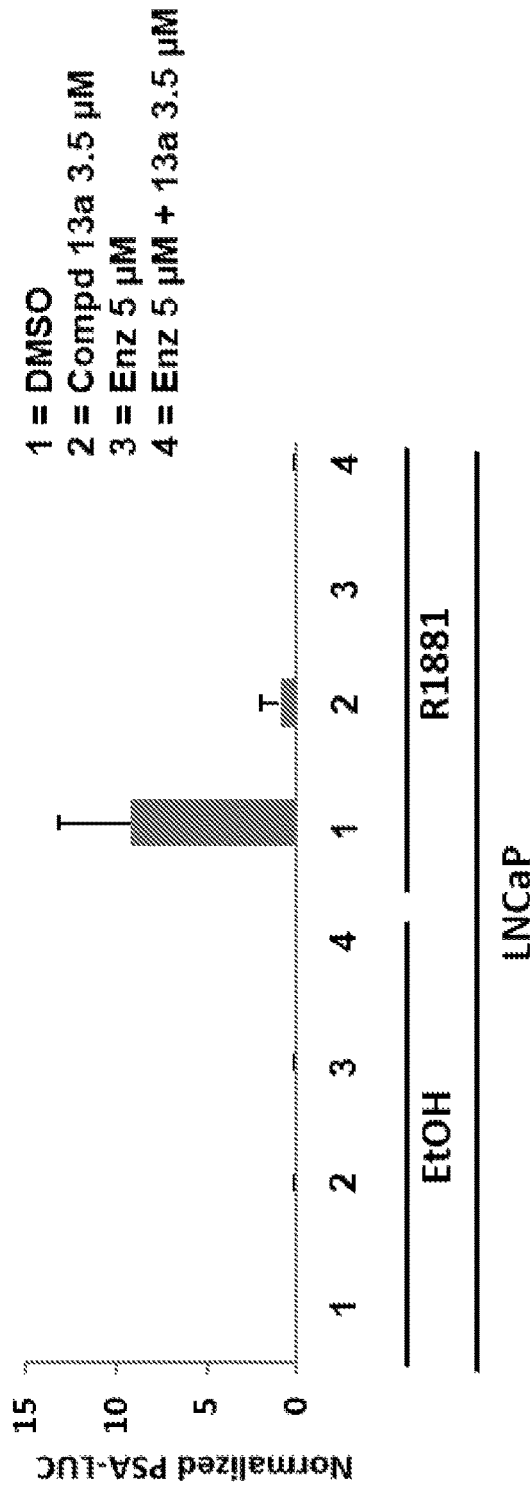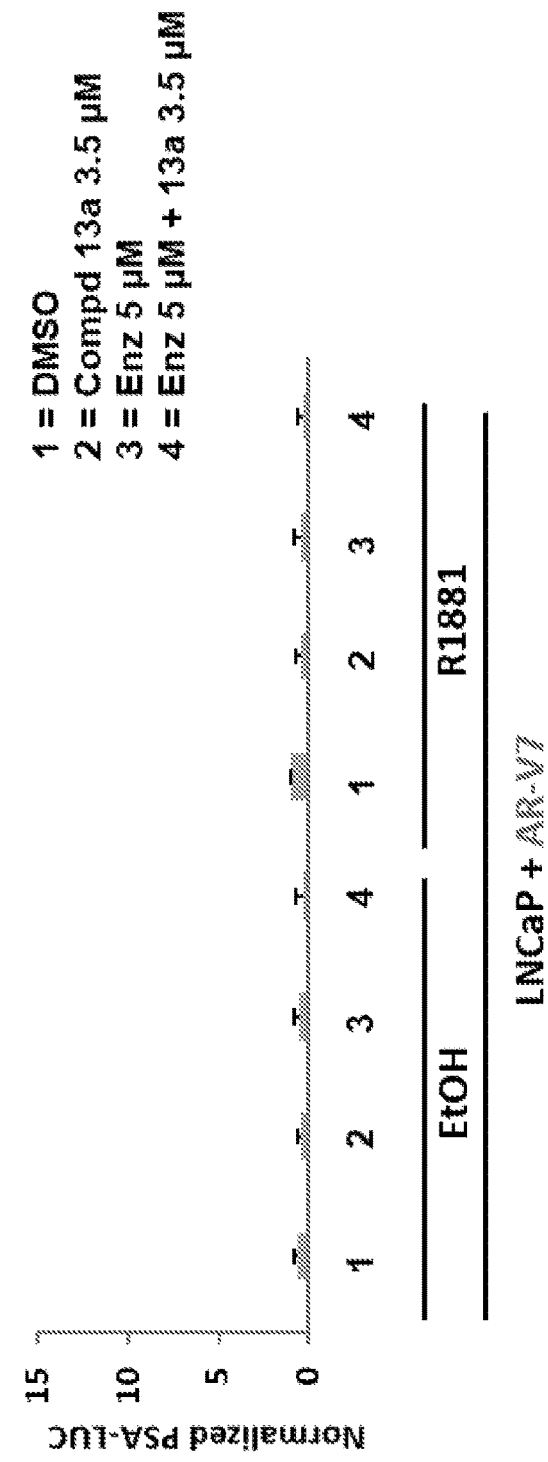

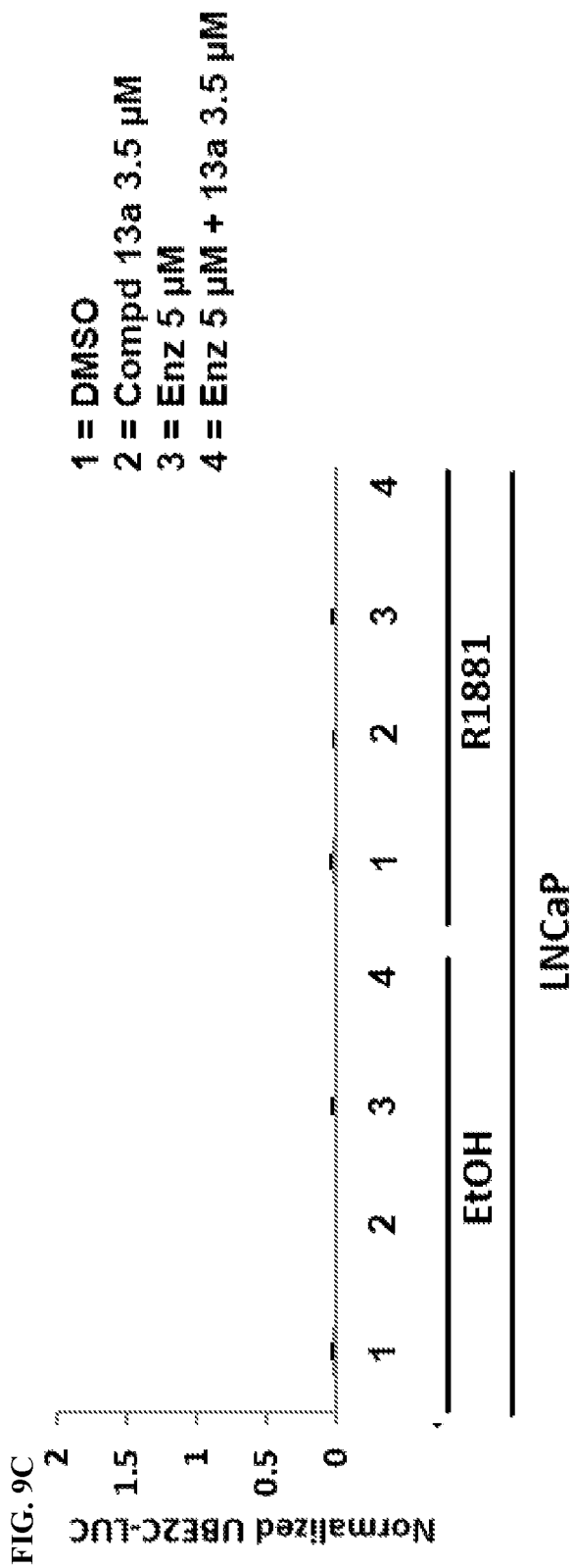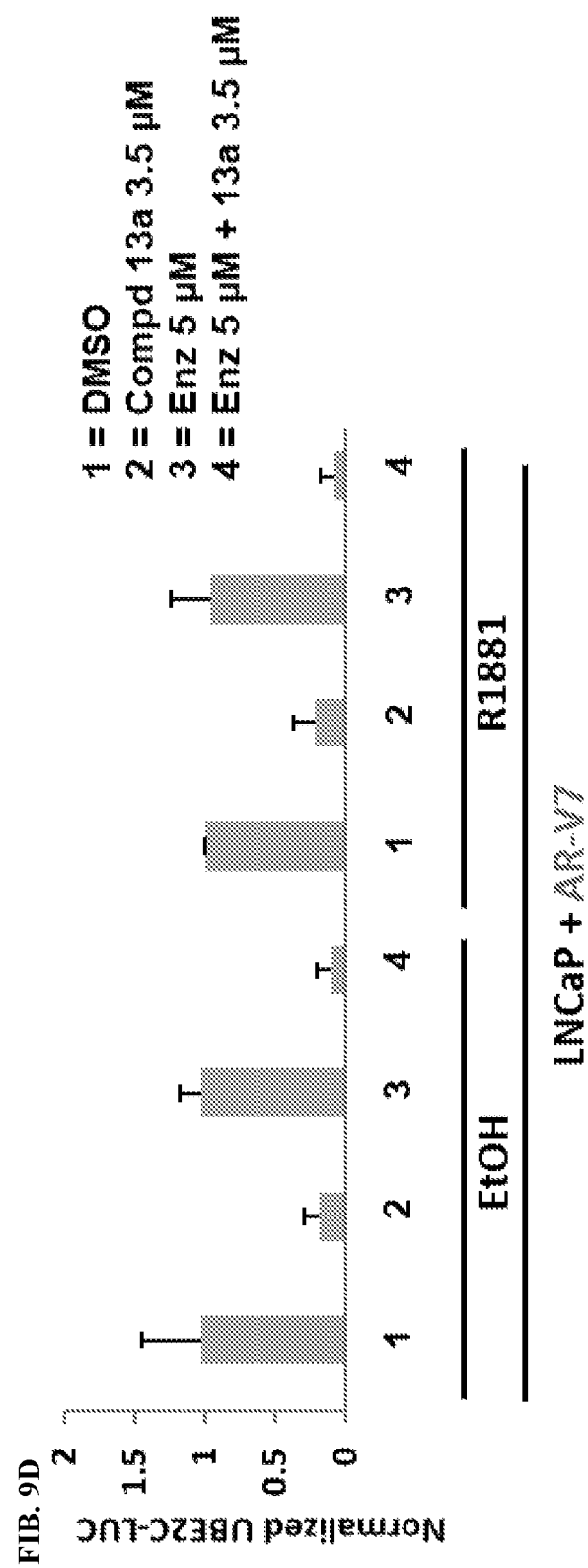
FIG. 9C
FIG. 9D

PHARMACEUTICAL COMPOSITIONS AND COMBINATIONS COMPRISING INHIBITORS OF THE ANDROGEN RECEPTOR AND USES THEREOF

CROSS-REFERENCE TO RELATED APPLICATIONS

This application is a U.S. National Stage application under 35 U.S.C. § 371 of International Application No. PCT/US2020/025545, filed Mar. 27, 2020, which claims priority to U.S. Provisional Application No. 62/825,440, filed Mar. 28, 2019, U.S. Provisional Application No. 62/825,450, filed Mar. 28, 2019, U.S. Provisional Application No. 62/842,980, filed May 3, 2019, and U.S. Provisional Application No. 62/857,519, filed Jun. 5, 2019, the disclosures of which are hereby incorporated by reference in their entireties for all purposes.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ESSA_042_01WO_SeqList_ST25.txt. The text file is ~2.4 KB, and was created on Mar. 27, 2020, and is being submitted electronically.

FIELD OF THE INVENTION

The present disclosure generally relates to pharmaceutical compositions and combinations comprising an androgen receptor N-terminal domain inhibitor or an inhibitor and an additional therapeutic agent, such as an cyclin-dependent kinase 4/6 (CDK 4/6) inhibitor, an Pin1 inhibitor (inhibitor of peptidyl-prolyl cis/trans isomerases), or an antiandrogen. In particular, the present disclosure relates to pharmaceutical compositions and combinations useful for treatment of various cancers, for example breast cancer and prostate cancer. Further, the present disclosure relates to administration of an androgen receptor N-terminal domain inhibitor in combination with radiation therapy for treating various cancers.

BACKGROUND OF THE INVENTION

Androgens mediate their effects through the androgen receptor (AR). Androgens play a role in a wide range of developmental and physiological responses and are involved in male sexual differentiation, maintenance of spermatogenesis, and male gonadotropin regulation (R. K. Ross, G. A. Coetzee, C. L. Pearce, J. K. Reichardt, P. Bretsky, L. N. Kolonel, B. E. Henderson, E. Lander, D. Altshuler & G. Daley, *Eur Urol* 35, 355-361 (1999); A. A. Thomson, *Reproduction* 121, 187-195 (2001); N. Tanji, K. Aoki & M. Yokoyama, *Arch Androl* 47, 1-7 (2001)). Several lines of evidence show that androgens are associated with the development of prostate carcinogenesis. Firstly, androgens induce prostatic carcinogenesis in rodent models (R. L. Noble, *Cancer Res* 37, 1929-1933 (1977); R. L. Noble, *Oncology* 34, 138-141 (1977)) and men receiving androgens in the form of anabolic steroids have a higher incidence of prostate cancer (J. T. Roberts & D. M. Essenhigh, *Lancet* 2, 742 (1986); J. A. Jackson, J. Waxman & A. M. Spiekerman, *Arch Intern Med* 149, 2365-2366 (1989); P. D. Guinan, W. Sadoughi, H. Alsheik, R. J. Ablin, D. Alrenga & I. M. Bush, *Am J Surg* 131, 599-600 (1976)). Secondly, prostate cancer does not develop if humans or dogs are castrated before puberty (J. D. Wilson & C. Roehrborn, *J Clin Endocrinol Metab* 84, 4324-4331 (1999); G. Wilding, *Cancer Surv* 14, 113-130 (1992)). Castration of adult males causes involution of the prostate and apoptosis of prostatic epithelium while eliciting no effect on other male external genitalia (E. M. Bruckheimer & N. Kyprianou, *Cell Tissue Res* 301, 153-162 (2000); J. T. Isaacs, *Prostate* 5, 545-557 (1984)). This dependency on androgens provides the underlying rationale for treating prostate cancer with chemical or surgical castration, also known as androgen ablation therapy (ABT) or androgen deprivation therapy (ADT).

Androgen receptor (AR) is a transcription factor that plays dual roles in breast cancer cells: promoting or inhibiting proliferation depending on expression and activity of estrogen receptor-alpha. Expression of AR is detected in up to 90% of all breast cancers.

Androgens also play a role in female diseases such as polycystic ovary syndrome as well as cancers. One example is ovarian cancer where elevated levels of androgens are associated with an increased risk of developing ovarian cancer (K. J. Helzlsouer, A. J. Alberg, G. B. Gordon, C. Longcope, T. L. Bush, S. C. Hoffman & G. W. Comstock, *JAMA* 274, 1926-1930 (1995); R. J. Edmondson, J. M. Monaghan & B. R. Davies, *Br J Cancer* 86, 879-885 (2002)). The AR has been detected in a majority of ovarian cancers (H. A. Risch, *J Natl Cancer Inst* 90, 1774-1786 (1998); B. R. Rao & B. J. Slotman, *Endocr Rev* 12, 14-26 (1991); G. M. Clinton & W. Hua, *Crit Rev Oncol Hematol* 25, 1-9 (1997)), whereas estrogen receptor-alpha (ERa) and the progesterone receptor are detected in less than 50% of ovarian tumors.

The only effective treatment available for advanced prostate cancer is the withdrawal of androgens which are essential for the survival of prostate luminal cells. Androgen ablation therapy causes a temporary reduction in tumor burden concomitant with a decrease in serum prostate-specific antigen (PSA). Unfortunately prostate cancer can eventually grow again in the absence of testicular androgens (castration-resistant disease) (Huber et al 1987 *Scand J. Urol Nephrol.* 104, 33-39). Castration-resistant prostate cancer that is still driven by AR is biochemically characterized before the onset of symptoms by a rising titre of serum PSA (Miller et al 1992 *J. Urol.* 147, 956-961). Once the disease becomes castration-resistant most patients succumb to their disease within two years.

The AR has distinct functional domains that include the carboxy-terminal ligand-binding domain (LBD), a DNA-binding domain (DBD) comprising two zinc finger motifs, and an N-terminus domain (NTD) that contains two transcriptional activation units (tau1 and tau5) within activation function-1 (AF-1). Binding of androgen (ligand) to the LBD of the AR results in its activation such that the receptor can effectively bind to its specific DNA consensus site, termed the androgen response element (ARE), on the promoter and enhancer regions of "normally" androgen regulated genes, such as PSA, to initiate transcription. The AR can be activated in the absence of androgen by stimulation of the cAMP-dependent protein kinase (PKA) pathway, with interleukin-6 (IL-6) and by various growth factors (Culig et al 1994 *Cancer Res.* 54, 5474-5478; Nazareth et al 1996 *J. Biol. Chem.* 271, 19900-19907; Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The mechanism of ligand-independent transformation of the AR has been shown to involve: 1) increased nuclear AR protein suggesting nuclear translocation; 2) increased AR/ARE complex formation; and 3) the AR-NTD (Sadar 1999 *J. Biol. Chem.* 274, 7777-7783; Ueda et al 2002 A *J. Biol. Chem.* 277, 7076-7085; and Ueda et al 2002 B *J. Biol. Chem.* 277, 38087-38094). The AR can be activated in the absence of testicular androgens by alternative signal transduction pathways in castration-resistant disease, which is consistent with the finding that nuclear AR protein is present in secondary prostate cancer tumors (Kim et al 2002 *Am. J. Pathol.* 160, 219-226; and van der Kwast et al 1991 *Inter. J. Cancer* 48, 189-193).

Clinically available inhibitors of the AR include nonsteroidal antiandrogens such as bicalutamide (Casodex™), nilutamide, flutamide, and enzalutamide. There is also a class of steroidal antiandrogens, such as cyproterone acetate and spironolactone. Both steroidal and non-steroidal antiandrogens target the LBD of the AR and predominantly fail presumably due to poor affinity and mutations that lead to activation of the AR by these same antiandrogens (Taplin, M. E., Bubley, G. J., Kom Y. J., Small E. J., Uptonm M., Rajeshkumarm B., Balkm S. P., *Cancer Res.*, 59, 2511-2515 (1999)), and constitutively active AR splice variants. Antiandrogens have no effect on the constitutively active AR splice variants that lack the ligand-binding domain (LBD) and are associated with castration-recurrent prostate cancer (Dehm S M, Schmidt L J, Heemers H V, Vessella R L, Tindall D J., *Cancer Res* 68, 5469-77, 2008; Guo Z, Yang X, Sun F, Jiang R, Linn D E, Chen H, Chen H, Kong X, Melamed J, Tepper C G, Kung H J, Brodie A M, Edwards J, Qiu Y., *Cancer Res.* 69, 2305-13, 2009; Hu et al 2009 Cancer Res. 69, 16-22; Sun et al 2010 *J Clin Invest.* 2010 120, 2715-30) and resistant to abiraterone and enzalutamide (Antonarakis et al., *N Engl J Med.* 2014, 371, 1028-38; Scher et al *JAMA Oncol.* 2016 doi: 10.1001). Conventional therapy has concentrated on androgen-dependent activation of the AR through its C-terminal domain.

Other relevant AR antagonists previously reported (see, WO 2010/000066, WO 2011/082487; WO 2011/082488; WO 2012/145330; WO 2015/031984; WO 2016/058080; and WO 2016/058082) that bind to full-length AR and/or truncated AR splice variants that are currently being developed include: AR degraders such as niclosamide (Liu C et al 2014), galeterone (Njar et al 2015; Yu Z at al 2014), and ARV-330/Androgen receptor PROTAC (Neklesa et al 2016 *J Clin Oncol* 34 suppl 2S; abstr 267); AR DBD inhibitor VPC-14449 (Dalal K et al 2014 *J Biol Chem.* 289(38): 26417-29; Li H et al 2014 *J Med Chem.* 57(15):6458-67; antiandrogens apalutamide (Clegg N J et al 2012), ODM-201 (Moilanen A M et al 2015), ODM-204 (Kallio et al *J Clin Oncol* 2016 vol. 34 no. 2_suppl 230), TAS3681 (Minamiguchi et al 2015 *J Clin Oncol* 33, suppl 7; abstr 266); and AR NTD inhibitors 3E10-AR441bsAb (Goicochea N L et al 2015), and sintokamide (Sadar et al 2008; Banuelos et al 2016).

The AR-NTD is also a target for drug development (e.g. WO 2000/001813; Myung et al. *J Clin. Invest* 2013, 123, 2948), since the NTD contains Activation-Function-1 (AF-1) which is the essential region required for AR transcriptional activity (Jenster et al 1991. *Mol Endocrinol.* 5, 1396-404). The AR-NTD importantly plays a role in activation of the AR in the absence of androgens (Sadar, M. D. 1999 *J. Biol. Chem.* 274, 7777-7783; Sadar M D et al 1999 *Endocr Relat Cancer.* 6, 487-502; Ueda et al 2002 *J. Biol. Chem.* 277, 7076-7085; Ueda 2002 *J. Biol. Chem.* 277, 38087-38094; Blaszczyk et al 2004 *Clin Cancer Res.* 10, 1860-9; Dehm et al 2006 *J Biol Chem.* 28, 27882-93; Gregory et al 2004 *J Biol Chem.* 279, 7119-30). The AR-NTD is important in hormonal progression of prostate cancer as shown by application of decoy molecules (Quayle et al 2007, *Proc Natl Acad Sci USA.* 104, 1331-1336).

While the crystal structure has been resolved for the AR C-terminus LBD, this has not been the case for the NTD due to its high flexibility and intrinsic disorder in solution (Reid et al 2002 *J. Biol. Chem.* 277, 20079-20086) thereby hampering virtual docking drug discovery approaches. Compounds that modulate AR, potentially through interaction with NTD domain, include the bisphenol compounds disclosed in published PCT Nos: WO 2010/000066, WO 2011/082487; WO 2011/082488; WO 2012/145330; WO 2012/139039; WO 2012/145328; WO 2013/028572; WO 2013/028791; WO 2014/179867; WO 2015/031984; WO 2016/058080; WO 2016/058082; WO 2016/112455; WO 2016/141458; WO 2017/177307; WO 2017/210771; and WO 2018/045450, and which are hereby incorporated by reference in their entireties.

Transcriptionally active androgen receptor plays a major role in CRPC in spite of reduced blood levels of androgen (Karantanos, T. et al *Oncogene* 2013, 32, 5501-5511; Harris, W. P. et al *Nature Clinical Practice Urology,* 2009, 6, 76-85). AR mechanisms of resistance to ADT include: overexpression of AR (Visakorpi, T. et al *Nature Genetics* 1995, 9, 401-406; Koivisto, P. et al *Scandinavian Journal of Clinical and Laboratory Investigation Supplementum* 1996, 226, 57-63); gain-of-function mutations in the AR LBD (Culig Z. et al *Molecular Endocrinology* 1993, 7, 1541-1550); intratumoral androgen synthesis (Cai, C. et al *Cancer Research* 2011, 71, 6503-6513); altered expression and function of AR coactivators (Ueda, T. et al *The Journal of Biological Chemistry* 2002, 277, 38087-38094; Xu J. et al *Nature Reviews Cancer* 2009, 9, 615-630); aberrant post-translational modifications of AR (Gioeli D. et al *Molecular and Cellular Endocrinology* 2012, 352, 70-78; van der Steen T. et al *International Journal of Molecular Sciences* 2013, 14, 14833-14859); and expression of AR splice variants (AR-Vs) which lack the ligand-binding domain (LBD) (Karantanos, T. et al *Oncogene* 2013, 32, 5501-5511; Andersen R. J. et al Cancer Cell 2010, 17, 535-546; Myung J. K. et al *The Journal of Clinical Investigation* 2013, 123, 2948-2960; Sun S. et al *The Journal of Clinical Investigation* 2010, 120, 2715-2730). Anti-androgens such as bicalutamide and enzalutamide target AR LBD, but have no effect on truncated constitutively active AR-Vs such as AR-V7 (Li Y. et al *Cancer Research* 2013, 73, 483-489). Expression of AR-V7 is associated with resistance to current hormone therapies (Li Y. et al *Cancer Research* 2013, 73, 483-489; Antonarakis E. S. et al *The New England Journal of Medicine* 2014, 371, 1028-1038).

The intrinsically disordered AR NTD is essential for its transcriptional activity. It harbors six putative binding sites for Pin1, a proline isomerase that regulates protein conformation at specific phosphorylated-Ser/Thr-Pro motifs. All-trans retinoic acid (ATRA) is a validated and potent Pin1 inhibitor. Since conformational changes within the AR NTD are required for transactivation, perturbation of its structure may be a promising approach to block its activity.

While significant advances have been made in this field, there remains a need for improved treatment for AR-mediated disorders including breast cancer and prostate cancer. Currently there is no FDA-approved targeted therapy for triple-negative breast cancer (TNBC). AR plays a role in the proliferation of breast cancer cells by either promoting proliferation or inhibiting proliferation depending on the expression of estrogen receptor (ER) and human epidermal growth factor receptor 2 (HER2). AR expression is detected in up to 90% of all breast cancers and in up to approximately 35% of TNBC. AR-Vs have been detected in primary breast cancer specimens and in breast cancer cell lines. AR-V7 expression was detected in circulating-tumor cells of patients with metastatic breast cancer and was associated with bone metastases. Targeting AR is a potential therapeutic strategy for AR-positive TNBC.

Cyclin-dependent kinases 4 and 6 (CDK4/6) are activated by cyclin D1 to phosphorylate Rb and are critical in the transition from G1 to S phase in cell cycle. Luminal AR subtype of triple negative breast cancer is particularly sensitive to CDK4/6 inhibitors and this sensitivity is associated with AR expression. Thus, androgen receptor N-terminal domain inhibitors in combination with CDK4/6 inhibitors can be a way to target treatment of AR-mediated diseases and conditions.

In addition, targeting Pin1 activity with an Pin1 inhibitor that may disrupt the AR NTD could enhance inhibition the AR NTD by androgen receptor modulators which bind to Tau-5 in the NTD.

In addition, a combination approach using AR modulating therapeutics with radiation could provide a promising option for the treatment of metastatic castration resistant prostate cancer (mCRPC) as targeted radiotherapy with radium 223 dichloride for mCRPChas been shown to increase overall survival (OS) of patients with bone metastases by approximately 3 months. All currently approved AR modulating drugs, such as enzalutamide and abiraterone, either directly or indirectly target the AR C-terminus ligand-binding domain (LBD). Such drugs are often unsuccessful due to the emergence of AR splice variants (ARV-7, ARv567es) that are constitutively active and lack a LBD. The presently disclosed method explores the use of androgen receptor N-terminal domain inhibitors that can bind to full-length AR and/or truncated AR splice variants in combination with radiation therapy.

SUMMARY OF THE INVENTION

The present disclosure relates to pharmaceutical compositions and combinations comprising an androgen receptor N-terminal domain inhibitor and a second therapeutically active agent. In one embodiment, the pharmaceutical composition comprises a CDK4/6 inhibitor and an androgen receptor N-terminal domain inhibitor. In one embodiment, the pharmaceutical composition comprises an androgen receptor N-terminal domain inhibitor and an androgen receptor ligand-binding domain inhibitor. In one embodiment, the pharmaceutical composition comprises an androgen receptor N-terminal domain inhibitor and a Pin1 inhibitor. In one embodiment, the pharmaceutical composition comprises an androgen receptor N-terminal domain inhibitor and a Pin1 inhibitor, wherein the androgen receptor N-terminal domain inhibitor is not 3-(4-(2-(4-(3-chloro-2-hydroxypropoxy)phenyl)propan-2-yl)phenoxy)propane-1,2-diol, 3-(4-(2-(4-(2-acetoxy-3-chloropropoxy)phenyl)propan-2-yl)phenoxy)propane-1,2-diyl diacetate, or stereoisomers thereof.

The present disclosure also relates to a method of treating cancer comprising administering an androgen receptor N-terminal domain inhibitor and a radiation therapy. In one embodiment, the radiation therapy is ionizing radiation therapy.

In one embodiment of the pharmaceutical compositions or combinations or the methods of the present disclosure, the androgen receptor N-terminal domain inhibitor has the structure of formula (i):

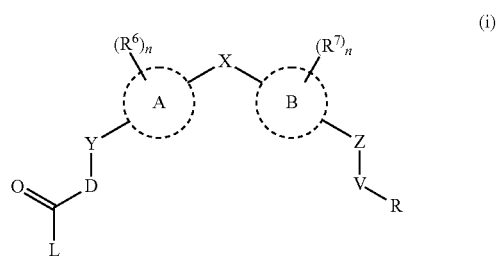

or a pharmaceutically acceptable salt, tautomer, stereoisomer or prodrug thereof, wherein:

A and B are each independently aryl or heteroaryl;

X is a bond, —$(CR^8R^9)_t$—, —O—, —C(=O)—, —$S(O)_n$—, —$NR^{10}$—, —$CONR^{10}$—, —$NR^{10}CO$—, —$SO_2NR^{10}$—, or —$NR^{10}SO_2$—;

Y and Z are each independently a bond, —$(CR^8R^9)_t$—, —O—, —$S(O)_n$—, —$NR^{10}$—, —$CONR^{10}$—, —$NR^{10}CO$—, —$SO_2NR^{10}$—, or —$NR^{10}SO_2$—;

V is a bond, optionally substituted —$(CR^{11}R^{12})_m$—, —C(=O)—, —$N(R^{10})CO$—, —$CONR^{10}$—, or —$NSO_2R^{10}$—;

R is —$(CR^{4a}R^{4b})$—$(CR^{5a}R^{5b})$—W or W;

W is hydrogen, halogen, —$CF_3$, —$CF_2R^{10}$, —CN, —$OR^{13}$, —$NR^{13}R^{14}$, optionally substituted —$CONR^{13}R^{14}$, optionally substituted carbocyclyl, optionally substituted heterocyclyl, optionally substituted aryl, or optionally substituted heteroaryl;

D is —$(CR^{1a}R^{1b})_q$—, —O—, or —$NR^{10}$—;

L is —$(CR^{2a}R^{2b})$—$R^3$ or -E-$R^3$;

E is —$(CR^{2a}R^{2b})_g$—, —O—, —$NR^{10}$—, or —$NR^{10}$—$(CR^{2a}R^{2b})_g$—;

$R^{1a}$, $R^{1b}$, $R^{2a}$, and $R^{2b}$ are each independently hydrogen, halogen, hydroxy, optionally substituted $C_{1-6}$ alkyl, optionally substituted $C_2$-$C_6$ alkenyl, optionally substituted $C_2$-$C_6$ alkynyl, optionally substituted $C_{1-6}$ alkoxy, optionally substituted —$OCO(C_1$-$C_6$ alkyl), —$NR^{13}R^{14}$, optionally substituted —$(C_1$-$C_6$ alkyl)-$NR^{13}R^{14}$, —$NR^{14}COR^{16}$, optionally substituted —$(C_1$-$C_6$ alkyl)-$NR^{14}COR^{16}$, —$CONR^{14}R^{15}$, optionally substituted —$(C_1$-$C_6$ alkyl)-$CONR^{14}R^{15}$, optionally substituted carbocyclyl, optionally substituted heterocyclyl, optionally substituted aryl, or optionally substituted heteroaryl;

or alternatively, $R^{1a}$ and $R^{1b}$ taken together form an optionally substituted carbocyclyl, optionally substituted heterocyclyl, optionally substituted aryl, or optionally substituted heteroaryl;

or alternatively, $R^{2a}$ and $R^{2b}$ taken together form a CO, optionally substituted carbocyclyl, optionally substituted heterocyclyl, optionally substituted aryl, or optionally substituted heteroaryl;

or alternatively, $R^{1a}$, $R^{1b}$, $R^{2a}$ and $R^{2b}$ taken together form an optionally substituted carbocyclyl, optionally substituted heterocyclyl, optionally substituted aryl, or optionally substituted heteroaryl;

$R^{4a}$, $R^{4b}$, $R^{5a}$, and $R^{5b}$ are each independently hydrogen, halogen, hydroxy, optionally substituted $C_{1-6}$ alkyl, optionally substituted $C_2$-$C_6$ alkenyl, optionally substituted $C_2$-$C_6$ alkynyl, optionally substituted $C_{1-6}$ alkoxy, optionally substituted —$OCO(C_1$-$C_6$ alkyl), —$NR^{13}R^{14}$, optionally substituted —$(C_1$-$C_6$ alkyl)-$NR^{13}R^{14}$, —$NR^{14}COR^{16}$, optionally substituted —$(C_1$-$C_6$ alkyl)-$NR^{14}COR^{16}$, —$CONR^{14}R^{15}$, optionally substituted —$(C_1$-$C_6$ alkyl)-$CONR^{14}R^{15}$, optionally substituted carbocyclyl, optionally substituted heterocyclyl, optionally substituted aryl, or optionally substituted heteroaryl;

or alternatively, $R^{4a}$ and $R^{4b}$ taken together form a CO, optionally substituted carbocyclyl, optionally substituted heterocyclyl, optionally substituted aryl, or optionally substituted heteroaryl;

or alternatively, $R^{4a}$, $R^{4b}$, $R^{5a}$ and $R^{5b}$ taken together form an optionally substituted carbocyclyl, optionally substituted heterocyclyl, optionally substituted aryl, or optionally substituted heteroaryl;

$R^3$ is absent, hydrogen, —CN, —CF$_3$, —OH, optionally substituted $C_1$-$C_6$ alkyl, optionally substituted $C_2$-$C_6$ alkenyl, optionally substituted $C_2$-$C_6$ alkynyl, optionally substituted —OR$^{15}$, optionally substituted $C_1$-$C_6$ alkoxy, —NH$_2$, —NR$^{16}$R$^{17}$, —NR$^{16}$COR$^{18}$, —NR$^{16}$S(O)$_p$R$^{18}$, —CONR$^{14}$R$^{15}$, —SONR$^{14}$R$^{15}$, —SO$_2$NR$^{14}$R$^{15}$, optionally substituted —S(O)$_p$R$^{18}$, —N$_3$, optionally substituted carbocyclyl, optionally substituted heterocyclyl, optionally substituted aryl, or optionally substituted heteroaryl;

or alternatively, $R^{2a}$, $R^{2b}$ and $R^3$ taken together form an optionally substituted carbocyclyl, optionally substituted heterocyclyl, optionally substituted aryl, or optionally substituted heteroaryl;

or alternatively, $R^{2a}$ and $R^{10}$ taken together form an optionally substituted heterocyclyl;

$R^6$ and $R^7$ are each independently H, methyl, methoxy, —CN, F, Cl, Br, I, $^{123}$I, —CF$_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —NR$^{13}$R$^{14}$, optionally substituted —($C_1$-$C_6$ alkyl)-NR$^{13}$R$^{14}$, —NR$^{14}$SO$_2$R$^{16}$, optionally substituted —($C_1$-$C_6$ alkyl)NR$^{14}$SO$_2$R$^{16}$, —NR$^{14}$COR$^{16}$, optionally substituted —($C_1$-$C_6$ alkyl)-NR$^{14}$COR$^{16}$, —CONR$^{14}$R$^{15}$, optionally substituted —($C_1$-$C_6$ alkyl)-CONR$^{14}$R$^{15}$, —SO$_2$NR$^{14}$R$^{15}$, optionally substituted —($C_1$-$C_6$ alkyl)-SO$_2$NR$^{14}$R$^{15}$, optionally substituted —SO$_2$R$^{16}$, or optionally substituted —($C_1$-$C_6$ alkyl)-SO$_2$R$^{16}$, optionally substituted carbocyclyl, optionally substituted heterocyclyl, optionally substituted aryl, or optionally substituted heteroaryl;

$R^8$, $R^9$, $R^{11}$ and $R^{12}$ are each independently hydrogen, —OH, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ alkylamino, optionally substituted —OCO($C_1$-$C_6$ alkyl), —NR$^{13}$R$^{14}$, optionally substituted —($C_1$-$C_6$ alkyl)-NR$^{13}$R$^{14}$, —NR$^{14}$COR$^{16}$, optionally substituted —($C_1$-$C_6$ alkyl)-NR$^{14}$COR$^{16}$, —CONR$^{14}$R$^{15}$, optionally substituted —($C_1$-$C_6$ alkyl)-CONR$^{14}$R$^{15}$, optionally substituted carbocyclyl, optionally substituted heterocyclyl, optionally substituted aryl, or optionally substituted heteroaryl;

or alternatively, $R^8$ and $R^9$ taken together form an optionally substituted carbocyclyl or optionally substituted heterocyclyl;

or alternatively, $R^{11}$ and $R^{12}$, on a same carbon atom or a different carbon atom, taken together form an optionally substituted carbocyclyl, optionally substituted heterocyclyl, optionally substituted aryl, or optionally substituted heteroaryl;

$R^{10}$ is hydrogen, halogen, optionally substituted $C_1$-$C_6$ alkyl, optionally substituted $C_1$-$C_6$ alkoxy, —CO($C_1$-$C_6$ alkyl), optionally substituted $C_1$-$C_6$ alkylamino, optionally substituted carbocyclyl, optionally substituted heterocyclyl, optionally substituted aryl, or optionally substituted heteroaryl;

$R^{13}$, $R^{14}$, $R^{15}$, $R^{16}$, $R^{17}$ and $R^{18}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl;

or alternatively, $R^{14}$ and $R^{15}$ are taken together to form an optionally substituted heterocyclyl, or optionally substituted heteroaryl;

or alternatively, $R^{16}$ and $R^{17}$ are taken together to form an optionally substituted heterocyclyl, or optionally substituted heteroaryl;

m is 0, 1, 2, 3, or 4;

each n is independently 0, 1 or 2;

each p is independently 0, 1 or 2;

q is 0, 1 or 2;

each g is independently 0, 1, 2, 3, or 4; and each t is independently 1 or 2.

In one embodiment of the pharmaceutical compositions or combinations or the methods of the present disclosure, the androgen receptor N-terminal domain inhibitor has the structure of formula (ii):

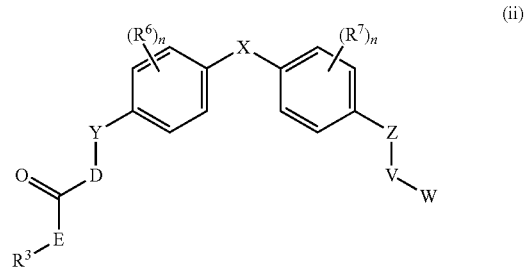

or a pharmaceutically acceptable salt, tautomer, stereoisomer or prodrug thereof, wherein:

X is a bond, —NR$^{10}$—, or —(CR$^{8a}$R$^{9a}$)$_t$—;

Y and Z are each independently a bond, —CH$_2$—, —C(CH$_3$)H—, —O—, —S—, —NH—, —NCH$_3$—, or —N(COCH$_3$)—;

V is —CH$_2$—, —CH$_2$CH$_2$—, —CH$_2$CH$_2$CH$_2$—, —CH$_2$CH(CH$_3$)CH$_2$—, —CH$_2$CH(OH)CH$_2$—, or —CH$_2$C(OH)(CH$_3$)CH$_2$—;

W is halogen, —NH$_2$, or —CF$_3$.

D is —NR$^{10}$— and E is —(CR$^{2a}$R$^{2b}$)$_g$—, —NR$^{10}$—, or —NR$^{10}$—(CR$^{2a}$R$^{2b}$)$_g$—;

or alternatively, E is —NR$^{10}$— or —NR$^{10}$—(CR$^{2a}$R$^{2b}$)$_g$—, and D is —(CR$^{1a}$R$^{1b}$)$_q$— or —NR$^{10}$—;

$R^{1a}$, $R^{1b}$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —NR$^{13}$R$^{14}$, —($C_1$-$C_3$ alkyl)-NR$^{13}$R$^{14}$, —NR$^{14}$COR$^{16}$, —($C_1$-$C_3$ alkyl)-NR$^{14}$COR$^{16}$, —CONR$^{14}$R$^{15}$, or —($C_1$-$C_6$ alkyl)-CONR$^{14}$R$^{15}$; or ($R^{1a}$ and $R^{1b}$) or ($R^{2a}$ and $R^{2b}$) taken together form an oxo (=O), an optionally substituted carbocyclyl, or an optionally substituted heterocyclyl;

$R^3$ is selected from hydrogen, —$C_1$-$C_6$ alkyl, —OR$^{15}$, —SR$^{18}$, —$C_1$-$C_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, —SOR$^{18}$, or —SO$_2$R$^{18}$;

$R^6$ and $R^7$ are each independently H, halogen, —CN, —$CF_3$, —OH, or $C_1$-$C_3$ alkyl;

$R^{8a}$ and $R^{9a}$ are each independently hydrogen, halogen, —OH, or $C_1$-$C_3$ alkyl; or $R^{8a}$ and $R^{9a}$ taken together form an 3- to 6-membered carbocyclyl or heterocyclyl;

$R^{10}$ is each independently hydrogen, $C_1$-$C_3$ alkyl, $C_2$-$C_3$ alkenyl, $C_2$-$C_3$ alkynyl, or —CO($C_1$-$C_3$ alkyl);

$R^{13}$, $R^{14}$, $R^{15}$, $R^{16}$, $R^{17}$ and $R^{18}$ are each independently hydrogen, $C_1$-$C_3$ alkyl, $C_2$-$C_3$ alkenyl, or $C_2$-$C_3$ alkynyl; or $R^{14}$ and $R^{15}$ taken together form an optionally substituted 5- or 6-membered heterocyclyl;

each n is independently 0, 1 or 2;

q is 0, 1 or 2;

each g is independently 0, 1, 2, 3, or 4; and each t is independently 1 or 2.

In one embodiment of the pharmaceutical compositions or combinations or the methods of the present disclosure, the androgen receptor N-terminal domain inhibitor has the structure of formula (iii):

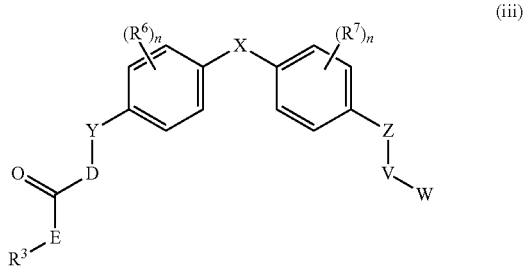

or a pharmaceutically acceptable salt, tautomer, stereoisomer or prodrug thereof, wherein:

X is a bond, —$NR^{10}$—, or —$(CR^{8a}R^{9a})_t$—;

Y and Z are each independently a bond, —$CH_2$—, —$C(CH_3)H$—, —O—, —S—, —NH—, —$NCH_3$—, or —$N(COCH_3)$—;

V is —$CH_2$—, —$CH_2CH_2$—, —$CH_2CH_2CH_2$—, —$CH_2CH(CH_3)CH_2$—, —$CH_2CH(OH)CH_2$—, or —$CH_2C(OH)(CH_3)CH_2$—;

W is halogen, —$NH_2$ or —$CF_3$;

D is —O— or —$NR^{10}$— and E is —$(CR^{2a}R^{2b})_{gg}$—;

or alternatively, E is —O—, —$NR^{10}$— or —$NR^{10}$—$(CR^{2a}R^{2b})_g$—, and D is —$(CR^{1a}R^{1b})_q$—;

$R^{1a}$, $R^{1b}$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_6$ alkyl)-$CONR^{14}R^{15}$; or ($R^{1a}$ and $R^{1b}$) or ($R^{2a}$ and $R^{2b}$) taken together form an oxo (=O), an optionally substituted carbocyclyl, or an optionally substituted heterocyclyl;

$R^3$ is selected from hydrogen, —$C_1$-$C_6$ alkyl, —$OR^{15}$, —$SR^{18}$, —$C_1$-$C_6$ alkoxy, —$NR^{16}R^{17}$, —$NR^{16}SR^{18}$, —$NR^{16}SOR^{18}$, —$NR^{16}SO_2R^{18}$, —$NR^{16}COR^{18}$, —$CONR^{14}R^{15}$, —$SONR^{14}R^{15}$, —$SO_2NR^{14}R^{15}$, —$SOR^{18}$, or —$SO_2R^{18}$;

$R^6$ and $R^7$ are each independently H, halogen, —CN, —$CF_3$, —OH, $C_1$-$C_3$ alkyl;

$R^{8a}$ and $R^{9a}$ are each independently hydrogen, halogen, —OH, or $C_1$-$C_3$ alkyl; or $R^{8a}$ and $R^{9a}$ taken together form an 3- to 6-membered carbocyclyl or heterocyclyl;

$R^{10}$ is each independently hydrogen, $C_1$-$C_3$ alkyl, $C_2$-$C_3$ alkenyl, $C_2$-$C_3$ alkynyl, or —CO($C_1$-$C_3$ alkyl);

$R^{13}$, $R^{14}$, $R^{15}$, $R^{16}$, $R^{17}$ and $R^{18}$ are each independently hydrogen, $C_1$-$C_3$ alkyl, $C_2$-$C_3$ alkenyl, or $C_2$-$C_3$ alkynyl; or $R^{14}$ and $R^{15}$ taken together form an optionally substituted 5- or 6-membered heterocyclyl;

m is 0, 1, 2, 3, or 4;

each n is independently 0, 1 or 2;

q is 1 or 2;

g is 0, 1, 2, 3, or 4;

gg is 1, 2, 3, or 4; and t is 1 or 2.

In one embodiment of the pharmaceutical compositions or combinations or the methods of the present disclosure, the androgen receptor N-terminal domain inhibitor has the structure of formula (iv):

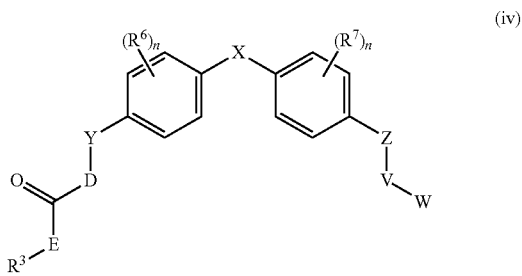

or a pharmaceutically acceptable salt, tautomer, stereoisomer or prodrug thereof, wherein:

X is a bond, —$NR^{10}$—, or —$(CR^{8a}R^{9a})_t$—;

Y and Z are each independently a bond, —$CH_2$—, —$C(CH_3)H$—, —O—, —S—, —NH—, —$NCH_3$—, or —$N(COCH_3)$—;

V is —$CH_2$—, —$CH_2CH_2$—, —$CH_2CH_2CH_2$—, —$CH_2CH(CH_3)CH_2$—, —$CH_2CH(OH)CH_2$—, or —$CH_2C(OH)(CH_3)CH_2$—;

W is —$CF_2R^{10}$, —$NR^{13}R^{14}$, optionally substituted carbocyclyl, optionally substituted heterocyclyl, optionally substituted aryl, or optionally substituted heteroaryl;

D is —$(CR^{1a}R^{1b})_q$—;

E is —$(CR^{2a}R^{2b})_g$—;

$R^{1a}$, $R^{1b}$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —$NR^{13}R^{14}$, —($C_1$-$C_3$ alkyl)-$NR^{13}R^{14}$, —$NR^{14}COR^{16}$, —($C_1$-$C_3$ alkyl)-$NR^{14}COR^{16}$, —$CONR^{14}R^{15}$, or —($C_1$-$C_6$ alkyl)-$CONR^{14}R^{15}$; or ($R^{1a}$ and $R^{1b}$) or ($R^{2a}$ and $R^{2b}$) taken together form an oxo (=O), an optionally substituted carbocyclyl, or an optionally substituted heterocyclyl;

$R^3$ is selected from hydrogen, —$C_1$-$C_6$ alkyl, —$OR^{15}$, —$SR^{18}$, —$C_1$-$C_6$ alkoxy, —$NR^{16}R^{17}$, —$NR^{16}SR^{18}$, —$NR^{16}SOR^{18}$, —$NR^{16}SO_2R^{18}$, —$NR^{16}COR^{18}$, —$CONR^{14}R^{15}$, —$SONR^{14}R^{15}$, —$SO_2NR^{14}R^{15}$, —$SOR^{18}$, or —$SO_2R^{18}$;

$R^6$ and $R^7$ are each independently H, halogen, —CN, —$CF_3$, —OH, or $C_1$-$C_3$ alkyl;

$R^{8a}$ and $R^{9a}$ are each independently hydrogen, halogen, —OH, or $C_1$-$C_3$ alkyl; or $R^{8a}$ and $R^{9a}$ taken together form an optionally substituted carbocyclyl or optionally substituted heterocyclyl;

$R^{10}$ is each independently hydrogen, $C_1$-$C_3$ alkyl, $C_2$-$C_3$ alkenyl, $C_2$-$C_3$ alkynyl, or —CO($C_1$-$C_3$ alkyl);

$R^{13}$, $R^{14}$, $R^{15}$, $R^{16}$, $R^{17}$ and $R^{18}$ are each independently hydrogen, $C_1$-$C_3$ alkyl, $C_2$-$C_3$ alkenyl, or $C_2$-$C_3$ alkynyl; or R$^{14}$ and R$^{15}$ taken together form an optionally substituted 5- or 6-membered heterocyclyl;
m is 0, 1, 2, 3, or 4;
each n is independently 0, 1 or 2;
q is 0, 1 or 2;
g is 0, 1, 2, 3, or 4; and
t is 1 or 2.

In one embodiment of the pharmaceutical compositions or combinations or the methods of the present disclosure, the androgen receptor is selected from Table A.

In one embodiment (a):

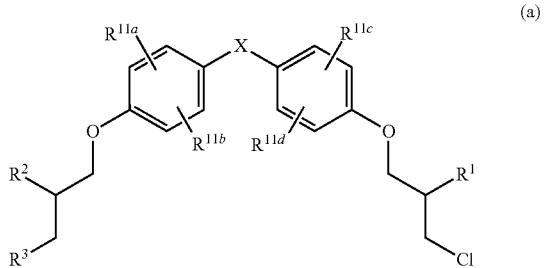

(a)

wherein:
X is —S(O)$_n$— or —C(R$^8$R$^9$)—;
R$^1$ is H, hydroxyl or —OC(=O)R$^{13}$;
R$^2$ is hydroxyl or —OC(=O)R$^{13}$;
R$^3$ is halo, —OH, —OR$^4$; —OC(=O)R$^{13}$, —NH$_2$, —NHC(=O)R$^{13}$, —N(C(=O)R$^{13}$)$_2$, —NHS(O)$_n$R$^5$, —N(C(=O)R$^{13}$)(S(O)$_n$R$^5$), —N(C$_1$-C$_6$ alkyl)(S(O)$_n$R$^5$), —S(O)$_n$R$^5$, —N$_3$, aryl, carbocyclyl, heteroaryl or heterocyclyl which are optionally substituted with one or more R$^6$;
R$^4$ is C$_1$-C$_6$ alkyl, C$_2$-C$_6$ alkenyl, C$_2$-C$_6$ alkynyl, aryl, carbocyclyl, heteroaryl or heterocyclyl which are optionally substituted with one or more R$^6$
R$^5$ is each independently C$_1$-C$_6$ alkyl or aryl which are optionally substituted with one or more R$^6$
R$^6$ is each independently selected from the group consisting of H, F, Cl, Br, I, $^{123}$I, hydroxyl, oxo, C$_1$-C$_6$ alkyl, C$_2$-C$_6$ alkenyl, C$_2$-C$_6$ alkynyl, C$_1$-C$_6$ alkoxy, C$_6$-C$_{12}$ aryl, wherein each R$^6$ is optionally substituted with one or more of halogen, $^{123}$I, $^{18}$F, hydroxyl, —OS(O)$_2$-aryl, C$_1$-C$_6$ alkyl, C$_2$-C$_6$ alkenyl, or C$_2$-C$_6$ alkynyl;
R$^8$ and R$^9$ are each independently H or C$_1$-C$_6$ alkyl;
R$^{11a}$, R$^{11b}$, R$^{11c}$ and R$^{11d}$ are each independently H, methyl, —CN, F, Cl, Br, I, or $^{123}$I;
R$^{13}$ is C$_1$-C$_6$ alkyl; and
n is 0, 1, or 2;
wherein at least one of R$^{11a}$, R$^{11b}$, R$^{11c}$ and R$^{11d}$ is methyl, —CN, F, Cl, Br, I, or $^{123}$I.

In one embodiment the compounds of formula (a), the compound has at least two of R$^{11a}$, R$^{11b}$, R$^{11c}$ and R$^{11d}$ are methyl, —CN, F, Cl, Br, I, or $^{123}$I. In one embodiment, R$^{11c}$ and R$^{11d}$ are each independently methyl, —CN, Cl, or Br. In some embodiments, R$^{11c}$ and R$^{11d}$ are each Cl or —CN.

In one embodiment the compounds of formula (a), X is —C(R$^8$R$^9$)— and R$^8$ and R$^9$ are each independently C$_1$-C$_3$ alkyl.

In one embodiment the compounds of formula (a), R$^8$ an R$^9$ are each methyl.

In one embodiment the compounds of formula (a), R$^1$ and R$^2$ are both hydroxyl.

In one embodiment the compounds of formula (a), R$^3$ is an optionally substituted 5 or 6 membered heteroaryl or an optionally substituted 3 to 7 membered heterocyclyl, wherein said heteroaryl or said heterocyclyl respectively comprise at least one N atom.

In one embodiment the compounds of formula (a), R$^3$ is selected from a group consisting of pyrrole, furan, thiophene, pyrazole, pyridine, pyridazine, pyrimidine, imidazole, thiazole, isoxazole, oxadiazole, thiadiazole, oxazole, triazole, isothiazole, oxazine, triazine, azepine, pyrrolidine, pyrroline, imidazoline, imidazolidine, pyrazoline, pyrazolidine, piperidine, dioxane, morpholine, dithiane, thiomorpholine, piperazine, and tetrazine. In one embodiment, R$^3$ is —NH$_2$, —NHC(=O)R$^{13}$, —N(C(=O)R$^{13}$)$_2$, —NHS(O)$_n$R$^5$, —N(C(=O)R$^{13}$)(S(O)$_n$R$^5$), —N(C$_1$-C$_6$ alkyl)(S(O)$_n$R$^5$) or —S(O)$_n$R$^5$. In some embodiments, R$^3$ is —NH$_2$, —NHC(=O)(C1-C4 alkyl), —N[(C(=O)(C1-C4 alkyl)]$_2$, —NHS(O)$_n$(C1-C3 alkyl), —N[C(=O)(C1-C4 alkyl)][(S(O)$_n$(C1-C3 alkyl)], —N[C$_1$-C$_6$ alkyl][S(O)$_n$(C1-C3 alkyl)], or —S(O)$_n$(C1-C3 alkyl).

In one embodiment of the pharmaceutical compositions or combinations or the methods of the present disclosure, the androgen receptor N-terminal domain inhibitor is selected from Table B.

In one embodiment of the method of treating cancer, the method further comprises administering a second therapeutically active agent.

In one embodiment of the pharmaceutical compositions or combinations or the methods of the present disclosure, the second therapeutically active agent is selected from a poly (ADP-ribose) polymerase (PARP) inhibitor, an androgen receptor ligand-binding domain inhibitor, an inhibitor of CYP17, a microtubule inhibitor, a modulator of PD-1 or PD-L1, a gonadotropin releasing hormone agonist, a 5-alpha reductase inhibitor, a vascular endothelial growth factor inhibitor, a histone deacetylase inhibitor, an integrin alpha-v-beta-3 inhibitor, a receptor tyrosine kinase, a phosphoinositide 3-kinase inhibitor, an anaplastic lymphoma kinase (ALK) inhibitor, an endothelin receptor A antagonist, an anti-CTLA4 inhibitor, an heat shock protein 27 (HSP27) inhibitor, an androgen receptor degrader, a androgen receptor DNA-binding domain inhibitor, a bromodomain and extra-terminal motif (BET) inhibitor, an androgen receptor N-terminal domain inhibitor, an alpha-particle emitting radioactive therapeutic agent, niclosamide, a selective estrogen receptor modulator (SERM), a selective estrogen receptor degrader (SERD), an aromatase inhibitor, selective progesterone receptor modulator (SPRM), a glucocorticoid receptor inhibitor, a CDK4/6 inhibitor, a HER2 receptor antagonist, a mammalian target of rapamycin (mTOR) inhibitor, an AKT inhibitor, a B-cell lymphoma-2 (Bcl-2) inhibitor, an aurora kinase inhibitor, a Wnt-targeting antagonist, a CYP11a inhibitor, a selective androgen receptor N-terminal domain inhibitor, or enhancer of zeste homolog 2 (EZH2) inhibitor.

In one embodiment of the pharmaceutical compositions or combinations or the methods of the present disclosure, the CDK4/6 inhibitor is selected from palbociclib, ribociclib, trilaciclib or abemaciclib. In one embodiment, the CDK4/6 inhibitor is Palbociclib.

In one embodiment of the pharmaceutical compositions or combinations or the methods of the present disclosure, the androgen receptor ligand-binding domain inhibitor is enzalutamide, apalutamide, darolutamide, bicalutamide, nilutamide, flutamide, ODM-204, or TAS3681. In one embodiment, the androgen receptor ligand-binding domain inhibitor is enzalutamide.

In one embodiment of the pharmaceutical compositions or combinations of the present disclosure, the Pin1 inhibitor is selected from juglone, plumbagin, PiB, PiJ, epigallocatechin gallate (EGCG), all-trans retinoic acid (ATRA), dipentamethylene thiauram monosulfide, TME-001 (2-(3-chloro-4-fluoro-phenyl)-isothiazol-3-one), KPT-6566, API-1, buparvaquone, or a pharmaceutically acceptable salt thereof.

In one embodiment of the pharmaceutical compositions or combinations of the present disclosure, the Pin1 inhibitor is selected from Table C or a pharmaceutically acceptable salt thereof. In one embodiment of the pharmaceutical compositions or combinations of the present disclosure, the Pin1 inhibitor is selected from Table D or a pharmaceutically acceptable salt thereof.

In one embodiment of the pharmaceutical compositions or combinations of the present disclosure, the Pin1 inhibitor is CRYPEVEIC, wherein the cysteine residues of said peptide are cyclized by a disulfide bond (SEQ ID NO: 1); Ac-Lys (N-biotinoyl)-AlaAla-Bth-D-Thr($PO_3H_2$)-Pip-Nal-Gln-$NH_2$ (SEQ ID NO: 2); Ac-Phe-D-Thr($PO_3H_2$)-Pip-Nal-Gln-$NH_2$ (SEQ ID NO: 3); and Ac-Phe-Phe-pSer-Ψ(Z)CHdC-Pro-Arg-$NH_2$ (SEQ ID NO: 4).

In one embodiment of the pharmaceutical compositions or combinations of the present disclosure, the Pin1 inhibitor is selected from 5-hydroxy-1,4-naphthalenedione, (1-piperidinecarbodithioic acid, anhydrosulfide), or diethyl-1,3,6,8-tetrahydro-1,3,6,8tetraoxobenzo[1mn] phenanthroline-2,7-diacetate, or a pharmaceutically acceptable salt thereof.

In one embodiment of the pharmaceutical compositions or combinations of the present disclosure, the Pin1 inhibitor is ATRA.

In one embodiment, the pharmaceutical compositions or combinations of the present disclosure comprises Compound 13a and enzalutamide. In one embodiment, the pharmaceutical compositions or combinations of the present disclosure comprises Compound 13a and Palbociclib. In one embodiment, the pharmaceutical compositions or combinations of the present disclosure comprises Compound 13a and ATRA.

In one embodiment of the pharmaceutical compositions or combinations or the methods of the present disclosure, the composition or the combination further comprises a pharmaceutically acceptable carrier is provided.

In one embodiment, the present disclosure relates to methods for modulating androgen receptor activity, comprising administering the pharmaceutical compositions or combinations of the present disclosure, to a subject in need thereof.

In one embodiment of any one of the method as disclosed herein, the modulating androgen receptor activity is for treating a condition or disease selected from prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, or age-related macular degeneration.

In one embodiment, the present disclosure relates to methods for treating cancer, comprising administering the pharmaceutical compositions or combinations of the present disclosure, to a subject in need thereof. In one embodiment, the cancer is selected from prostate cancer, breast cancer, ovarian cancer, bladder cancer, pancreatic cancer, hepatocellular cancer, endometrial cancer, or salivary gland carcinoma. In one embodiment, the cancer is prostate cancer.

In one embodiment of the methods as disclosed herein, the cancer is breast cancer. In one embodiment, the breast cancer is AR-positive triple negative breast cancer.

In one embodiment of the methods as disclosed herein, the prostate cancer is primary or localized prostate cancer, locally advanced prostate cancer, recurrent prostate cancer, advanced prostate cancer, metastatic prostate cancer, metastatic castration-resistant prostate cancer, and hormone-sensitive prostate cancer. In some embodiments, the prostate cancer is metastatic castration-resistant prostate cancer. In other embodiments, the prostate cancer expresses full-length androgen receptor or truncated androgen receptor splice variant. In one embodiment, the prostate cancer is resistant to enzalutamide monotherapy.

In one embodiment of the methods as disclosed herein comprising administering the pharmaceutical compositions or combinations comprising an androgen receptor N-terminal domain inhibitor and a second therapeutically active agent, the methods further comprising administering radiation therapy the subject.

In one embodiment of the method of administering radiation lutetium-177 is administered concurrently with radiation. In one embodiment, lutetium-177 is targeted to prostate cancer cells.

In one embodiment of any one of the methods disclosed herein, the radiation therapy is ionizing radiation therapy. In one embodiment, the administering the androgen receptor N-terminal domain inhibitor or a pharmaceutical composition thereof and the administering radiation therapy occurs during same treatment period or during different treatment period.

BRIEF DESCRIPTION OF THE DRAWINGS

FIG. 9A shows effects of Compound 13a and/or enzalutamide on androgen-induced PSA-luciferase activity in LNCaP cells. FIG. 9B shows effects of Compound 13a and/or enzalutamide on AR-V7 induced PSA-luciferase activity in LNCaP cells.

FIG. 9C shows effects of Compound 13a and/or enzalutamide on levels of V7BS3-luciferase activity in LNCaP cells. FIG. 9D shows effects of Compound 13a and/or enzalutamide on AR-V7-induced V7BS3-luciferase activity in LNCaP cells.

FIG. 10 shows cell proliferation assay results for VCaP-MDVR cell lines treated enzalutamide (ENZ) alone or in combination with Compound 13a.

FIG. 11 B shows cell proliferation assay results for C4-2B-MDVR cell lines treated enzalutamide (ENZ) alone or in combination with Compound 13a in the presence of R1881.

DETAILED DESCRIPTION

Figure 1:
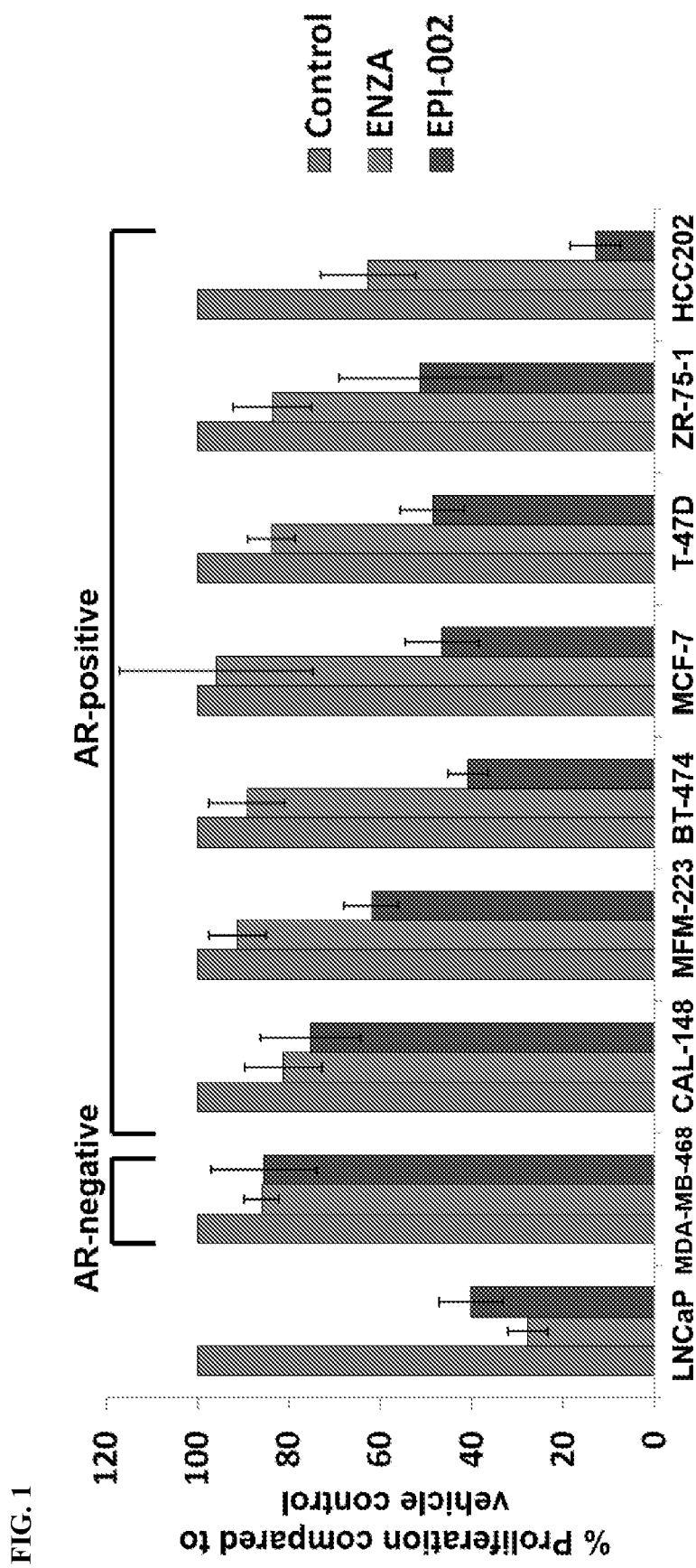
FIG. 1 shows cell proliferation assay results for breast cancer and prostate cancer cell lines treated with control, enzalutamide (ENZ), or EPI-002.
Figure 2A:
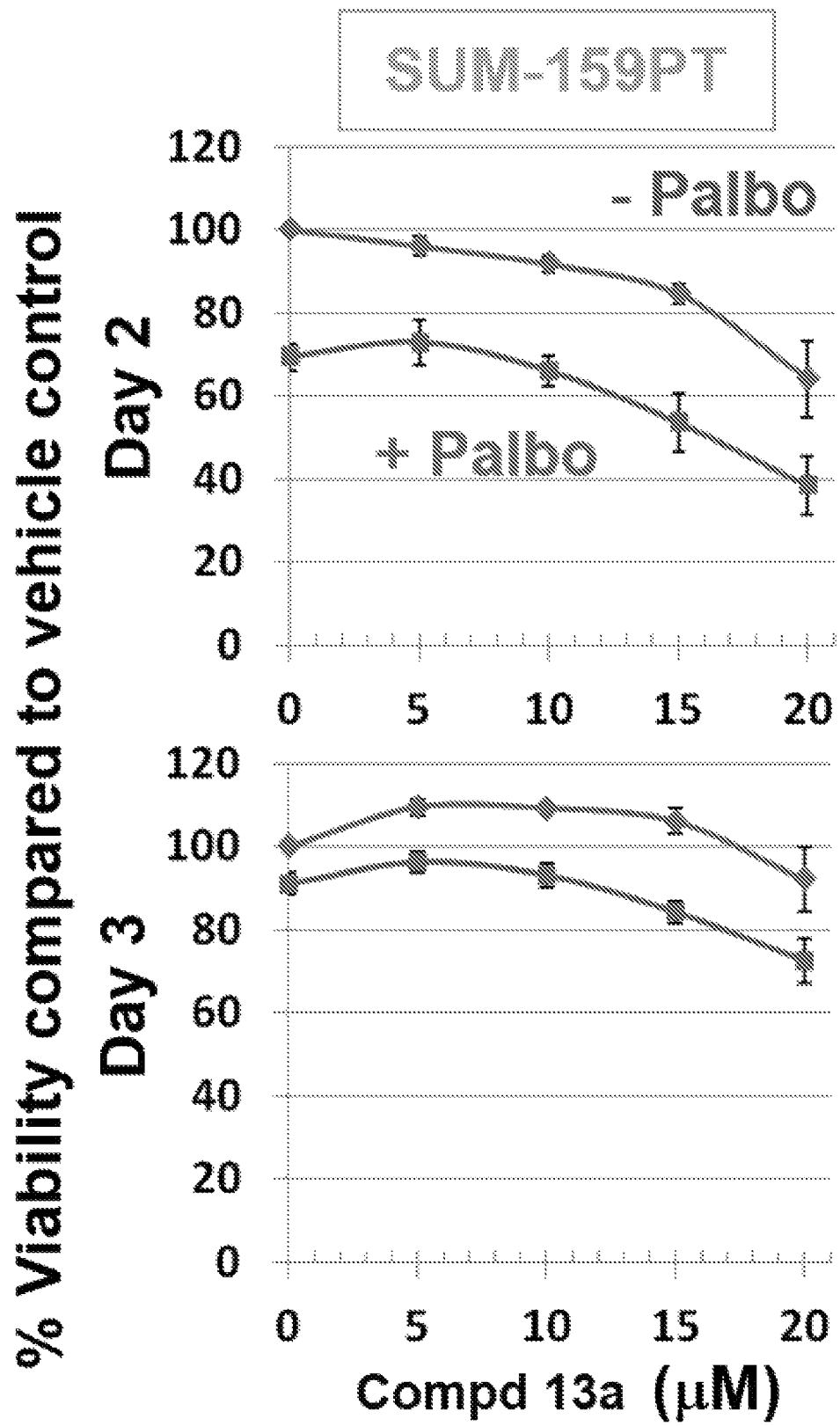
FIG. 2A shows cell viability of SUM-159PT cells treated with Compound 13a with and without palbociclib (Palbo).
Figure 2B:
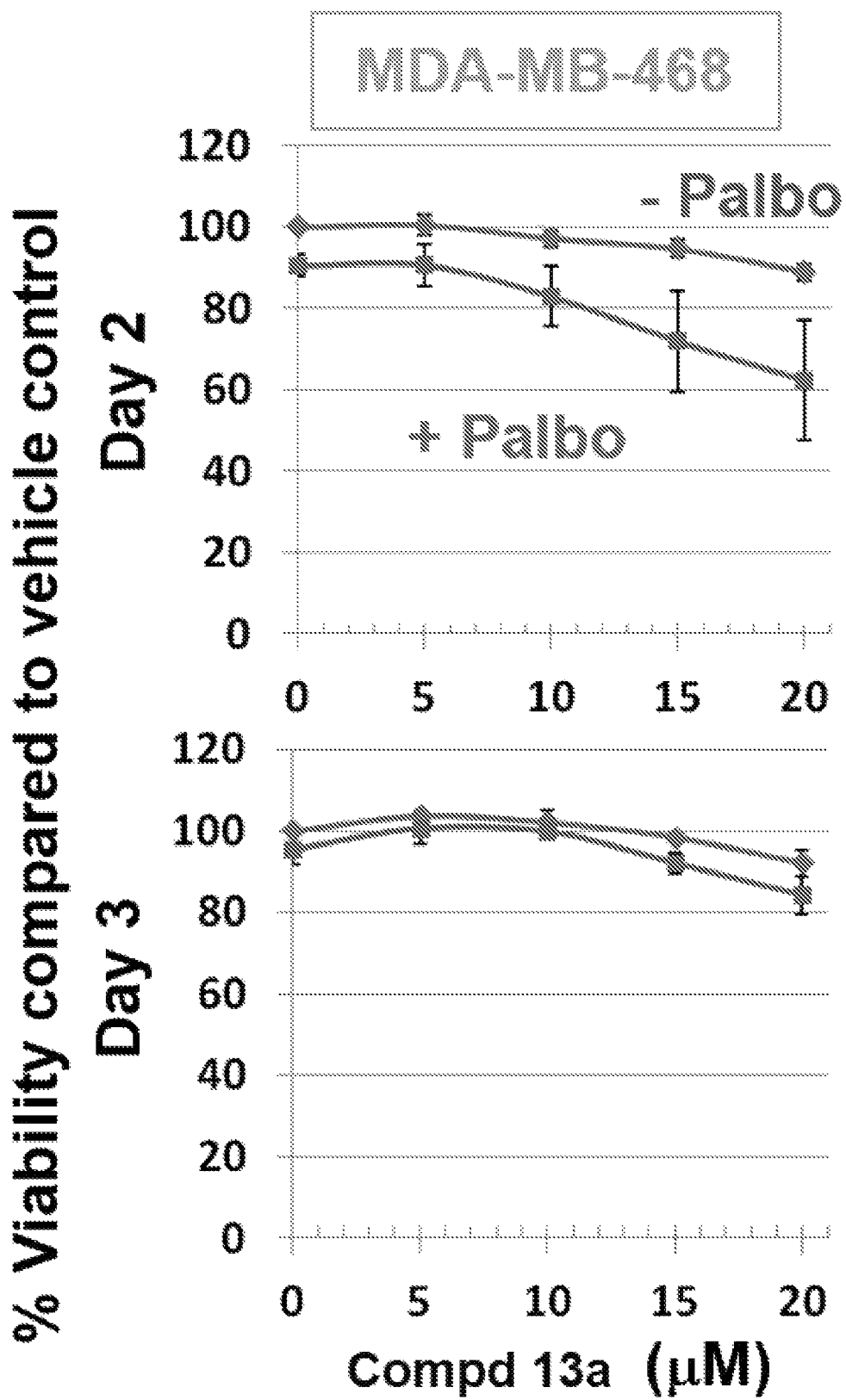
FIG. 2B shows cell viability of MDA-MB-468 cells treated with Compound 13a with and without palbociclib (Palbo).
Figure 2C:
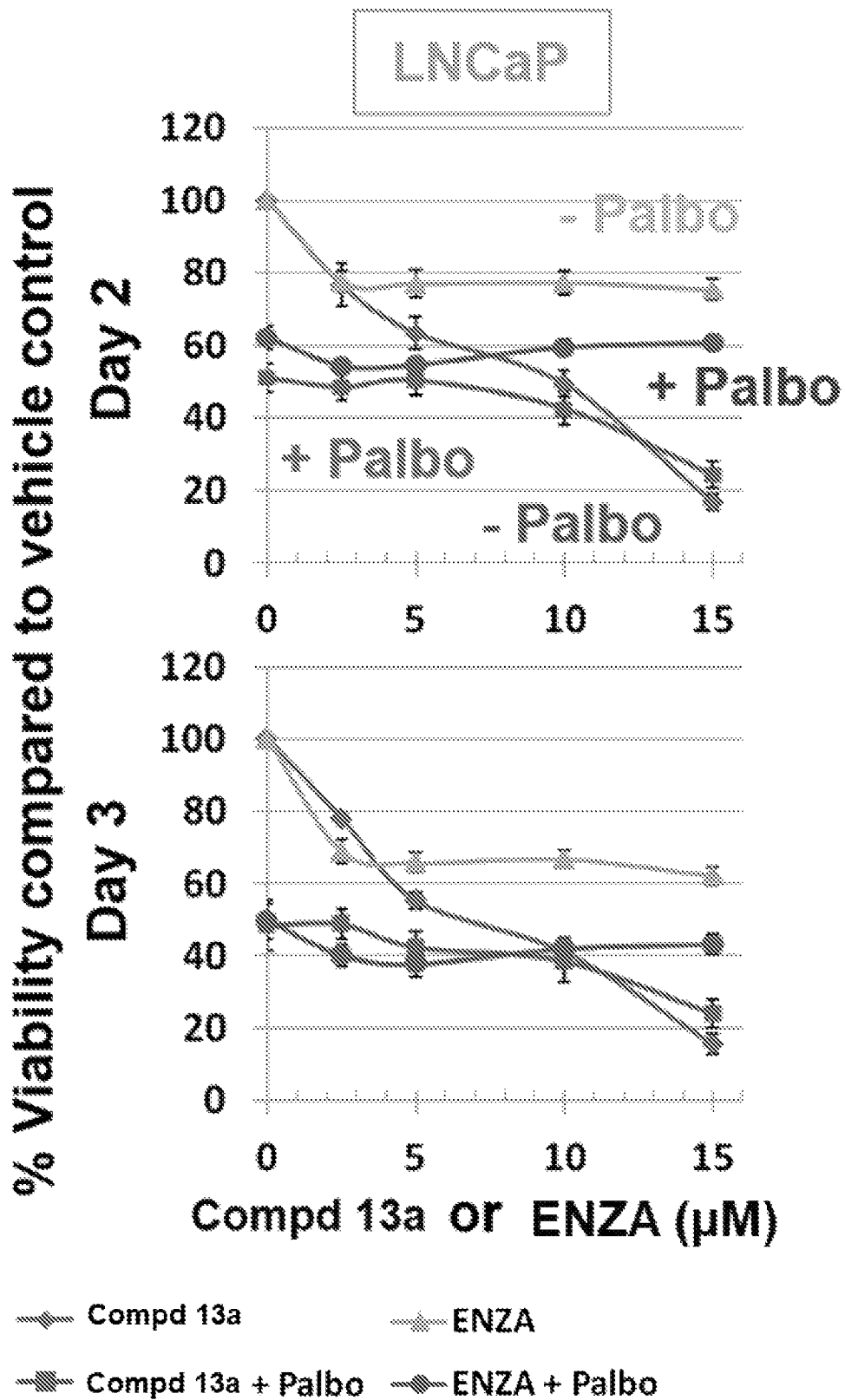
FIG. 2C shows cell viability of LNCaP cells treated with Compound 13a or enzalutamide (ENZ) with and without palbociclib (Palbo).
Figure 2D:
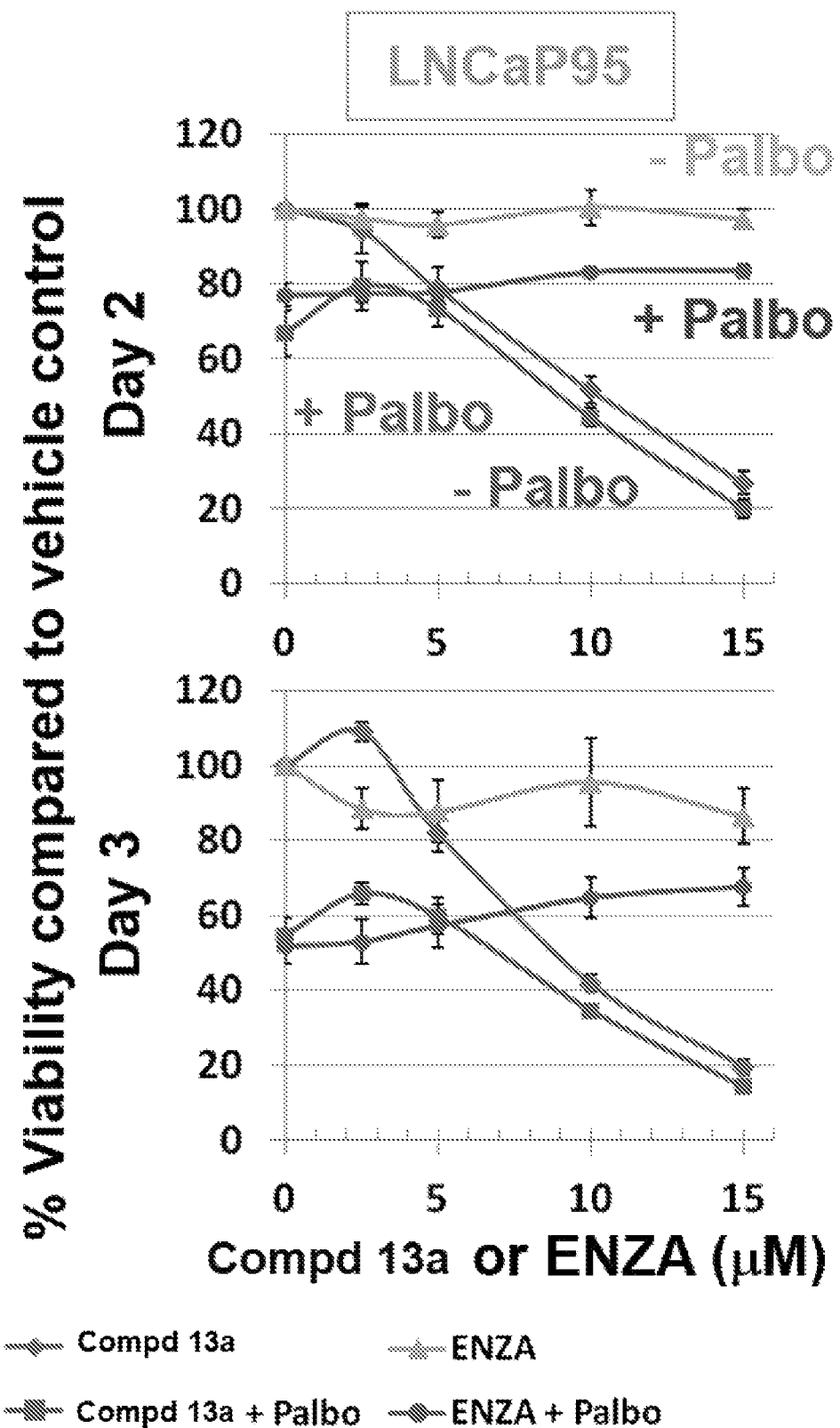
FIG. 2D shows cell viability of LNCaP95 cells treated with Compound 13a or enzalutamide (ENZ) with and without palbociclib (Palbo).

All publications, patents and patent applications, including any drawings and appendices therein are incorporated by reference in their entirety for all purposes to the same extent as if each individual publication, patent or patent application, drawing, or appendix was specifically and individually indicated to be incorporated by reference in its entirety for all purposes.

Definitions

While the following terms are believed to be well understood by one of ordinary skill in the art, the following definitions are set forth to facilitate explanation of the presently disclosed subject matter.

Throughout the present specification, the terms "about" and/or "approximately" may be used in conjunction with numerical values and/or ranges. The term "about" is understood to mean those values near to a recited value. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The term "a" or "an" refers to one or more of that entity; for example, "a androgen receptor N-terminal domain inhibitor" refers to one or more androgen receptor N-terminal domain inhibitors or at least one androgen receptor N-terminal domain inhibitor. As such, the terms "a" (or "an"), "one or more" and "at least one" are used interchangeably herein. In addition, reference to "an inhibitor" by the indefinite article "a" or "an" does not exclude the possibility that more than one of the inhibitors is present, unless the context clearly requires that there is one and only one of the inhibitors.

As used herein, the verb "comprise" as is used in this description and in the claims and its conjugations are used in its non-limiting sense to mean that items following the word are included, but items not specifically mentioned are not excluded. The present invention may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

The term "pharmaceutically acceptable salts" includes both acid and base addition salts. Pharmaceutically acceptable salts include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

The term "treating" means one or more of relieving, alleviating, delaying, reducing, improving, or managing at least one symptom of a condition in a subject. The term "treating" may also mean one or more of arresting, delaying the onset (i.e., the period prior to clinical manifestation of the condition) or reducing the risk of developing or worsening a condition.

The compounds of the invention, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present disclosure is meant to include all such possible isomers, as well as their racemic and optically pure forms whether or not they are specifically depicted herein. Optically active (+) and (−), (R)- and (S)-, or (D)- and (L)-isomers can be prepared using chiral synthons or chiral reagents, or resolved using conventional techniques, for example, chromatography and fractional crystallization. Conventional techniques for the preparation/ isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present disclosure includes tautomers of any said compounds.

A "prodrug" refers to a derivative of a compound of the present disclosure that will be converted to the compound in vivo. In one embodiment of the present disclosure, a prodrug includes a compound of formula (i)-(iii) and (a), having a free hydroxyl group (—OH) that is acetylated (—OCOMe) or acylated at one or more positions.

An "effective amount" means the amount of a formulation according to the invention that, when administered to a patient for treating a state, disorder or condition is sufficient to effect such treatment. The "effective amount" will vary depending on the active ingredient, the state, disorder, or condition to be treated and its severity, and the age, weight, physical condition and responsiveness of the mammal to be treated.

The term "therapeutically effective" applied to dose or amount refers to that quantity of a compound or pharmaceutical formulation that is sufficient to result in a desired clinical benefit after administration to a patient in need thereof.

As used herein, the term "ionizing radiation" refers to ionizing radiation from any source that is capable of ionizing atoms or molecules of a cell. Non-limiting examples of ionizing radiation include: X-rays, ultraviolet light, gamma rays, alpha particles, beta particles, and neutrons. Depending on the wavelength, ultraviolet light may be considered either-ionizing or non-ionizing radiation.

As used herein, a "subject" can be a human, non-human primate, mammal, rat, mouse, cow, horse, pig, sheep, goat, dog, cat and the like. The subject can be suspected of having or at risk for having a cancer, such as prostate cancer, breast cancer, ovarian cancer, salivary gland carcinoma, or endometrial cancer, or suspected of having or at risk for having acne, hirsutism, alopecia, benign prostatic hyperplasia, ovarian cysts, polycystic ovary disease, precocious puberty, spinal and bulbar muscular atrophy, or age-related macular degeneration. Diagnostic methods for various cancers, such as prostate cancer, breast cancer, ovarian cancer, bladder cancer, pancreatic cancer, hepatocellular cancer, salivary gland carcinoma, or endometrial cancer, and diagnostic methods for acne, hirsutism, alopecia, benign prostatic hyperplasia, ovarian cysts, polycystic ovary disease, precocious puberty, spinal and bulbar muscular atrophy, or age-related macular degeneration and the clinical delineation of cancer, such as prostate cancer, breast cancer, ovarian cancer, bladder cancer, pancreatic cancer, hepatocellular cancer, salivary gland carcinoma, or endometrial cancer, diagnoses and the clinical delineation of acne, hirsutism, alopecia, benign prostatic hyperplasia, ovarian cysts, polycystic ovary disease, precocious puberty, spinal and bulbar muscular atrophy, or age-related macular degeneration are known to those of ordinary skill in the art.

"Mammal" includes humans and both domestic animals such as laboratory animals (e.g., mice, rats, monkeys, dogs, etc.) and household pets (e.g., cats, dogs, swine, cattle, sheep, goats, horses, rabbits), and non-domestic animals such as wildlife and the like.

All weight percentages (i.e., "% by weight" and "wt. %" and w/w) referenced herein, unless otherwise indicated, are measured relative to the total weight of the pharmaceutical composition.

As used herein, "substantially" or "substantial" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking, the nearness of completion will be so as to have the same overall result as if absolute and total completion were obtained. The use of "substantially" is equally applicable when used in a negative connotation to refer to the complete or near complete lack of action, characteristic, property, state, structure, item, or result. For example, a composition that is "substantially free of" other active agents would either completely lack other active agents, or so nearly completely lack other active agents that the effect would be the same as if it completely lacked other active agents. In other words, a composition that is "substantially free of" an ingredient or element or another active agent may still contain such an item as long as there is no measurable effect thereof "Electrophile" as used herein relates to species that is attracted to an electron rich center. In chemistry, an electrophile is a reagent attracted to electrons. It participates in a chemical reaction by accepting an electron pair in order to bond to a nucleophile. Because electrophiles accept electrons, they are Lewis acids. Most electrophiles are positively charged, have an atom that carries a partial positive charge, or have an atom that does not have an octet of electrons.

The terms below, as used herein, have the following meanings, unless indicated otherwise:

"Amino" refers to the —NH$_2$ radical.

"Cyano" refers to the —CN radical.

"Halo" or "halogen" refers to bromo, chloro, fluoro or iodo radical, including their radioisotopes. "$^{123}$I" refers to the radioactive isotope of iodine having atomic mass 123. The compounds of Formula I can comprise at least one $^{123}$I moiety. Throughout the present application, where structures depict a $^{123}$I moiety at a certain position it is meant that the I moiety at this position is enriched for $^{123}$I. In other words, the compounds contain more than the natural abundance of $^{123}$I at the indicated position(s). It is not required that the compounds comprise 100% $^{123}$I at the indicated positions, provided $^{123}$I is present in more than the natural abundance. Typically the $^{123}$I isotope is enriched to greater than 50%, greater than 60%, greater than 70%, greater than, 80% or greater than 90%, relative to $^{127}$I. "$^{18}$F" refers to the radioactive isotope of fluorine having atomic mass 18. "F" or "$^{19}$F" refers to the abundant, non-radioactive fluorine isotope having atomic mass 19. The compounds of Formula I can comprise at least one $^{18}$F moiety. Throughout the present application, where structures depict a $^{18}$F moiety at a certain position it is meant that the F moiety at this position is enriched for $^{18}$F. In other words, the compounds contain more than the natural abundance of $^{18}$F at the indicated position(s). It is not required that the compounds comprise 100% $^{18}$F at the indicated positions, provided $^{18}$F is present in more than the natural abundance. Typically the $^{18}$F isotope is enriched to greater than 50%, greater than 60%, greater than 70%, greater than 80% or greater than 90%, relative to $^{19}$F.

"Hydroxy" or "hydroxyl" refers to the —OH radical.

"Imino" refers to the =NH substituent.

"Nitro" refers to the —NO$_2$ radical.

"Oxo" refers to the =O substituent.

"Thioxo" refers to the =S substituent.

"Alkyl" or "alkyl group" refers to a fully saturated, straight or branched hydrocarbon chain radical having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl group comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes $C_{11}$ and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —OR$_a$ where R$_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula —NHR$_a$ or —NR$_a$R$_a$ where each R$_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —C(=O)R$_a$ moiety, wherein R$_a$ is an alkyl, alkenyl or alkynyl radical as defined above. A non-limiting example of an alkyl carbonyl is the methyl carbonyl ("acetal") moiety. Alkylcarbonyl groups can also be referred to as "Cw-Cz acyl" where w and z depicts the range of the number of carbon in R$_a$, as defined above. For example, "C1-$C_{10}$ acyl" refers to alkylcarbonyl group as defined above, where R$_a$ is $C_1$-$C_{10}$ alkyl, $C_1$-$C_{10}$ alkenyl, or $C_1$-$C_{10}$ alkynyl radical as defined above. Unless stated otherwise specifically in the specification, an alkyl carbonyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" or "arylalkyl" refers to a radical of the formula —R$_b$—R$_c$ where R$_b$ is an alkylene group as defined above and R$_c$ is one or more aryl radicals as defined above, for example, benzyl, diphenylmethyl and the like. Unless stated otherwise specifically in the specification, an aralkyl group can be optionally substituted.

"Aralkenyl" or "arylalkenyl" refers to a radical of the formula —R$_b$—R$_c$ where R$_b$ is an alkenylene o group as defined above and R$_c$ is one or more aryl radicals as defined above. Unless stated otherwise specifically in the specification, an aralkenyl group can be optionally substituted.

"Aralkynyl" or "arylalkynyl" refers to a radical of the formula —R$_b$—R$_c$ where R$_b$ is an alkynylene group as defined above and R$_C$ is one or more aryl radicals as defined above. Unless stated otherwise specifically in the specification, an aralkynyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl. cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula —R$_b$—R$_d$ where R$_b$ is an alkylene, alkenylene, or alkynylene group as defined above and R$_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkenyl group can be optionally substituted.

"Heterocyclyl," "heterocyclic ring" or "heterocycle" refers to a stable 3- to 20-membered non-aromatic, partially aromatic, or aromatic ring radical which consists of two to twelve carbon atoms and from one to six heteroatoms selected from the group consisting of nitrogen, oxygen and sulfur. Heterocyclcl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclyl group can be optionally substituted.

"Heterocyclylalkyl" refers to a radical of the formula —$R_b$—$R_e$ where $R_b$ is an alkylene group as defined above and $R_e$ is a heterocyclyl radical as defined above. Unless stated otherwise specifically in the specification, a heterocycloalkylalkyl group can be optionally substituted.

"Heterocyclylalkenyl" refers to a radical of the formula —$R_b$—$R_e$ where $R_b$ is an alkenylene group as defined above and $R_e$ is a heterocyclyl radical as defined above. Unless stated otherwise specifically in the specification, a heterocycloalkylalkenyl group can be optionally substituted.

"Heterocyclylalkynyl" refers to a radical of the formula —$R_b$—$R_e$ where $R_b$ is an alkynylene group as defined above and $R_e$ is a heterocyclyl radical as defined above. Unless stated otherwise specifically in the specification, a heterocycloalkylalkynyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1, 4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophene), benzotriazolyl, benzo[4,6]imidazo[1,2-a]pyridinyl, carbazolyl, cinnolinyl, dibenzofuranyl, dibenzothiophene, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophene (i.e. thienyl). Unless stated otherwise specifically in the specification, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula —$R_b$—$R_f$ where $R_b$ is an alkylene chain as defined above and $R_f$ is a heteroaryl radical as defined above. Unless stated otherwise specifically in the specification, a heteroarylalkyl group can be optionally substituted.

"Heteroarylalkenyl" refers to a radical of the formula —$R_b$—$R_f$ where $R_b$ is an alkenylene, chain as defined above and $R_f$ is a heteroaryl radical as defined above. Unless stated otherwise specifically in the specification, a heteroarylalkenyl group can be optionally substituted.

"Heteroarylalkynyl" refers to a radical of the formula —$R_b$—$R_f$ where $R_b$ is an alkynylene chain as defined above and $R_f$ is a heteroaryl radical as defined above. Unless stated otherwise specifically in the specification, a heteroarylalkynyl group can be optionally substituted.

"Ring" refers to a cyclic group which can be fully saturated, partially saturated, or fully unsaturated. A ring can be monocyclic, bicyclic, tricyclic, or tetracyclic. Unless stated otherwise specifically in the specification, a ring can be optionally substituted.

"Thioalkyl" refers to a radical of the formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (i.e., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups.

"Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the symbol

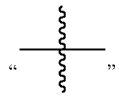

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

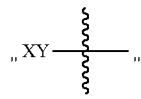

indicates that the chemical entity "XY" is bonded to another chemical entity via the point of attachment bond. Furthermore, the specific point of attachment to the non-depicted chemical entity can be specified by inference. For example, the compound CH$_3$—R$^3$, wherein R$^3$ is H or

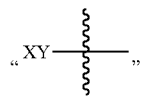

infers that when R$^3$ is "XY", the point of attachment bond is the same bond as the bond by which R$^3$ is depicted as being bonded to CH$_3$.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring can be replaced with a nitrogen atom.

The following description includes information that may be useful in understanding the present invention. It is not an admission that any of the information provided herein is prior art or relevant to the presently claimed inventions, or that any publication specifically or implicitly referenced is prior art.

Androgen Receptor N-Terminal Domain Inhibitors of the Present Disclosure

The pharmaceutical compositions or combinations of the present disclosure can be useful for modulating (including inhibiting) androgen receptors. Further, the pharmaceutical compositions or combinations of the present disclosure can be useful for treating various diseases and conditions including, but not limited to, cancer.

In one embodiment of the present disclosure, the pharmaceutical compositions or combinations comprises an androgen receptor N-terminal domain inhibitor and a CDK4/6 inhibitor.

In one embodiment, the pharmaceutical composition comprises an androgen receptor N-terminal domain inhibitor and a Pin1 inhibitor. In one embodiment, the pharmaceutical composition comprises an androgen receptor N-terminal domain inhibitor and a Pin1 inhibitor, wherein the androgen receptor N-terminal domain inhibitor is not 3-(4-(2-(4-(3-chloro-2-hydroxypropoxy)phenyl)propan-2-yl)phenoxy)propane-1,2-diol, 3-(4-(2-(4-(2-acetoxy-3-chloropropoxy)phenyl)propan-2-yl)phenoxy)propane-1,2-diyl diacetate, or stereoisomers thereof.

In one embodiment of the present disclosure, the pharmaceutical compositions or combinations comprises an androgen receptor N-terminal domain inhibitor and an androgen receptor ligand-binding domain inhibitor.

The androgen receptor N-terminal domain inhibitors of the present disclosure can, alone, be useful for treating various diseases and conditions including, but not limited to, cancer. In some embodiments, the cancer is prostate cancer.

In one embodiment, the present disclosure provides androgen receptor N-terminal domain inhibitors selected from compounds of formula (i):

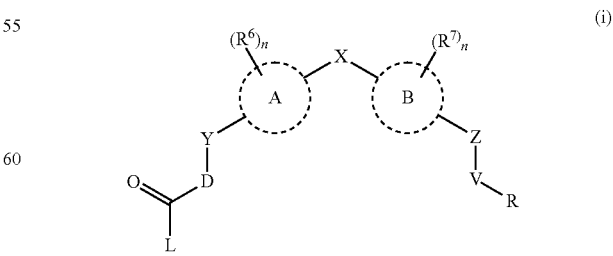

or a pharmaceutically acceptable salt, tautomer, stereoisomer or prodrug thereof, wherein:

A and B are each independently aryl or heteroaryl;

X is a bond, $-(CR^8R^9)_t-$, $-O-$, $-C(=O)-$, $-S(O)_n-$, $-NR^{10}-$, $-CONR^{10}-$, $-NR^{10}CO-$, $-SO_2NR^{10}-$, or $-NR^{10}SO_2-$;

Y and Z are each independently a bond, $-(CR^8R^9)_t-$, $-O-$, $-S(O)_n-$, $-NR^{10}-$, $-CONR^{10}-$, $-NR^{10}CO-$, $-SO_2NR^{10}-$, or $-NR^{10}SO_2-$;

V is a bond, optionally substituted $-(CR^{11}R^{12})_m-$, $-C(=O)-$, $-N(R^{10})CO-$, $-CONR^{10}-$, or $-NSO_2R^{10}-$;

R is $-(CR^{4a}R^{4b})-(CR^{5a}R^{5b})-W$ or W;

W is hydrogen, halogen, $-CF_3$, $-CF_2R^{10}$, $-CN$, $-OR^{13}$, $-NR^{13}R^{14}$, optionally substituted $-CONR^{13}R^{14}$, optionally substituted carbocyclyl, optionally substituted heterocyclyl, optionally substituted aryl, or optionally substituted heteroaryl;

D is $-(CR^{1a}R^{1b})_q-$, $-O-$, or $-NR^{10}-$;

L is $-(CR^{2a}R^{2b})-R^3$ or $-E-R^3$;

E is $-(CR^{2a}R^{2b})_g-$, $-O-$, $-NR^{10}-$, or $-NR^{10}-(CR^{2a}R^{2b})_g-$;

$R^{1a}$, $R^{1b}$, $R^{2a}$, and $R^{2b}$ are each independently hydrogen, halogen, hydroxy, optionally substituted $C_{1-6}$ alkyl, optionally substituted $C_2$-$C_6$ alkenyl, optionally substituted $C_2$-$C_6$ alkynyl, optionally substituted $C_{1-6}$ alkoxy, optionally substituted $-OCO(C_1$-$C_6$ alkyl), $-NR^{13}R^{14}$, optionally substituted $-(C_1$-$C_6$ alkyl)-$NR^{13}R^{14}$, $-NR^{14}COR^{16}$, optionally substituted $-(C_1$-$C_6$ alkyl)-$NR^{14}COR^{16}$, $-CONR^{14}R^{15}$, optionally substituted $-(C_1$-$C_6$ alkyl)-$CONR^{14}R^{15}$, optionally substituted carbocyclyl, optionally substituted heterocyclyl, optionally substituted aryl, or optionally substituted heteroaryl;

or alternatively, $R^{1a}$ and $R^{1b}$ taken together form an optionally substituted carbocyclyl, optionally substituted heterocyclyl, optionally substituted aryl, or optionally substituted heteroaryl;

or alternatively, $R^{2a}$ and $R^{2b}$ taken together form a CO, optionally substituted carbocyclyl, optionally substituted heterocyclyl, optionally substituted aryl, or optionally substituted heteroaryl;

or alternatively, $R^{1a}$, $R^{1b}$, $R^{2a}$ and $R^{2b}$ taken together form an optionally substituted carbocyclyl, optionally substituted heterocyclyl, optionally substituted aryl, or optionally substituted heteroaryl;

$R^{4a}$, $R^{4b}$, $R^{5a}$, and $R^{5b}$ are each independently hydrogen, halogen, hydroxy, optionally substituted $C_{1-6}$ alkyl, optionally substituted $C_2$-$C_6$ alkenyl, optionally substituted $C_2$-$C_6$ alkynyl, optionally substituted $C_{1-6}$ alkoxy, optionally substituted $-OCO(C_1$-$C_6$ alkyl), $-NR^{13}R^{14}$, optionally substituted $-(C_1$-$C_6$ alkyl)-$NR^{13}R^{14}$, $-NR^{14}COR^{16}$, optionally substituted $-(C_1$-$C_6$ alkyl)-$NR^{14}COR^{16}$, $-CONR^{14}R^{15}$, optionally substituted $-(C_1$-$C_6$ alkyl)-$CONR^{14}R^{15}$, optionally substituted carbocyclyl, optionally substituted heterocyclyl, optionally substituted aryl, or optionally substituted heteroaryl;

or alternatively, $R^{4a}$ and $R^{4b}$ taken together form a CO, optionally substituted carbocyclyl, optionally substituted heterocyclyl, optionally substituted aryl, or optionally substituted heteroaryl;

or alternatively, $R^{4a}$, $R^{4b}$, $R^{5a}$ and $R^{5b}$ taken together form an optionally substituted carbocyclyl, optionally substituted heterocyclyl, optionally substituted aryl, or optionally substituted heteroaryl;

$R^3$ is absent, hydrogen, $-CN$, $-CF_3$, $-OH$, optionally substituted $C_1$-$C_6$ alkyl, optionally substituted $C_2$-$C_6$ alkenyl, optionally substituted $C_2$-$C_6$ alkynyl, optionally substituted $-OR^{15}$, optionally substituted $C_1$-$C_6$ alkoxy, $-NH_2$, $-NR^{16}R^{17}$, $-NR^{16}COR^{18}$, $-NR^{16}S(O)_pR^{18}$, $-CONR^{14}R^{15}$, $-SONR^{14}R^{15}$, $-SO_2NR^{14}R^{15}$, optionally substituted $-S(O)_pR^{18}$, $-N_3$, optionally substituted carbocyclyl, optionally substituted heterocyclyl, optionally substituted aryl, or optionally substituted heteroaryl;

$R^{2a}$, $R^{2b}$ and $R^3$ taken together form an optionally substituted carbocyclyl, optionally substituted heterocyclyl, optionally substituted aryl, or optionally substituted heteroaryl;

$R^6$ and $R^7$ are each independently H, halogen, $-CN$, $-CF_3$, $-OH$, optionally substituted $C_1$-$C_6$ alkyl, optionally substituted $C_1$-$C_6$ alkoxy, optionally substituted $-(C_1$-$C_6$ alkyl)-$(C_1$-$C_6$ alkoxy), optionally substituted $-(C_1$-$C_6$ alkyl)-OH, $-NR^{13}R^{14}$ optionally substituted $-(C_1$-$C_6$ alkyl)-$NR^{13}R^{14}$, $-NR^{14}SO_2R^{16}$, optionally substituted $-(C_1$-$C_6$ alkyl)$NR^{14}SO_2R^{16}$, $-NR^{14}COR^{16}$, optionally substituted $-(C_1$-$C_6$ alkyl)-$NR^{14}COR^{16}$, $-CONR^{14}R^{15}$, optionally substituted $-(C_1$-$C_6$ alkyl)-$CONR^{14}R^{15}$, $-SO_2NR^{14}R^{15}$, optionally substituted $-(C_1$-$C_6$ alkyl)-$SO_2NR^{14}R^{15}$, optionally substituted $-SO_2R^{16}$, optionally substituted $-(C_1$-$C_6$ alkyl)-$SO_2R^{16}$, optionally substituted carbocyclyl, optionally substituted heterocyclyl, optionally substituted aryl, or optionally substituted heteroaryl;

$R^8$, $R^9$, $R^{11}$ and $R^{12}$ are each independently hydrogen, $-OH$, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ alkylamino, optionally substituted $-OCO(C_1$-$C_6$ alkyl), $-NR^{13}R^{14}$, optionally substituted $-(C_1$-$C_6$ alkyl)-$NR^{13}R^{14}$, $-NR^{14}COR^{16}$, optionally substituted $-(C_1$-$C_6$ alkyl)-$NR^{14}COR^{16}$, $-CONR^{14}R^{15}$, optionally substituted $-(C_1$-$C_6$ alkyl)-$CONR^{14}R^{15}$, optionally substituted carbocyclyl, optionally substituted heterocyclyl, optionally substituted aryl, or optionally substituted heteroaryl;

or alternatively, $R^8$ and $R^9$ taken together form an optionally substituted carbocyclyl or optionally substituted heterocyclyl;

or alternatively, $R^{11}$ and $R^{12}$, on a same carbon atom or a different carbon atom, taken together form an optionally substituted carbocyclyl, optionally substituted heterocyclyl, optionally substituted aryl, or optionally substituted heteroaryl;

$R^{10}$ is hydrogen, halogen, optionally substituted $C_1$-$C_6$ alkyl, optionally substituted $C_1$-$C_6$ alkoxy, $-CO(C_1$-$C_6$ alkyl), optionally substituted $C_1$-$C_6$ alkylamino, optionally substituted carbocyclyl, optionally substituted heterocyclyl, optionally substituted aryl, or optionally substituted heteroaryl;

or alternatively, $R^{2a}$ and $R^{10}$ taken together form an optionally substituted heterocyclyl;

$R^{13}$, $R^{14}$, $R^{15}$, $R^{16}$, $R^{17}$ and $R^{18}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl;

or alternatively, $R^{14}$ and $R^{15}$ are taken together to form an optionally substituted heterocyclyl, or optionally substituted heteroaryl;

or alternatively, $R^{16}$ and $R^{17}$ are taken together to form an optionally substituted heterocyclyl, or optionally substituted heteroaryl;

m is 0, 1, 2, 3, or 4;

each n is independently 0, 1 or 2;

each p is independently 0, 1 or 2;

q is 0, 1 or 2;

each g is independently 0, 1, 2, 3, or 4; and each t is independently 1 or 2.

In one embodiment, the present disclosure provides androgen receptor N-terminal domain inhibitors selected from compounds of formula (ii):

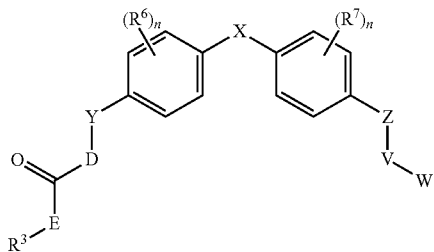

(ii)

or a pharmaceutically acceptable salt, tautomer, stereoisomer or prodrug thereof, wherein:

X is a bond, —$NR^{10}$—, or —$(CR^{8a}R^{9a})_t$—;

Y and Z are each independently a bond, —$CH_2$—, —$C(CH_3)H$—, —O—, —S—, —NH—, —$NCH_3$—, or —$N(COCH_3)$—;

V is —$CH_2$—, —$CH_2CH_2$—, —$CH_2CH_2CH_2$—, —$CH_2CH(CH_3)CH_2$—, —$CH_2CH(OH)CH_2$—, or —$CH_2C(OH)(CH_3)CH_2$—;

W is halogen, —$NH_2$, or —$CF_3$.

D is —$NR^{10}$— and E is —$(CR^{2a}R^{2b})_g$—, —$NR^{10}$—, or —$NR^{10}$—$(CR^{2a}R^{2b})_g$—.

or alternatively, E is —$NR^{10}$— or —$NR^{10}$—$(CR^{2a}R^{2b})_g$—, and D is —$(CR^{1a}R^{1b})_q$— or —$NR^{10}$—;

$R^{1a}$, $R^{1b}$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —$OCO(C_1$-$C_3$ alkyl), —$NR^{13}R^{14}$, —$(C_1$-$C_3$ alkyl)-$NR^{13}R^{14}$, —$NR^{14}COR^{16}$, —$(C_1$-$C_3$ alkyl)-$NR^{14}COR^{16}$, —$CONR^{14}R^{15}$, or —$(C_1$-$C_6$ alkyl)-$CONR^{14}R^{15}$; or ($R^{1a}$ and $R^{1b}$) or ($R^{2a}$ and $R^{2b}$) taken together form an oxo (=O), an optionally substituted carbocyclyl, or an optionally substituted heterocyclyl;

$R^3$ is selected from hydrogen, —$C_1$-$C_6$ alkyl, —$OR^{15}$, —$SR^{18}$, —$C_1$-$C_6$ alkoxy, —$NR^{16}R^{17}$, —$NR^{16}SR^{18}$, —$NR^{16}SOR^{18}$, —$NR^{16}SO_2R^{18}$, —$NR^{16}COR^{18}$, —$CONR^{14}R^{15}$, —$SONR^{14}R^{15}$, —$SO_2NR^{14}R^{15}$, —$SOR^{18}$, or —$SO_2R^{18}$;

$R^6$ and $R^7$ are each independently H, halogen, —CN, —$CF_3$, —OH, $C_1$-$C_3$ alkyl;

$R^{8a}$ and $R^{9a}$ are each independently hydrogen, halogen, —OH, or $C_1$-$C_3$ alkyl;

$R^{10}$ is each independently hydrogen, $C_1$-$C_3$ alkyl, $C_2$-$C_3$ alkenyl, $C_2$-$C_3$ alkynyl, —$CO(C_1$-$C_3$ alkyl);

$R^{13}$, $R^{14}$, $R^{15}$, $R^{16}$, $R^{17}$ and $R^{18}$ are each independently hydrogen, $C_1$-$C_3$ alkyl, $C_2$-$C_3$ alkenyl, or $C_2$-$C_3$ alkynyl; or $R^{14}$ and $R^{15}$ taken together form an optionally substituted 5- or 6-membered heterocyclyl;

each n is independently 0, 1 or 2;

q is 0, 1 or 2;

each g is independently 0, 1, 2, 3, or 4; and each t is independently 1 or 2.

In one embodiment, the present disclosure provides androgen receptor N-terminal domain inhibitors selected from compounds of formula (iii):

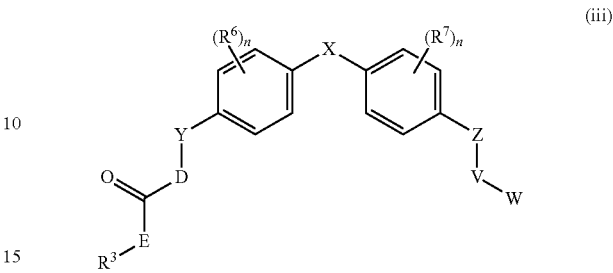

(iii)

or a pharmaceutically acceptable salt, tautomer, stereoisomer or prodrug thereof, wherein:

X is a bond, —$NR^{10}$—, or —$(CR^{8a}R^{9a})_t$—;

Y and Z are each independently a bond, —$CH_2$—, —$C(CH_3)H$—, —O—, —S—, —NH—, —$NCH_3$—, or —$N(COCH_3)$—;

V is —$CH_2$—, —$CH_2CH_2$—, —$CH_2CH_2CH_2$—, —$CH_2CH(CH_3)CH_2$—, —$CH_2CH(OH)CH_2$—, or —$CH_2C(OH)(CH_3)CH_2$—;

W is halogen, —$NH_2$ or —$CF_3$;

D is —$NR^{10}$— and E is —$(CR^{2a}R^{2b})_{gg}$—;

or alternatively, E is —$NR^{10}$— or —$NR^{10}$—$(CR^{2a}R^{2b})_g$—, and D is —$(CR^{1a}R^{1b})_q$—;

$R^{1a}$, $R^{1b}$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —$OCO(C_1$-$C_3$ alkyl), —$NR^{13}R^{14}$; —$(C_1$-$C_3$ alkyl)-$NR^{13}R^{14}$, —$NR^{14}COR^{16}$, —$(C_1$-$C_3$ alkyl)-$NR^{14}COR^{16}$, —$CONR^{14}R^{15}$, or —$(C_1$-$C_6$ alkyl)-$CONR^{14}R^{15}$; or ($R^{1a}$ and $R^{1b}$) or ($R^{2a}$ and $R^{2b}$) taken together form an oxo (=O), an optionally substituted carbocyclyl, or an optionally substituted heterocyclyl;

$R^3$ is selected from hydrogen, —$C_1$-$C_6$ alkyl, —$OR^{15}$, —$SR^{18}$, —$C_1$-$C_6$ alkoxy, —$NR^{16}R^{17}$, —$NR^{16}SR^{18}$, —$NR^{16}SOR^{18}$, —$NR^{16}SO_2R^{18}$, —$NR^{16}COR^{18}$, —$CONR^{14}R^{15}$, —$SONR^{14}R^{15}$, —$SO_2NR^{14}R^{15}$, —$SOR^{18}$, or —$SO_2R^{18}$;

$R^6$ and $R^7$ are each independently H, halogen, —CN, —$CF_3$, —OH, or $C_1$-$C_3$ alkyl;

$R^{8a}$ and $R^{9a}$ are each independently hydrogen, halogen, —OH, or $C_1$-$C_3$ alkyl;

$R^{10}$ is each independently hydrogen, $C_1$-$C_3$ alkyl, $C_2$-$C_3$ alkenyl, $C_2$-$C_3$ alkynyl, or —$CO(C_1$-$C_3$ alkyl);

$R^{13}$, $R^{14}$, $R^{15}$, $R^{16}$, $R^{17}$ and $R^{18}$ are each independently hydrogen, $C_1$-$C_3$ alkyl, $C_2$-$C_3$ alkenyl, or $C_2$-$C_3$ alkynyl; or $R^{14}$ and $R^{15}$ taken together form an optionally substituted 5- or 6-membered heterocyclyl;

m is 0, 1, 2, 3, or 4;

each n is independently 0, 1 or 2;

q is 1 or 2;

g is 0, 1, 2, 3, or 4;

gg is 1, 2, 3, or 4; and t is 1 or 2.

In one embodiment, the present disclosure provides androgen receptor N-terminal domain inhibitors selected from compounds of formula (iv):

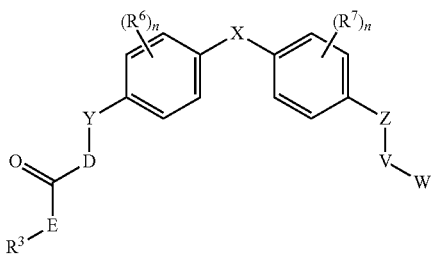

(iv)

or a pharmaceutically acceptable salt, tautomer, stereoisomer or prodrug thereof, wherein:

X is a bond, —NR$^{10}$—, or —(CR$^{8a}$R$^{9a}$)$_t$—;

Y and Z are each independently a bond, —CH$_2$—, —C(CH$_3$)H—, —O—, —S—, —NH—, —NCH$_3$—, or —N(COCH$_3$)—;

V is —CH$_2$—, —CH$_2$CH$_2$—, —CH$_2$CH$_2$CH$_2$—, —CH$_2$CH(CH$_3$)CH$_2$—, —CH$_2$CH(OH)CH$_2$—, or —CH$_2$C(OH)(CH$_3$)CH$_2$—;

W is —CF$_2$R$^{10}$, —NR$^{13}$R$^{14}$, optionally substituted carbocyclyl, optionally substituted heterocyclyl, optionally substituted aryl, or optionally substituted heteroaryl; D is —(CR$^{1a}$R$^{1b}$)$_q$—;

E is —(CR$^{2a}$R$^{2b}$)$_g$—;

R$^{1a}$, R$^{1b}$, R$^{2a}$, and R$^{2b}$ are each independently hydrogen, halogen, —OH, C$_1$-C$_3$ alkyl, C$_2$-C$_3$ alkenyl, C$_2$-C$_3$ alkynyl, C$_1$-C$_3$ alkoxy, —OCO(C$_1$-C$_3$ alkyl), —NR$^{13}$R$^{14}$, —(C$_1$-C$_3$ alkyl)-NR$^{13}$R$^{14}$, —NR$^{14}$COR$^{16}$, —(C$_1$-C$_3$ alkyl)-NR$^{14}$COR$^{16}$, —CONR$^{14}$R$^{15}$, or —(C$_1$-C$_6$ alkyl)-CONR$^{14}$R$^{15}$; or (R$^{1a}$ and R$^{1b}$) or (R$^{2a}$ and R$^{2b}$) taken together form an oxo (=O), an optionally substituted carbocyclyl, or an optionally substituted heterocyclyl;

R$^3$ is selected from hydrogen, —C$_1$-C$_6$ alkyl, —OR$^{15}$, —SR$^{18}$, —C$_1$-C$_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, —SOR$^{18}$, or —SO$_2$R$^{18}$;

R$^6$ and R$^7$ are each independently H, halogen, —CN, —CF$_3$, —OH, or C$_1$-C$_3$ alkyl;

R$^{8a}$ and R$^{9a}$ are each independently hydrogen, halogen, —OH, or C$_1$-C$_3$ alkyl; or R$^{8a}$ and R$^{9a}$ taken together form an optionally substituted carbocyclyl or optionally substituted heterocyclyl;

R$^{10}$ is each independently hydrogen, C$_1$-C$_3$ alkyl, C$_2$-C$_3$ alkenyl, C$_2$-C$_3$ alkynyl, or —CO(C$_1$-C$_3$ alkyl);

R$^{13}$, R$^{14}$, R$^{15}$, R$^{16}$, R$^{17}$ and R$^{18}$ are each independently hydrogen, C$_1$-C$_3$ alkyl, C$_2$-C$_3$ alkenyl, or C$_2$-C$_3$ alkynyl; or R$^{14}$ and R$^{15}$ taken together form an optionally substituted 5- or 6-membered heterocyclyl;

m is 0, 1, 2, 3, or 4;

each n is independently 0, 1 or 2;

q is 0, 1 or 2;

g is 0, 1, 2, 3, or 4; and t is 1 or 2.

In one embodiment of the compounds of formula (i), R is W.

In one embodiment of the compounds of formula (i), W is hydrogen, halogen, —CF$_3$, or —NR$^{13}$R$^{14}$. In one embodiment, W is hydrogen, halogen, —CF$_3$, or —NH$_2$. In some embodiments, W is aryl, optionally substituted with halogen, C$_1$-C$_3$ alkyl, —CN, —CF$_3$, —OH, C$_1$-C$_3$ alkoxy, —NR$^{13}$R$^{14}$ or —SO$_2$R$^{16}$. In another embodiment, W is a phenyl, optionally substituted with halogen, C$_1$-C$_3$ alkyl, —CN, —CF$_3$, —OH, or C$_1$-C$_3$ alkoxy.

In one embodiment of the compounds of formula (i)-(iii), W is hydrogen, halogen, —CF$_3$, or —NH$_2$. In one embodiment, W is a halogen. In one embodiment, W is Cl, Br, I, or F. In other embodiments, W is Cl.

In one embodiment of the compounds of formula (i), L is -E-R$^3$.

In one embodiment of the compounds of formula (i)-(iv), X is a bond, —NR$^{10}$—, or —(CR$^{8a}$R$^{9a}$)$_t$—. In one embodiment, X is a bond. In other embodiments, X is —(CR$^8$R$^9$)$_t$— or —NR$^{10}$—. In another embodiment, X is —NR$^{10}$—.

In one embodiment of the compounds of formula (i)-(iv), X is —NR$^{10}$—, wherein R$^{10}$ is hydrogen or optionally substituted C$_1$-C$_6$ alkyl. In another embodiment, R$^{10}$ is hydrogen. In some embodiments, X is —NR$^{10}$—, wherein R$^{10}$ is methyl. In one embodiment, X is —NR$^{10}$—, wherein R$^{10}$ is H, C$_1$-C$_6$ alkyl, or —CO(C$_1$-C$_6$ alkyl). In one embodiment, X is —NR$^{10}$—, wherein R$^{10}$ is H, C$_1$-C$_6$ alkyl, or —CO(C$_1$-C$_6$ alkyl). In one embodiment, X is —NR$^{10}$—, wherein R$^{10}$ is H, C$_1$-C$_3$ alkyl, or —CO(C$_1$-C$_3$ alkyl).

In one embodiment of the compounds of formula (i)-(iv), X is —(CR$^8$R$^9$)$_t$—. In one embodiment, X is —(CR$^8$R$^9$)$_t$—, wherein R$^8$ and R$^9$ are each selected from H, halogen, —OH, or C$_1$-C$_6$ alkyl. In one embodiment, X is a bond or —(CR$^{8a}$R$^{9a}$)$_t$—, wherein R$^{8a}$ and R$^{9a}$ are each selected from H, halogen, —OH, or C$_1$-C$_6$ alkyl and t is 1, or 2. In some embodiments, X is —(CR$^8$R$^9$)$_t$—, wherein each R$^8$ and R$^9$ are independently hydrogen or optionally substituted C$_1$-C$_6$ alkyl. In some embodiments, X is —(CR$^8$R$^9$)$_t$—, wherein each R$^8$ and R$^9$ are hydrogen. In some embodiments, X is —(CR$^8$R$^9$)$_t$—, wherein each R$^8$ and R$^9$ are methyl.

In one embodiment of the compounds of formula (i)-(iv), X is a bond or —(CR$^{8a}$R$^{9a}$)$_t$—, wherein t is 1, or 2.

In one embodiment of the compounds of formula (i)-(iv), the instance of t when X is —(CR$^8$R$^9$)$_t$— is 1. In other embodiments, the instance of t when X is —(CR$^8$R$^9$)$_t$- is 2.

In one embodiment of the compounds of formula (i)-(iv), X —(CR$^{8a}$R$^{9a}$)$_t$—, wherein R$^{8a}$ and R$^{9a}$ taken together form an optionally substituted carbocyclyl or optionally substituted heterocyclyl. In one embodiment, X —(CR$^{8a}$R$^{9a}$)$_t$—, wherein R$^{8a}$ and R$^{9a}$ taken together form an optionally substituted 3- to 6-membered carbocyclyl or an optionally substituted 3- to 6-membered heterocyclyl containing one heteroatom selected from O, S, or N. In one embodiment, X —(CR$^{8a}$R$^{9a}$)$_t$—, wherein R$^{8a}$ and R$^{9a}$ taken together form a 3- to 6-membered carbocyclyl or a 3- to 6-membered heterocyclyl containing one heteroatom selected from O, S, or N. In one embodiment, X —(CR$^{8a}$R$^{9a}$)$_t$—, wherein R$^{8a}$ and R$^{9a}$ taken together form a 4-membered heterocyclyl containing one O.

In one embodiment of the compounds of formula (i)-(iv), X is a bond, —NR$^{10}$—, or —(CR$^{8a}$R$^{9a}$)$_t$—. In one embodiment, X is a bond, —CH$_2$—, —C(CH$_3$)$_2$—, —CH$_2$CH$_2$—, —NH—, —N(CH$_3$)—, —N(iPr)—, or —N(COCH$_3$)—. In other embodiments, X is a bond, —NH—, —CH$_2$—, —C(CH$_3$)$_2$—, or —CH$_2$CH$_2$—. In other embodiments, X is a bond, —NH—, —N(COCH$_3$)—, —N(C$_1$-C$_3$ alkyl)-, —CH$_2$—, —CH(CH$_3$)—, —C(CH$_3$)$_2$—, —CH$_2$CH$_2$—, —CH(OH)—, —CHF—, or —CHF$_2$—. In other embodiments, X is a bond, —CH$_2$—, —C(CH$_3$)$_2$—, —CH$_2$CH$_2$—, —NH—, —N(CH$_3$)—, —N(iPr)—, or —N(COCH$_3$)—.

In one embodiment of the compounds of formula (i), Y is —(CR$^8$R$^9$)$_t$—, —O—, or —NR$^{10}$—. In other embodiments, Y is —O—. In another embodiment, Y is —(CR$^8$R$^9$)$_t$—. In another embodiment, Y is —(CR$^8$R$^9$)$_t$—, wherein each R$^8$ and R$^9$ are hydrogen.

In one embodiment of the compounds of formula (i), the instance of t when Y is —(CR$^8$R$^9$)$_t$— is 1.

In one embodiment of the compounds of formula (i), Y is —NR$^{10}$—. In another embodiment, Y is —NR$^{10}$—, wherein R$^{10}$ is hydrogen or optionally substituted C$_1$-C$_6$ alkyl. In another embodiment, Y is —NR$^{10}$—, R$^{10}$ is hydrogen. In another embodiment, Y is —NR$^{10}$—, R$^{10}$ is methyl.

In one embodiment of the compounds of formula (i)-(iv), Y is a bond, —CH$_2$—, —C(CH$_3$)H—, —O—, —S—, —NH—, —NCH$_3$—, or —N(COCH$_3$)—. In one embodiment, Y is a —CH$_2$—, —C(CH$_3$)H—, —O—, —S—, —NH—, —NCH$_3$—, or —N(COCH$_3$)—. In one embodiment, Y is —CH$_2$—, —O—, —NH—, or —NCH$_3$—. In some embodiments, Y is a bond, —CH$_2$—, —O—, or —NCH$_3$—. In some embodiments, Y is a bond, —CH$_2$—, —O—, or —NH—. In some embodiments, Y is —O—.

In one embodiment of the compounds of formula (i), Z is —(CR$^8$R$^9$)$_t$—, O, or NR$^{10}$. In one embodiment, Z is O. In some embodiments, Z is —(CR$^8$R$^9$)$_t$—. In another embodiment, Z is —(CR$^8$R$^9$)$_t$—, wherein each R$^8$ and R$^9$ are hydrogen.

In one embodiment of the compounds of formula (i), the instance of t when Z is —(CR$^8$R$^9$)$_t$— is 1.

In one embodiment of the compounds of formula (i), Z is —NR$^{10}$—. In some embodiments, Z is —NR$^{10}$—, wherein R$^{10}$ is hydrogen or optionally substituted C$_1$-C$_6$ alkyl. In some embodiments, Z is —NR$^{10}$—, wherein R$^{10}$ is hydrogen. In some embodiments, Z is —NR$^{10}$—, wherein R$^{10}$ is methyl.

In one embodiment of the compounds of formula (i)-(iii), Z is a bond, —CH$_2$—, —C(CH$_3$)H—, —O—, —S—, —NH—, —NCH$_3$—, or —N(COCH$_3$)—. In one embodiment, Z is —CH$_2$—, —C(CH$_3$)H—, —O—, —S—, —NH—, —NCH$_3$—, or —N(COCH$_3$)—. In one embodiment, Z is —CH$_2$—, —O—, —NH—, —NCH$_3$—, or —N(COCH$_3$)—. In some embodiments, Z is a bond, —CH$_2$—, —O—, or —NCH$_3$—. In some embodiments, Z is a bond, —CH$_2$—, —O—, or —NH—. In some embodiments, Z is —O—.

In one embodiment of the compounds of formula (i), V is a bond, —(CR$^{11}$R$^{12}$)$_m$—, —C(=O)—, —N(R$^{10}$)CO—, —CONR$^{10}$—, or —NSO$_2$R$^{10}$—. In one embodiment, V is a bond. In other embodiments, V is optionally substituted —C(R$^{11}$R$^{12}$)$_m$—. In one embodiment, is optionally substituted —C(R$^{11}$R$^{12}$)$_m$—, wherein each R$^{11}$ and R$^{12}$ are hydrogen. In some embodiments, V is —(CR$^{11}$R$^{12}$)$_m$—.

In one embodiment of the compounds of formula (i), V is —(CR$^{11}$R$^{12}$)$_m$—, wherein m is 1, 2, or 3. In some embodiments, V is —(CR$^{11}$R$^{12}$)$_m$—, wherein R$^{11}$ and R$^{12}$ are each selected from H, halogen, —OH, or C$_1$-C$_6$ alkyl. In some embodiments, V is —(CR$^{11}$R$^{12}$)$_m$—, wherein m is 1, 2, or 3. In some embodiments, V is —(CR$^{11}$R$^{12}$)$_m$—, wherein R$^{11}$ and R$^{12}$ are each selected from H, halogen, —OH, or C$_1$-C$_3$ alkyl.

In one embodiment of the compounds of formula (i)-(iv), V is —CH$_2$—, —CH$_2$CH$_2$—, —CH$_2$CH$_2$CH$_2$—, —CH$_2$CH(CH$_3$)CH$_2$—, —CH$_2$CH(OH)CH$_2$—, or —CH$_2$C(OH)(CH$_3$)CH$_2$—.

In one embodiment of the compounds of formula (i), Z is a bond, —CH$_2$—, —C(CH$_3$)H—, —O—, —S—, —NH—, —NCH$_3$—, or —N(COCH$_3$)—; and V is —(CR$^{11}$R$^{12}$)$_m$—.

In one embodiment of the compounds of formula (i)-(iv), Z is a bond, —CH$_2$—, —C(CH$_3$)H—, —O—, —S—, —NH—, —NCH$_3$—, or —N(COCH$_3$)—; V is —CH$_2$—, —CH$_2$CH$_2$—, —CH$_2$CH$_2$CH$_2$—, —CH$_2$CH(CH$_3$)CH$_2$—, —CH$_2$CH(OH)CH$_2$—, or —CH$_2$C(OH)(CH$_3$)CH$_2$—; and W is halogen, —NH$_2$, or —CF$_3$.

In one embodiment of the compounds of formula (i)-(iv), Z is a bond, —CH$_2$—, —C(CH$_3$)H—, —O—, —S—, —NH—, —NCH$_3$—, or —N(COCH$_3$)—; V is —CH$_2$—, —CH$_2$CH$_2$—, —CH$_2$CH$_2$CH$_2$—, —CH$_2$CH(CH$_3$)CH$_2$—, —CH$_2$CH(OH)CH$_2$—, or —CH$_2$C(OH)(CH$_3$)CH$_2$—; and W is halogen, —NH$_2$, or —CF$_3$.

In one embodiment of the compounds of formula (i), m is 1 or 2. In some embodiments, m is 1.

In one embodiment of the compounds of formula (i), each R$^8$ and R$^9$ are independently hydrogen or optionally substituted C$_1$-C$_6$ alkyl.

In one embodiment of the compounds of formula (i), R$^{1a}$ and R$^{1b}$ are each hydrogen or optionally substituted C$_{1-6}$ alkyl. In other embodiments, R$^{1a}$ and R$^{1b}$ are each hydrogen.

In one embodiment of the compounds of formula (i), R$^{2a}$ and R$^{2b}$ are each hydrogen or optionally substituted C$_{1-6}$ alkyl. In other embodiments, R$^{2a}$ and R$^{2b}$ are each hydrogen.

In one embodiment of the compounds of formula (i)-(iv), R$^3$ is selected from hydrogen, optionally substituted C$_1$-C$_6$ alkyl, optionally substituted —OR$^{15}$, optionally substituted —SR$^{18}$, optionally substituted C$_1$-C$_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, optionally substituted —SOR$^{18}$, or optionally substituted —SO$_2$R$^{18}$. In one embodiment, R$^3$ is selected from hydrogen, —C$_1$-C$_3$ alkyl, —NR$^{16}$SO(C$_1$-C$_3$ alkyl), —NR$^{16}$SO$_2$(C$_1$-C$_3$ alkyl), —SONR$^{14}$R$^{15}$, —SO$_2$NR$^{14}$R$^{15}$, —SOR$^{18}$, or —SO$_2$R$^{18}$. In other embodiments, R$^3$ is selected from —NHSO$_2$(C$_1$-C$_3$ alkyl), —NCH$_3$SO$_2$(C$_1$-C$_3$ alkyl), or —SO$_2$(C$_1$-C$_3$ alkyl).

In one embodiment of the compounds of formula (i)-(iv), R$^3$ is —NR$^{16}$R$^{17}$, —NR$^{16}$COR$^{18}$, —NR$^{16}$S(O)$_p$R$^{18}$, —S(O)$_p$R$^{18}$, optionally substituted carbocyclyl, optionally substituted heterocyclyl, optionally substituted aryl, or optionally substituted heteroaryl. In other embodiments, R$^3$ is —NR$^{16}$R$^{17}$. In one embodiment, R$^3$ is —NR$^{16}$S(O)$_p$R$^{18}$ or —S(O)$_p$R$^{18}$.

In one embodiment of the compounds of formula (i)-(iv), R$^3$ is hydrogen, —CN, —CF$_3$, —OH, optionally substituted C$_1$-C$_6$ alkyl, optionally substituted C$_2$-C$_6$ alkenyl, optionally substituted C$_2$-C$_6$ alkynyl, optionally substituted —OR$^{15}$, optionally substituted C$_1$-C$_6$ alkoxy, —NH$_2$, —NR$^{16}$R$^{17}$, —NR$^{16}$COR$^{18}$, —NR$^{16}$S(O)$_p$R$^{18}$, —CONR$^{14}$R$^{11}$, —SONR$^{14}$R$^{15}$, —SO$_2$NR$^{14}$R$^{15}$, optionally substituted —S(O)$_p$R$^{18}$, —N$_3$, optionally substituted carbocyclyl, optionally substituted heterocyclyl, optionally substituted aryl, or optionally substituted heteroaryl. In some embodiments, R$^3$ is hydrogen, —CN, —CF$_3$, —OH, optionally substituted C$_1$-C$_3$ alkyl, optionally substituted C$_2$-C$_3$ alkenyl, optionally substituted C$_2$-C$_3$ alkynyl, optionally substituted —OR$^{15}$, optionally substituted C$_1$-C$_3$ alkoxy, —NH$_2$, —NR$^{16}$R$^{17}$, —NR$^{16}$COR$^{18}$, —NR$^{16}$S(O)$_p$R$^{18}$, —CONR$^{14}$R$^{15}$, —SONR$^{14}$R$^{15}$, —SO$_2$NR$^{14}$R$^{15}$, optionally substituted —S(O)$_p$R$^{18}$, —N$_3$, optionally substituted 3- to 7-membered carbocyclyl, optionally substituted 3- to 7-membered heterocyclyl, optionally substituted 6- to 12-membered aryl, or optionally substituted 5- to 12-membered heteroaryl. In other embodiments, R$^3$ is hydrogen, —CN, —CF$_3$, —OH, optionally substituted C$_1$-C$_3$ alkyl, optionally substituted C$_2$-C$_3$ alkenyl, optionally substituted C$_2$-C$_3$ alkynyl, optionally substituted —OR$^{15}$, optionally substituted C$_1$-C$_3$ alkoxy, —NH$_2$, —NR$^{16}$R$^{17}$, —NR$^{16}$COR$^{18}$, —NR$^{16}$S(O)$_p$R$^{18}$, —CONR$^{14}$R$^{15}$, —SONR$^{14}$R$^{15}$, —SO$_2$NR$^{14}$R$^{15}$, optionally substituted —S(O)$_p$R$^{18}$, or —N$_3$. In one embodiment, R$^3$ is optionally substituted 3- to 7-membered carbocyclyl, optionally substituted 3- to 7-membered heterocyclyl, optionally substituted 6-membered aryl, or optionally substituted 5- to 6-membered heteroaryl.

In one embodiment of the compounds of formula (i)-(iv), $R^3$ is selected from hydrogen, $C_1$-$C_6$ alkyl, $C_1$-$C_6$ alkoxy, —NHSO$_2$($C_1$-$C_6$ alkyl), —NCH$_3$SO$_2$($C_1$-$C_6$ alkyl), —SO$_2$($C_1$-$C_6$ alkyl), —NHCO($C_1$-$C_6$ alkyl), or —N($C_1$-$C_6$ alkyl)CO($C_1$-$C_6$ alkyl). In another embodiment, $R^3$ is hydrogen, $C_1$-$C_3$ alkyl, $C_1$-$C_3$ alkoxy, —NHSO$_2$($C_1$-$C_3$ alkyl), —NCH$_3$SO$_2$($C_1$-$C_3$ alkyl), —SO$_2$($C_1$-$C_3$ alkyl), —NHCO($C_1$-$C_3$ alkyl), or —N($C_1$-$C_3$ alkyl)CO($C_1$-$C_3$ alkyl). In other embodiments, $R^3$ is selected from —NHSO$_2$($C_1$-$C_3$ alkyl), —NCH$_3$SO$_2$($C_1$-$C_3$ alkyl), or —SO$_2$($C_1$-$C_3$ alkyl). In one embodiment, $R^3$ is selected from hydrogen, $C_1$-$C_3$ alkyl, $C_2$-$C_3$ alkenyl, $C_2$-$C_3$ alkynyl, $C_1$-$C_3$ alkoxy, —S($C_1$-$C_3$ alkyl), —SO($C_1$-$C_3$ alkyl), —SO$_2$($C_1$-$C_3$ alkyl), —NHSO$_2$CH$_3$, —N(CH$_3$)SO$_2$CH$_3$, —CH$_2$NHSO$_2$CH$_3$, —CH$_2$N(CH$_3$)SO$_2$CH$_3$, —SO$_2$NH$_2$, —CONH$_2$, —CON($C_1$-$C_3$ alkyl)$_2$, —CONH($C_1$-$C_3$ alkyl), —NHCO($C_1$-$C_3$ alkyl), or —N(CH$_3$)CO($C_1$-$C_3$ alkyl). In one embodiment, $R^3$ is selected from hydrogen, methyl, ethyl, propyl, isopropyl, methoxy, —SO$_2$CH$_3$, —NHSO$_2$CH$_3$, or —N(CH$_3$)SO$_2$CH$_3$. In one embodiment, $R^3$ is selected from —SO$_2$CH$_3$, —NHSO$_2$CH$_3$, or —N(CH$_3$)SO$_2$CH$_3$.

In one embodiment of the compounds of formula (i)-(iv), $R^3$ is $C_1$-$C_6$ alkyl.

In one embodiment of the compounds of formula (i)-(iv), $R^3$ is —NR$^{16}$R$^{17}$, wherein R$^{16}$ and R$^{17}$ are taken together to form an 3- to 7-membered optionally substituted heterocyclyl. In one embodiment, $R^3$ is —NR$^{16}$R$^{17}$, wherein R$^{16}$ and R$^{17}$ are taken together to form a 6-membered optionally substituted heterocycle. In one embodiment, $R^3$ is —NR$^{16}$R$^{17}$, wherein R$^{16}$ and R$^{17}$ are taken together to form a 6-membered optionally substituted heterocycle. In one embodiment, $R^3$ is —NR$^{16}$R$^{17}$, wherein R$^{16}$ and R$^{17}$ are taken together to form an optionally substituted piperizine. In one embodiment, $R^3$ is —NR$^{16}$R$^{17}$, wherein R$^{16}$ and R$^{17}$ are taken together to form a piperizine, optionally substituted with —SO$_2$CH$_3$, —NHSO$_2$CH$_3$, or —N(CH$_3$)SO$_2$CH$_3$. In one embodiment, $R^3$ is

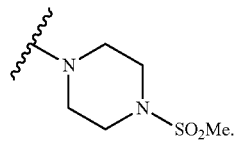

In one embodiment of the compounds of formula (i)-(iv), R$^{16}$ and R$^{17}$ are taken together with the intervening atom to form an optionally substituted heterocyclyl, or optionally substituted heteroaryl. In some embodiments, R$^{16}$ and R$^{17}$ are taken together to form an optionally substituted heterocyclyl. In some embodiments, R$^{16}$ and R$^{17}$ are taken together to form an 3- to 7-membered optionally substituted heterocyclyl. In some embodiments, R$^{16}$ and R$^{17}$ are taken together to form an 3- to 7-membered optionally substituted heterocyclyl, comprising one or more heteroatoms selected from N, O, or S.

In one embodiment of the compounds of formula (i)-(iv), R$^{16}$ is hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl. In one embodiment, R$^{16}$ is hydrogen or optionally substituted $C_1$-$C_6$ alkyl. In some embodiments, R$^{16}$ is hydrogen or $C_1$-$C_6$ alkyl. In some embodiments, R$^{16}$ is hydrogen or $C_1$-$C_3$ alkyl.

In one embodiment of the compounds of formula (i)-(iv), R$^{17}$ is hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl. In one embodiment, R$^{17}$ is hydrogen or optionally substituted $C_1$-$C_6$ alkyl. In some embodiments, R$^{17}$ is hydrogen or $C_1$-$C_6$ alkyl. In some embodiments, R$^{17}$ is hydrogen or $C_1$-$C_3$ alkyl.

In one embodiment of the compounds of formula (i)-(iv), R$^{18}$ is hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl. In one embodiment, R$^{18}$ is hydrogen or optionally substituted $C_1$-$C_6$ alkyl. In some embodiments, R$^{18}$ is hydrogen or $C_1$-$C_6$ alkyl. In some embodiments, R$^{18}$ is hydrogen or $C_1$-$C_3$ alkyl.

In one embodiment of the compounds of formula (i), R$^{18}$ is $C_1$-$C_6$ alkyl; and p is 2.

In one embodiment of the compounds of formula (i), R$^{2a}$, R$^{2b}$ and R$^3$ taken together with the intervening atom are optionally substituted carbocyclyl, optionally substituted heterocyclyl, optionally substituted aryl, or optionally substituted heteroaryl. In other embodiments, R$^{2a}$, R$^{2b}$ and R$^3$ taken together with the intervening atom are optionally substituted heteroaryl. In some embodiments, R$^{2a}$, R$^{2b}$ and R$^3$ taken together with the intervening atom are optionally substituted tetrazolyl, imidazolyl, 1,2,3-triazolyl, oxazole, pyrazinyl, pyrimidinyl, or 1,3,5-triazinyl.

In one embodiment of the compounds of formula (i), R$^{4a}$ is hydrogen, halogen, optionally substituted $C_{1-6}$ alkyl, or optionally substituted $C_{1-6}$ alkoxy. In some embodiments, R$^{4a}$ is optionally substituted $C_{1-6}$ alkyl or hydrogen. In other embodiments, R$^{4a}$ is hydroxy.

In one embodiment of the compounds of formula (i), R$^{4b}$ is hydrogen, halogen, optionally substituted $C_{1-6}$ alkyl, or optionally substituted $C_{1-6}$ alkoxy. In some embodiments, R$^{4b}$ is hydrogen.

In one embodiment of the compounds of formula (i), R$^{5a}$ is hydrogen, halogen, optionally substituted $C_{1-6}$ alkyl, or optionally substituted $C_{1-6}$ alkoxy. In one embodiment, R$^{5a}$ is hydrogen.

In one embodiment of the compounds of formula (i), R$^{5b}$ is hydrogen, halogen, optionally substituted $C_{1-6}$ alkyl, or optionally substituted $C_{1-6}$ alkoxy. In one embodiment, R$^{5b}$ is hydrogen.

In one embodiment of the compounds of formula (i), n is 1. In other embodiments, n is 2.

In one embodiment of the compounds of formula (i), R$^6$ and R$^7$ are each independently halogen, —CN, —CF$_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —NR$^{13}$R$^{14}$, optionally substituted —($C_1$-$C_6$ alkyl)-NR$^{13}$R$^{14}$, —NR$^{14}$SO$_2$R$^{16}$, optionally substituted —($C_1$-$C_6$ alkyl)NR$^{14}$SO$_2$R$^{16}$, —NR$^{14}$COR$^{16}$, optionally substituted —($C_1$-$C_6$ alkyl)-NR$^{14}$COR$^{16}$, —CONR$^{14}$R$^{15}$, optionally substituted —($C_1$-$C_6$ alkyl)-CONR$^{14}$R$^{15}$, —SO$_2$NR$^{14}$R$^{15}$, optionally substituted —($C_1$-$C_6$ alkyl)-SO$_2$NR$^{14}$R$^{15}$, optionally substituted —SO$_2$R$^{16}$, or optionally substituted —($C_1$-$C_6$ alkyl)-SO$_2$R$^{16}$. In one embodiment, R$^6$ and R$^7$ are each independently halogen, —CN, —CF$_3$, —OH, optionally substituted $C_1$-$C_3$ alkyl, $C_1$-$C_3$ alkoxy, optionally substituted-($C_1$-$C_3$ alkyl)-($C_1$-$C_3$ alkoxy), optionally substituted- (C$_1$-C$_3$ alkyl)-OH, —NR$^{13}$R$^{14}$, —(C$_1$-C$_3$ alkyl)-NR$^{13}$R$^{14}$, —NR$^{14}$SO$_2$R$^{16}$, optionally substituted —(C$_1$-C$_3$ alkyl)NR$^{14}$SO$_2$R$^{16}$, —NR$^{14}$COR$^{16}$, optionally substituted —(C$_1$-C$_3$ alkyl)-NR$^{14}$COR$^{16}$, —CONR$^{14}$R$^{15}$, optionally substituted —(C$_1$-C$_3$ alkyl)-CONR$^{14}$R$^{15}$, —SO$_2$NR$^{14}$R$^{15}$, optionally substituted —(C$_1$-C$_3$ alkyl)-SO$_2$NR$^{14}$R$^{15}$, —SO$_2$R$^{16}$, or optionally substituted —(C$_1$-C$_3$ alkyl)-SO$_2$R$^{16}$. In one embodiment, R$^6$ and R$^7$ are each independently halogen, —CN, —CF$_3$, —OH, C$_1$-C$_3$ alkyl, C$_1$-C$_3$ alkoxy, —(C$_1$-C$_3$ alkyl)-(C$_1$-C$_3$ alkoxy), —(C$_1$-C$_3$ alkyl)-OH, —NR$^{13}$R$^{14}$, —(C$_1$-C$_3$ alkyl)-NR$^{13}$R$^{14}$, —NR$^{14}$SO$_2$R$^{16}$, —(C$_1$-C$_3$ alkyl)NR$^{14}$SO$_2$R$^{16}$, —NR$^{14}$COR$^{16}$, —(C$_1$-C$_3$ alkyl)-NR$^{14}$COR$^{16}$, —CONR$^{14}$R$^{15}$, —(C$_1$-C$_3$ alkyl)-CONR$^{14}$R$^{15}$, —SO$_2$NR$^{14}$R$^{15}$, —(C$_1$-C$_3$ alkyl)-SO$_2$NR$^{14}$R$^{15}$, —SO$_2$R$^{16}$, or —(C$_1$-C$_3$ alkyl)-SO$_2$R$^{16}$. In one embodiment, R$^6$ and R$^7$ are each independently halogen, —CN, —CF$_3$, —OH, C$_1$-C$_3$ alkyl, or —CONR$^{14}$R$^1$. In some embodiments, R$^6$ and R$^7$ are each independently halogen, —CN, —CF$_3$, —OH, methyl, methoxy, or —CONH$_2$. In one embodiment, R$^6$ and R$^7$ are each independently Cl, —CN, —CF$_3$, —OH, methyl, methoxy, or —CONH$_2$.

In one embodiment of the compounds of formula (i), R$^6$ and R$^7$ are each independently optionally substituted carbocyclyl, optionally substituted heterocyclyl, optionally substituted aryl, or optionally substituted heteroaryl. In one embodiment, R$^6$ and R$^7$ are each independently 3- to 7-membered carbocyclyl, 3- to 7-membered heterocyclyl, phenyl, or 5- to 6-membered heteroaryl.

In one embodiment of the compounds of formula (i)-(iv), R$^6$ and R$^7$ is each independently halogen, —CN, —CF$_3$, —OH, methyl, or methoxy. In one embodiment, R$^6$ and R$^7$ are each independently halogen, —CN, —CF$_3$, —OH, or methyl. In one embodiment, R$^6$ and R$^7$ are each independently H, halogen, —CN, or methyl. In another embodiment, R$^6$ and R$^7$ is each independently Cl, —CN, —CF$_3$, —OH, methyl, or methoxy. In one embodiment, R$^6$ and R$^7$ is independently H, methyl, methoxy, CN, F, Cl, Br, or I. In one embodiment of the compounds of formula (i)-(iv), R$^6$ and R$^7$ is independently H, methyl, methoxy, CN, F, Cl, Br, I, $^{123}$I or CF$_3$. In other embodiments, R$^6$ and R$^7$ is F, Cl, Br, or I. In one embodiment, each occurrence of R$^6$ and R$^7$ is Cl.

In one embodiment of the compounds of formula (i)-(iv), R$^6$ have one of the connectivity as shown below with respect to X and Y:

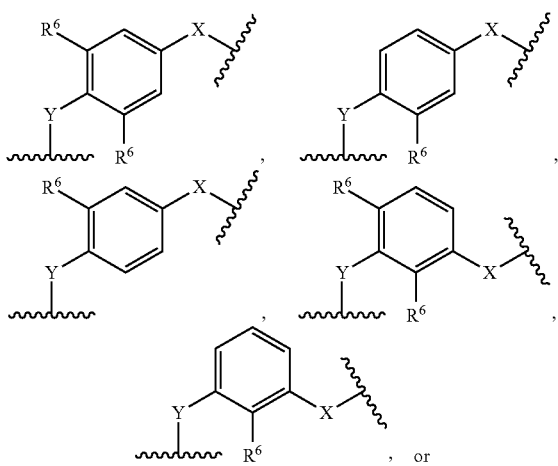

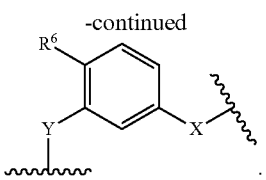

In one embodiment of the compounds of formula (i)-(iv), R$^7$ have one of the connectivity as shown below with respect to X and Z:

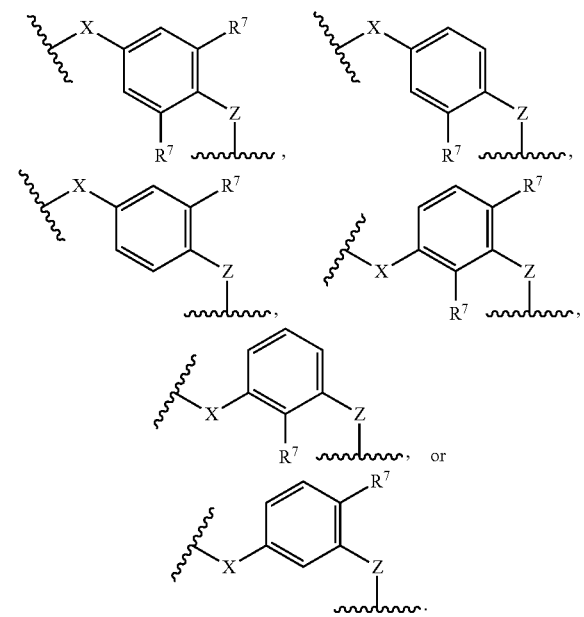

In one embodiment of the compounds of formula (i)-(iv), n in —(R$^6$)$_n$ is 0, 1, or 2. In some embodiments, n is 0 or 1. In other embodiments, n is 0. In some embodiments, n is 1.

In one embodiment of the compounds of formula (i)-(iv), n in —(R$^7$)$_n$ is 0, 1, or 2. In some embodiments, n is 0 or 1. In other embodiments, n is 0. In some embodiments, n is 1.

In one embodiment of the compounds of formula (i)-(iv), the sum of n in —(R$^6$)$_n$ and —(R$^7$)$_n$ is 0, 1, 2, 3, or 4. In some embodiments, the sum of n in —(R$^6$)$_n$ and —(R$^7$)$_n$ isv1, 2, 3, or 4. In some embodiments, the sum of n in —(R$^6$)$_n$ and —(R$^7$)$_n$ is 2 or 4. In some embodiments, the sum of n in —(R$^6$)$_n$ and —(R$^7$)$_n$ is 2.

In one embodiment of the compounds of formula (i), A and B are each independently 5- or 6-membered aryl or heteroaryl. In other embodiments, A and B are each independently selected from phenyl, pyridyl, pyrimidyl, or thiophene. In one embodiment, A and B are each phenyl.

In one embodiment of the compounds of formula (i), A has a meta or para connectivity with X and Y. In one embodiment of the compounds of formula (i), B has a meta or para connectivity with X and Z.

In one embodiment of the compounds of formula (i)-(iv), D is —CH$_2$—, —CH(CH$_3$)—, —C(CH$_3$)$_2$—, or —CH$_2$CH$_2$—. In one embodiment, D is —(CH$_2$)$_2$—.

In one embodiment of the compounds of formula (i), D is —(CR$^{1a}$R$^{1b}$)$_q$—; E is —O—, —NR$^{10}$—, or —NR$^{10}$—(CR$^{2a}$R$^{2b}$)$_g$—; and q is 1 or 2.

In one embodiment of the compounds of formula (i), D is —O— or —NR$^{10}$—; E is —(CR$^{2a}$R$^{2b}$)$_g$—; and g is 1, 2, 3, or 4.

In one embodiment of the compounds of formula (i), D is —O— or —NR$^{10}$—; and E is —O—, —NR$^{10}$— or —NR$^{10}$—(CR$^{2a}$R$^{2b}$)$_g$—.

In one embodiment of the compounds of formula (i), R$^{8b}$ and R$^{9b}$ are each independently hydrogen, halogen, optionally substituted C$_1$-C$_6$ alkyl, optionally substituted C$_2$-C$_6$ alkenyl, optionally substituted C$_2$-C$_6$ alkynyl, optionally substituted C$_1$-C$_6$ alkoxy, —NR$^{13}$R$^{14}$, optionally substituted —(C$_1$-C$_6$ alkyl)-NR$^{13}$R$^{14}$, —NR$^{14}$COR$^{16}$, optionally substituted —(C$_1$-C$_6$ alkyl)-NR$^{14}$COR$^{16}$, —CONR$^{14}$R$^{15}$, optionally substituted —(C$_1$-C$_6$ alkyl)-CONR$^{14}$R$^{15}$, optionally substituted carbocyclyl, optionally substituted heterocyclyl, optionally substituted aryl, or optionally substituted heteroaryl. In one embodiment, R$^{11}$ and R$^{12}$ are not —OH.

In one embodiment of the compounds of formula (i), R$^{11}$ and R$^{12}$ are each independently hydrogen, halogen, —OH, or C$_1$-C$_3$ alkyl.

In one embodiment of the compounds of formula (i), g is independently 0, 1, 2, or 3.

In one embodiment of the compounds of formula (i), R$^{1a}$, R$^{1b}$, R$^{2a}$, and R$^{2b}$ are each independently hydrogen, halogen, —OH, C$_1$-C$_3$ alkyl, C$_2$-C$_3$ alkenyl, C$_2$-C$_3$ alkynyl, C$_1$-C$_3$ alkoxy, —OCO(C$_1$-C$_3$ alkyl), —NR$^{13}$R$^{14}$, —(C$_1$-C$_3$ alkyl)-NR$^{13}$R$^{14}$, —NR$^{14}$COR$^{16}$, —(C$_1$-C$_3$ alkyl)-NR$^{14}$COR$^{16}$, —CONR$^{14}$R$^{15}$, or —(C$_1$-C$_6$ alkyl)-CONR$^{14}$R$^{15}$; or (R$^{1a}$ and R$^{1b}$) or (R$^{2a}$ and R$^{2b}$) taken together form an oxo (=O), an optionally substituted carbocyclyl, or an optionally substituted heterocyclyl.

In one embodiment of the compounds of formula (i)-(iii), q is 0.

In one embodiment of the compounds of formula (i)-(iii), E is —CH$_2$—, —CH(CH$_3$)—, —C(CH$_3$)$_2$—, —CH$_2$CH$_2$—, or —CH$_2$CH$_2$CH$_2$—.

In one embodiment of the compounds of formula (i)-(iii), g is 0.

In one embodiment of the compounds of formula (i)-(iii), at least one of Z and Y is —O—.

In one embodiment of the compounds of formula (i) or (iv), Y is —O—, D is —(CR$^{1a}$R$^{1b}$)$_q$—, L is —(CR$^{2a}$R$^{2b}$)—R$^3$, and R$^3$ is —NR$^{16}$S(O)$_p$R$^{18}$. In one embodiment, Y is —O—, D is —(CR$^{1a}$R$^{1b}$)-L is —(CR$^{2a}$R$^{2b}$)—R$^3$, and R$^3$ is —NR$^{16}$S(O)$_2$(C$_1$-C$_3$ alkyl). In one embodiment, Y is —O—, D is —CH$_2$—, —CH(CH$_3$)—, or —C(CH$_3$)$_2$—, L is —CH$_2$—R$^3$, and R$^3$ is —NHS(O)$_2$CH$_3$.

In one embodiment of the compounds of formula (i)-(iii), when E is —O—, R$^3$ is hydrogen, —CF$_3$, optionally substituted C$_1$-C$_6$ alkyl, optionally substituted C$_2$-C$_6$ alkenyl, optionally substituted C$_2$-C$_6$ alkynyl, optionally substituted carbocyclyl, optionally substituted heterocyclyl, optionally substituted aryl, or optionally substituted heteroaryl. In other embodiments, when E is —O—, R$^3$ is hydrogen, —CF$_3$, C$_1$-C$_3$ alkyl, C$_2$-C$_3$ alkenyl, C$_2$-C$_3$ alkynyl, carbocyclyl, heterocyclyl, aryl, or heteroaryl.

In one embodiment of the compounds of formula (i)-(iv), at least one of Z and Y is —O—.

In one embodiment of the compounds of formula (i)-(iv), -D-C(O)-E-R$^3$ is

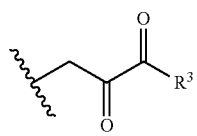

or its tautomeric form

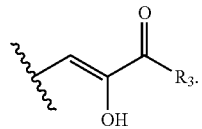

In one embodiment of the compounds of formula (i)-(iv), —Y-D-C(O)-E-R$^3$ is

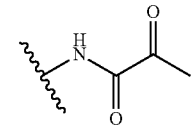 [SMILES: *NC(=O)C(C)=O]

or its tautomeric form

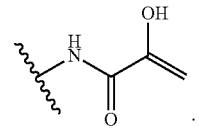

In one embodiment of the compounds of formula (i), -D-C(O)-E-R$^3$ is

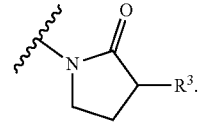

In one embodiment of the compounds of formula (i)-(iv), R$^{1a}$, and R$^{1b}$ are each independently hydrogen, halogen, —OH, C$_1$-C$_3$ alkyl, C$_2$-C$_3$ alkenyl, C$_2$-C$_3$ alkynyl, C$_1$-C$_3$ alkoxy, —OCO(C$_1$-C$_3$ alkyl), —NR$^{13}$R$^{14}$, —(C$_1$-C$_3$ alkyl)-NR$^{13}$R$^{14}$, —NR$^{14}$COR$^{16}$, —(C$_1$-C$_3$ alkyl)-NR$^{14}$COR$^{16}$, —CONR$^{14}$R$^{15}$, —(C$_1$-C$_6$ alkyl)-CONR$^{14}$R$^{15}$; or R$^{1a}$ and R$^{1b}$ taken together form an oxo (=O), an optionally substituted carbocyclyl, or an optionally substituted heterocyclyl. In some embodiments, R$^{1a}$, and R$^{1b}$ are each independently hydrogen, halogen, —OH, C$_1$-C$_3$ alkyl, C$_2$-C$_3$ alkenyl, C$_2$-C$_3$ alkynyl, C$_1$-C$_3$ alkoxy, —OCO(C$_1$-C$_3$ alkyl), —NR$^{13}$R$^{14}$, —(C$_1$-C$_3$ alkyl)-NR$^{13}$R$^{14}$, —NR$^{14}$COR$^{16}$, —(C$_1$-C$_3$ alkyl)-NR$^{14}$COR$^{16}$, —CONR$^{14}$R$^{15}$, or —(C$_1$-C$_6$ alkyl)-CONR$^{14}$R$^{15}$. In one embodiment, R$^{1a}$ and R$^{1b}$ are each hydrogen or R$^{1a}$ and R$^{1b}$ taken together form an oxo (=O).

In one embodiment of the compounds of formula (i)-(iv), R$^{2a}$ and R$^{2b}$ are each independently hydrogen, halogen, —OH, C$_1$-C$_3$ alkyl, C$_2$-C$_3$ alkenyl, C$_2$-C$_3$ alkynyl, C$_1$-C$_3$ alkoxy, —OCO(C$_1$-C$_3$ alkyl), —NR$^{13}$R$^{14}$, —(C$_1$-C$_3$ alkyl)-NR$^{13}$R$^{14}$, —NR$^{14}$COR$^{16}$, —(C$_1$-C$_3$ alkyl)-NR$^{14}$COR$^{16}$, —CONR$^{14}$R$^{15}$, or —(C$_1$-C$_6$ alkyl)-CONR$^{14}$R$^{15}$; or R$^{2a}$ and R$^{2b}$ taken together form an oxo (=O), an optionally substituted carbocyclyl, or an optionally substituted heterocyclyl. In some embodiments, R$^{2a}$ and R$^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —NR$^{13}$R$^{14}$, —($C_1$-$C_3$ alkyl)-NR$^{13}$R$^{14}$, —NR$^{14}$COR$^{16}$, —($C_1$-$C_3$ alkyl)-NR$^{14}$COR$^{16}$, —CONR$^{14}$R$^{15}$, or —($C_1$-$C_6$ alkyl)-CONR$^{14}$R$^{15}$. In one embodiment, R$^{2a}$ and R$^{2b}$ are each hydrogen or R$^{2a}$ and R$^{2b}$ taken together form an oxo (=O).

In one embodiment of the compounds of formula (ii)-(iii) R$^{8a}$ and R$^{9a}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, —NR$^{13}$R$^{14}$, optionally substituted —($C_1$-$C_6$ alkyl)-NR$^{13}$R$^{14}$, —NR$^{14}$COR$^{16}$, optionally substituted —($C_1$-$C_6$ alkyl)-NR$^{14}$COR$^{16}$, —CONR$^{14}$R$^{15}$, optionally substituted —($C_1$-$C_6$ alkyl)-CONR$^{14}$R$^{15}$, optionally substituted carbocyclyl, optionally substituted heterocyclyl, optionally substituted aryl, or optionally substituted heteroaryl. In one embodiment, R$^{8a}$ and R$^{9a}$ are each independently hydrogen, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, —NR$^{13}$R$^{14}$, optionally substituted —($C_1$-$C_6$ alkyl)-NR$^{13}$R$^{14}$, —NR$^{14}$COR$^{16}$, optionally substituted —($C_1$-$C_6$ alkyl)-NR$^{14}$COR$^{16}$, —CONR$^{14}$R$^{15}$, or optionally substituted —($C_1$-$C_6$ alkyl)-CONR$^{14}$R$^{15}$. In one embodiment, R$^{8a}$ and R$^{9a}$ hydrogen, halogen, —OH, or $C_1$-$C_3$ alkyl. In one embodiment, R$^{8a}$ and R$^{9a}$ hydrogen, halogen, —OH, or methyl. In one embodiment, R$^{8a}$ and R$^{9a}$ hydrogen, F, —OH, or methyl.

In one embodiment of the compounds of formula (i)-(iv), R$^{10}$ is hydrogen, halogen, optionally substituted $C_1$-$C_6$ alkyl, or optionally substituted $C_1$-$C_6$ alkoxy. In some embodiments, R$^{10}$ is hydrogen, $C_1$-$C_6$ alkyl, or $C_1$-$C_6$ alkoxy. In some embodiments, R$^{10}$ is hydrogen, $C_1$-$C_3$ alkyl, or $C_1$-$C_3$ alkoxy.

In one embodiment of the compounds of formula (i), R$^{2a}$ and R$^{10}$ taken together form an optionally substituted heterocyclyl. In one embodiment, R$^{2a}$ and R$^{10}$ taken together form an optionally substituted 5- or 6-membered heterocyclyl.

In one embodiment of the compounds of formula (i)-(iv), R$^{13}$ is hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl. In one embodiment, R$^{13}$ is hydrogen or optionally substituted $C_1$-$C_6$ alkyl. In some embodiments, R$^{13}$ is hydrogen or $C_1$-$C_6$ alkyl. In some embodiments, R$^{13}$ is hydrogen or $C_1$-$C_3$ alkyl.

In one embodiment of the compounds of formula (i)-(iv), R$^{14}$ is hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl. In one embodiment, R$^{14}$ is hydrogen or optionally substituted $C_1$-$C_6$ alkyl. In some embodiments, R$^{14}$ is hydrogen or $C_1$-$C_6$ alkyl. In some embodiments, R$^{14}$ is hydrogen or $C_1$-$C_3$ alkyl.

In one embodiment of the compounds of formula (i)-(iv), R$^{15}$ is hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl. In one embodiment, R$^{15}$ is hydrogen or optionally substituted $C_1$-$C_6$ alkyl. In some embodiments, R$^{15}$ is hydrogen or $C_1$-$C_6$ alkyl. In some embodiments, R$^{15}$ is hydrogen or $C_1$-$C_3$ alkyl.

In one embodiment of the compounds of formula (i)-(iv), R$^{14}$ and R$^{15}$ are taken together to form an optionally substituted heterocyclyl, or optionally substituted heteroaryl. In some embodiments, R$^{14}$ and R$^{15}$ are taken together to form an optionally substituted heterocyclyl. In some embodiments, R$^{14}$ and R$^{15}$ are taken together to form an 3- to 7-membered optionally substituted heterocyclyl. In some embodiments, R$^{14}$ and R$^{15}$ are taken together to form an 3- to 7-membered optionally substituted heterocyclyl, comprising one or more heteroatoms selected from N, O, or S.

In one embodiment of the compounds of formula (i)-(iv), R$^{11}$ and R$^{12}$ are each independently hydrogen, halogen, —OH, or $C_1$-$C_3$ alkyl. In one embodiment, R$^{11}$ and R$^{12}$ are each independently hydrogen, halogen, or $C_1$-$C_3$ alkyl. In one embodiment, R$^{11}$ and R$^{12}$ are not —OH.

In one embodiment of the compounds of formula (i)-(iv), g is independently 0, 1, 2, or 3. In one embodiment, g is 0. In another embodiment, g is 1, 2, or 3. In some embodiments, g is 1 or 2.

In one embodiment of the compounds of formula (i), n is S(O)$_n$ is 2. In another embodiment, n is 1 or 2. In some embodiments, n is 0.

In one embodiment of the compounds of formula (i)-(iv), p is 2. In another embodiment, p is 1 or 2. In some embodiments, p is 0.

In one embodiment of the compounds of formula (i)-(iv), q is 0. In another embodiment, q is 1. In one embodiment, q is 2.

In one embodiment of the compounds of formula (i)-(iv), t is 1. In one embodiment, t is 2.

In one embodiment of the compounds of formula (iii), gg is 1, 2, or 3. In some embodiments, gg is 1 or 2.

In one embodiment of the compounds of formula (i), Z and V are not both a bond or absent (e.g., m is 0 in —(CR$^{11}$R$^{12}$)$_m$—).

In one embodiment, the present disclosure provides compounds as disclosed in Table A or a pharmaceutically acceptable salt, tautomer, stereoisomer or prodrug thereof. In one embodiment, the present disclosure provides androgen receptor N-terminal domain inhibitors selected from Compounds AA1-AA98, or a pharmaceutically acceptable salt, tautomer, stereoisomer or prodrug thereof. In one embodiment, the present disclosure provides androgen receptor N-terminal domain inhibitors selected from Compounds AA99-AA104, or a pharmaceutically acceptable salt, tautomer, stereoisomer or prodrug thereof. In one embodiment, the present disclosure provides androgen receptor N-terminal domain inhibitors selected from Compounds AA1-AA104, or a pharmaceutically acceptable salt, tautomer, stereoisomer or prodrug thereof.

The compounds disclosed in WO 2019/226991 can be useful androgen receptor N-terminal domain inhibitors for the present invention. The disclosure of WO 2019/226991 is incorporated by reference in its entirety for all purposes.

TABLE A

Androgen Receptor Modulators

| Compound ID | Structure |
|---|---|
| AA1 | 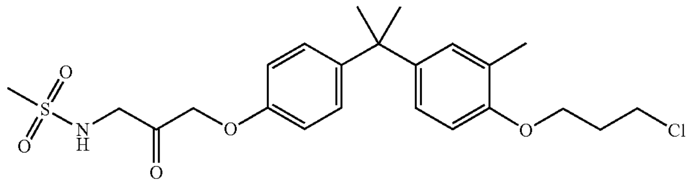 [SMILES: Cc1cc(C(C)(C)c2ccc(OCC(=O)CNS(C)(=O)=O)cc2)ccc1OCCCCl] |
| AA2 | 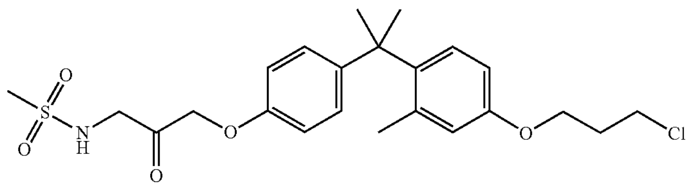 [SMILES: Cc1cc(OCCCCl)ccc1C(C)(C)c1ccc(OCC(=O)CNS(C)(=O)=O)cc1] |
| AA3 | 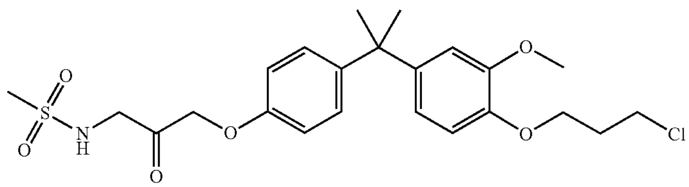 [SMILES: COc1cc(C(C)(C)c2ccc(OCC(=O)CNS(C)(=O)=O)cc2)ccc1OCCCCl] |
| AA4 | 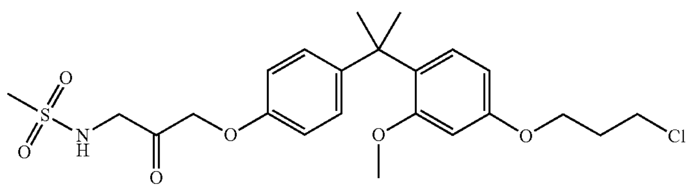 [SMILES: COc1cc(OCCCCl)ccc1C(C)(C)c1ccc(OCC(=O)CNS(C)(=O)=O)cc1] |
| AA5 | 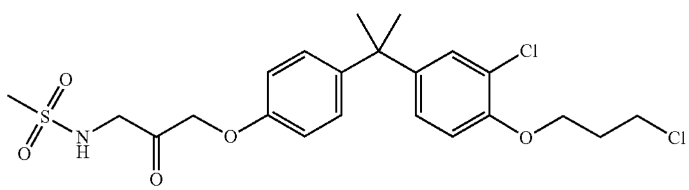 [SMILES: CC(C)(c1ccc(OCC(=O)CNS(C)(=O)=O)cc1)c1ccc(OCCCCl)c(Cl)c1] |
| AA6 | 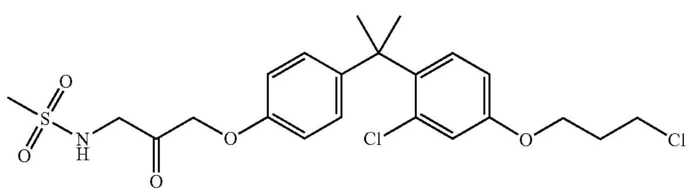 [SMILES: CC(C)(c1ccc(OCC(=O)CNS(C)(=O)=O)cc1)c1ccc(OCCCCl)cc1Cl] |
| AA7 | 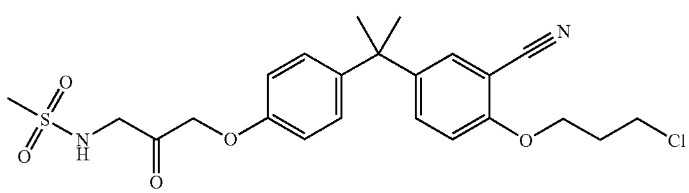 [SMILES: CC(C)(c1ccc(OCC(=O)CNS(C)(=O)=O)cc1)c1ccc(OCCCCl)c(C#N)c1] |
| AA8 | 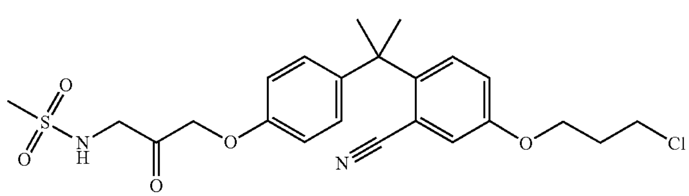 [SMILES: CC(C)(c1ccc(OCC(=O)CNS(C)(=O)=O)cc1)c1ccc(OCCCCl)cc1C#N] |

TABLE A-continued

Androgen Receptor Modulators

| Compound ID | Structure |
| --- | --- |
| AA9 | 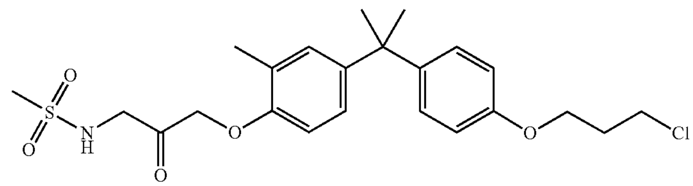 [SMILES: Cc1cc(C(C)(C)c2ccc(OCCCCl)cc2)ccc1OCC(=O)CNS(C)(=O)=O] |
| AA10 | 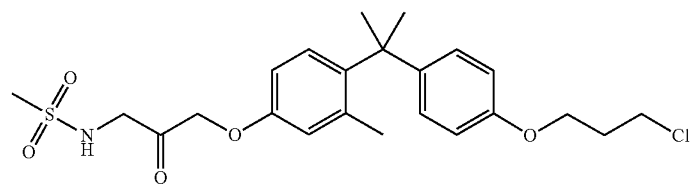 [SMILES: Cc1cc(OCC(=O)CNS(C)(=O)=O)ccc1C(C)(C)c1ccc(OCCCCl)cc1] |
| AA11 | 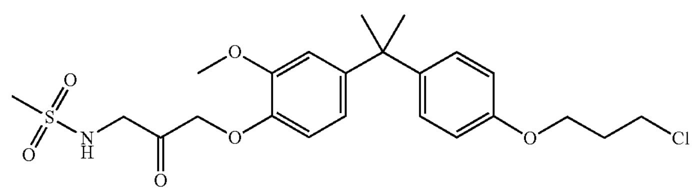 [SMILES: COc1cc(C(C)(C)c2ccc(OCCCCl)cc2)ccc1OCC(=O)CNS(C)(=O)=O] |
| AA12 | 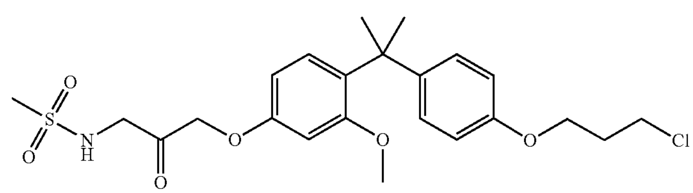 [SMILES: COc1cc(OCC(=O)CNS(C)(=O)=O)ccc1C(C)(C)c1ccc(OCCCCl)cc1] |
| AA13 | 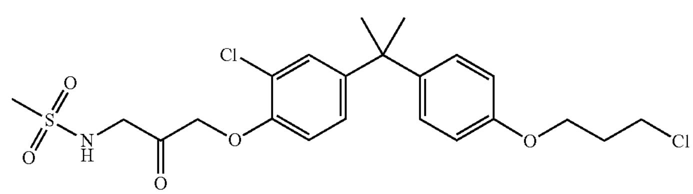 [SMILES: CC(C)(c1ccc(OCCCCl)cc1)c1ccc(OCC(=O)CNS(C)(=O)=O)c(Cl)c1] |
| AA14 | 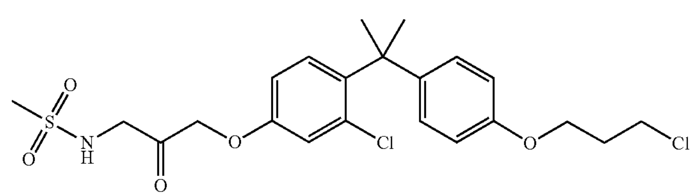 [SMILES: CC(C)(c1ccc(OCCCCl)cc1)c1ccc(OCC(=O)CNS(C)(=O)=O)cc1Cl] |
| AA15 | 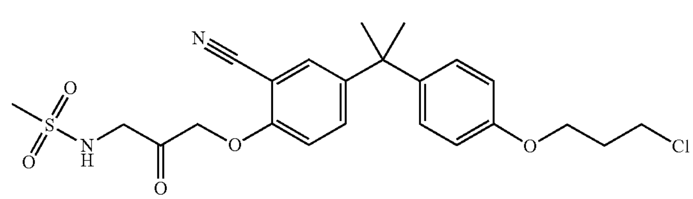 [SMILES: CC(C)(c1ccc(OCCCCl)cc1)c1ccc(OCC(=O)CNS(C)(=O)=O)c(C#N)c1] |

TABLE A-continued

Androgen Receptor Modulators

| Compound ID | Structure |
|---|---|
| AA16 | 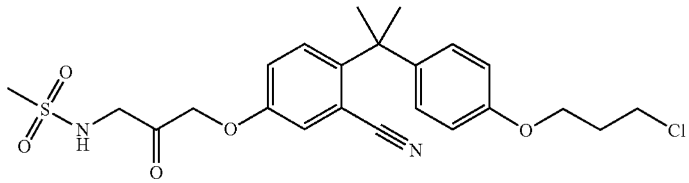 [SMILES: CC(C)(c1ccc(OCCCCl)cc1)c1ccc(OCC(=O)CNS(C)(=O)=O)cc1C#N] |
| AA17 | 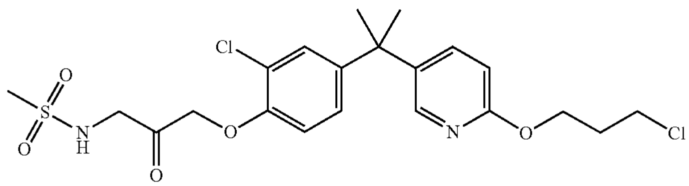 [SMILES: CC(C)(c1ccc(OCCCCl)nc1)c1ccc(OCC(=O)CNS(C)(=O)=O)c(Cl)c1] |
| AA18 | 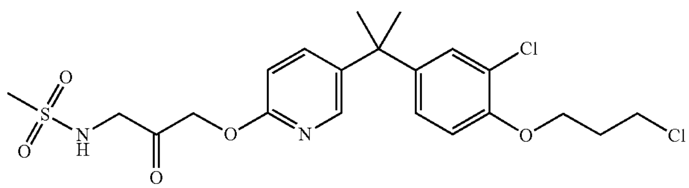 [SMILES: CC(C)(c1ccc(OCC(=O)CNS(C)(=O)=O)nc1)c1ccc(OCCCCl)c(Cl)c1] |
| AA19 | 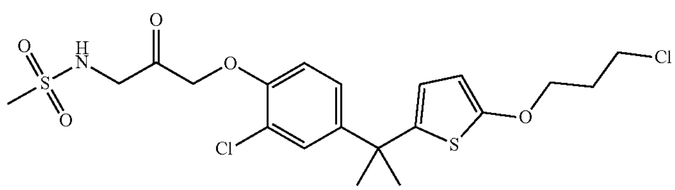 [SMILES: CC(C)(c1ccc(OCC(=O)CNS(C)(=O)=O)c(Cl)c1)c1ccc(OCCCCl)s1] |
| AA20 | 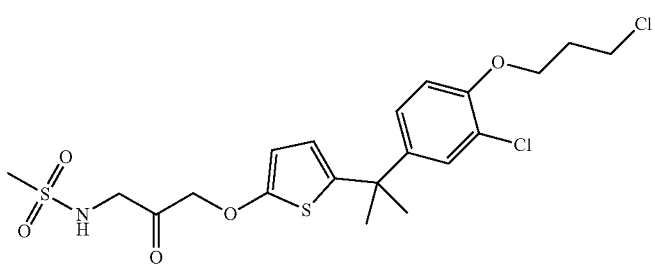 [SMILES: CC(C)(c1ccc(OCCCCl)c(Cl)c1)c1ccc(OCC(=O)CNS(C)(=O)=O)s1] |
| AA21 | 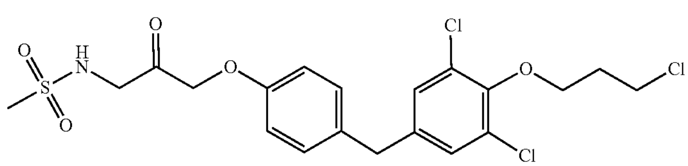 [SMILES: CS(=O)(=O)NCC(=O)COc1ccc(Cc2cc(Cl)c(OCCCCl)c(Cl)c2)cc1] |
| AA22 | 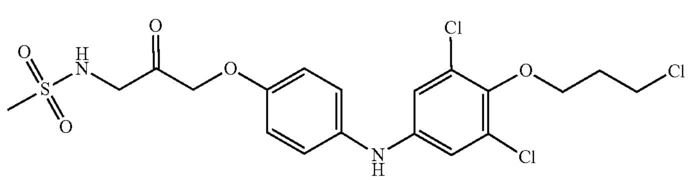 [SMILES: CS(=O)(=O)NCC(=O)COc1ccc(Nc2cc(Cl)c(OCCCCl)c(Cl)c2)cc1] |

TABLE A-continued
Androgen Receptor Modulators
| Compound ID | Structure |
|---|---|
| AA23 | 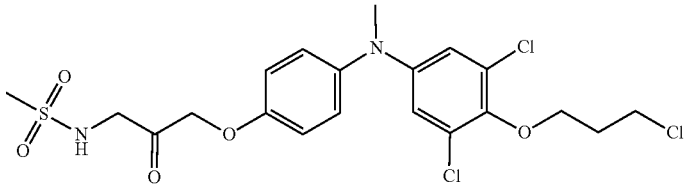 [SMILES: CN(c1ccc(OCC(=O)CNS(C)(=O)=O)cc1)c1cc(Cl)c(OCCCCl)c(Cl)c1] |
| AA24 | 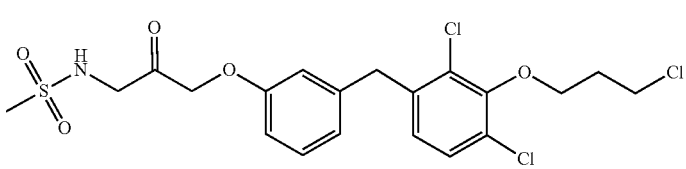 [SMILES: CS(=O)(=O)NCC(=O)COc1cccc(Cc2ccc(Cl)c(OCCCCl)c2Cl)c1] |
| AA25 | 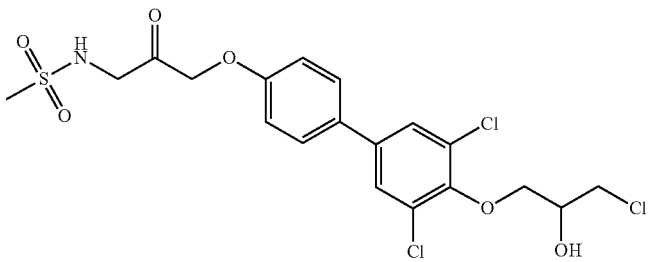 [SMILES: CS(=O)(=O)NCC(=O)COc1ccc(-c2cc(Cl)c(OCC(O)CCl)c(Cl)c2)cc1] |
| AA26 | 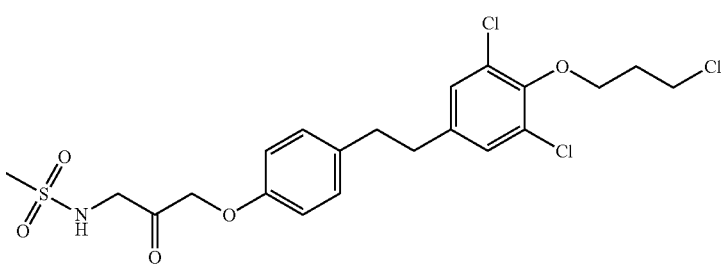 [SMILES: CS(=O)(=O)NCC(=O)COc1ccc(CCc2cc(Cl)c(OCCCCl)c(Cl)c2)cc1] |
| AA27 | 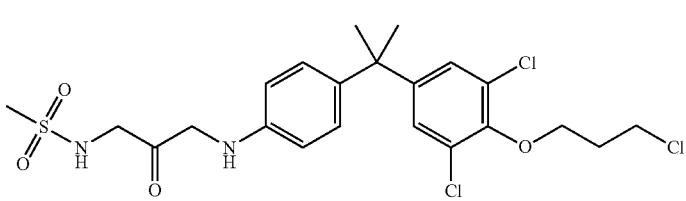 [SMILES: CC(C)(c1ccc(NCC(=O)CNS(C)(=O)=O)cc1)c1cc(Cl)c(OCCCCl)c(Cl)c1] |
| AA28 | 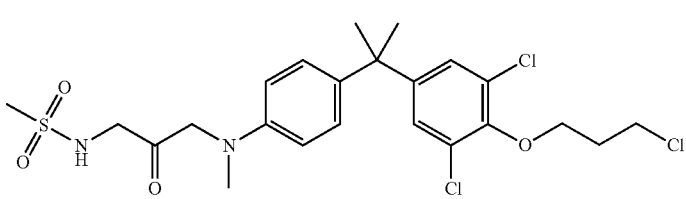 [SMILES: CN(CC(=O)CNS(C)(=O)=O)c1ccc(C(C)(C)c2cc(Cl)c(OCCCCl)c(Cl)c2)cc1] |
| AA29 | 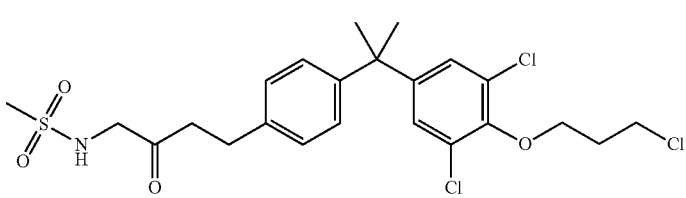 [SMILES: CC(C)(c1ccc(CCC(=O)CNS(C)(=O)=O)cc1)c1cc(Cl)c(OCCCCl)c(Cl)c1] |

TABLE A-continued
Androgen Receptor Modulators
| Compound ID | Structure |
|---|---|
| AA30 | 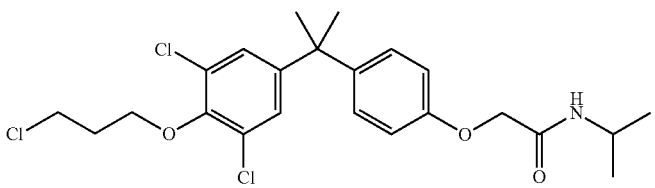 [SMILES: CC(C)NC(=O)COc1ccc(C(C)(C)c2cc(Cl)c(OCCCCl)c(Cl)c2)cc1] |
| AA31 | 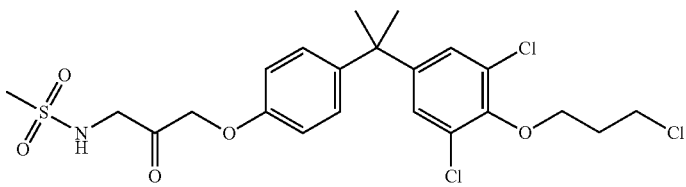 [SMILES: CC(C)(c1ccc(OCC(=O)CNS(C)(=O)=O)cc1)c1cc(Cl)c(OCCCCl)c(Cl)c1] |
| AA32 | 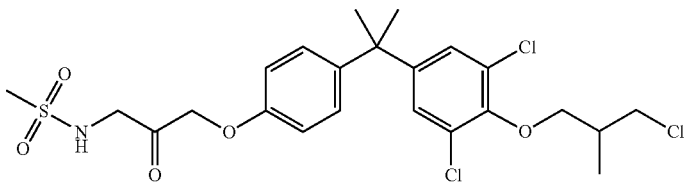 [SMILES: CC(CCl)COc1c(Cl)cc(C(C)(C)c2ccc(OCC(=O)CNS(C)(=O)=O)cc2)cc1Cl] |
| AA33 | 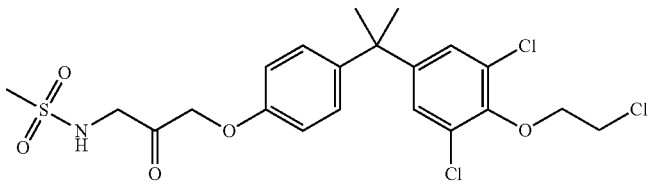 [SMILES: CC(C)(c1ccc(OCC(=O)CNS(C)(=O)=O)cc1)c1cc(Cl)c(OCCCl)c(Cl)c1] |
| AA34 | 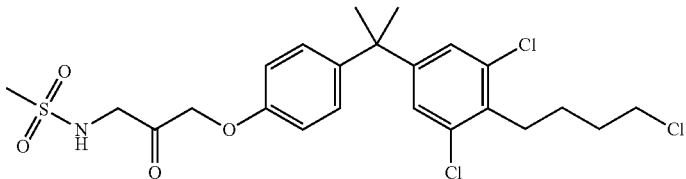 [SMILES: CC(C)(c1ccc(OCC(=O)CNS(C)(=O)=O)cc1)c1cc(Cl)c(CCCCCl)c(Cl)c1] |
| AA35 | 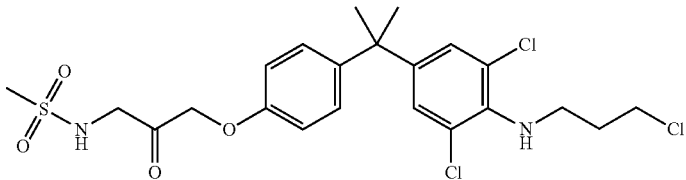 [SMILES: CC(C)(c1ccc(OCC(=O)CNS(C)(=O)=O)cc1)c1cc(Cl)c(NCCCCl)c(Cl)c1] |
| AA36 | 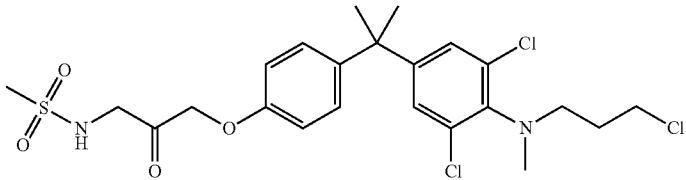 [SMILES: CN(CCCCl)c1c(Cl)cc(C(C)(C)c2ccc(OCC(=O)CNS(C)(=O)=O)cc2)cc1Cl] |

TABLE A-continued

Androgen Receptor Modulators

| Compound ID | Structure |
|---|---|
| AA37 | 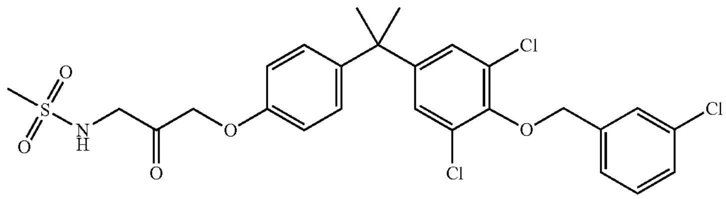 [SMILES: CC(C)(c1ccc(OCC(=O)CNS(C)(=O)=O)cc1)c1cc(Cl)c(OCc2cccc(Cl)c2)c(Cl)c1] |
| AA38 | 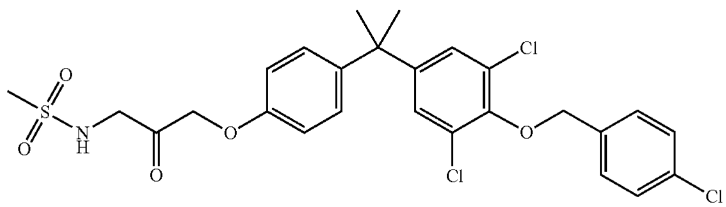 [SMILES: CC(C)(c1ccc(OCC(=O)CNS(C)(=O)=O)cc1)c1cc(Cl)c(OCc2ccc(Cl)cc2)c(Cl)c1] |
| AA39 | 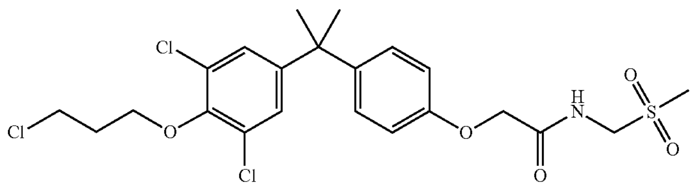 [SMILES: CC(C)(c1ccc(OCC(=O)NCS(C)(=O)=O)cc1)c1cc(Cl)c(OCCCCl)c(Cl)c1] |
| AA40 | 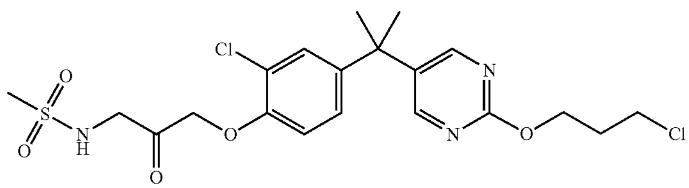 [SMILES: CC(C)(c1cnc(OCCCCl)nc1)c1ccc(OCC(=O)CNS(C)(=O)=O)c(Cl)c1] |
| AA41 | 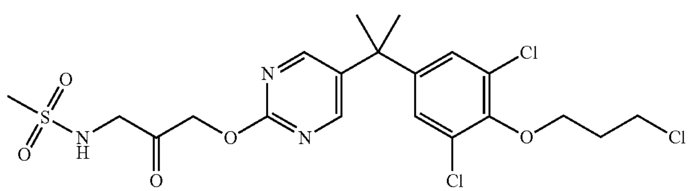 [SMILES: CC(C)(c1cnc(OCC(=O)CNS(C)(=O)=O)nc1)c1cc(Cl)c(OCCCCl)c(Cl)c1] |
| AA42 | 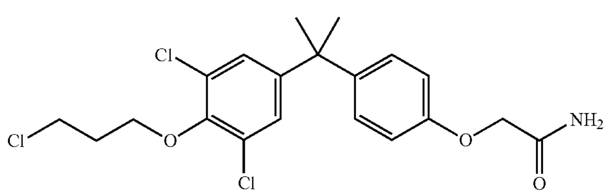 [SMILES: CC(C)(c1ccc(OCC(N)=O)cc1)c1cc(Cl)c(OCCCCl)c(Cl)c1] |
| AA43 | 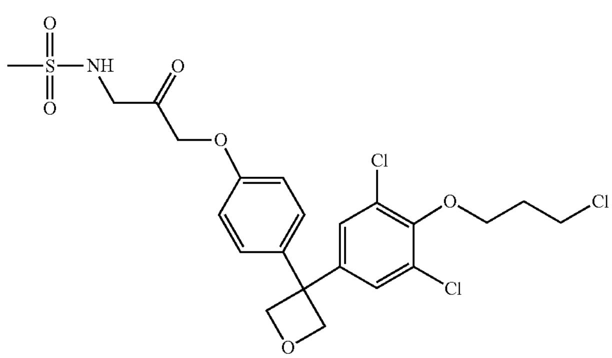 [SMILES: CS(=O)(=O)NCC(=O)COc1ccc(C2(c3cc(Cl)c(OCCCCl)c(Cl)c3)COC2)cc1] |

TABLE A-continued

Androgen Receptor Modulators

| Compound ID | Structure |
|---|---|
| AA44 | 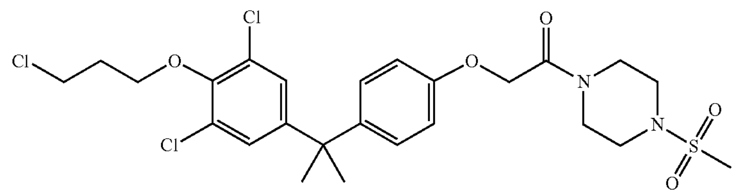 [SMILES: CC(C)(c1ccc(OCC(=O)N2CCN(S(C)(=O)=O)CC2)cc1)c1cc(Cl)c(OCCCCl)c(Cl)c1] |
| AA45 | 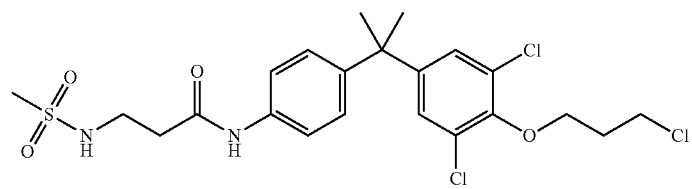 [SMILES: CC(C)(c1ccc(NC(=O)CCNS(C)(=O)=O)cc1)c1cc(Cl)c(OCCCCl)c(Cl)c1] |
| AA46 | 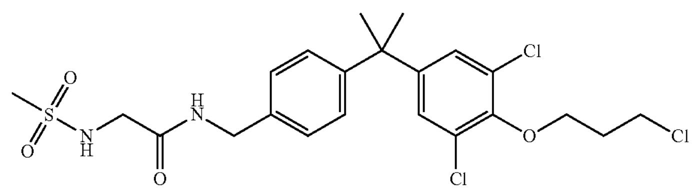 [SMILES: CC(C)(c1ccc(CNC(=O)CNS(C)(=O)=O)cc1)c1cc(Cl)c(OCCCCl)c(Cl)c1] |
| AA47 | 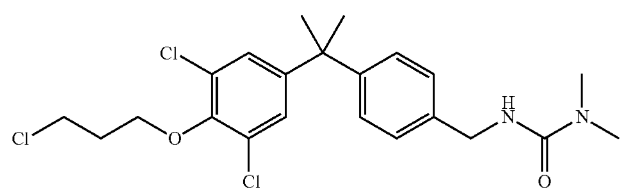 [SMILES: CN(C)C(=O)NCc1ccc(C(C)(C)c2cc(Cl)c(OCCCCl)c(Cl)c2)cc1] |
| AA48 | 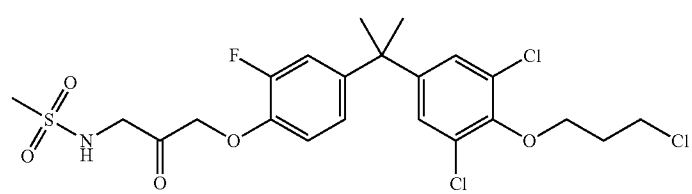 [SMILES: CC(C)(c1ccc(OCC(=O)CNS(C)(=O)=O)c(F)c1)c1cc(Cl)c(OCCCCl)c(Cl)c1] |
| AA49 | 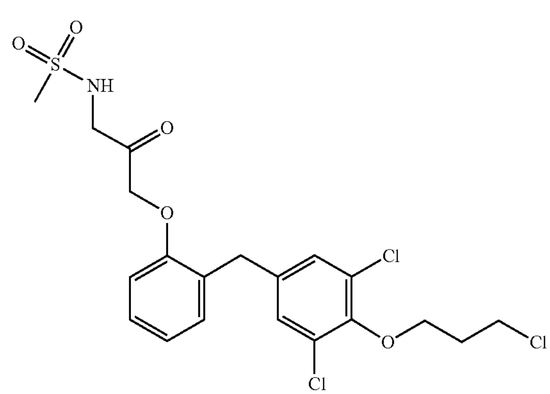 [SMILES: CS(=O)(=O)NCC(=O)COc1ccccc1Cc1cc(Cl)c(OCCCCl)c(Cl)c1] |

TABLE A-continued

Androgen Receptor Modulators

| Compound ID | Structure |
|---|---|
| AA50 | 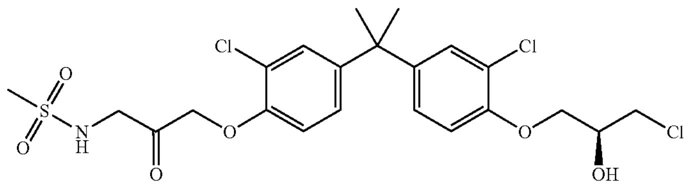 [SMILES: CC(C)(c1ccc(OCC(=O)CNS(C)(=O)=O)c(Cl)c1)c1ccc(OC[C@H](O)CCl)c(Cl)c1] |
| AA51 | 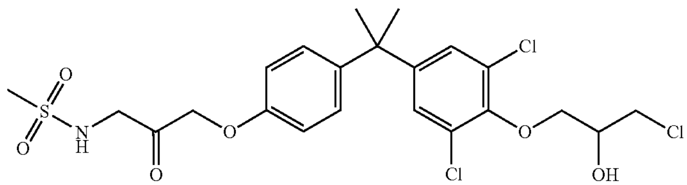 [SMILES: CC(C)(c1ccc(OCC(=O)CNS(C)(=O)=O)cc1)c1cc(Cl)c(OCC(O)CCl)c(Cl)c1] |
| AA51(S) | 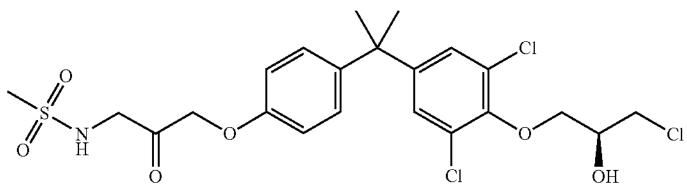 [SMILES: CC(C)(c1ccc(OCC(=O)CNS(C)(=O)=O)cc1)c1cc(Cl)c(OC[C@H](O)CCl)c(Cl)c1] |
| AA51(R) | 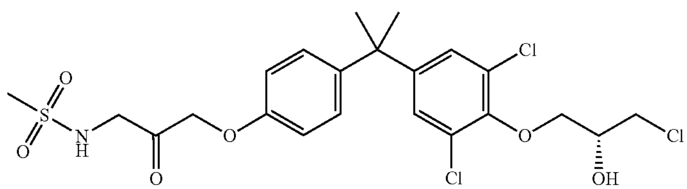 [SMILES: CC(C)(c1ccc(OCC(=O)CNS(C)(=O)=O)cc1)c1cc(Cl)c(OC[C@@H](O)CCl)c(Cl)c1] |
| AA52 | 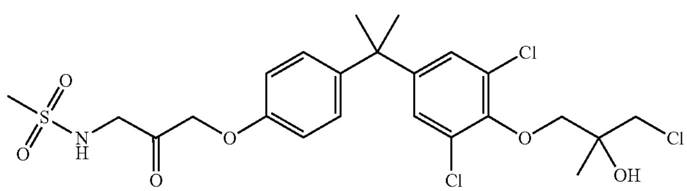 [SMILES: CC(O)(CCl)COc1c(Cl)cc(C(C)(C)c2ccc(OCC(=O)CNS(C)(=O)=O)cc2)cc1Cl] |
| AA52(S) | 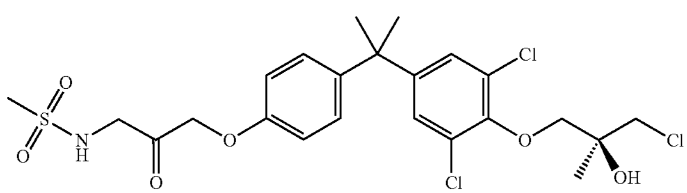 [SMILES: CC(C)(c1ccc(OCC(=O)CNS(C)(=O)=O)cc1)c1cc(Cl)c(OC[C@](C)(O)CCl)c(Cl)c1] |
| AA52(R) | 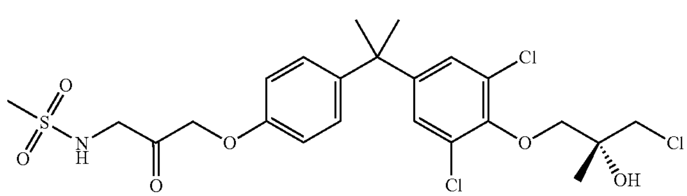 [SMILES: CC(C)(c1ccc(OCC(=O)CNS(C)(=O)=O)cc1)c1cc(Cl)c(OC[C@@](C)(O)CCl)c(Cl)c1] |
| AA53 | 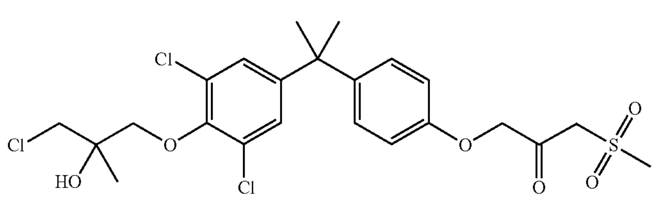 [SMILES: CC(O)(CCl)COc1c(Cl)cc(C(C)(C)c2ccc(OCC(=O)CS(C)(=O)=O)cc2)cc1Cl] |

TABLE A-continued
Androgen Receptor Modulators
| Compound ID | Structure |
|---|---|
| AA53(S) | 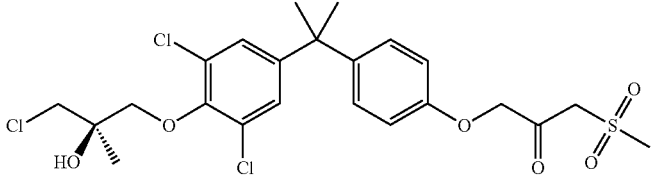 [SMILES: CC(C)(c1ccc(OCC(=O)CS(C)(=O)=O)cc1)c1cc(Cl)c(OC[C@@](C)(O)CCl)c(Cl)c1] |
| AA53(R) | 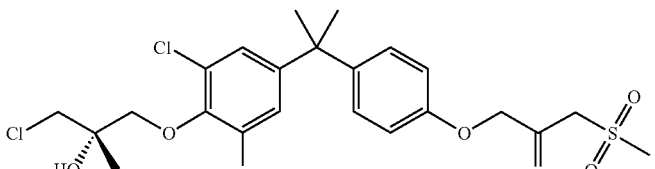 |
| AA54 | 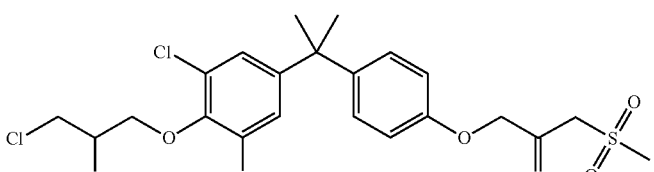 |
| AA54(S) | 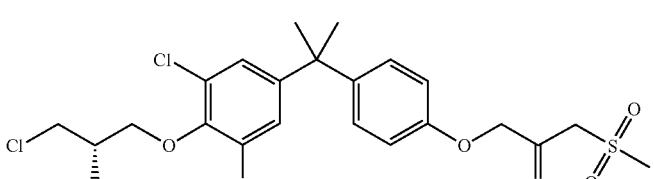 |
| AA54(R) | 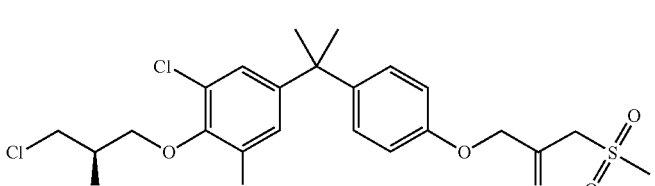 |
| AA55 | 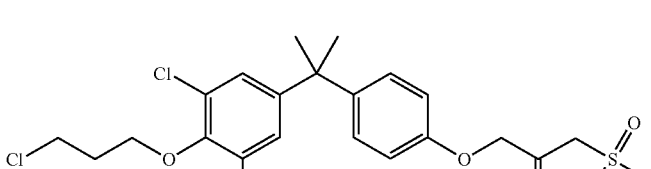 |
| AA56 | 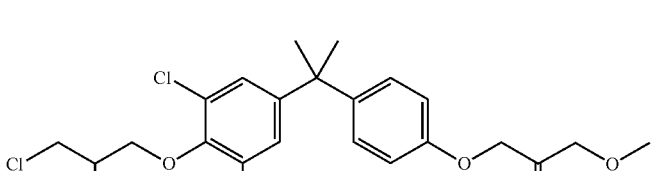 |

TABLE A-continued

Androgen Receptor Modulators

| Compound ID | Structure |
|---|---|
| AA56(S) | 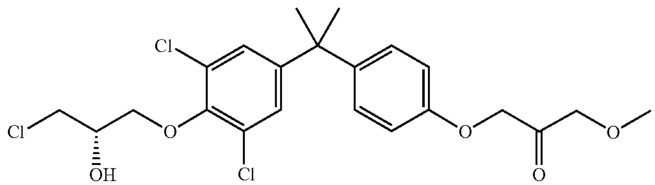 [SMILES: COCC(=O)COc1ccc(C(C)(C)c2cc(Cl)c(OC[C@H](O)CCl)c(Cl)c2)cc1] |
| AA56(R) | 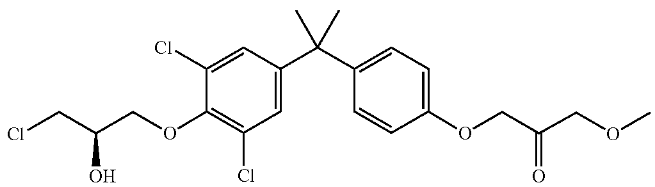 |
| AA57 | 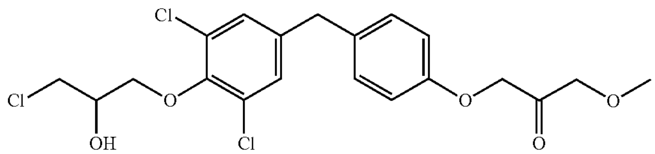 |
| AA57(S) | 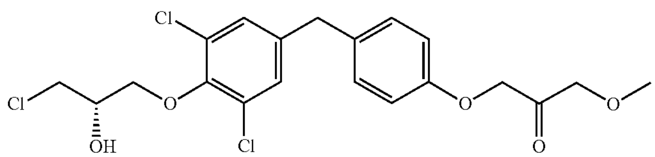 [SMILES: COCC(=O)COc1ccc(Cc2cc(Cl)c(OCC(O)CCl)c(Cl)c2)cc1] |
| AA57(R) | 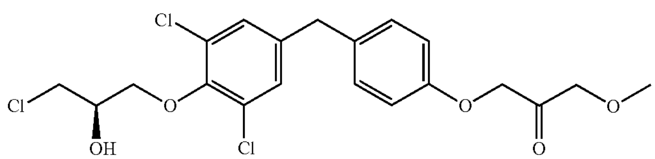 |
| AA58 | 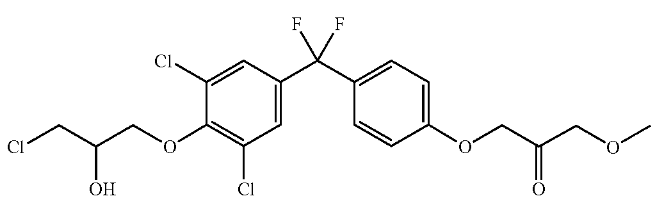 [SMILES: COCC(=O)COc1ccc(C(F)(F)c2cc(Cl)c(OCC(O)CCl)c(Cl)c2)cc1] |
| AA58(S) | 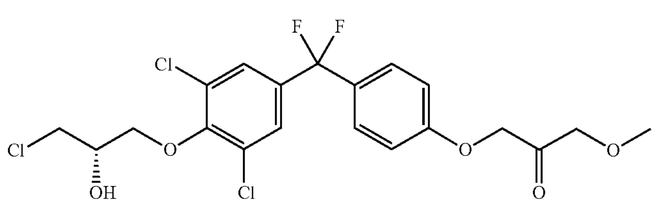 [SMILES: COCC(=O)COc1ccc(C(F)(F)c2cc(Cl)c(OC[C@H](O)CCl)c(Cl)c2)cc1] |
| AA58(R) | 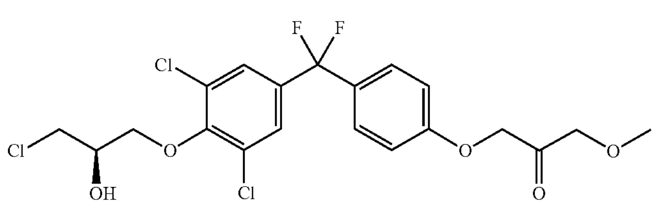 [SMILES: COCC(=O)COc1ccc(C(F)(F)c2cc(Cl)c(OC[C@@H](O)CCl)c(Cl)c2)cc1] |

TABLE A-continued

Androgen Receptor Modulators

| Compound ID | Structure |
| --- | --- |
| AA59 | 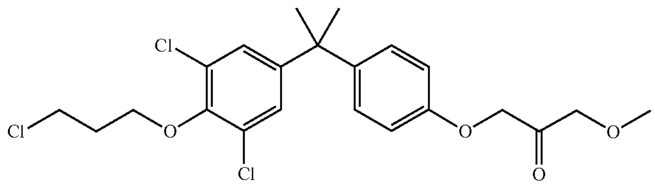 [SMILES: COCC(=O)COc1ccc(C(C)(C)c2cc(Cl)c(OCCCCl)c(Cl)c2)cc1] |
| AA60 | 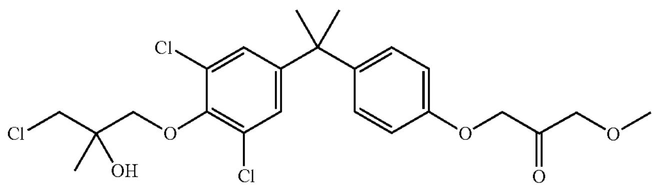 [SMILES: COCC(=O)COc1ccc(C(C)(C)c2cc(Cl)c(OCC(C)(O)CCl)c(Cl)c2)cc1] |
| AA60(S) | 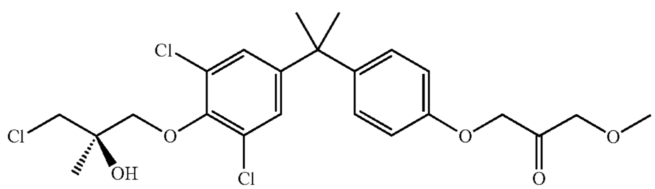 [SMILES: COCC(=O)COc1ccc(C(C)(C)c2cc(Cl)c(OC[C@@](C)(O)CCl)c(Cl)c2)cc1] |
| AA60(R) | 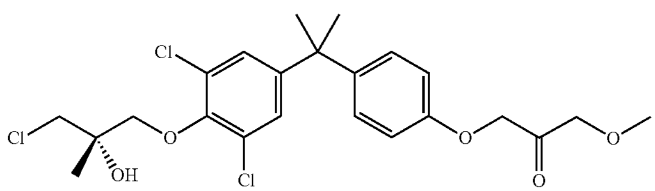 [SMILES: COCC(=O)COc1ccc(C(C)(C)c2cc(Cl)c(OC[C@](C)(O)CCl)c(Cl)c2)cc1] |
| AA61 | 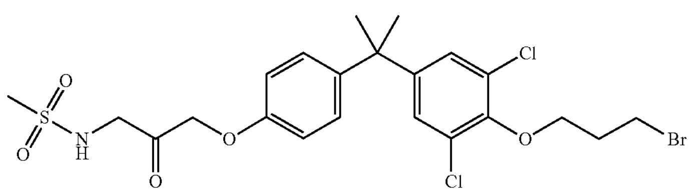 [SMILES: CC(C)(c1ccc(OCC(=O)CNS(C)(=O)=O)cc1)c1cc(Cl)c(OCCCBr)c(Cl)c1] |
| AA62 | 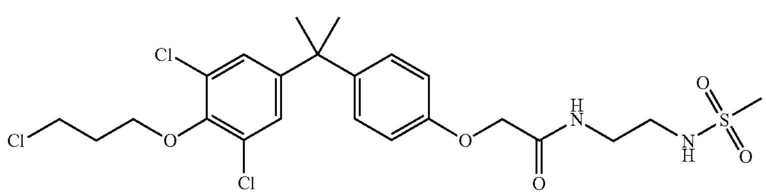 [SMILES: CC(C)(c1ccc(OCC(=O)NCCNS(C)(=O)=O)cc1)c1cc(Cl)c(OCCCCl)c(Cl)c1] |
| AA63 | |
| AA64 | 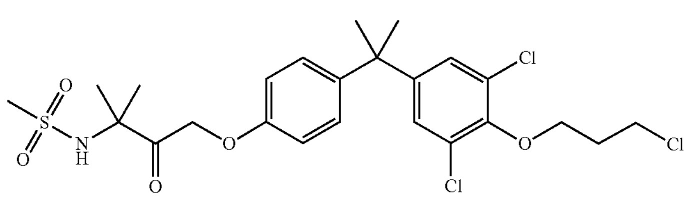 [SMILES: CC(C)(NS(C)(=O)=O)C(=O)COc1ccc(C(C)(C)c2cc(Cl)c(OCCCCl)c(Cl)c2)cc1] |

TABLE A-continued
Androgen Receptor Modulators
| Compound ID | Structure |
|---|---|
| AA65 | 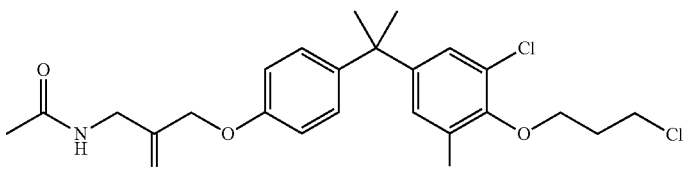 |
| AA66 | 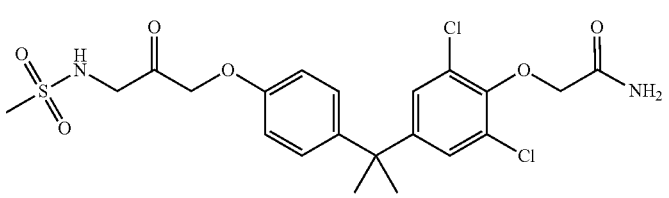 [SMILES: CC(C)(c1ccc(OCC(=O)CNS(C)(=O)=O)cc1)c1cc(Cl)c(OCC(N)=O)c(Cl)c1] |
| AA67 | 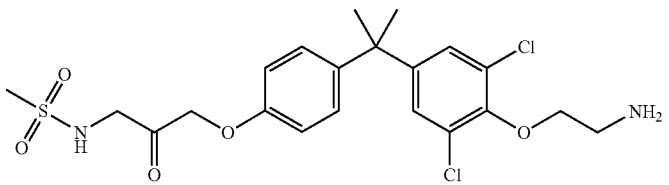 [SMILES: CC(C)(c1ccc(OCC(=O)CNS(C)(=O)=O)cc1)c1cc(Cl)c(OCCN)c(Cl)c1] |
| AA68 | 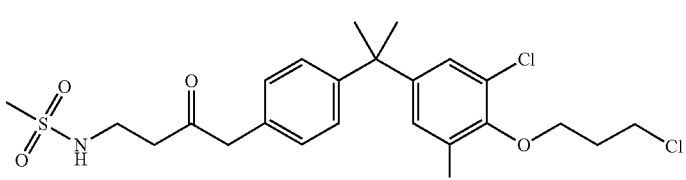 |
| AA69 | 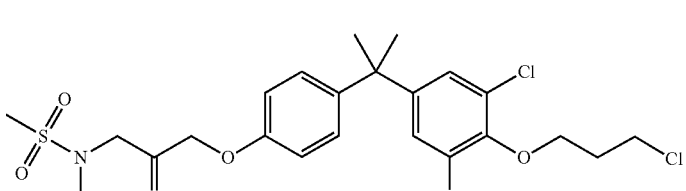 |
| AA70 | 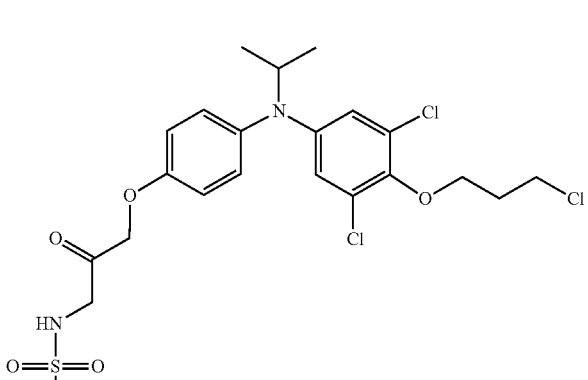 |

TABLE A-continued

Androgen Receptor Modulators

| Compound ID | Structure |
|---|---|
| AA71 | 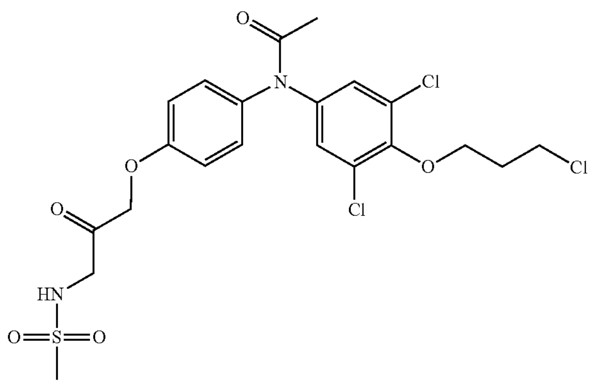 [SMILES: CC(=O)N(c1ccc(OCC(=O)CNS(C)(=O)=O)cc1)c1cc(Cl)c(OCCCCl)c(Cl)c1] |
| AA72 | 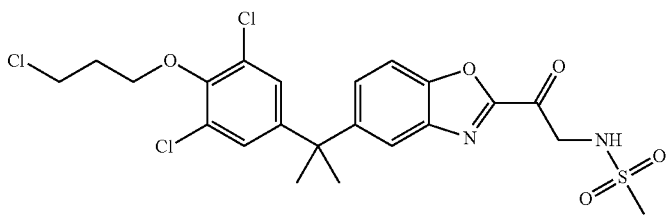 [SMILES: CC(C)(c1cc(Cl)c(OCCCCl)c(Cl)c1)c1ccc2oc(C(=O)CNS(C)(=O)=O)nc2c1] |
| AA73 | 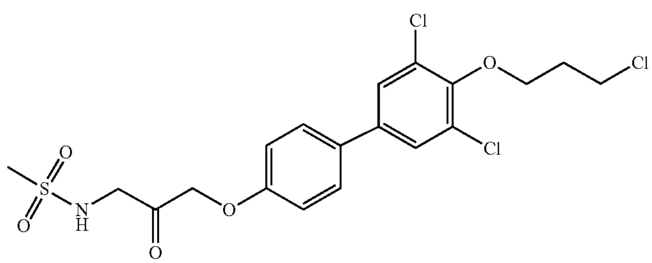 [SMILES: CS(=O)(=O)NCC(=O)COc1ccc(-c2cc(Cl)c(OCCCCl)c(Cl)c2)cc1] |
| AA74 | 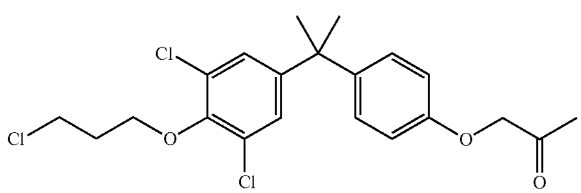 [SMILES: CC(=O)COc1ccc(C(C)(C)c2cc(Cl)c(OCCCCl)c(Cl)c2)cc1] |
| A75 | 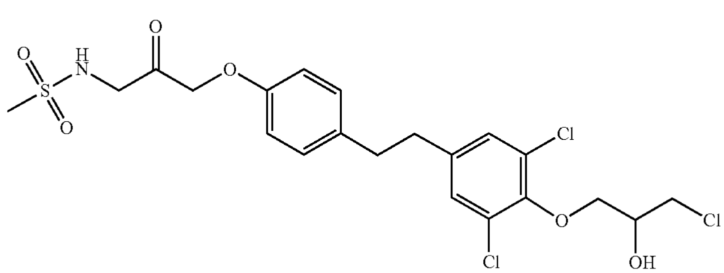 [SMILES: CS(=O)(=O)NCC(=O)COc1ccc(CCc2cc(Cl)c(OCC(O)CCl)c(Cl)c2)cc1] |

TABLE A-continued
Androgen Receptor Modulators
| Compound ID | Structure |
|---|---|
| AA76 | 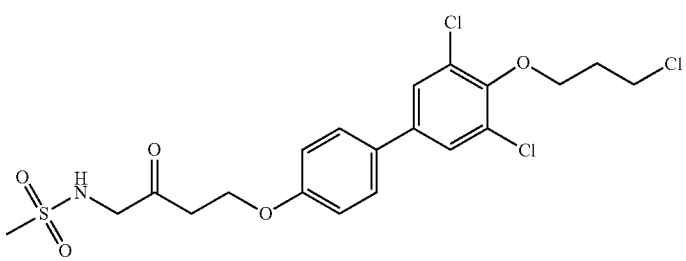 [SMILES: CS(=O)(=O)NCC(=O)CCOc1ccc(-c2cc(Cl)c(OCCCCl)c(Cl)c2)cc1] |
| AA77 | 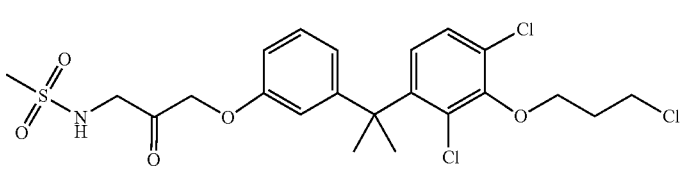 [SMILES: CC(C)(c1cccc(OCC(=O)CNS(C)(=O)=O)c1)c1ccc(Cl)c(OCCCCl)c1Cl] |
| A78 | 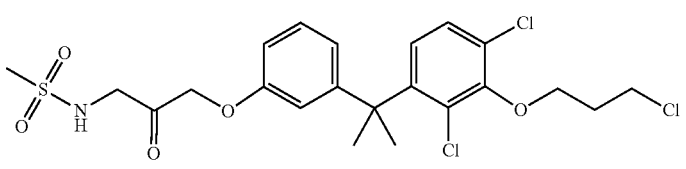 [SMILES: CC(C)(c1cccc(OCC(=O)CNS(C)(=O)=O)c1)c1ccc(Cl)c(OCCCCl)c1Cl] |
| AA79 | 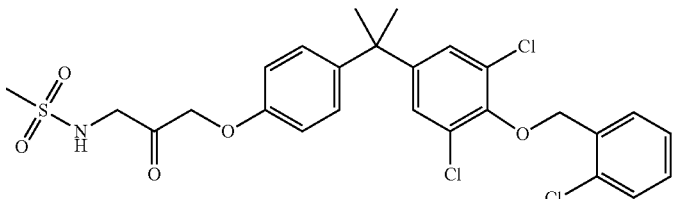 |
| AA80 | 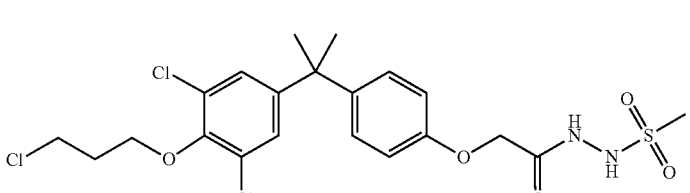 |
| AA81 | 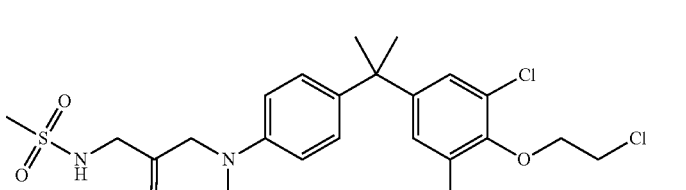 |
| AA82 | 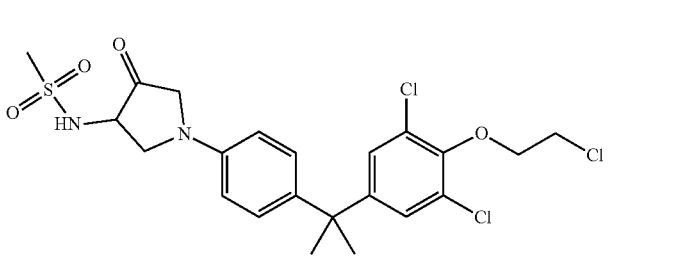 [SMILES: CC(C)(c1ccc(N2CC(=O)C(NS(C)(=O)=O)C2)cc1)c1cc(Cl)c(OCCCl)c(Cl)c1] |

TABLE A-continued

Androgen Receptor Modulators

| Compound ID | Structure |
|---|---|
| AA83 | 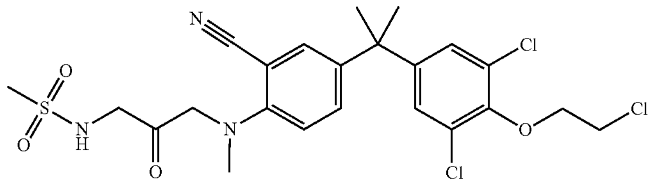 [SMILES: CN(CC(=O)CNS(C)(=O)=O)c1ccc(C(C)(C)c2cc(Cl)c(OCCCl)c(Cl)c2)cc1C#N] |
| AA84 | 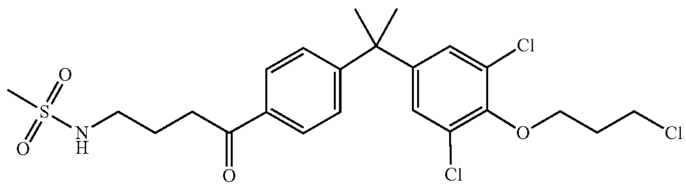 [SMILES: CC(C)(c1ccc(C(=O)CCCNS(C)(=O)=O)cc1)c1cc(Cl)c(OCCCCl)c(Cl)c1] |
| AA85 | 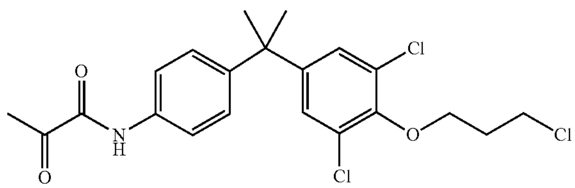 [SMILES: CC(=O)C(=O)Nc1ccc(C(C)(C)c2cc(Cl)c(OCCCCl)c(Cl)c2)cc1] |
| AA86 | 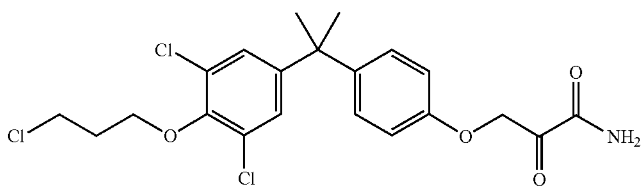 [SMILES: CC(C)(c1ccc(OCC(=O)C(N)=O)cc1)c1cc(Cl)c(OCCCCl)c(Cl)c1] |
| AA87 | 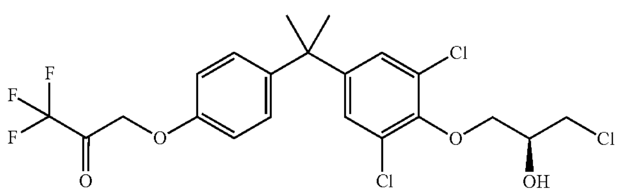 [SMILES: CC(C)(c1ccc(OCC(=O)C(F)(F)F)cc1)c1cc(Cl)c(OC[C@H](O)CCl)c(Cl)c1] |
| AA88 | 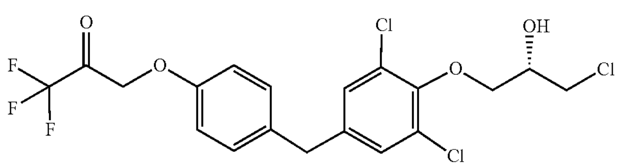 [SMILES: O=C(COc1ccc(Cc2cc(Cl)c(OC[C@H](O)CCl)c(Cl)c2)cc1)C(F)(F)F] |
| AA89 | 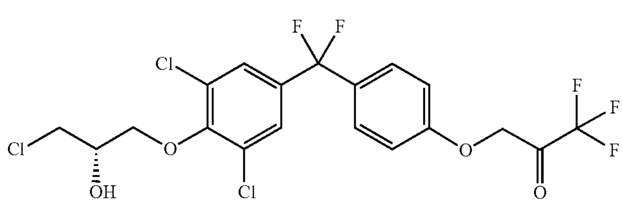 [SMILES: O=C(COc1ccc(C(F)(F)c2cc(Cl)c(OC[C@H](O)CCl)c(Cl)c2)cc1)C(F)(F)F] |
| AA90 | 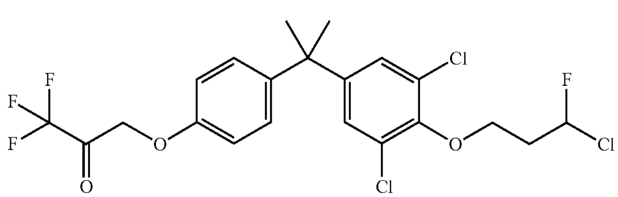 |

TABLE A-continued

Androgen Receptor Modulators

| Compound ID | Structure |
|---|---|
| AA91 | 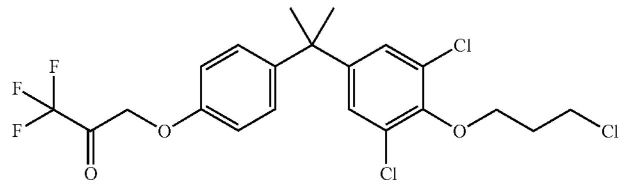 [SMILES: CC(C)(c1ccc(OCC(=O)C(F)(F)F)cc1)c1cc(Cl)c(OCCCCl)c(Cl)c1] |
| AA92 | 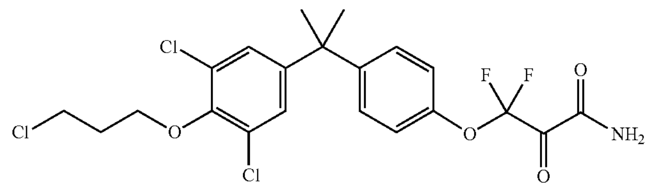 [SMILES: CC(C)(c1ccc(OC(F)(F)C(=O)C(N)=O)cc1)c1cc(Cl)c(OCCCCl)c(Cl)c1] |
| AA93 | 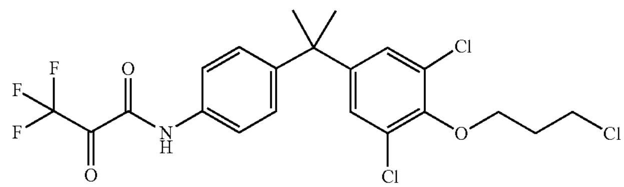 [SMILES: CC(C)(c1ccc(NC(=O)C(=O)C(F)(F)F)cc1)c1cc(Cl)c(OCCCCl)c(Cl)c1] |
| AA94 | 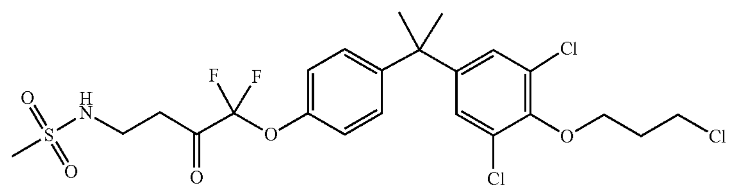 [SMILES: CC(C)(c1ccc(OC(F)(F)C(=O)CCNS(C)(=O)=O)cc1)c1cc(Cl)c(OCCCCl)c(Cl)c1] |
| AA95 | 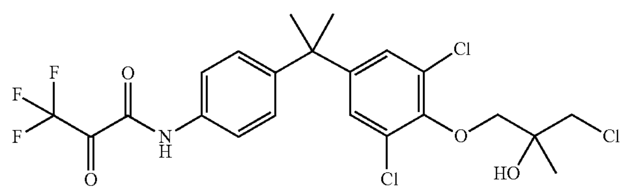 [SMILES: CC(O)(CCl)COc1c(Cl)cc(C(C)(C)c2ccc(NC(=O)C(=O)C(F)(F)F)cc2)cc1Cl] |
| AA96 | 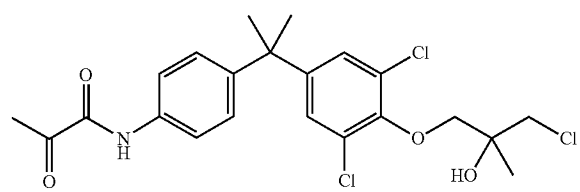 [SMILES: CC(=O)C(=O)Nc1ccc(C(C)(C)c2cc(Cl)c(OCC(C)(O)CCl)c(Cl)c2)cc1] |
| AA97 | 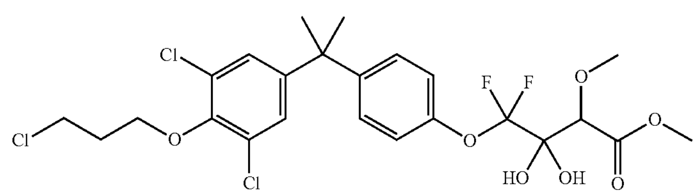 [SMILES: COC(=O)C(OC)C(O)(O)C(F)(F)Oc1ccc(C(C)(C)c2cc(Cl)c(OCCCCl)c(Cl)c2)cc1] |
| AA98 | 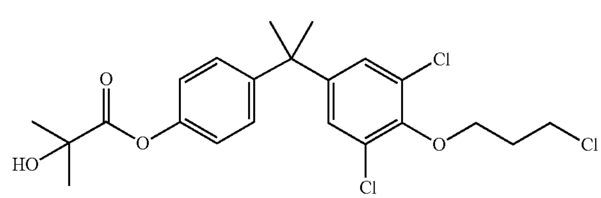 [SMILES: CC(C)(O)C(=O)Oc1ccc(C(C)(C)c2cc(Cl)c(OCCCCl)c(Cl)c2)cc1] |

TABLE A-continued

Androgen Receptor Modulators

| Compound ID | Structure |
|---|---|
| AA99 | 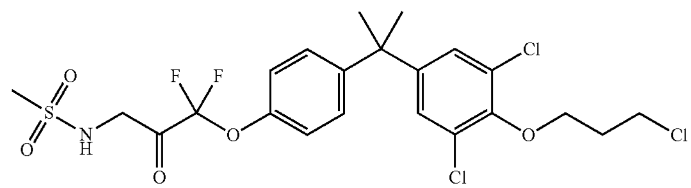 [SMILES: CC(C)(c1ccc(OC(F)(F)C(=O)CNS(C)(=O)=O)cc1)c1cc(Cl)c(OCCCCl)c(Cl)c1] |
| AA100 | 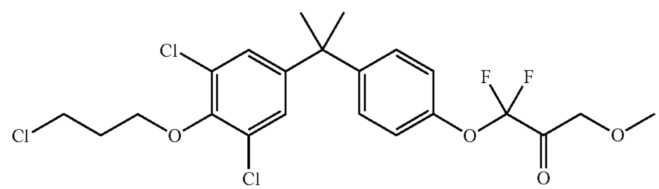 [SMILES: COCC(=O)C(F)(F)Oc1ccc(C(C)(C)c2cc(Cl)c(OCCCCl)c(Cl)c2)cc1] |
| AA101 | 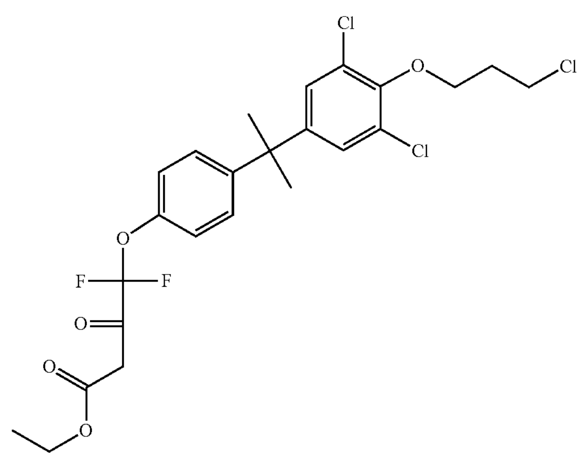 [SMILES: CCOC(=O)CC(=O)C(F)(F)Oc1ccc(C(C)(C)c2cc(Cl)c(OCCCCl)c(Cl)c2)cc1] |
| AA102 | 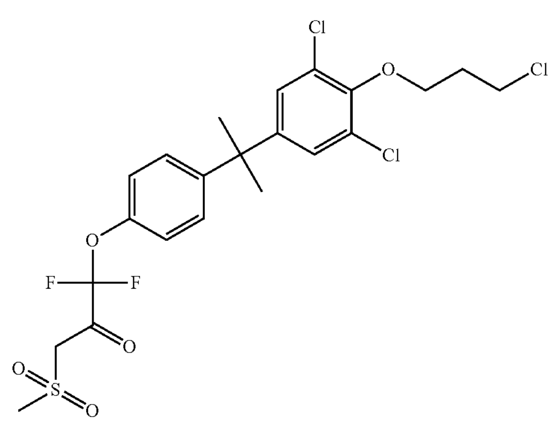 [SMILES: CC(C)(c1ccc(OC(F)(F)C(=O)CS(C)(=O)=O)cc1)c1cc(Cl)c(OCCCCl)c(Cl)c1] |

TABLE A-continued

Androgen Receptor Modulators

| Compound ID | Structure |
|---|---|
| AA103 | 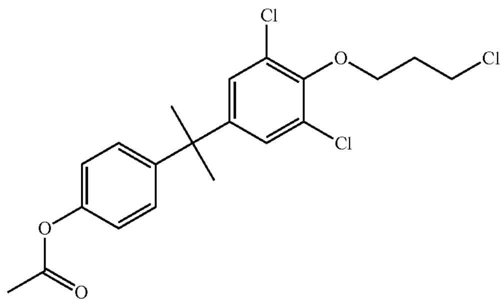 [SMILES: CC(=O)Oc1ccc(C(C)(C)c2cc(Cl)c(OCCCCl)c(Cl)c2)cc1] |
| AA104 | 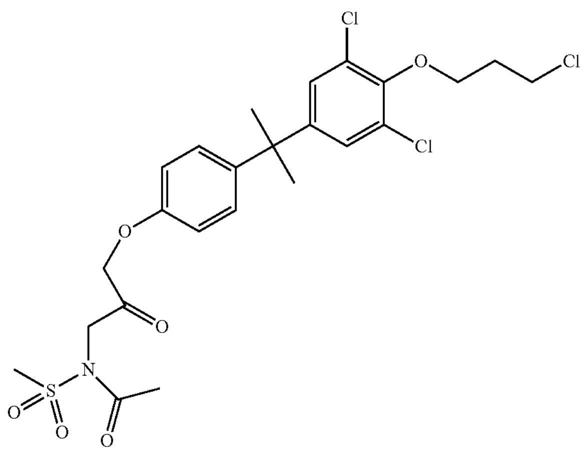 [SMILES: CC(=O)N(CC(=O)COc1ccc(C(C)(C)c2cc(Cl)c(OCCCCl)c(Cl)c2)cc1)S(C)(=O)=O] |

In one embodiment, the present disclosure provides androgen receptor N-terminal domain inhibitors selected from compounds of formula (a):

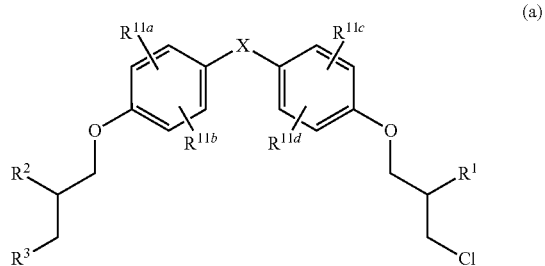

or a pharmaceutically acceptable salt, tautomer or stereoisomer thereof, wherein:
X is —S(O)$_n$— or —C(R$^8$R$^9$)—;
R$^1$ is H, —OH, or —OC(=O)R$^{13}$;
R$^2$ is —OH, or —OC(=O)R$^{13}$;
R$^3$ is halo, —OH, —OR$^4$, —OC(=O)R$^{13}$, —NH$_2$, —NHC(=O)R$^{13}$, —N(C(=O)R$^{13}$)$_2$, —NHS(O)$_n$R$^5$, —N(C(=O)R$^{13}$)(S(O)$_n$R$^5$), —N(C$_1$-C$_6$ alkyl)(S(O)$_n$R$^5$), —S(O)$_n$R$^5$, —N$_3$, aryl, carbocyclyl, heteroaryl or heterocyclyl which are optionally substituted with one or more R$^6$;
R$^4$ is C$_1$-C$_6$ alkyl, C$_2$-C$_6$ alkenyl, C$_2$-C$_6$ alkynyl, aryl, carbocyclyl, heteroaryl or heterocyclyl which are optionally substituted with one or more R$^6$;
R$^5$ is each independently C$_1$-C$_6$ alkyl or aryl which are optionally substituted with one or more R$^6$;
R$^6$ is each independently selected from the group consisting of H, F, Cl, Br, I, $^{123}$I, —OH, oxo, C$_1$-C$_6$ alkyl, C$_2$-C$_6$ alkenyl, C$_2$-C$_6$ alkynyl, C$_1$-C$_6$ alkoxy, C$_6$-C$_{12}$ aryl, wherein each R$^6$ is optionally substituted with one or more of halogen, $^{123}$I, $^{18}$F, —OH, —OS(O)$_2$-aryl, C$_1$-C$_6$ alkyl, C$_2$-C$_6$ alkenyl, or C$_2$-C$_6$ alkynyl;
R$^8$ and R$^9$ are each independently H or C$_1$-C$_6$ alkyl;
R$^{11a}$, R$^{11b}$, R$^{11c}$ and R$^{11d}$ are each independently H, methyl, —CN, F, Cl, Br, I, or $^{123}$I;
R$^{13}$ is C$_1$-C$_6$ alkyl; and
n is 0, 1, or 2;
wherein at least one of R$^{11a}$, R$^{11b}$, R$^{11c}$ and R$^{11d}$ is methyl, —CN, F, Cl, Br, I, or $^{123}$I.

In one embodiment of the compounds of formula (a), X is —C(R$^8$R$^9$)—. In one embodiment X is —C(R$^8$R$^9$)—, wherein R$^8$ and R$^9$ are each independently H or C$_1$-C$_3$ alkyl. In another embodiment, X is —C(R$^8$R$^9$)—, wherein R$^8$ and R$^9$ are each C$_1$ alkyl. In some embodiments, X is —S(O)$_2$— or —C(CH$_3$)$_2$—.

In one embodiment of the compounds of formula (a), R$^1$ is —OH. In another embodiment, R$^1$ is —OC(=O)R$^{13}$. In some embodiments, R$^1$ is —OC(=O)R$^{13}$, wherein R$^{13}$ is C$_1$-C$_4$ alkyl. In other embodiments, R$^1$ is —OC(=O)R$^{13}$, wherein R$^{13}$ is methyl. In one embodiment, R$^1$ is H.

In one embodiment of the compounds of formula (a), R$^2$ is —OH. In another embodiment, R$^2$ is —OC(=O)R$^{13}$. In some embodiments, R$^2$ is —OC(=O)R$^{13}$, wherein R$^{13}$ is C$_1$-C$_4$ alkyl. In other embodiments, R$^2$ is —OC(=O)R$^{13}$, wherein R$^{13}$ is methyl.

In one embodiment of the compounds of formula (a), at least one of $R^1$, $R^2$, or $R^3$ is —OH. In some embodiments, at least two of $R^1$, $R^2$, or $R^3$ are each —OH. In other embodiments, $R^1$ and $R^2$ are each —OH.

In one embodiment of the compounds of formula (a), at least one of $R^1$, $R^2$, or $R^3$ is —OC(=O)$R^{13}$, wherein $R^{13}$ is $C_1$-$C_4$ alkyl. In another embodiment, at least one of $R^1$, $R^2$, or $R^3$ is —OC(=O)$R^{13}$, wherein $R^{13}$ is methyl. In some embodiments, at least two of $R^1$, $R^2$, or $R^3$ are each —OC(=O)$R^{13}$, wherein $R^{13}$ is $C_1$-$C_4$ alkyl. In another embodiment, at least two of $R^1$, $R^2$, or $R^3$ are each —OC(=O)$R^{13}$, wherein $R^{13}$ is methyl. In other embodiments, $R^1$ and $R^2$ are each —OC(=O)$R^{13}$, wherein $R^{13}$ is methyl.

In one embodiment of the compounds of formula (a), $R^3$ is —$NH_2$, —NHC(=O)$R^{13}$, —N(C(=O)$R^{13}$)$_2$, —NHS(O)$_n$$R^5$, —N(C(=O)$R^{13}$)(S(O)$_n$$R^5$), or —N($C_1$-$C_6$ alkyl)(S(O)$_n$$R^5$). In one embodiment, $R^3$ is a —$NH_2$. In one embodiment, $R^3$ is a —NHC(=O)$R^{13}$. In one embodiment, $R^3$ is a —N(C(=O)$R^{13}$)$_2$. In another embodiment, $R^3$ is a —NHS(O)$_n$$R^5$. In some embodiments, $R^3$ is a —NHS(O)$_2$$R^5$. In other embodiments, $R^3$ is a —NHS(O)$_2$$R^5$, wherein $R^5$ is $C_1$-$C_3$ alkyl. In one embodiment, $R^3$ is a —NHS(O)$_2$$R^5$, wherein $R^5$ is $C_1$ alkyl. In one embodiment, $R^3$ is a —N(C(=O)$R^{13}$)(S(O)$_n$$R^5$). In one embodiment, $R^3$ is a —N($C_1$-$C_6$ alkyl)(S(O)$_n$$R^5$). In one embodiment, $R^3$ is a —NHS(O)$_2$$CH_3$.

In one embodiment of the compounds of formula (a), $R^3$ is —$NH_2$, —NHC(=O)($C_1$-$C_4$ alkyl), —N[(C(=O)($C_1$-$C_4$ alkyl)]$_2$, —NHS(O)$_n$($C_1$-$C_3$ alkyl), —N[C(=O)($C_1$-$C_4$ alkyl)][(S(O)$_n$($C_1$-$C_3$ alkyl)], or —N[$C_1$-$C_6$ alkyl][S(O)$_n$($C_1$-$C_3$ alkyl)]. In some embodiments, $R^3$ is —NH(C(=O)$CH_3$) or —N(C(=O)$CH_3$)$_2$. In other embodiments, $R^3$ is —NHS(O)$_2$$CH_3$. In other embodiments, $R^3$ is —N(C(=O)$CH_3$)(S(O)$_2$$CH_3$).

In one embodiment of the compounds of formula (a), $R^3$ is a —S(O)$_n$$R^5$. In one embodiment, $R^3$ is a —S(O)$_2$$R^5$. In another embodiment, $R^3$ is a —S(O)$_2$($C_1$-$C_3$ alkyl). In other embodiments, $R^3$ is a —S(O)$_2$$CH_3$. In other embodiments, $R^3$ is a —S(O)$_2$$CH_2$$CH_3$.

In one embodiment of the compounds of formula (a), $R^3$ is an optionally substituted 5 or 6 membered heteroaryl or an optionally substituted 3 to 7 membered heterocyclyl, wherein said heteroaryl or said heterocyclyl respectively comprise at least one N atom in the ring. In one embodiment, $R^3$ is selected from a group consisting of pyrrole, furan, thiophene, pyrazole, pyridine, pyridazine, pyrimidine, imidazole, thiazole, isoxazole, oxadiazole, thiadiazole, oxazole, triazole, isothiazole, oxazine, triazine, azepine, pyrrolidine, pyrroline, imidazoline, imidazolidine, pyrazoline, pyrazolidine, piperidine, dioxane, morpholine, dithiane, thiomorpholine, piperazine, and tetrazine. In a certain embodiment, $R^3$ is

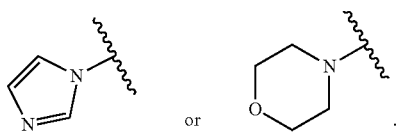 [SMILES: *n1ccnc1 ; *N1CCOCC1]

In one embodiment of the compounds of formula (a), $R^3$ is —O$R^4$. In one embodiment, $R^3$ is —O$R^4$, wherein $R^4$ is $C_1$-$C_6$ alkyl. In another embodiment, $R^3$ is —O$R^4$, wherein $R^4$ is $C_1$-$C_3$ alkyl. In one embodiment, $R^3$ is —O$R^4$, wherein $R^4$ is methyl, ethyl, n-propyl, or i-propyl. In one embodiment, $R^3$ is —O$R^4$, wherein $R^4$ is methyl. In another embodiment, $R^3$ is —O$R^4$, wherein $R^4$ is i-propyl.

In one embodiment of the compounds of formula (a), $R^3$ is a halogen. In other embodiments, $R^3$ is F, Cl, Br, or I. In one embodiment, $R^3$ is F.

In one embodiment of the compounds of formula (a), at least one of $R^{11a}$, $R^{11b}$, $R^{11c}$ and $R^{11d}$ is Cl. In another embodiment, at least one of $R^{11a}$, $R^{11b}$, $R^{11c}$ and $R^{11d}$ is Br. In some embodiments, at least one of $R^{11a}$, $R^{11b}$, $R^{11c}$ and $R^{11d}$ is methyl. In some embodiments, at least one of $R^{11a}$, $R^{11b}$, $R^{11c}$ and $R^{11d}$ is —CN, In one embodiment of the compounds of formula (a), at least two of $R^{11a}$, $R^{11b}$, $R^{11c}$ and $R^{11d}$ are methyl, F, Cl, Br, I, or $^{123}$I. In another embodiment, exactly two of $R^{11a}$i, $R^{11b}$, $R^{11c}$ and $R^{11d}$ are methyl, F, Cl, Br, I, or $^{123}$I.

In one embodiment of the compounds of formula (a), $R^{11a}$ and $R^{11b}$ are each H and $R^{11c}$ and $R^{11d}$ are each independently methyl, F, Cl, Br, I, or $^{123}$I. In one embodiment, $R^{11a}$ and $R^{11b}$ are each H, and $R^{11c}$ and $R^{11d}$ are each Cl. In one embodiment, $R^{11a}$ and $R^{11b}$ are each H, and $R^{11c}$ and $R^{11d}$ are each Br. In one embodiment, $R^{11a}$ and $R^{11b}$ are each H, and $R^{11c}$ and $R^{11d}$ are each methyl.

In one embodiment of the compounds of formula (a), $R^{11a}$ and $R^{11c}$ are each H, and $R^{11b}$ and $R^{11d}$ are each independently methyl, F, Cl, Br, I, or $^{123}$I. In one embodiment, $R^{11a}$ and $R^{11c}$ are each H, and $R^{11b}$ and $R^{11d}$ are each Cl. In one embodiment, $R^{11a}$ and $R^{11c}$ are each H, and $R^{11b}$ and $R^{11d}$ are each Br. In one embodiment, $R^{11a}$ and $R^{11c}$ are each H, and $R^{11b}$ and $R^{11d}$ are each methyl.

In one embodiment of the compounds of formula (a), $R^{13}$ is $C_1$-$C_3$ alkyl. In other embodiments, $R^{13}$ is methyl, ethyl, or propyl. In one embodiment, $R^{13}$ is a methyl.

In one embodiment of the compounds of formula (a), n is 0. In another embodiment n is 1. In some embodiments, n is 2.

In one embodiment of the compounds of formula (a), the compound comprises one or more of F, Cl, Br, I or $^{123}$I substitutions for $R^3$. In one embodiment, the compound comprises one or more of I or $^{123}$I substitutions for $R^3$.

In one embodiment of the compounds of formula (a), the compound comprises at least one $R^6$ substituent on $R^3$, wherein at least one $R^6$ is further substituted with at least one of F, Cl, Br, I or $^{123}$I. In another embodiment, $R^6$ substituent on $R^3$ is further substituted with at least one of I or $^{123}$I.

In some more specific embodiments of the compounds of Formula (a), the compound has one of the following structures from Table B, or a pharmaceutically acceptable salt, tautomer, or stereoisomer thereof. In one embodiment, the compounds of Formula (a) is selected from Compounds 1, 1a, 1A, 1aA, 5, 5a, 5A, 5aA, 7, 7a, 7A, 7aA, 8, 8a, 8A, 8aA, 9, 9a, 9A, 9aA, 11, 11a, 11A, 11aA, 12, 12a, 13, 13a, 13A, 13aA, 14, 14a, 14A, 14aA, 22, or 22a, or a pharmaceutically acceptable salt, tautomer, or stereoisomer thereof.

The compounds disclosed in WO 2017/177307 can be useful androgen receptor modulators for the present invention. The disclosure of WO 2017/177307 is incorporated by reference in its entirety for all purposes.

TABLE B

Androgen receptor N-terminal domain inhibitors

| Comp ID | Structure |
|---|---|
| 1 | 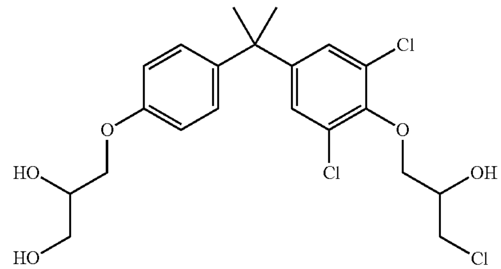 [SMILES: CC(C)(c1ccc(OCC(O)CO)cc1)c1cc(Cl)c(OCC(O)CCl)c(Cl)c1] |
| 1A | |
| 1a | |
| 1aA | 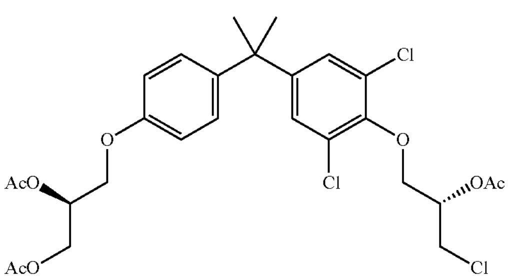 [SMILES: CC(=O)OC[C@H](COc1ccc(C(C)(C)c2cc(Cl)c(OC[C@@H](CCl)OC(C)=O)c(Cl)c2)cc1)OC(C)=O] |
| 5 | 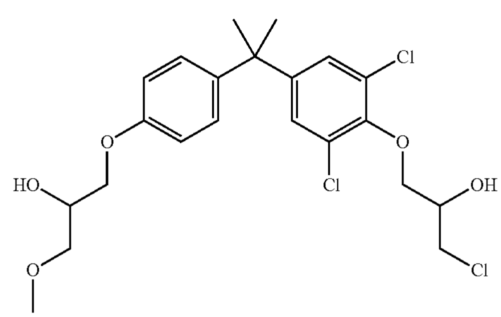 [SMILES: COCC(O)COc1ccc(C(C)(C)c2cc(Cl)c(OCC(O)CCl)c(Cl)c2)cc1] |
| 5A | |
| 5a | |
| 5aA | |
| 7 | |

TABLE B-continued

Androgen receptor N-terminal domain inhibitors

| Comp ID | Structure |
|---|---|
| 7A | (structure) |
| 7a | (structure) |
| 7aA | (structure) |
| 8 | (structure) |
| 8A | (structure) |
| 8a | (structure) |
| 8aA | (structure) |
| 9 | (structure) |
| 9A | (structure) |
| 9a | (structure) |

TABLE B-continued

Androgen receptor N-terminal domain inhibitors

| Comp ID | Structure |
|---|---|
| 9aA | 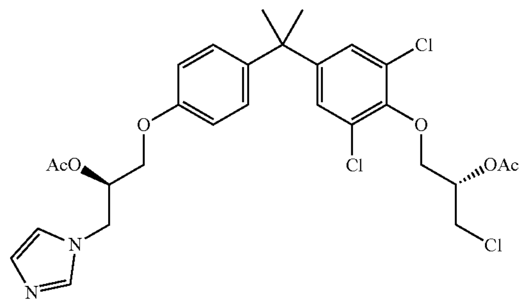 [SMILES: CC(=O)O[C@H](CCl)COc1c(Cl)cc(C(C)(C)c2ccc(OC[C@@H](Cn3ccnc3)OC(C)=O)cc2)cc1Cl] |
| 11 | 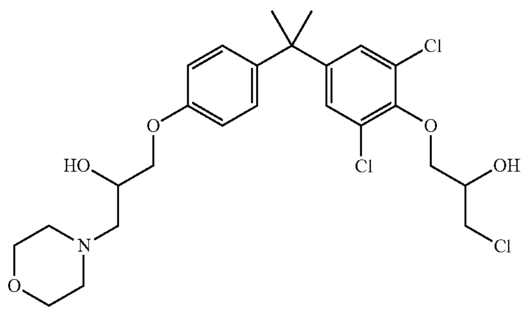 [SMILES: CC(C)(c1ccc(OCC(O)CN2CCOCC2)cc1)c1cc(Cl)c(OCC(O)CCl)c(Cl)c1] |
| 11A | |
| 11a | |
| 11aA | 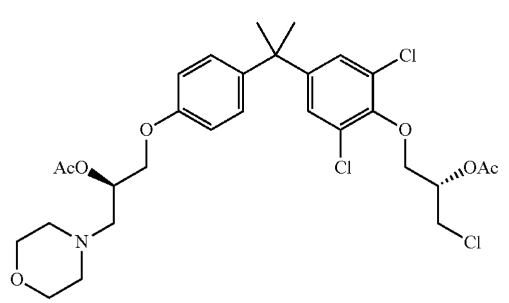 [SMILES: CC(=O)O[C@H](CCl)COc1c(Cl)cc(C(C)(C)c2ccc(OC[C@@H](CN3CCOCC3)OC(C)=O)cc2)cc1Cl] |
| 12 | |
| 12a | |
| 13 | |
| 13A | |
| 13a | |

TABLE B-continued

Androgen receptor N-terminal domain inhibitors

| Comp ID | Structure |
|---|---|
| 13aA | [Structure: bisphenol-type core with 3,5-dichlorophenyl and phenyl rings; left side bears –O–CH$_2$–CH(OAc)–CH$_2$–N(Ac)–S(=O)$_2$–CH$_3$ (methanesulfonamide N-acetyl); right side bears –O–CH$_2$–CH(,,,OAc)–CH$_2$–Cl] |
| 14 | [Structure: bisphenol core, left: –O–CH$_2$–CH(OH)–CH$_2$–S(=O)$_2$–Et; right: –O–CH$_2$–CH(OH)–CH$_2$–Cl; central ring 3,5-dichloro] |
| 14A | [Structure: as 14 with acetylated hydroxyls (OAc in place of OH)] |
| 14a | [Structure: as 14 with defined stereochemistry (HO,,, and ,,,OH)] |
| 14aA | [Structure: as 14A with defined stereochemistry (AcO,,, and ,,,OAc)] |
| 22 | [Structure: bis(3-methylphenyl)propane core; both aryl ethers: –O–CH$_2$–CH(OH)–CH$_2$–OH on left and –O–CH$_2$–CH(OH)–CH$_2$–Cl on right] |
| 22a | [Structure: as 22 with defined stereochemistry at both CH(OH) centers] |

In one embodiment, the compounds as disclosed herein is an androgen receptor N-terminal domain inhibitor. In one embodiment, the compounds as disclosed herein binds to androgen receptor. In another embodiment, the compounds as disclosed herein binds to androgen receptor N-terminal domain.

In one embodiment, the pharmaceutical compositions and the pharmaceutical combinations of present disclosure comprises a compound of formula (i)-(iv) or (a), or a pharmaceutically acceptable salt thereof and a second therapeutically active agent. In one embodiment, the pharmaceutical compositions and the pharmaceutical combinations of present disclosure comprises a compound of formula (i)-(iv) or a compound of Table A, or a pharmaceutically acceptable salt, tautomer, stereoisomer or prodrug thereof, and a CDK4/6 inhibitor or an androgen receptor ligand-binding domain inhibitor. In one embodiment, the pharmaceutical compositions and the pharmaceutical combinations of present disclosure comprises a compound of formula (i)-(iv) or a compound of Table A, or a pharmaceutically acceptable salt, tautomer, stereoisomer or prodrug thereof, and a CDK4/6 inhibitor or an androgen receptor ligand-binding domain inhibitor. In one embodiment, the pharmaceutical compositions and the pharmaceutical combinations of present disclosure comprises a compound selected from Compounds AA1-AA98, or a pharmaceutically acceptable salt, tautomer, stereoisomer or prodrug thereof, and a CDK4/6 inhibitor or an androgen receptor ligand-binding domain inhibitor. In one embodiment, the pharmaceutical compositions and the pharmaceutical combinations of present disclosure comprises a compound selected from Compounds AA1-AA104, or a pharmaceutically acceptable salt, tautomer, stereoisomer or prodrug thereof, and a CDK4/6 inhibitor or an androgen receptor ligand-binding domain inhibitor. In one embodiment, the pharmaceutical compositions and the pharmaceutical combinations of present disclosure comprises a compound of formula (a) or a compound of Table B, or a pharmaceutically acceptable salt, tautomer, stereoisomer or prodrug thereof, and a CDK4/6 inhibitor or an androgen receptor ligand-binding domain inhibitor. In one embodiment, the pharmaceutical compositions and the pharmaceutical combinations of present disclosure comprises a compound is selected from Compounds 1, 1a, 1A, 1aA, 5, 5a, 5A, 5aA, 7, 7a, 7A, 7aA, 8, 8a, 8A, 8aA, 9, 9a, 9A, 9aA, 11, 11a, 11A, 11aA, 12, 12a, 13, 13a, 13A, 13aA, 14, 14a, 14A, 14aA, 22, or 22a, or a pharmaceutically acceptable salt, tautomer, stereoisomer or prodrug thereof, and a CDK4/6 inhibitor or an androgen receptor ligand-binding domain inhibitor.

In one embodiment, the pharmaceutical compositions and the pharmaceutical combinations of present disclosure further comprises a pharmaceutically acceptable carrier or a pharmaceutically acceptable excipient.

CDK4/6 Inhibitors

The G1/S transition is a stage in the cell cycle between the G1 (GAP 1) phase, when the cell grows, and the S (Synthesis) phase, when DNA is replicated. The G1/S transition is a cell cycle check point where DNA integrity is assessed and the cell cycle can pause, for example, in response to improperly or partially replicated DNA. During this transition the cell can decide to become quiescent (enter G0), differentiate, make DNA repairs, or proliferate based on molecular signaling inputs and environmental inputs. The G1/S transition occurs late in G1 phase and the absence or improper application of this highly regulated check point can lead to cellular transformation and disease states such as cancer by deregulated state of proliferation.

The retinoblastoma tumor suppressor protein ($R_b$) governs this key cell-cycle checkpoint (at G1/S transition) that normally prevents G1 phase cells from entering S phase in the absence of appropriate mitogenic signals. Cancer cells frequently overcome or bypass $R_b$-dependent growth suppression via constitutive phosphorylation and inactivation of $R_b$ function by cyclin-dependent kinase (CDK) 4 or CDK6 partnered with D-type cyclins (cyclin D).

During this G1/S transition, G1 cyclin D-CDK4/6 dimer complex phosphorylates $R_b$ (phosphorylated $R_b$=pRb) releasing transcription factor E2F, which then drives the transition from G1 to S phase. Once the G1 cyclin D-CDK4/6 dimer complex causes pRb to release E2F by conformational change in E2F-bounded $R_b$ upon phosphorylation, E2F drives the expression of other cyclins, such as cyclin E and cyclin A, which push the cell through the cell cycle by activating cyclin-dependent kinases, and a molecule called proliferating cell nuclear antigen, or PCNA, which speeds DNA replication and repair by helping to attach polymerase to DNA.

Thus, the activity/expression level of cyclin D and control of the G1/S transition by $R_b$ and/or pRb is critical for cell proliferation. Many cancers harbor mutations in the protein present in this $R_b$ checkpoint pathway that controls progression of the cell cycle. Thus, there is a need for treatment of cancer which is effective for treating subjects who have abnormally high expression levels in the $R_b$ checkpoint pathway or harbor mutations in the protein present in the $R_b$ checkpoint pathway.

Cyclin D1 activates CDK4/6 to phosphorylate $R_b$ and other proteins involved in the transition from G1 phase to S phase during cell cycle. Luminal androgen receptor (LAR) subtype of TNBC is particularly sensitive to CDK4/6 inhibitors. This sensitivity is associated with AR expression and low cyclin E1 levels.

In one embodiment, any known CDK4/6 inhibitors can be used in the pharmaceutical compositions and combinations of the present disclosure.

In one embodiment, the CDK4/6 inhibitors useful for the pharmaceutical compositions and combinations as disclosed herein, is selected from palbociclib, ribociclib, trilaciclib or abemaciclib. In one embodiment, the CDK4/6 inhibitor is selected from palbociclib, abemaciclib, or ribociclib. In one embodiment, the CDK4/6 inhibitor is palbociclib.

Androgen Receptor Ligand-Binding Domain Inhibitor

In one embodiment, the androgen receptor N-terminal domain inhibitor compound of formula (i)-(iv) or (a), or a pharmaceutically acceptable salt thereof are androgen receptor N-terminal domain inhibitors. In one embodiment, androgen receptor N-terminal domain inhibitors can be useful when used in combination with an androgen receptor ligand-binding domain inhibitor. In some embodiments, an androgen receptor N-terminal domain inhibitor and an androgen receptor ligand-binding domain inhibitor can act synergistically.

In one embodiment, the androgen receptor ligand-binding domain inhibitor is enzalutamide, apalutamide, darolutamide, bicalutamide, nilutamide, flutamide, ODM-204, or TAS3681. In one embodiment, the androgen receptor ligand-binding domain inhibitor is enzalutamide.

Pin1 Inhibitors

Pin1 is a unique isomerase that regulates the proline conformation of a phosphorylated motif (pSer/Thr-Pro). Pin1 levels are often elevated in prostate cancer and correlate with risk for developing castration-resistant prostate cancer (CRPC).

Since the cis trans conformations of proline are dramatically different, they may influence protein structure and function. There are several putative Pin1 sites located on the AR (androgen receptor), and many are within the intrinsically disordered N-terminal domain (NTD).

The intrinsically disordered AR NTD (androgen receptor N-terminal domain) is essential for its transcriptional activity. It harbors six putative binding sites for Pin1, a proline isomerase that regulates protein conformation at specific phosphorylated-Ser/Thr-Pro motifs. Since conformational changes within the ARNTD are required for transactivation, perturbation of its structure can lead to blocking AR NTD activity. Thus, Pin1 inhibitors used in combination with an androgen receptor N-terminal domain inhibitor can lead to enhanced inhibition of the androgen receptor, including AR NTD.

In one embodiment, any known Pin1 inhibitors can be used in combination with androgen receptor N-terminal domain inhibitor as disclosed herein.

In one embodiment, Pin1 inhibitor is selected from juglone, plumbagin, PiB, PiJ, epigallocatechin gallate (EGCG), all-trans retinoic acid (ATRA), dipentamethylene thiauram monosulfide, TME-001 (2-(3-chloro-4-fluoro-phenyl)-isothiazol-3-one), KPT-6566, API-1, buparvaquone, or a pharmaceutically acceptable salt thereof.

In one embodiment, Pin1 inhibitor is selected from Table C or a pharmaceutically acceptable salt thereof.

TABLE C
Pin1 Inhibitors
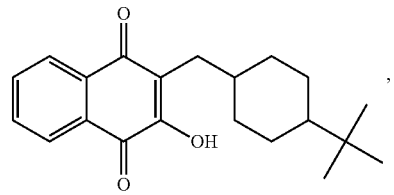 [SMILES: CC(C)(C)C1CCC(CC2=C(O)C(=O)c3ccccc3C2=O)CC1]
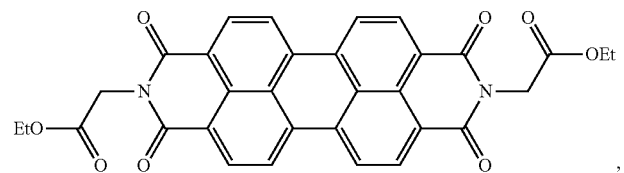 [SMILES: CCOC(=O)CN1C(=O)c2ccc3c4ccc5c6c(ccc(c7ccc(c2c37)C1=O)c64)C(=O)N(CC(=O)OCC)C5=O ; ","]
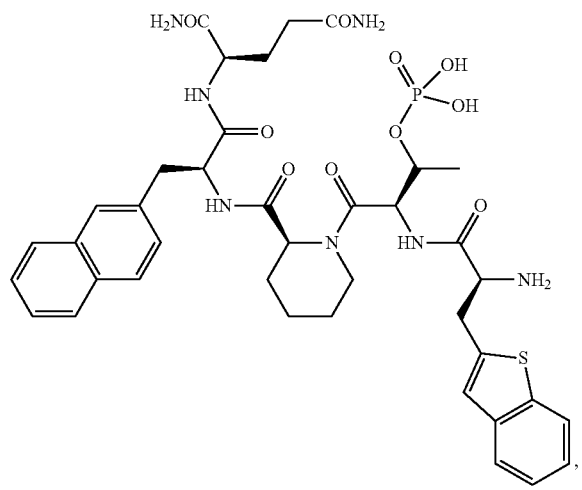 [SMILES: CC(OP(=O)(O)O)[C@@H](NC(=O)[C@@H](N)Cc1cc2ccccc2s1)C(=O)N1CCCC[C@H]1C(=O)N[C@@H](Cc1ccc2ccccc2c1)C(=O)N[C@H](CCC(N)=O)C(N)=O]
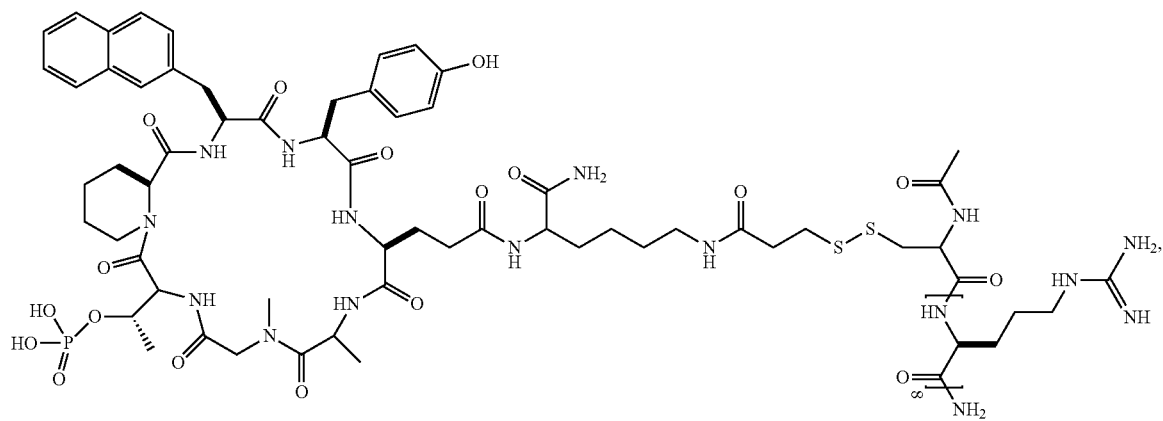
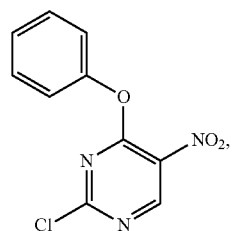 [SMILES: O=[N+]([O-])c1cnc(Cl)nc1Oc1ccccc1]

TABLE C-continued
Pin1 Inhibitors
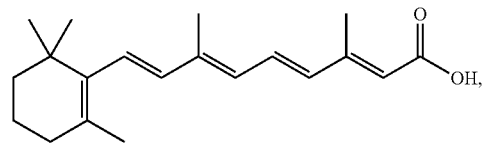 [SMILES: CC1=C(/C=C/C(C)=C/C=C/C(C)=C/C(=O)O)C(C)(C)CCC1]
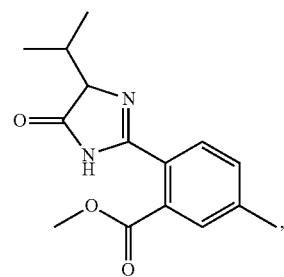 [SMILES: COC(=O)c1cc(C)ccc1C1=NC(C(C)C)C(=O)N1]
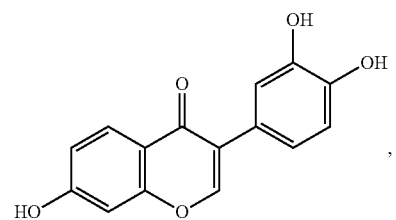 [SMILES: O=c1c(-c2ccc(O)c(O)c2)coc2cc(O)ccc12 ; ","]
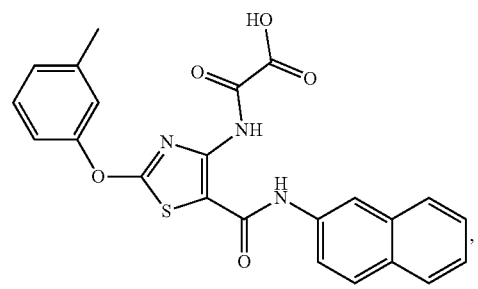 [SMILES: Cc1cccc(Oc2nc(NC(=O)C(=O)O)c(C(=O)Nc3ccc4ccccc4c3)s2)c1]
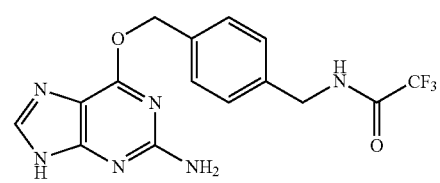 [SMILES: Nc1nc(OCc2ccc(CNC(=O)C(F)(F)F)cc2)c2nc[nH]c2n1]

In some embodiments, the Pin1 inhibitor is an analogue of retinoic acid. In yet other embodiments, the Pin1 inhibitor is selected from Table D, or a pharmaceutically acceptable salt thereof.
TABLE D
Pin1 inhibitors
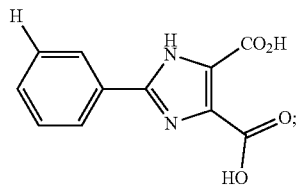
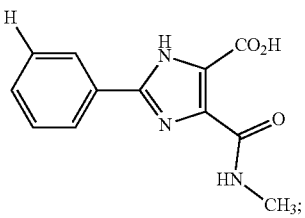 [SMILES: CNC(=O)c1nc(-c2ccccc2)[nH]c1C(=O)O]
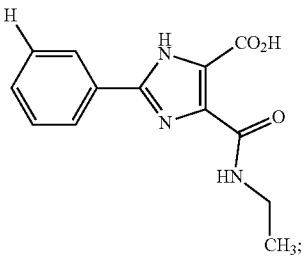 [SMILES: CCNC(=O)c1nc(-c2ccccc2)[nH]c1C(=O)O]
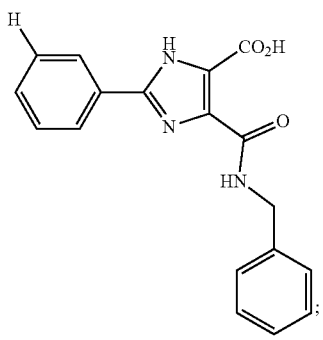 [SMILES: O=C(NCc1ccccc1)c1nc(-c2ccccc2)[nH]c1C(=O)O]
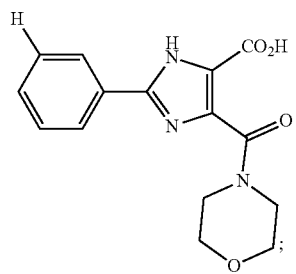 [SMILES: O=C(O)c1[nH]c(-c2ccccc2)nc1C(=O)N1CCOCC1]
TABLE D-continued
Pin1 inhibitors
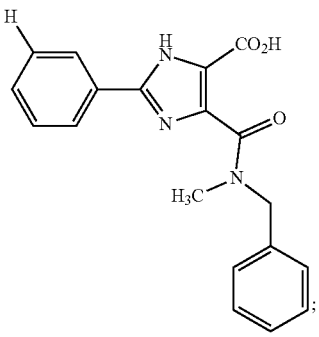 [SMILES: CN(Cc1ccccc1)C(=O)c1nc(-c2ccccc2)[nH]c1C(=O)O]
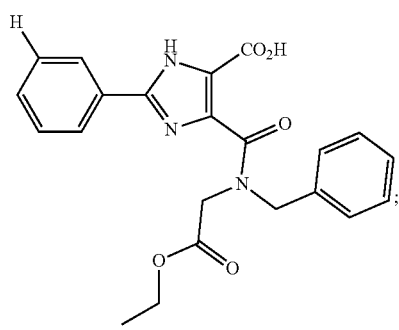 [SMILES: CCOC(=O)CN(Cc1ccccc1)C(=O)c1nc(-c2ccccc2)[nH]c1C(=O)O]
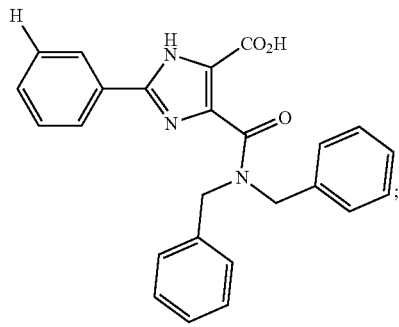 [SMILES: O=C(O)c1[nH]c(-c2ccccc2)nc1C(=O)N(Cc1ccccc1)Cc1ccccc1]
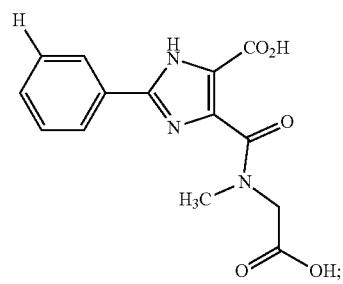 [SMILES: CN(CC(=O)O)C(=O)c1nc(-c2ccccc2)[nH]c1C(=O)O]
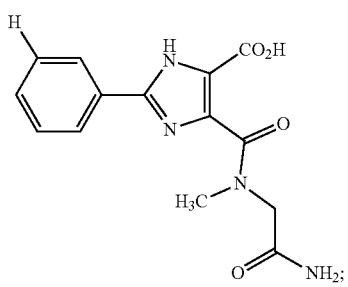 [SMILES: CN(CC(N)=O)C(=O)c1nc(-c2ccccc2)[nH]c1C(=O)O]

TABLE D-continued

Pin1 inhibitors

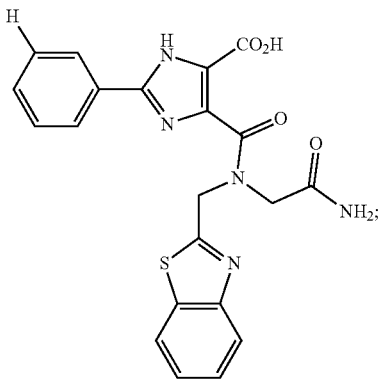 [SMILES: NC(=O)CN(Cc1nc2ccccc2s1)C(=O)c1nc(-c2ccccc2)[nH]c1C(=O)O]

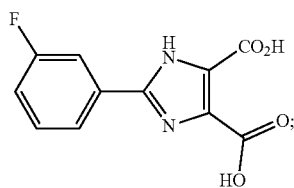 [SMILES: O=C(O)c1nc(-c2cccc(F)c2)[nH]c1C(=O)O]

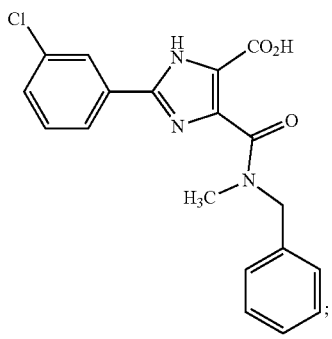 [SMILES: CN(Cc1ccccc1)C(=O)c1nc(-c2cccc(Cl)c2)[nH]c1C(=O)O]

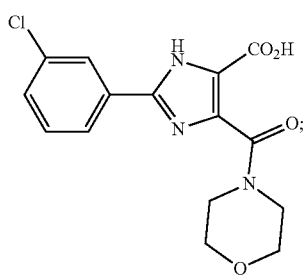 [SMILES: O=C(O)c1[nH]c(-c2cccc(Cl)c2)nc1C(=O)N1CCOCC1]

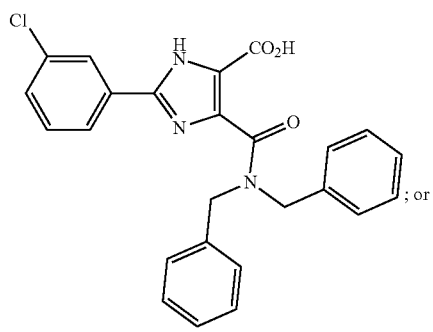 [SMILES: O=C(O)c1[nH]c(-c2cccc(Cl)c2)nc1C(=O)N(Cc1ccccc1)Cc1ccccc1]

TABLE D-continued

Pin1 inhibitors

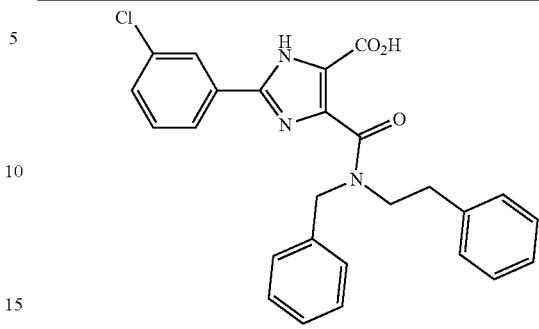

In yet other embodiments, the Pin1 inhibitor is a peptide. In some such embodiments, the peptide is selected from: CRYPEVEIC, wherein the cysteine residues of said peptide are cyclized by a disulfide bond (SEQ ID NO: 1); Ac-Lys (N-biotinoyl)-AlaAla-Bth-D-Thr(PO₃H₂)-Pip-Nal-Gln-NH₂ (SEQ ID NO: 2); Ac-Phe-D-Thr(PO₃H₂)-Pip-Nal-Gln-NH₂ (SEQ TD NO: 3); and Ac-Phe-Phe-pSer-Ψ[(Z)CHdC-Pro-Arg-NH₂ (SEQ ID NO: 4).

In one embodiment, Pin1 inhibitor is selected from 5-hydroxy-1,4-naphthalenedione, (1-piperidinecarbodithioic acid, anhydrosulfide), or diethyl-1,3,6,8-tetrahydro-1,3,6, 8tetraoxobenzo[1mn] phenanthroline-2,7-diacetate, or a pharmaceutically acceptable salt thereof.

In one embodiment, Pin1 inhibitor is juglone or ATRA. In one embodiment, Pin1 inhibitor is ATRA.

Other Therapeutically Active Agents

The pharmaceutical composition of the present disclosure comprises a second therapeutically active agent. The second therapeutically active agent can be selected from a poly (ADP-ribose) polymerase (PARP) inhibitor, an androgen receptor ligand-binding domain inhibitor, an inhibitor of CYP17, a microtubule inhibitor, a modulator of PD-1 or PD-L1, a gonadotropin releasing hormone agonist, a 5-alpha reductase inhibitor, a vascular endothelial growth factor inhibitor, a histone deacetylase inhibitor, an integrin alpha-v-beta-3 inhibitor, a receptor tyrosine kinase, a phosphoinositide 3-kinase inhibitor, an anaplastic lymphoma kinase (ALK) inhibitor, an endothelin receptor A antagonist, an anti-CTLA4 inhibitor, an heat shock protein 27 (HSP27) inhibitor, an androgen receptor degrader, a androgen receptor DNA-binding domain inhibitor, a bromodomain and extra-terminal motif (BET) inhibitor, an androgen receptor N-terminal domain inhibitor, an alpha-particle emitting radioactive therapeutic agent, niclosamide, a selective estrogen receptor modulator (SERM), a selective estrogen receptor degrader (SERD), an aromatase inhibitor, selective progesterone receptor modulator (SPRM), a glucocorticoid receptor inhibitor, a CDK4/6 inhibitor, a HER2 receptor antagonist, a mammalian target of rapamycin (mTOR) inhibitor, an AKT inhibitor, a B-cell lymphoma-2 (Bcl-2) inhibitor, an aurora kinase inhibitor, a Wnt-targeting antagonist, a CYP11a inhibitor, a selective androgen receptor N-terminal domain inhibitor, or enhancer of zeste homolog 2 (EZH2) inhibitor.

The pharmaceutical composition of the present disclosure comprises a second therapeutically active agent. The second therapeutically active agent can be selected from a poly (ADP-ribose) polymerase (PARP) inhibitor, an androgen receptor ligand-binding domain inhibitor, an inhibitor of CYP17, a microtubule inhibitor, a modulator of PD-1 or PD-L1, a gonadotropin releasing hormone agonist, a 5-alpha reductase inhibitor, a vascular endothelial growth factor inhibitor, a histone deacetylase inhibitor, an integrin alpha-v-beta-3 inhibitor, a receptor tyrosine kinase, a phosphoinositide 3-kinase inhibitor, an anaplastic lymphoma kinase (ALK) inhibitor, an endothelin receptor A antagonist, an anti-CTLA4 inhibitor, an heat shock protein 27 (HSP27) inhibitor, an androgen receptor degrader, a androgen receptor DNA-binding domain inhibitor, a bromodomain and extra-terminal motif (BET) inhibitor, an androgen receptor N-terminal domain inhibitor, an alpha-particle emitting radioactive therapeutic agent, niclosamide, a selective estrogen receptor modulator (SERM), a selective estrogen receptor degrader (SERD), an aromatase inhibitor, selective progesterone receptor modulator (SPRM), a glucocorticoid receptor inhibitor, a CDK4/6 inhibitor, a HER2 receptor antagonist, or a mammalian target of rapamycin (mTOR) inhibitor.

In one embodiment, the second therapeutically active agent is selected from a poly (ADP-ribose) polymerase (PARP) inhibitor including but not limited to olaparib, niraparib, rucaparib, talazoparib; an androgen receptor ligand-binding domain inhibitor including but not limited to enzalutamide, apalutamide, darolutamide, bicalutamide, nilutamide, flutamide, ODM-204, TAS3681; an inhibitor of CYP17 including but not limited to galeterone, abiraterone, abiraterone acetate; a microtubule inhibitor including but not limited to docetaxel, paclitaxel, cabazitaxel (XRP-6258); a modulator of PD-1 or PD-L1 including but not limited to pembrolizumab, durvalumab, nivolumab, atezolizumab; a gonadotropin releasing hormone agonist including but not limited to cyproterone acetate, leuprolide; a 5-alpha reductase inhibitor including but not limited to finasteride, dutasteride, turosteride, bexlosteride, izonsteride, FCE 28260, SKF105,111; a vascular endothelial growth factor inhibitor including but not limited to bevacizumab (Avastin); a histone deacetylase inhibitor including but not limited to OSU-HDAC42; an integrin alpha-v-beta-3 inhibitor including but not limited to VITAXIN; a receptor tyrosine kinase including but not limited to sunitumib; a phosphoinositide 3-kinase inhibitor including but not limited to alpelisib, buparlisib, idealisib; an anaplastic lymphoma kinase (ALK) inhibitor including but not limited to crizotinib, alectinib; an endothelin receptor A antagonist including but not limited to ZD-4054; an anti-CTLA4 inhibitor including but not limited to MDX-010 (ipilimumab); an heat shock protein 27 (HSP27) inhibitor including but not limited to OGX 427; an androgen receptor degrader including but not limited to ARV-330, ARV-110; a androgen receptor DNA-binding domain inhibitor including but not limited to VPC-14449; a bromodomain and extra-terminal motif (BET) inhibitor including but not limited to BI-894999, GSK25762, GS-5829; an N-terminal domain inhibitor including but not limited to a sintokamide; an alpha-particle emitting radioactive therapeutic agent including but not limited to radium 233 or a salt thereof; niclosamide; or related compounds thereof; a selective estrogen receptor modulator (SERM) including but not limited to tamoxifen, raloxifene, toremifene, arzoxifene, bazedoxifene, pipindoxifene, lasofoxifene, enclomiphene; a selective estrogen receptor degrader (SERD) including but not limited to fulvestrant, ZB716, OP-1074, elacestrant, AZD9496, GDC0810, GDC0927, GW5638, GW7604; an aromatase inhibitor including but not limited to anastrazole, exemestane, letrozole; selective progesterone receptor modulators (SPRM) including but not limited to mifepristone, lonaprison, onapristone, asoprisnil, lonaprisnil, ulipristal, telapristone; a glucocorticoid receptor inhibitor including but not limited to mifepristone, COR108297, COR125281, ORIC-101, PT150; CDK4/6 inhibitors including palbociclib, abemaciclib, ribociclib; HER2 receptor antagonist including but not limited to trastuzumab, neratinib; or a mammalian target of rapamycin (mTOR) inhibitor including but not limited to everolimus, temsirolimus, an AKT inhibitor including but not limited to MK-2206; a Bcl-2 inhibitor including but not limited to venetoclax; an aurora kinase inhibitor including but not limited to alisertib; a Wnt-targeting antagonist including but not limited to DKK-1-4 proteins (Dikhopf), secreted Frazzle related proteins (sFRP); a CYP11a inhibitor including but not limited to ODM-208; a selective androgen receptor N-terminal domain inhibitor including but not limited to LY2452473; or EZH2 inhibitor including but not limited to CPI-1205.

In one embodiment, the second therapeutically active agent is selected from a poly (ADP-ribose) polymerase (PARP) inhibitor including but not limited to olaparib, niraparib, rucaparib, talazoparib; an androgen receptor ligand-binding domain inhibitor including but not limited to enzalutamide, apalutamide, darolutamide, bicalutamide, nilutamide, flutamide, ODM-204, TAS3681; an inhibitor of CYP17 including but not limited to galeterone, abiraterone, abiraterone acetate; a microtubule inhibitor including but not limited to docetaxel, paclitaxel, cabazitaxel (XRP-6258); a modulator of PD-1 or PD-L1 including but not limited to pembrolizumab, durvalumab, nivolumab, atezolizumab; a gonadotropin releasing hormone agonist including but not limited to cyproterone acetate, leuprolide; a 5-alpha reductase inhibitor including but not limited to finasteride, dutasteride, turosteride, bexlosteride, izonsteride, FCE 28260, SKF105,111; a vascular endothelial growth factor inhibitor including but not limited to bevacizumab (Avastin); a histone deacetylase inhibitor including but not limited to OSU-HDAC42; an integrin alpha-v-beta-3 inhibitor including but not limited to VITAXIN; a receptor tyrosine kinase including but not limited to sunitumib; a phosphoinositide 3-kinase inhibitor including but not limited to alpelisib, buparlisib, idealisib; an anaplastic lymphoma kinase (ALK) inhibitor including but not limited to crizotinib, alectinib; an endothelin receptor A antagonist including but not limited to ZD-4054; an anti-CTLA4 inhibitor including but not limited to MDX-010 (ipilimumab); an heat shock protein 27 (HSP27) inhibitor including but not limited to OGX 427; an androgen receptor degrader including but not limited to ARV-330, ARV-110; a androgen receptor DNA-binding domain inhibitor including but not limited to VPC-14449; a bromodomain and extra-terminal motif (BET) inhibitor including but not limited to BI-894999, GSK25762, GS-5829; an N-terminal domain inhibitor including but not limited to a sintokamide; an alpha-particle emitting radioactive therapeutic agent including but not limited to radium 233 or a salt thereof; niclosamide; or related compounds thereof; a selective estrogen receptor modulator (SERM) including but not limited to tamoxifen, raloxifene, toremifene, arzoxifene, bazedoxifene, pipindoxifene, lasofoxifene, enclomiphene; a selective estrogen receptor degrader (SERD) including but not limited to fulvestrant, ZB716, OP-1074, elacestrant, AZD9496, GDC0810, GDC0927, GW5638, GW7604; an aromatase inhibitor including but not limited to anastrazole, exemestane, letrozole; selective progesterone receptor modulators (SPRM) including but not limited to mifepristone, lonaprison, onapristone, asoprisnil, lonaprisnil, ulipristal, telapristone; a glucocorticoid receptor inhibitor including but not limited to mifepristone, COR108297, COR125281, ORIC-101, PT150; CDK4/6 inhibitors including palbociclib, abemaciclib, ribociclib; HER2 receptor antagonist including but not limited to trastuzumab, neratinib; or a mammalian target of rapamycin (mTOR) inhibitor including but not limited to everolimus, temsirolimus.

In one embodiment, the second therapeutically active agent is a microtubule inhibitor. In one embodiment, the microtubule inhibitor is selected from docetaxel, paclitaxel, or cabazitaxel (XRP-6258). In one embodiment, the microtubule inhibitor is docetaxel.

In one embodiment, the second therapeutically active agent is a Bcl-2 inhibitor. In one embodiment, the Bcl-2 inhibitor is venetoclax.

Therapeutic Use

The pharmaceutical compositions and combinations of the present disclosure find use in any number of methods. For example, in some embodiments the compounds are useful in methods for modulating androgen receptor (AR). In some embodiments the compounds are useful in methods for inhibiting androgen receptor (AR). In some embodiments the compounds are useful in methods for inhibiting AR N-terminal domain. In some embodiments, inhibiting androgen receptor (AR) activity is in a mammalian cell. In some embodiments, inhibiting androgen receptor (AR) can be in a subject in need thereof (e.g., a mammalian subject) and for treatment of any of the described conditions or diseases.

In other embodiments, inhibiting androgen receptor (AR) activity is for treatment of at least one indication selected from the group consisting of: prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, age related macular degeneration, and combinations thereof. For example in some embodiments, the indication is prostate cancer. In other embodiments, the prostate cancer is primary/localized prostate cancer, locally advanced prostate cancer, recurrent prostate cancer, metastatic prostate cancer, advanced prostate cancer, or metastatic castration-resistant prostate cancer (CRPC), or hormone-sensitive prostate cancer. While in other embodiments, the prostate cancer is androgen dependent prostate cancer. In other embodiments, the spinal and bulbar muscular atrophy is Kennedy's disease.

In one embodiment of the present disclosure, a method of treating a condition associated with cell proliferation in a patient in need thereof is provided, comprising administering a pharmaceutical composition or a combination as disclosed herein, comprising a CDK4/6 inhibitor and an androgen receptor N-terminal domain inhibitor having the structure of formula (i)-(iv) or (a), or a pharmaceutically acceptable salt, tautomer, stereoisomer or prodrug thereof, to a subject in need thereof. In one embodiment, the present invention provides a method of treating cancer or tumors. In another embodiment, the present invention provides a method of treating prostate cancer or breast cancer. In another embodiment, the present invention provides a method of treating prostate cancer.

In one embodiment of the present disclosure, a method of reducing, inhibiting, or ameliorating proliferation, comprising administering a therapeutically effective amount of a pharmaceutical composition or a combination comprising a CDK4/6 inhibitor and an androgen receptor N-terminal domain inhibitor having the structure of formula (i)-(iv) or (a), or a pharmaceutically acceptable salt, tautomer, stereoisomer or prodrug thereof, is provided. In one embodiment, the reducing, inhibiting, or ameliorating in the method disclosed herein, is in vivo. In another embodiment, the reducing, inhibiting, or ameliorating is in vitro.

In one embodiment, the cells in the method disclosed herein, are a cancer cells. In one embodiment, the cancer cells are a prostate cancer cells. In one embodiment, the prostate cancer cells are cells of primary/localized prostate cancer (newly diagnosed or early stage), locally advanced prostate cancer, recurrent prostate cancer (e.g., prostate cancer which was not cured with primary therapy), metastatic prostate cancer, advanced prostate cancer (e.g., after castration for recurrent prostate cancer), metastatic castration-resistant prostate cancer (CRPC), or hormone-sensitive prostate cancer. In another embodiment, the prostate cancer cells are cells of a metastatic castration-resistant prostate cancer. In other embodiments, the prostate cancer cells are an androgen-dependent prostate cancer cells or an androgen-independent prostate cancer cells. In one embodiment, the cancer cells are breast cancer cells.

In one embodiment, the condition or disease associated with cell proliferation is cancer. In one embodiment of any one of the methods disclosed herein, the cancer is selected from the group consisting of: prostate cancer, breast cancer, ovarian cancer, endometrial cancer, salivary gland carcinoma, hair loss, acne, hirsutism, ovarian cysts, polycystic ovary disease, precocious puberty, spinal and bulbar muscular atrophy, and age-related macular degeneration. In one embodiment, the condition or disease is prostate cancer. In one embodiment, prostate cancer is selected from primary/localized prostate cancer, locally advanced prostate cancer, recurrent prostate cancer, metastatic prostate cancer, advanced prostate cancer, metastatic castration-resistant prostate cancer (CRPC), or hormone-sensitive prostate cancer. In another embodiment, the prostate cancer is a metastatic castration-resistant prostate cancer. In some embodiments, the prostate cancer is an androgen-dependent prostate cancer cells or an androgen-independent prostate cancer. In one embodiment, the condition or disease is breast cancer. In one embodiment, the breast cancer is triple negative breast cancer. In some embodiments, the breast cancer is AR-positive triple negative breast cancer.

In another embodiment of the present disclosure, a method for reducing or preventing tumor growth, comprising contacting tumor cells with a pharmaceutical composition or a combination as disclosed herein, comprising a CDK4/6 inhibitor and an androgen receptor N-terminal domain inhibitor having the structure of formula (i)-(iv) or (a), or a pharmaceutically acceptable salt, tautomer, stereoisomer or prodrug thereof is provided.

In one embodiment, reducing or preventing tumor growth includes reduction in tumor volume. In one embodiment, reducing or preventing tumor growth includes complete elimination of tumors. In one embodiment, reducing or preventing tumor growth includes stopping or halting the existing tumor to grow. In one embodiment, reducing or preventing tumor growth includes reduction in the rate of tumor growth. In one embodiment, reducing or preventing tumor growth includes reduction in the rate of tumor growth such that the rate of tumor growth before treating a patient with the methods disclosed herein (r1) is faster than the rate of tumor growth after said treatment (r2) such that r1>r2.

In one embodiment, the reducing or preventing in the method disclosed herein is in vivo. In another embodiment, the treating is in vitro.

In one embodiment, the tumor cell in the method disclosed herein is selected from prostate cancer, breast cancer, ovarian cancer, endometrial cancer, or salivary gland carcinoma. In one embodiment, the tumor cells are prostate cancer tumor cells. In one embodiment, the prostate cancer tumor cells are tumor cells of primary/localized prostate cancer, locally advanced prostate cancer, recurrent prostate cancer, metastatic prostate cancer, advanced prostate cancer, metastatic castration-resistant prostate cancer (CRPC), or hormone-sensitive prostate cancer. In other embodiments, the prostate cancer is a metastatic castration-resistant prostate cancer. In some embodiments, the prostate cancer is androgen-dependent prostate cancer or androgen-independent prostate cancer. In another embodiment, the tumor cells are is breast cancer tumor cells.

The present disclosure also relates to use of the androgen receptor N-terminal domain inhibitors or compositions thereof as disclosed herein for treatment of cancer in combination with radiation therapy.

In one embodiment of the methods with radiation therapy, the type of radiation can include X-rays gamma rays, high energy electrons and high LET (Linear Energy Transfer) radiation, such as, protons, neutron, and alpha particles. The ionizing radiation can be employed by techniques well known to those skilled in the art. For example, X-rays and gamma rays are applied by external and/or interstitial means from linear accelerators or radioactive sources. High-energy electrons can be produced by linear accelerators and high LET radiation is also applied from radioactive sources implanted interstitially. The total dose of radiation employed by one skilled in the art can range from 18 to 160 Gray (Gy). (One Gray unit of measure is equal to 100 rads) The total dose of radiation can be divided into 5 to 7 continuous weeks of therapy. In one embodiment, one week of radiation is divided into 5 daily fractions. A daily fraction of radiation consists of a dose from 1.2 to 2.5 Gray. The total amount of radiation used in brachytherapy may be 160 Gy. The exact dosage of radiation can dependent on a variety of factors including but not limited to the volume of the cancerous tissue to be irradiated, normal tissue surrounding the cancerous tissue, age of the patient, medical history of the patient, and other clinical factors. See, R. Arriagada, Hematology/Oncology Clinics of North America, Vol. 11, pgs. 461-472 (1997) and S. Hellman, Principles of Cancer Management: Radiation Therapy, in Cancer: Principles and Practice of Oncology, 5$^{th}$ Ed., Lippincott Publishers, pgs. 307-332 (1997); the disclosure of which is herein incorporated by reference.

In one embodiment of the method with radiation therapy, the radiation therapy is administered in the same treatment period as the androgen receptor N-terminal domain inhibitor or the composition/combination thereof. That is, the subject receives radiation therapy on the same day or the same week as the androgen receptor N-terminal domain inhibitor or the composition/combination thereof. In one embodiment, the radiation therapy is administered within 24 hours of administration of the androgen receptor N-terminal domain inhibitor or a composition/combination thereof.

In one embodiment of the method with radiation therapy, the radiation therapy is administered in a different treatment period as the androgen receptor N-terminal domain inhibitor or the composition/combination thereof. That is, the subject first receives treatment with the androgen receptor N-terminal domain inhibitor or the composition/combination thereof for a duration as prescribed by a medical professional and upon completion of the androgen receptor modulator treatment, is administered radiation therapy, or vice versa.

In one embodiment of the methods disclosed herein, radiation therapy is administered concurrently with lutetium-177 or other alpha emitters, to a subject who has been treated or in treatment with the androgen receptor N-terminal domain inhibitor or the composition/combination thereof as disclosed herein. In one embodiment lutetium-177 is targeted for prostate cancer cells.

In one embodiment of the methods disclosed herein, radiation therapy is administered concurrently with a prostate specific membrange antigen (PSMA) ligand. In one embodiment, PSMA ligand is targeted for prostate cancer cells.

In one embodiment of the methods disclosed herein, Compound 13a is administered in a patient in need thereof in combination with radiation therapy. In one embodiment, the method of combining administration of Compound 13a with radiation therapy increases accumulation of DNA damage. In one embodiment, the method of combining administration of Compound 13a with radiation therapy increases accumulation of DNA damage.

Pharmaceutical Compositions and Formulations

The pharmaceutical composition or a combination as disclosed herein, can further comprise a pharmaceutically acceptable carrier or excipient.

In one embodiment, pharmaceutical composition or a combination comprises an androgen receptor N-terminal domain inhibitor selected from Table A, or a pharmaceutically acceptable salt or solvate thereof, a second therapeutically effective agent, and a pharmaceutically acceptable carrier or excipient. In one embodiment, the pharmaceutical composition or the combination comprises a Pin1 inhibitor, an androgen receptor N-terminal domain inhibitor selected from Table A, or a pharmaceutically acceptable salt or solvate thereof, and a pharmaceutically acceptable carrier or excipient. In one embodiment, pharmaceutical composition or a combination comprises ATRA, an androgen receptor modulator selected from Table A, or a pharmaceutically acceptable salt or solvate thereof, and a pharmaceutically acceptable carrier or excipient. In one embodiment, the pharmaceutical composition or the combination comprises a CDK4/6 inhibitor, an androgen receptor N-terminal domain inhibitor selected from Table A, or a pharmaceutically acceptable salt or solvate thereof, and a pharmaceutically acceptable carrier or excipient. In one embodiment, the pharmaceutical composition or the combination comprises palbociclib, an androgen receptor N-terminal domain inhibitor selected from Table A, or a pharmaceutically acceptable salt or solvate thereof, and a pharmaceutically acceptable carrier or excipient. In one embodiment, the pharmaceutical composition or the combination comprises a Bcl-2 inhibitor, an androgen receptor N-terminal domain inhibitor selected from Table A, or a pharmaceutically acceptable salt or solvate thereof, and a pharmaceutically acceptable carrier or excipient. In one embodiment, the pharmaceutical composition or the combination comprises venetoclax, an androgen receptor N-terminal domain inhibitor selected from Table A, or a pharmaceutically acceptable salt or solvate thereof, and a pharmaceutically acceptable carrier or excipient. In one embodiment, the pharmaceutical composition or the combination comprises an androgen receptor ligand-binding domain inhibitor, an androgen receptor N-terminal domain inhibitor selected from Table A, or a pharmaceutically acceptable salt or solvate thereof, and a pharmaceutically acceptable carrier or excipient. In one embodiment, the pharmaceutical composition or the combination comprises a) enzalutamide, apalutamide, or darolutamide, b) an androgen receptor N-terminal domain inhibitor selected from Table A, or a pharmaceutically acceptable salt or solvate thereof, and c) a pharmaceutically acceptable carrier or excipient. In one embodiment, the pharmaceutical composition or the combination comprises a microtubule inhibitor, an androgen receptor N-terminal domain inhibitor selected from Table A, or a pharmaceutically acceptable salt or solvate thereof, and a pharmaceutically acceptable carrier or excipient. In one embodiment, the pharmaceutical composition or the combination comprises docetaxel, an androgen receptor N-terminal domain inhibitor selected from Table A, or a pharmaceutically acceptable salt or solvate thereof, and a pharmaceutically acceptable carrier or excipient.

In one embodiment, pharmaceutical composition or a combination comprises an androgen receptor N-terminal domain inhibitor selected from Table B, or a pharmaceutically acceptable salt or solvate thereof, a second therapeutically effective agent, and a pharmaceutically acceptable carrier or excipient. In one embodiment, the pharmaceutical composition or the combination comprises a Pin1 inhibitor, an androgen receptor N-terminal domain inhibitor selected from Table B, or a pharmaceutically acceptable salt or solvate thereof, and a pharmaceutically acceptable carrier or excipient. In one embodiment, pharmaceutical composition or a combination comprises ATRA, an androgen receptor modulator selected from Table B, or a pharmaceutically acceptable salt or solvate thereof, and a pharmaceutically acceptable carrier or excipient. In one embodiment, the pharmaceutical composition or the combination comprises a CDK4/6 inhibitor, an androgen receptor N-terminal domain inhibitor selected from Table B, or a pharmaceutically acceptable salt or solvate thereof, and a pharmaceutically acceptable carrier or excipient. In one embodiment, the pharmaceutical composition or the combination comprises palbociclib, an androgen receptor N-terminal domain inhibitor selected from Table B, or a pharmaceutically acceptable salt or solvate thereof, and a pharmaceutically acceptable carrier or excipient. In one embodiment, the pharmaceutical composition or the combination comprises a Bcl-2 inhibitor, an androgen receptor N-terminal domain inhibitor selected from Table B, or a pharmaceutically acceptable salt or solvate thereof, and a pharmaceutically acceptable carrier or excipient. In one embodiment, the pharmaceutical composition or the combination comprises venetoclax, an androgen receptor N-terminal domain inhibitor selected from Table B, or a pharmaceutically acceptable salt or solvate thereof, and a pharmaceutically acceptable carrier or excipient. In one embodiment, the pharmaceutical composition or the combination comprises an androgen receptor ligand-binding domain inhibitor, an androgen receptor N-terminal domain inhibitor selected from Table B, or a pharmaceutically acceptable salt or solvate thereof, and a pharmaceutically acceptable carrier or excipient. In one embodiment, the pharmaceutical composition or the combination comprises a) enzalutamide, apalutamide, or darolutamide, b) an androgen receptor N-terminal domain inhibitor selected from Table B, or a pharmaceutically acceptable salt or solvate thereof, and c) a pharmaceutically acceptable carrier or excipient. In one embodiment, the pharmaceutical composition or the combination comprises a microtubule inhibitor, an androgen receptor N-terminal domain inhibitor selected from Table B, or a pharmaceutically acceptable salt or solvate thereof, and a pharmaceutically acceptable carrier or excipient. In one embodiment, the pharmaceutical composition or the combination comprises docetaxel, an androgen receptor N-terminal domain inhibitor selected from Table B, or a pharmaceutically acceptable salt or solvate thereof, and a pharmaceutically acceptable carrier or excipient.

In one embodiment, pharmaceutical composition or a combination comprises ATRA, Compound 13a, or a pharmaceutically acceptable salt or solvate thereof, and a pharmaceutically acceptable carrier or excipient. In one embodiment, pharmaceutical composition or a combination comprises palbociclib, Compound 13a, or a pharmaceutically acceptable salt or solvate thereof, and a pharmaceutically acceptable carrier or excipient. In one embodiment, pharmaceutical composition or a combination comprises venetoclax, Compound 13a, or a pharmaceutically acceptable salt or solvate thereof, and a pharmaceutically acceptable carrier or excipient.

In one embodiment, pharmaceutical composition or a combination comprises enzalutamide, Compound 13a, or a pharmaceutically acceptable salt or solvate thereof, and a pharmaceutically acceptable carrier or excipient.

In one embodiment, a pharmaceutical composition, as described herein, further comprises one or more additional therapeutically active agents. In one embodiment, one or more additional therapeutically active agents are selected from therapeutics useful for treating cancer, neurological disease, a disorder characterized by abnormal accumulation of a-synuclein, a disorder of an aging process, cardiovascular disease, bacterial infection, viral infection, mitochondrial related disease, mental retardation, deafness, blindness, diabetes, obesity, autoimmune disease, glaucoma, Leber's Hereditary Optic Neuropathy, and rheumatoid arthritis.

In some embodiments, the one or more additional therapeutic agents is a poly (ADP-ribose) polymerase (PARP) inhibitor including but not limited to olaparib, niraparib, rucaparib, talazoparib; an androgen receptor ligand-binding domain inhibitor including but not limited to enzalutamide, apalutamide, darolutamide, bicalutamide, nilutamide, flutamide, ODM-204, TAS3681; an inhibitor of CYP17 including but not limited to galeterone, abiraterone, abiraterone acetate; a microtubule inhibitor including but not limited to docetaxel, paclitaxel, cabazitaxel (XRP-6258); a modulator of PD-1 or PD-L1 including but not limited to pembrolizumab, durvalumab, nivolumab, atezolizumab; a gonadotropin releasing hormone agonist including but not limited to cyproterone acetate, leuprolide; a 5-alpha reductase inhibitor including but not limited to finasteride, dutasteride, turosteride, bexlosteride, izonsteride, FCE 28260, SKF105,111; a vascular endothelial growth factor inhibitor including but not limited to bevacizumab (Avastin); a histone deacetylase inhibitor including but not limited to OSU-HDAC42; an integrin alpha-v-beta-3 inhibitor including but not limited to VITAXIN; a receptor tyrosine kinase including but not limited to sunitumib; a phosphoinositide 3-kinase inhibitor including but not limited to alpelisib, buparlisib, idealisib; an anaplastic lymphoma kinase (ALK) inhibitor including but not limited to crizotinib, alectinib; an endothelin receptor A antagonist including but not limited to ZD-4054; an anti-CTLA4 inhibitor including but not limited to MDX-010 (ipilimumab); an heat shock protein 27 (HSP27) inhibitor including but not limited to OGX 427; an androgen receptor degrader including but not limited to ARV-330, ARV-110; a androgen receptor DNA-binding domain inhibitor including but not limited to VPC-14449; a bromodomain and extra-terminal motif (BET) inhibitor including but not limited to BI-894999, GSK25762, GS-5829; an N-terminal domain inhibitor including but not limited to a sintokamide; an alpha-particle emitting radioactive therapeutic agent including but not limited to radium 233 or a salt thereof; niclosamide; or related compounds thereof; a selective estrogen receptor modulator (SERM) including but not limited to tamoxifen, raloxifene, toremifene, arzoxifene, bazedoxifene, pipindoxifene, lasofoxifene, enclomiphene; a selective estrogen receptor degrader (SERD) including but not limited to fulvestrant, ZB716, OP-1074, elacestrant, AZD9496, GDC0810, GDC0927, GW5638, GW7604; an aromatase inhibitor including but not limited to anastrazole, exemestane, letrozole; selective progesterone receptor modulators (SPRM) including but not limited to mifepristone, lonaprison, onapristone, asoprisnil, lonaprisnil, ulipristal, telapristone; a glucocorticoid receptor inhibitor including but not limited to mifepristone, COR108297, COR125281, ORIC-101, PT150; CDK4/6 inhibitors including palbociclib, abemaciclib, ribociclib; HER2 receptor antagonist including but not limited to trastuzumab, neratinib; a mammalian target of rapamycin (mTOR) inhibitor including but not limited to everolimus, temsirolimus.

In a further embodiment of the present disclosure, a pharmaceutical composition or combination as disclosed herein comprises a pharmaceutically acceptable carrier, excipient or adjuvant is provided. The pharmaceutically acceptable carriers, excipients and adjuvants are added to the composition or formulation for a variety of purposes. In one embodiment, a pharmaceutically acceptable carrier includes a pharmaceutically acceptable excipient, binder, and/or diluent. In one embodiment, suitable pharmaceutically acceptable excipients include, but are not limited to, water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, the pharmaceutical compositions of the present disclosure may additionally contain other adjunct components conventionally found in pharmaceutical compositions, at their art-established usage levels. Thus, for example, the pharmaceutical compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

For the purposes of this disclosure, the compounds of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

The compounds disclosed herein can be formulated in accordance with the routine procedures adapted for desired administration route. Accordingly, the compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in Remington: The Science and Practice of Pharmacy, A. Gennaro, ed., 20th edition, Lippincott, Williams & Wilkins, Philadelphia, PA.

In certain embodiments, a pharmaceutical composition of the present disclosure is prepared using known techniques, including, but not limited to mixing, dissolving, granulating, dragee-making, levigating, emulsifying, encapsulating, entrapping or tableting processes.

In one embodiment, suitable pharmaceutically acceptable carriers include, but are not limited to, inert solid fillers or diluents and sterile aqueous or organic solutions. Pharmaceutically acceptable carriers are well known to those skilled in the art and include, but are not limited to, from about 0.01 to about 0.1 M and preferably 0.05M phosphate buffer or 0.8% saline. Such pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate. Aqueous carriers suitable for use in the present application include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellant.

Solid carriers suitable for use in the present application include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Parenteral carriers suitable for use in the present application include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Diluents may be added to the formulations of the present invention. Diluents increase the bulk of a solid pharmaceutical composition and/or combination, and may make a pharmaceutical dosage form containing the composition and/or combination easier for the patient and care giver to handle. Diluents for solid compositions and/or combinations include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Additional embodiments relate to the pharmaceutical formulations wherein the formulation is selected from the group consisting of a solid, powder, liquid and a gel. In certain embodiments, a pharmaceutical composition of the present invention is a solid (e.g., a powder, tablet, a capsule, granulates, and/or aggregates). In certain of such embodiments, a solid pharmaceutical composition comprising one or more ingredients known in the art, including, but not limited to, starches, sugars, diluents, granulating agents, lubricants, binders, and disintegrating agents.

Solid pharmaceutical compositions that are compacted into a dosage form, such as a tablet, may include excipients whose functions include helping to bind the active ingredient and other excipients together after compression. Binders for solid pharmaceutical compositions and/or combinations include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition and/or combination. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of a non-compacted solid composition and/or combination and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition and/or combination to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition and/or combination of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

Liquid pharmaceutical compositions can be prepared where the solid or amorphous components are dissolved or suspended in a liquid carrier such as water, vegetable oil, alcohol, polyethylene glycol, propylene glycol, or glycerin.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Liquid pharmaceutical compositions can contain emulsifying agents to disperse uniformly throughout the composition and/or combination an active ingredient or other excipient that is not soluble in the liquid carrier. Emulsifying agents that may be useful in liquid compositions and/or combinations of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition can also contain a buffer such as gluconic acid, lactic acid, citric acid or acetic acid, sodium gluconate, sodium lactate, sodium citrate, or sodium acetate. Selection of excipients and the amounts used may be readily determined by the formulation scientist based upon experience and consideration of standard procedures and reference works in the field.

In one embodiment, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables. Formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80 and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

Appropriate pharmaceutical compositions of the present disclosure can be determined according to any clinically-acceptable route of administration of the composition to the subject. The manner in which the composition is administered is dependent, in part, upon the cause and/or location. One skilled in the art will recognize the advantages of certain routes of administration. The method includes administering an effective amount of the agent or compound (or composition comprising the agent or compound) to achieve a desired biological response, e.g., an amount effective to alleviate, ameliorate, or prevent, in whole or in part, a symptom of a condition to be treated, e.g., oncology and neurology disorders. In various aspects, the route of administration is systemic, e.g., oral or by injection. The agents or compounds, or pharmaceutically acceptable salts or derivatives thereof, are administered orally, nasally, transdermally, pulmonary, inhalationally, buccally, sublingually, intraperintoneally, subcutaneously, intramuscularly, intravenously, rectally, intrapleurally, intrathecally, intraportally, and parenterally. Alternatively or in addition, the route of administration is local, e.g., topical, intra-tumor and peri-tumor. In some embodiments, the compound is administered orally.

In certain embodiments, a pharmaceutical composition of the present disclosure is prepared for oral administration. In certain of such embodiments, a pharmaceutical composition is formulated by combining one or more agents and pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In other embodiments the compound of the present disclosure are administered by the intravenous route. In further embodiments, the parenteral administration may be provided in a bolus or by infusion.

In certain embodiments, a pharmaceutical composition is prepared for rectal administration, such as a suppository or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more compounds of formula (i)-(iv) or (a), or a pharmaceutically acceptable salt or solvate thereof are formulated as a prodrug. In certain embodiments, upon in vivo administration, a prodrug is chemically converted to the biologically, pharmaceutically or therapeutically more active form. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

In various aspects, the androgen receptor N-terminal domain inhibitors in the pharmaceutical composition or combination as disclosed herein can be administered at about 0.001 mg/kg to about 100 mg/kg body weight (e.g., about 0.01 mg/kg to about 10 mg/kg or about 0.1 mg/kg to about 5 mg/kg).

The concentration of a disclosed compound in a pharmaceutically acceptable mixture will vary depending on several factors, including the dosage of the compound to be administered, the pharmacokinetic characteristics of the compound(s) employed, and the route of administration. The agent may be administered in a single dose or in repeat doses. The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. Treatments may be administered daily or more frequently depending upon a number of factors, including the overall health of a patient, and the formulation and route of administration of the selected compound(s). An ordinarily skilled physician or veterinarian can readily determine and prescribe the effective amount of the drug required to prevent, counter or arrest the progress of the condition.

The compounds or pharmaceutical compositions of the present disclosure may be manufactured and/or administered in single or multiple unit dose forms.

Having now generally described the invention, the same will be more readily understood through reference to the following examples, which are provided by way of illustration and are not intended to be limiting of the present invention.

EXAMPLES

The disclosure now being generally described, it will be more readily understood by reference to the following examples which are included merely for purposes of illustration of certain aspects and embodiments of the present invention, and are not intended to limit the invention.
Synthetic Preparation The novel compounds of the present invention can be prepared in a variety of ways known to one skilled in the art of organic synthesis. The compounds of the present invention can be synthesized using the methods as hereinafter described below, together with synthetic methods known in the art of synthetic organic chemistry or variations thereon as appreciated by those skilled in the art.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis,* 44th. Ed., Wiley & Sons, 2006, as well as in Jerry March, *Advanced Organic Chemistry,* $4^{th}$ edition, John Wiley & Sons, publisher, New York, 1992 which are incorporated herein by reference in their entirety.

Compounds of the present invention can be prepared by the literature methods cited in the following text. The following schemes depict established, known syntheses of these scaffolds.

The groups and/or the substituents of the compounds of the present invention can be synthesized and attached to these scaffolds by the literature methods cited in the following text. The following schemes depict the known techniques for accomplishing this joinder.
General Synthesis Compounds of the present invention can be synthesized using the following methods. General reaction conditions are given, and reaction products can be purified by general known methods including crystallization, silica gel chromatography using various organic solvents such as hexane, cyclohexane, ethyl acetate, methanol and the like, preparative high pressure liquid chromatography or preparative reverse phase high pressure liquid chromatography.
Representative Synthesis of Androgen Receptor N-Terminal Domain Inhibitors For synthesis of Compounds in Table A, see WO 2019/226991 for procedures. The disclosures of WO 2019/226991 are hereby incorporated by reference in their entireties.

Example 1: (S)—N-(3-(4-(2-(3,5-dichloro-4-(3-chloro-2-hydroxypropoxy)phenyl) propan-2-yl)phenoxy)-2-oxopropyl)methanesulfonamide (AA51(S))

To a solution of (R)—N-(3-(4-(2-(3,5-dichloro-4-(oxiran-2-ylmethoxy)phenyl)propan-2-yl)phenoxy)-2-oxopropyl) methanesulfonamide (1g) (30 mg, 0.06 mmol, 1.0 eq.) in MeCN (6 mL) was added $CeCl_3 \cdot 7H_2O$ (34 mg, 0.09 mmol, 1.5 eq.) and the solution was heated to reflux for 16 hours.

The resulting white paste was collected by filtration and washed with ethyl acetate and the clear suspension was concentrated under reduced pressure. The resulting residue was purified by flash silica gel column chromatography (elution: ethyl acetate in hexane) to provide (S)—N-(3-(4-(2-(3,5-dichloro-4-(3-chloro-2-hydroxypropoxy)phenyl)propan-2-yl)phenoxy)-2-oxopropyl)methanesulfonamide (AA51(S)): (13.7 mg, 42.4%) as a colorless oil. LRMS (M+Na$^+$) m/z: calcd 560.05; found 560.0. $^1$HNMR (400 MHz, DMSO-d6): δ 7.44 (t, J=5.6 Hz, 1H), 7.23 (s, 2H), 7.15 (d, J=8.8 Hz, 2H), 6.84 (d, J=8.8 Hz, 2H), 5.55 (d, J=5.2 Hz, 1H), 4.91 (s, 2H), 4.01-4.10 (m, 3H), 3.96 (d, J=5.6 Hz, 2H), 3.82 (dd, J=4.0, 11.2 Hz, 2H), 3.70 (dd, J=4.0, 11.2 Hz, 2H), 2.93 (s, 3H), 1.60 (s, 6H).

Example 2: N-(3-(4-(2-(3,5-dichloro-4-(3-chloropropoxy)phenyl)propan-2-yl)phenoxy)-2-oxopropyl)methanesulfonamide (AA31)

To a solution of (R)—N-(3-(4-(2-(3,5-dichloro-4-(3-CHloropropoxy)phenyl)propan-2-yl)phenoxy)-2-hydroxypropyl)methanesulfonamide (2a) (25.0 mg, 0.048 mmol, 1.0 eq.) in anhydrous dichloromethane (3 mL) was treated Dess-Martin periodinane (41 mg, 0.096 mmol, 2.0 eq.) at 0° C. for 10 minutes. Then it was warmed to the room temperature for 16 hours. The reaction was quenched by the addition of a saturated solution of ammonium chloride (2 ml) and the mixture was extracted with ethyl acetate (2×30 ml). The combined organic layers were washed with deionized water (2×30 ml), dried over anhydrous magnesium sulfate, filtered, and concentrated under reduced pressure. The resulting residue was purified by gradient flash silica gel column chromatography (elution: acetate in hexane) to provide N-(3-(4-(2-(3,5-dichloro-4-(3-chloropropoxy)phenyl)propan-2-yl)phenoxy)-2-oxopropyl)methanesulfonamide (AA31) (30 mg, 88% yield) as a colorless oil. LRMS (M+Na$^+$) m/z: calcd 544.06; found 544.2. 1HNMR (400 MHz, DMSO-d6): δ 7.44 (t, J=5.6 Hz, 1H), 7.24 (s, 2H), 7.15 (d, J=8.8 Hz, 2H), 6.85 (d, J=8.8 Hz, 2H), 4.91 (s, 2H), 4.01 (m, 4H), 3.86 (t, J=6.4 Hz, 2H), 2.93 (s, 3H), 2.19 (m, 2H), 1.60 (s, 6H).

Example 3: 1-(4-(2-(3,5-dichloro-4-(3-chloropropoxy)phenyl)propan-2-yl)phenoxy)-3-(methylsulfonyl)propan-2-one (AA55)

Compound (AA55) was synthesized according to Compound (AA31) by using (S)-2,6-dichloro-4-(2-(4-(2-hydroxy-3-(methylsulfonyl)propoxy)phenyl)propan-2-yl)phenol (3d) Yield (94.1%). LRMS (M+Na$^+$) m/z: calcd 529.06; found 529.3. $^1$HNMR (400 MHz, DMSO-d6): δ 7.24 (s, 2H), 7.15 (d, J=9.2 Hz, 2H), 6.84 (d, J=8.8 Hz, 2H), 4.96 (s, 2H), 4.59 (s, 2H), 4.08 (t, J=6.0 Hz, 2H), 3.86 (t, J=6.0 Hz, 2H), 3.11 (s, 3H), 2.19 (m, 2H), 1.61 (s, 6H).

Example 4: N-(3-(4-(3-(3,5-dichloro-4-(3-chloropropoxy)phenyl)oxetan-3-yl)phenoxy)-2-oxopropyl)methanesulfonamide (AA43)

To a solution of tert-butyl N-(3-(4-(3-(3,5-dichloro-4-(3-chloropropoxy)phenyl)oxetan-3-yl)phenoxy)-2-oxo-propyl)-N-methylsulfonyl-carbamate (60 mg, 0.1 mmol) in DCM (2 mL) was added formic acid (1 mL) and the solution was stirred at 25° C. for 15 min. TLC showed the reaction was completed. The reaction was concentrated under reduced pressure. The residue was purified by prep-HPLC (HCO2H) to give N-(3-(4-(3-(3,5-dichloro-4-(3-chloropropoxy)phenyl)oxetan-3-yl)phenoxy)-2-oxopropyl)methanesulfonamide (6.7 mg, yield: 13.2%) as colorless oil. LCMS purity (220 nm): 94.5%. $^1$H NMR (400 MHz, CHCl$_3$-d) δ 7.18-7.10 (m, 4H), 6.93 (br d, J=7.7 Hz, 2H), 5.20 (br d, J=5.1 Hz, 2H), 5.12 (br d, J=5.3 Hz, 2H), 5.05 (br s, 1H), 4.69 (s, 2H), 4.41 (br d, J=4.2 Hz, 2H), 4.21-4.14 (m, 2H), 3.87 (br t, J=5.8 Hz, 2H), 3.01 (s, 3H), 2.30 (br t, J=5.8 Hz, 2H). %). LRMS (M+H$^+$) m/z: calcd 535.0; found 535.

Example 5: Synthesis of N-(4-(2-(3,5-dichloro-4-(3-chloropropoxy)phenyl)propan-2-yl)benzyl)-2-(methylsulfonamido)acetamide (AA46)

To a solution of 2-bromo-N-[[4-[1-[3,5-dichloro-4-(3-chloropropoxy)phenyl]-1-methyl-ethyl]phenyl]methyl]acetamide (5) (100 mg, 0.20 mol) and Cs$_2$CO$_3$ (321 mg, 0.98 mmol) in DMF (5 mL) was added methanesulfonamide (37.5 mg, 0.39 mmol). Then the resulting solution was stirred at 25° C. for 2 hours. LCMS showed the reaction was completed. The solution was poured into water (5 mL) and the organic layer was separated. The aqueous phase was extracted with EtOAc (3 mL×4). The combined organic layers were washed with brine (4 mL×3), dried over Na$_2$SO$_4$, filtered and concentrated. The crude product was purified by prep-HPLC (TFA) to give the N-[[4-[1-[3,5-dichloro-4-(3-chloropropoxy)phenyl]-1-methyl-ethyl]phenyl]methyl]-2-(methanesulfonamido)acetamide (24.1 mg, yield: 23.4%) as a yellow gum. HPLC purity (220 nm): 98.3%. $^1$H NMR (400 MHz, CHCl3-d) δ 7.26-7.18 (m, 4H), 7.14 (s, 2H), 6.34 (br s, 1H), 5.02 (br s, 1H), 4.49 (d, J=5.7 Hz, 2H), 4.18 (t, J=5.8 Hz, 2H), 3.92-3.85 (m, 4H), 3.03 (s, 3H), 2.31 (quin, J=6.1 Hz, 2H), 1.66 (s, 6H). LCMS (M+H$^+$) m/z: clcd 522.1; found 523.0.

Example 6: Synthesis of N-(3,5-dichloro-4-(3-chloropropoxy)phenyl)-N-(4-(3-(methylsulfonamido)-2-oxopropoxy)phenyl)acetamide (AA71)

A solution of tert-butyl (3-(4-(N-(3,5-dichloro-4-(3-chloropropoxy)phenyl)acetamido)phenoxy)-2-oxopropyl)(methylsulfonyl)carbamate (200 mg, 0.2 mmol) in HCl/EtOAc (4 M, 4 mL) was stirred at 25° C. for 15 min. TLC showed the reaction was completed. The reaction was concentrated under reduced pressure. The residue was purified by prep-HPLC (HCl) to give N-(3,5-dichloro-4-(3-chloropropoxy)phenyl)-N-(4-(3-(methylsulfonamido)-2-oxopropoxy)phenyl)acetamide (69 mg, yield: 59.0%) as yellow oil. HPLC purity (220 nm): 93.5%. $^1$H NMR (400 MHz, CHCl$_3$-d) δ=7.26-7.21 (m, 4H), 7.01-6.92 (m, 2H), 5.05 (br s, 1H), 4.70 (s, 2H), 4.40 (d, J=5.1 Hz, 2H), 4.15 (br s, 2H), 3.85 (t, J=6.4 Hz, 2H), 3.02 (s, 3H), 2.28 (quin, J=6.0 Hz, 2H), 2.10-2.01 (m, 3H). LCMS (M+H$^+$) m/z: clcd: 538.0; found: 539.0.

Example 7: Synthesis of N-(3-((3',5'-dichloro-4'-(3-chloropropoxy)-[1,1'-biphenyl]-4-yl)oxy)-2-oxopropyl)methanesulfonamide (AA73)

A solution of tert-butyl (3-((3',5'-dichloro-4'-(3-chloropropoxy)-[1,1'-biphenyl]-4-yl)oxy)-2-oxopropyl)(methylsulfonyl)carbamate (7) (70.0%, 0.13 g, 0.15 mol) in HCl/EtOAc (2 mL) was stirred at 20° C. for 0.5 hour. LCMS showed the reaction was completed. The solution was concentrated under reduced pressure. The crude product was purified by prep-HPLC (HCl) to give N-(3-((3',5'-dichloro-4'-(3-chloropropoxy)-[1,1'-biphenyl]-4-yl)oxy)-2-oxopropyl)methanesulfonamide (29 mg, yield: 27.0%) as brown oil. HPLC purity (220 nm): 90.5%. ¹H NMR (400 MHz, CHCl₃-d) δ=7.51-7.48 (d, J=8.8 Hz, 2H), 7.47 (s, 2H), 7.00-6.96 (d, J=8.6 Hz, 2H), 5.12-4.99 (m, 1H), 4.72 (s, 2H), 4.46-4.37 (d, J=5.2 Hz, 2H), 4.25-4.17 (t, J=5.7 Hz, 2H), 3.96-3.83 (t, J=6.4 Hz, 2H), 3.02 (s, 3H), 2.38-2.25 (m, 2H). LCMS (M+H⁺) m/z: clcd: 480.0; found 480.0.

Example 8: Synthesis of N-(3-(4-(3,5-dichloro-4-(3-chloro-2-hydroxypropoxy)phenethyl)phenoxy)-2-oxopropyl)methanesulfonamide (AA75)

A solution of tert-butyl N-(3-(4-(2-(3,5-dichloro-4-(3-chloro-2-(methoxymethoxy)propoxy)phenyl)ethyl)phenoxy)-2-oxo-propyl)-N-methylsulfonyl-carbamate (9) (180 mg, 0.27 mmol) in TFA (2 mL) and DCM (10 mL) was stirred at 20° C. for 3 hours. LCMS showed the reaction was completed. The resulting solution was concentrated under reduced pressure. The residue was purified by prep-HPLC (HCl) to give N-(3-(4-(2-(3, 5-dichloro-4-(3-chloro-2-hydroxy-propoxy)phenyl)ethyl)phenoxy)-2-oxo-propyl)methanesulfonamide (13.9 mg, yield: 9.84%) as white solid. HPLC purity (220 nm): 92%. ¹H NMR (400 MHz, CHCl3-d) δ ppm 7.06-7.11 (m, 4H), 6.80-6.86 (m, 2H), 5.02 (br s, 1H), 4.63-4.69 (m, 2H), 4.40 (d, J=5.14 Hz, 2H), 4.23 (br s, 1H), 4.12-4.20 (m, 2H), 3.74-3.90 (m, 2H), 3.00 (s, 3H), 2.83-2.86 (m, 2H), 2.79-2.83 (m, 2H).

Example 9: Synthesis of N-(3-((4-(2-(3,5-dichloro-4-(2-chloroethoxy)phenyl)propan-2-yl)phenyl)(methyl)amino)-2-oxopropyl)methanesulfonamide hydrochloride (AA81)

A solution of tert-butyl (3-((4-(2-(3,5-dichloro-4-(2-chloroethoxy)phenyl)propan-2-yl)phenyl)(methyl)amino)-2-oxopropyl) (methylsulfonyl)carbamate (100 mg, 0.2 mmol) in HCl/EtOAc (2 mL) was stirred at 25° C. for 15 min. TLC showed the reaction was completed. The reaction was concentrated under reduced pressure. The residue was purified by prep-HPLC (HCl) to give N-(3-((4-(2-(3,5-dichloro-4-(2-chloroethoxy)phenyl)propan-2-yl)phenyl)(methyl)amino)-2-oxopropyl)methanesulfonamide hydrochloride (7.6 mg, yield: 9.1%) as yellow oil. ¹H NMR (400 MHz, CHCl₃-d) δ 7.16 (br s, 2H), 7.12 (s, 2H), 6.95 (br s, 2H), 5.70 (br s, 1H), 4.49-4.22 (m, 4H), 4.15-3.81 (m, 4H), 3.18 (br s, 3H), 2.94 (br s, 3H), 1.62 (s, 6H). LCMS (M+H⁺) m/z: clcd: 520.1; found 521.0.

For synthesis of Compounds in Table B, see WO 2017/177307 for procedures. The disclosures of WO 2017/177307 are hereby incorporated by reference in their entireties.

Example 10: Synthesis of (R)-3-(4-(2-(3,5-dichloro-4-((S)-3-chloro-2-hydroxypropoxy)phenyl)propan-2-yl)phenoxy)propane-1,2-diol (Compound 1a)

To a solution of (S)-4-((4-(2-(3,5-dichloro-4-(((R)-oxiran-2-yl)methoxy)phenyl)propan-2-yl)phenoxy)methyl)-2,2-dimethyl-1,3-dioxolane (560 mg, 1.2 mmol, 1.0 equiv) in MeCN (12 mL) was added CeCl₃·7H₂O (1118 mg, 3.0 mmol, 2.5 equiv) and the mixture was heated to reflux for 16 h. The resulting white paste was collected by filtration and washed with ethyl acetate and the clear suspension was concentrated under reduced pressure. The resulting residue was purified by column chromatography to provide the titled compound (512 mg, 92%) as a sticky oil. ¹H NMR (600 MHz, CDCl₃) δ (ppm)=7.15-7.12 (m, 4H), 6.86 (d, J=9.0 Hz, 2H), 4.26-4.23 (m, 1H), 4.21-4.15 (m, 2H), 4.15-4.11 (m, 1H), 4.08-4.03 (m, 2H), 3.86 (dd, J=4.8 Hz, 10.8 Hz, 2H), 3.78 (dd, J=6.6 Hz, 12.6 Hz, 2H), 1.64 (s, 6H); ¹³C NMR (150 MHz, CDCl₃) δ (ppm)=156.76, 149.30, 148.26, 141.84, 128.52, 127.87, 127.67, 114.35, 73.69, 70.48, 69.26, 63.78, 45.55, 42.34, 30.79; ESI-LRMS calcd for [M+Na]⁺ 485.1, found 485.4.

Example 11: Synthesis of (R)-3-(4-(2-(3,5-dibromo-4-((S)-3-chloro-2-hydroxypropoxy)phenyl)propan-2-yl)phenoxy)propane-1,2-diol (Compound 3a)

Compound 3a was synthesized by a similar procedure used to prepare Compound 1a in Example 10. ¹H NMR (400 MHz, DMSO-D6) δ (ppm)=7.39 (s, 1H), 7.30 (dd, J=2.0 Hz, 34.4 Hz, 1H), 7.15 (d, J=8.8 Hz, 2H), 6.86 (d, J=8.8 Hz, 2H), 5.57-5.54 (m, 1H), 4.91 (d, J=4.8 Hz, 1H), 4.64 (t, J=5.6 Hz, 1H), 4.10-4.08 (m, 1H), 3.98-3.92 (m, 3H), 3.86-3.81 (m, 2H), 3.79-3.76 (m, 1H), 3.71 (dd, J=5.6 Hz, 11.2 Hz, 1H), 3.45-3.42 (m, 2H), 1.60 (s, 6H).

Example 12: Synthesis of (S)-1-chloro-3-(2,6-dichloro-4-(2-(4-((R)-2-hydroxy-3-methoxypropoxy)phenyl)propan-2-yl)phenoxy)propan-2-ol (Compound 5a)

To a solution of (S)-1-chloro-3-(2,6-dichloro-4-(2-(4-(((R)-oxiran-2-yl)methoxy)phenyl)propan-2-yl)phenoxy)propan-2-ol (15 mg, 0.034 mmol, 1.0 equiv) in anhydrous methanol (2 mL) was added Erbium (III) trifluoromethanesulfonate (2.1 mg, 0.0034 mmol, 0.1 equiv) and the mixture was stirred at room temperature for 40 h. The reaction was quenched by the addition of a saturated solution of ammonium chloride (0.5 ml) and the mixture was extracted with ethyl acetate (2×10 ml). The organic layer was washed with deionized water (2×10 ml), dried over anhydrous magnesium sulfate, filtered, and concentrated under reduced pressure. The resulting residue was purified by gradient flash column chromatography on silica gel (elution: 30% ethyl acetate in hexane to 50% ethyl acetate in hexane) to provide Compound 5a (12.5 mg, 77.1%) as a colorless oil. ¹H NMR (600 MHz, CDCl₃) δ (ppm)=7.14-7.10 (m, 4H), 6.87 (d, J=6.0 Hz, 2H), 4.26-4.22 (m, 1H), 4.21-4.15 (m, 3H), 4.06-4.01 (m, 2H), 3.87 (dd, J=6.0 Hz, 11.4 Hz, 1H), 3.79 (dd, J=5.4 Hz, 11.4 Hz, 1H), 3.61 (dd, J=4.2 Hz, 9.6 Hz, 1H), 3.57 (dd, J=6.0 Hz, 9.6 Hz, 1H), 3.44 (s, 3H), 1.64 (s, 6H); ¹³C NMR (150 MHz, CDCl₃) δ (ppm)=156.37, 148.81, 147.69, 141.04, 127.95, 127.25, 127.05, 113.81, 73.13, 73.00, 69.93, 68.58, 68.44, 58.88, 45.00, 41.78, 30.25.

Example 13: Synthesis of (S)-1-chloro-3-(2,6-dichloro-4-(2-(4-((R)-2-hydroxy-3-isopropoxypropoxy)phenyl)propan-2-yl)phenoxy)propan-2-ol (Compound 7a)

Compound 7a was synthesized by a similar procedure used to prepare Compound 3a in Example 11. ¹H NMR (400 MHz, CDCl₃) δ (ppm)=7.13-7.10 (m, 4H), 6.86 (d, J=8.8 Hz, 2H), 4.25-4.12 (m, 4H), 4.03-3.98 (m, 2H), 3.85 (dd, J=5.2 Hz, 10.8 Hz, 1H), 3.77 (dd, J=5.6 Hz, 11.2 Hz, 1H), 3.67-3.53 (m, 3H), 2.83 (s, 1H), 2.57 (s, 1H), 1.62 (s, 6H), 1.18 (d, J=6.0 Hz, 6H).

Example 14: Synthesis of (S)-1-chloro-3-(2,6-dichloro-4-(2-(4-((S)-3-fluoro-2-hydroxypropoxy)phenyl)propan-2-yl)phenoxy)propan-2-ol (Compound 8a)

To a solution of Compound 1a (1 equiv; synthesized according to Example 10) in dichloromethane were successively added triethylamine trihydrofluoride (2 equiv) and XtalFluor-M (2 equiv). After 3 h, the reaction mixture was quenched at room temperature with a 5% aqueous sodium bicarbonate solution and stirred for 15 min, and the resulting mixture was extracted twice with dichloromethane. The organic phases were combined, dried over anhydrous magnesium sulfate, and filtered. Solvents were evaporated, and the resulting crude material was purified by silica gel chromatography to provide Compound 8a. $^1$H NMR (600 MHz, CDCl$_3$) δ (ppm)=7.16-7.14 (m, 4H), 6.87 (d, J=8.4 Hz, 2H), 4.69-4.56 (m, 2H), 4.30-4.22 (m, 2H), 4.22-4.16 (m, 2H), 4.10-4.09 (m, 2H), 3.87 (dd, J=6.0 Hz, 11.4 Hz, 1H), 3.79 (dd, J=5.4 Hz, 10.8 Hz, 1H), 1.64 (s, 6H).

Example 15: Synthesis of (S)-1-chloro-3-(2,6-dichloro-4-(2-(4-((R)-2-hydroxy-3-(1H-imidazol-1-yl)propoxy)phenyl)propan-2-yl)phenoxy)propan-2-ol (Compound 9a)

To a solution of (5)-1-chloro-3-(2,6-dichloro-4-(2-(4-(((R)-oxiran-2-yl)methoxy)phenyl)propan-2-yl)phenoxy)propan-2-ol (12.6 mg, 0.028 mmol, 1.0 equiv) in anhydrous MeCN (2 mL) was added Bismuth (III) trifluoromethanesulfonate (1.8 mg, 0.0028 mmol, 0.1 equiv) and the mixture was stirred at room temperature for 40 h. The reaction was quenched by the addition of a saturated solution of ammonium chloride (0.5 ml) and the mixture was extracted with ethyl acetate (2×10 ml). The organic layer was washed with deionized water (2×10 ml), dried over anhydrous magnesium sulfate, filtered, and concentrated under reduced pressure. The resulting residue was purified by flash column chromatography to provide Compound 9a (8.7 mg, 60.4%) as a colorless oil. $^1$H NMR (600 MHz, CDCl$_3$) δ (ppm)=7.56 (s, 1H), 7.16-7.14 (m, 4H), 7.04 (s, 1H), 7.01 (s, 1H), 6.86 (d, J=8.4 Hz, 2H), 4.29-4.23 (m, 3H), 4.22-4.13 (m, 3H), 3.98-3.92 (m, 2H), 3.87 (dd, J=6.0 Hz, 11.4 Hz, 1H), 3.79 (dd, J=4.8 Hz, 10.8 Hz, 1H), 1.65 (s, 6H).

Example 16: Synthesis of (5)-1-chloro-3-(2,6-dichloro-4-(2-(4-((R)-2-hydroxy-3-morpholinopropoxy)phenyl)propan-2-yl)phenoxy)propan-2-ol (Compound 11a)

Compound 11a was synthesized by a similar procedure used to prepare Compound 9a in Example 15. $^1$H NMR (400 MHz, CDCl$_3$) δ (ppm)=7.16-7.11 (m, 4H), 6.88 (d, J=8.8 Hz, 2H), 4.27-4.13 (m, 4H), 4.07-3.98 (m, 2H), 3.90-3.77 (m, 6H), 2.84-2.80 (m, 2H), 2.73-2.72 (m, 2H), 2.71-2.67 (m, 2H), 1.65 (s, 6H); ESI-LRMS calcd for [M+H]$^+$ 532.1, found 534.6.

Example 17: Synthesis of (R)-1-amino-3-(4-(2-(3,5-dichloro-4-((S)-3-chloro-2-hydroxypropoxy)phenyl)propan-2-yl)phenoxy)propan-2-ol (Compound 12a) and N—((R)-3-(4-(2-(3,5-dichloro-4-((S)-3-chloro-2-hydroxypropoxy)phenyl)propan-2-yl)phenoxy)-2-hydroxypropyl)methanesulfonamide (Compound 13a)

Synthesis of (R)-1-amino-3-(4-(2-(3,5-dichloro-4-((S)-3-chloro-2-hydroxypropoxy)phenyl)propan-2-yl)phenoxy)propan-2-ol (Compound 12a). To a solution of (R)-1-azido-3-(4-(2-(3,5-dichloro-4-((S)-3-chloro-2-hydroxypropoxy)phenyl)propan-2-yl)phenoxy)propan-2-ol (57 mg, 0.117 mmol, 1.0 equiv) in MeCN (6 mL) was added triphenylphosphine (36.7 mg, 0.14 mmol, 1.2 equiv) and the mixture was heated to reflux for 16 h. The reaction was quenched by deionized water (2 ml) and the mixture was extracted with ethyl acetate (2×30 ml). The organic layer was washed with deionized water (2×30 ml), dried over anhydrous magnesium sulfate, filtered, and concentrated under reduced pressure. The resulting residue was purified by gradient flash column chromatography on Si gel (elution: 2% methanol in dichloromethane to 30% methanol in dichloromethane) to provide Compound 12a (24.3 mg, 44.9%) as a colorless oil. $^1$H NMR (400 MHz, CDCl$_3$) δ (ppm)=7.12-7.09 (m, 4H), 6.84 (d, J=8.4 Hz, 2H), 4.24-4.21 (m, 1H), 4.17-4.13 (m, 2H), 3.97 (m, 3H), 3.84 (dd, J=5.6 Hz, 11.2 Hz, 1H), 3.76 (dd, J=5.6 Hz, 11.2 Hz, 1H), 3.00-2.85 (m, 2H), 1.61 (s, 6H); $^{13}$C NMR (100 MHz, CDCl$_3$) δ (ppm)=157.00, 149.35, 148.31, 141.60, 128.52, 127.81, 127.61, 114.37, 73.78, 70.47, 70.42, 70.14, 45.65, 44.11, 42.34, 30.25; ESI-LRMS calcd for [M+H]$^+$ 462.1, found 463.9.

Synthesis of N—((R)-3-(4-(2-(3,5-dichloro-4-((S)-3-chloro-2-hydroxypropoxy)phenyl)propan-2-yl)phenoxy)-2-hydroxypropyl)methanesulfonamide (Compound 13a). To a solution of (R)-1-azido-3-(4-(2-(3,5-dichloro-4-((S)-3-chloro-2-hydroxypropoxy)phenyl)propan-2-yl)phenoxy)propan-2-ol (14.3 mg, 0.031 mmol, 1.0 equiv) in anhydrous dichloromethane (3 mL) was treated triethylamine (12.5 mg, 0.124 mmol, 4.0 equiv) and methane sulfonyl chloride (3.6 mg, 0.031 mmol, 1.0 equiv) sequentially at 0° C. for 10 minutes. Then it was warmed to room temperature for 16 hours. The reaction was quenched by the addition of a saturated solution of ammonium chloride (2 ml) and the mixture was extracted with ethyl acetate (2×20 ml). The organic layer was washed with deionized water (2×20 ml), dried over anhydrous magnesium sulfate, filtered, and concentrated under reduced pressure. The resulting residue was purified by gradient flash column chromatography on silica gel (elution: 50% ethyl acetate in hexane to 75% ethyl acetate in hexane) to provide Compound 13a (9.7 mg, 57.9%) as a colorless oil. $^1$H NMR (600 MHz, CDCl$_3$) δ (ppm)=7.15-7.13 (m, 4H), 6.87 (d, J=5.4 Hz, 2H), 4.93-4.90 (m, 1H), 4.26-4.23 (m, 1H), 4.21-4.13 (m, 3H), 4.06-4.01 (m, 2H), 3.87 (dd, J=5.4 Hz, 11.4 Hz, 1H), 3.79 (dd, J=5.4 Hz, 10.8 Hz, 1H), 3.50-3.45 (m, 1H), 3.26-3.31 (m, 1H), 3.03 (s, 3H), 1.64 (s, 6H); $^{13}$C NMR (150 MHz, CDCl$_3$) δ (ppm)=155.94, 148.69, 147.73, 141.57, 127.99, 127.39, 127.05, 113.81, 73.14, 69.92, 68.85, 68.54, 45.19, 44.99, 41.81, 39.98, 30.22.

Example 18: Synthesis of (S)-1-chloro-3-(2,6-dichloro-4-(2-(4-((S)-3-(ethylsulfonyl)-2-hydroxypropoxy)phenyl)propan-2-yl)phenoxy)propan-2-ol (Compound 14a)

To a solution of (S)-1-chloro-3-(2,6-dichloro-4-(2-(4-((S)-3-(ethylthio)-2-hydroxypropoxy)phenyl)propan-2-yl)phenoxy)propan-2-ol (14.6 mg, 0.029 mmol, 1.0 equiv) in anhydrous dichloromethane (3 mL) was treated 3-chloroperbenzoic acid (14.0 mg, 0.081 mmol, 2.8 equiv) at 0° C. for 10 minutes. Then it was warmed to room temperature for 3 hours. The reaction was quenched by the addition of a saturated solution of ammonium chloride (2 ml) and the mixture was extracted with ethyl acetate (2×20 ml). The organic layer was washed with saturated NaHCO$_3$ (20 ml), deionized water (2×20 ml), dried over anhydrous magnesium sulfate, filtered, and concentrated under reduced pressure. The resulting residue was purified by gradient flash column chromatography on Si gel (elution: 30% ethyl acetate in hexane to 75% ethyl acetate in hexane) to provide Compound 14a (4.7 mg, 31.0%) as a colorless oil. $^1$H NMR (400 MHz, CDCl$_3$) δ (ppm)=7.18-7.15 (m, 4H), 6.88 (d, J=8.8 Hz, 2H), 4.69-4.67 (m, 1H), 4.27-4.15 (m, 3H), 4.10-4.07 (m, 2H), 3.88 (dd, J=5.2 Hz, J=11.2 Hz, 1H), 3.80 (dd, J=5.2 Hz, J=10.8 Hz, 1H), 3.39-3.20 (m, 4H), 1.66 (s, 6H), 1.48 (t, J=7.2 Hz, 3H); ESI-LRMS calcd for [M+Na]$^+$ 561.1, found 561.5.

Example 19: Synthesis of (R)-3-(4-(2-(4-((S)-3-chloro-2-hydroxypropoxy)-3-methylphenyl)propan-2-yl)-2-methylphenoxy)propane-1,2-diol (Compound 22a)

Compound 22a was synthesized by a similar procedure used to prepare Compound 1a in Example 10. $^1$H NMR (400 MHz, DMSO-D6) δ (ppm)=6.97-6.94 (m, 4H), 6.81-6.76 (m, 2H), 5.50 (d, J=4.8 Hz, 1H), 4.86 (s, 1H), 4.61 (s, 1H), 4.06-4.00 (m, 1H), 3.97-3.89 (m, 3H), 3.86-3.76 (m, 3H), 3.69 (dd, J=5.6 Hz, 11.2 Hz, 1H), 3.50-3.44 (m, 2H), 2.10 (s, 6H), 1.55 (s, 6H); $^{13}$C NMR (100 MHz, DMSO-D6) δ (ppm)=155.14, 154.74, 143.23, 142.75, 129.32, 129.23, 125.66, 125.62, 125.22, 125.16, 111.28, 111.16, 70.67, 70.02, 69.48, 69.32, 63.43, 55.50, 47.53, 31.42, 16.86, 16.79.

Example 20: Synthesis (R)-1-(4-(2-(4-((R)-2-acetoxy-3-chloropropoxy)-3,5-dichlorophenyl)propan-2-yl)phenoxy)-3-methoxypropan-2-yl acetate (Compound 5dA)

Ac$_2$O (128 mg, 1.26 mmol, 6.0 equiv.), Et3N (127 mg, 1.26 mmol, 6.0 equiv.) and DMAP (26 mg, 0.21 mmol, 1.0 equiv.) were added to a solution of Compound 5a (100 mg, 0.21 mmol, 1.0 equiv., see Example 12) in anhydrous DCM (5 mL) at room temperature and the resultant mixture was stirred at the same temperature overnight. The mixture was diluted with EtOAc (30 mL) and the organic layer was washed with water (15 mL) and brine (15 mL). The organic layer was further dried over anhydrous MgSO$_4$ and evaporated under reduced pressure. The crude was loaded onto a silica gel column and eluted with Hexane/EtOAc (13/1 to 6/1) to give 111 mg of the titled compound as colorless oil (yield: 95.0%). $^1$H NMR (600 MHz, CHLOROFORM-d) δ 7.11-7.12 (m, 2H), 7.09-7.11 (m, 2H), 6.82-6.87 (m, 2H), 5.32-5.35 (m, 1H), 5.28-5.32 (m, 1H), 4.18-4.26 (m, 2H), 4.09-4.16 (m, 2H), 3.97 (dd, J=5.14, 11.74 Hz, 1H), 3.88 (dd, J=5.14, 11.74 Hz, 1H), 3.66 (dd, J=2.20, 4.40 Hz, 2H), 3.40 (s, 3H), 2.14 (s, 3H), 2.11 (s, 3H), 1.61 (s, 6H). $^{13}$C NMR (151 MHz, CHLOROFORM-d) δ 170.8, 170.4, 156.9, 149.4, 148.4, 141.8, 128.7, 127.9, 127.7, 114.5, 71.9, 71.1, 70.9, 66.4, 59.6, 42.7, 42.4, 30.9, 21.4, 21.2.

Example 21: Synthesis (R)-1-(4-(2-(4-((S)-2-acetoxy-3-chloropropoxy)-3,5-dichlorophenyl)propan-2-yl)phenoxy)-3-methoxypropan-2-yl acetate (Compound 5aA)

Acetic Anhydride (4.1 mg, 0.04 mmol, 4.0 equiv) was added to a solution of Compound 5a (5.0 mg, 0.01 mmol, 1.0 equiv, see Example 12), DMAP (0.1 mg, 0.001 mmol, 0.1 equiv) and Et$_3$N (4.1 mg, 0.04 mmol, 4.0 equiv) in anhydrous dichloromethane (1 mL). The resulting solution was stirred overnight at room temperature. Dichloromethane was removed under reduced pressure and the residue was purified by column chromatography to afford the title compound as a colorless oil (5.8 mg, 98.6%). $^1$H NMR (400 MHz, CDCl$_3$) δ (ppm)=7.11-7.08 (m, 4H), 6.83 (d, J=8.8 Hz, 2H), 5.35-5.26 (m, 2H), 4.26-4.17 (m, 2H), 4.16-4.07 (m, 2H), 3.96 (dd, J=5.2 Hz, 11.6 Hz, 1H), 3.86 (dd, J=5.6 Hz, 11.6 Hz, 1H), 3.66-3.61 (m, 2H), 3.38 (s, 3H), 2.13 (s, 3H), 2.10 (s, 3H), 1.60 (s, 6H); $^{13}$C NMR (150 MHz, CDCl$_3$) δ (ppm)=170.80, 170.45, 156.96, 149.41, 148.39, 141.80, 128.69, 127.90, 127.70, 114.54, 71.91, 71.12, 70.54, 66.44, 59.62, 42.73, 42.43, 30.90, 21.38, 21.18; ESI-LRMS calcd for [M+H]$^+$ 561.1, found 561.1.

Example 22: Synthesis of (R)-1-(4-(2-(4-((S)-2-acetoxy-3-chloropropoxy)-3,5-dichlorophenyl)propan-2-yl)phenoxy)-3-isopropoxypropan-2-yl acetate (Compound 7aA)

Compound 7aA was synthesized by a similar procedure used to prepare Compound 5aA in Example 21 by using Compound 7a prepared according to Example 13. Compound 7aA was obtained as a colorless oil (6.4 mg, 96.2%). $^1$H NMR (400 MHz, CDCl$_3$) δ (ppm)=7.12-7.08 (m, 4H), 6.85 (d, J=8.8 Hz, 2H), 5.36-5.30 (m, 1H), 5.28-5.22 (m, 1H), 4.27-4.09 (m, 4H), 3.97 (dd, J=5.2 Hz, 11.6 Hz, 1H), 3.87 (dd, J=5.6 Hz, 11.6 Hz, 1H), 3.71-3.57 (m, 3H), 2.14 (s, 3H), 2.09 (s, 3H), 1.61 (s, 6H), 1.15 (dd, J=2.0 Hz, 6.0 Hz, 6H); $^{13}$C NMR (150 MHz, CDCl$_3$) δ (ppm)=170.16, 169.78, 156.42, 148.77, 147.72, 141.03, 128.02, 127.20, 127.03, 113.91, 71.97, 71.25, 70.98, 70.30, 66.01, 65.72, 42.06, 41.76, 30.24, 21.60, 21.54, 20.74, 20.52; ESI-LRMS calcd for [M+Na]$^+$ 611.1, found 611.1.

Example 23: Synthesis of (S)-1-(4-(2-(4-((S)-2-acetoxy-3-(ethylsulfonyl)propoxy)phenyl)propan-2-yl)-2,6-dichlorophenoxy)-3-chloropropan-2-yl acetate (Compound 14aA)

Compound 14aA was synthesized by a similar procedure used to prepare Compound 5aA in Example 21 by using Compound 14a prepared according to Example 18. Compound 14aA was obtained as a colorless oil (3.4 mg, 97.3%). $^1$H NMR (400 MHz, CDCl$_3$) δ (ppm)=7.13-7.08 (m, 4H), 6.84 (d, J=8.8 Hz, 2H), 5.63-5.57 (m, 1H), 5.36-5.30 (m, 1H), 4.29-4.18 (m, 4H), 3.97 (dd, J=5.2 Hz, 12.0 Hz, 1H), 3.87 (dd, J=5.6 Hz, 11.6 Hz, 1H), 3.54-3.40 (m, 2H), 3.10 (q, J=7.2 Hz, 2H), 2.14 (s, 3H), 2.12 (s, 3H), 1.61 (s, 6H), 1.44 (t, J=7.2 Hz, 3H); $^{13}$C NMR (150 MHz, CDCl$_3$) δ (ppm)= 170.41, 170.16, 158.50, 154.94, 142.86, 142.39, 128.70, 128.03, 127.66, 114.48, 71.87, 71.46, 67.79, 67.05, 52.48, 48.82, 42.69, 42.44, 30.86, 21.15, 20.90, 6.80; ESI-LRMS calcd for [M+Na]$^+$ 645.1, found 645.1.

Example 24: Synthesis of (R)-1-(4-(2-(4-((S)-2-acetoxy-3-chloropropoxy)-3,5-dichlorophenyl)propan-2-yl)phenoxy)-3-morpholinopropan-2-yl acetate (Compound 11aA)

Compound 11aA was synthesized by a similar procedure used to prepare Compound 5aA in Example 21 by using Compound 11a prepared according to Example 16. Compound 11aA was obtained as a colorless oil (6.8 mg, 97.6%). $^1$H NMR (400 MHz, CDCl$_3$) δ (ppm)=7.14-7.07 (m, 4H), 6.83 (d, J=8.8 Hz, 2H), 5.72-5.70 (m, 1H), 5.36-5.30 (m, 1H), 4.47-4.40 (m, 1H), 4.39-4.32 (m, 1H), 4.29-4.14 (m, 4H), 3.99-3.94 (m, 3H), 3.87 (dd, J=5.6 Hz, 11.6 Hz, 1H), 3.58-3.37 (m, 4H), 2.97 (m, 2H), 2.23 (s, 3H), 2.14 (s, 3H), 1.61 (s, 6H); $^{13}$C NMR (150 MHz, CDCl$_3$) δ (ppm)=170.54, 170.37, 156.02, 149.12, 148.39, 142.61, 128.67, 128.06, 127.60, 114.34, 71.81, 70.90, 67.26, 65.89, 63.60, 58.52, 53.17, 52.58, 42.64, 42.40, 30.78, 29.87, 21.56, 21.11; ESI-LRMS calcd for [M+H]$^+$ 616.1, found 616.1.

Example 25: Synthesis of (S)-1-(4-(2-(4-((R)-2-acetoxy-3-(1H-imidazol-1-yl)propoxy)phenyl)propan-2-yl)-2,6-dichlorophenoxy)-3-chloropropan-2-yl acetate (Compound 9aA)

Compound 9aA was synthesized by a similar procedure used to prepare Compound 5aA in Example 21 by using Compound 9a prepared according to Example 15. Compound 9aA was obtained as a colorless oil (5.6 mg, 93.6%). $^1$H NMR (400 MHz, CDCl$_3$) δ (ppm)=9.40 (s, 1H), 7.39 (s, 1H), 7.20 (s, 1H), 7.14-7.10 (m, 4H), 6.82 (d, J=8.4, 2H), 5.50 (m, 1H), 5.35-5.31 (m, 1H), 4.78-4.70 (m, 2H), 4.27-4.18 (m, 4H), 3.96 (dd, J=5.6 Hz, 11.6 Hz, 1H), 3.87 (dd, J=5.6 Hz, 11.6 Hz, 1H), 2.14 (s, 3H), 2.11 (s, 3H), 1.61 (s, 6H); $^{13}$C NMR (150 MHz, CDCl$_3$) δ (ppm)=170.21, 169.67, 155.72, 148.93, 142.61, 136.02, 128.53, 127.97, 127.46, 121.62, 120.13, 114.19, 71.66, 70.76, 69.72, 65.27, 49.70, 42.49, 42.26, 30.65, 20.96, 20.91; ESI-LRMS calcd for [M+H]$^+$ 597.1, found 597.1.

Example 26: Synthesis of (S)-1-(4-(2-(4-((R)-2-acetoxy-3-(N-(methylsulfonyl)acetamido)propoxy)phenyl)propan-2-yl)-2,6-dichlorophenoxy)-3-chloropropan-2-yl acetate (Compound 13aA)

Compound 13aA was synthesized according to Example 21 by using Compound 13a. Compound 13aA was obtained as a colorless oil (6.0 mg, 100%). $^1$H NMR (400 MHz, CDCl$_3$) δ (ppm)=7.13-7.08 (m, 4H), 6.82 (d, J=8.4, 2H), 5.47-5.42 (m, 1H), 5.36-5.30 (m, 1H), 4.29-4.07 (m, 6H), 3.97 (dd, J=5.2 Hz, 11.6 Hz, 1H), 3.87 (dd, J=5.6 Hz, 11.6 Hz, 1H), 3.33 (s, 3H), 2.44 (s, 3H), 2.14 (s, 3H), 2.10 (s, 3H), 1.61 (s, 6H); $^{13}$C NMR (150 MHz, CDCl$_3$) δ (ppm)=171.33, 170.47, 170.29, 156.42, 149.13, 148.29, 142.17, 128.58, 127.88, 127.54, 114.33, 71.74, 70.82, 70.36, 67.19, 46.69, 42.66, 42.57, 42.31, 30.73, 24.49, 21.07, 20.03; ESI-LRMS calcd for [M+H]$^+$ 666.1, found 666.1.

Example 27: Synthesis of (S)-1-(4-(2-(4-((S)-2-acetoxy-3-chloropropoxy)-3,5-dichlorophenyl)propan-2-yl)phenoxy)-3-fluoropropan-2-yl acetate (Compound 8aA)

Compound 8aA was synthesized according to Example 21 by using Compound 8a prepared according to Example 14. Compound 8aA was obtained as a colorless oil (5.8 mg, 95.9%). $^1$H NMR (400 MHz, CDCl$_3$) δ (ppm)=7.13-7.10 (m, 4H), 6.84 (d, J=8.8 Hz, 2H), 5.39-5.29 (m, 2H), 4.79-4.71 (m, 1H), 4.67-4.59 (m, 1H), 4.27-4.18 (m, 2H), 4.16-4.14 (m, 2H), 3.97 (dd, J=5.2 Hz, 11.6 Hz, 1H), 3.87 (dd, J=5.6 Hz, 11.6 Hz, 1H), 2.14 (s, 3H), 2.13 (s, 3H), 1.61 (s, 6H); $^{13}$C NMR (150 MHz, CDCl$_3$) δ (ppm)=170.58, 170.46, 156.65, 149.33, 148.43, 142.14, 128.73, 127.99, 127.70, 114.48, 82.13, 80.99 (d, J=513.0 Hz), 71.92, 70.98, 70.77, 70.64 (d, J=19.5 Hz), 65.19, 65.15 (d, J=6.0 Hz), 42.73, 42.46, 30.91, 21.22, 21.19; ESI-LRMS calcd for [M+H]$^+$ 549.1, found 549.1.

Example 28: Synthesis of (S)-3-(4-(2-(4-((S)-2-acetoxy-3-chloropropoxy)-3,5-dichlorophenyl)propan-2-yl)phenoxy)propane-1,2-diyl diacetate (Compound 1aA)

Compound 1aA was synthesized according to Example 21 by using Compound 1a prepared according to Example 10. Compound 1aA was obtained as a colorless oil (63.0 mg, 97.1%). $^1$H NMR (600 MHz, CDCl$_3$) δ (ppm)=7.14-7.11 (m, 4H), 6.85 (d, J=12.0 Hz, 2H), 5.39-5.33 (m, 2H), 4.45 (dd, J=4.2 Hz, 12.0 Hz, 1H), 4.32 (dd, J=6.0 Hz, 12.0 Hz, 1H), 4.26 (dd, J=4.8 Hz, 10.2 Hz, 1H), 4.22 (dd, J=4.8 Hz, 10.2 Hz, 1H), 4.13-4.12 (m, 2H), 3.98 (dd, J=5.4 Hz, 12.0 Hz, 1H), 3.89 (dd, J=5.4 Hz, 12.0 Hz, 1H), 2.16 (s, 3H), 2.12 (s, 3H), 2.10 (s, 3H), 1.63 (s, 6H); $^{13}$C NMR (150 MHz, CDCl$_3$) δ (ppm)=170.21, 169.90, 169.77, 156.07, 148.66, 147.76, 141.40, 128.04, 127.28, 127.02, 113.88, 71.24, 70.31, 69.30, 65.55, 62.10, 42.05, 41.77, 30.23, 20.56, 20.50, 20.35; ESI-LRMS calcd for [M+Na]$^+$ 611.1, found 611.0.

Biological Assays

Example 29: Activity of Exemplary Compounds in Cellular Assays

LNCaP cells were transiently transfected with the PSA (6.1 kb)-luciferase reporter for 24 h, and then treated with indicated concentration of representative compounds with synthetic androgen, R1881 (1 nM) for 24 h. After 24 h of incubation with R1881, the cells were harvested, and relative luciferase activities were determined. To determine the IC$_{50}$, treatments were normalized to the maximum activity with androgen-induction (in the absence of test compounds, vehicle only) (Table 1).

Luciferase Assay: Lysates were thawed on ice then collected into V-bottom 96-well tissue culture plates. Lysates were centrifuged at 4° C. for 5 minutes at 4000 rpm. To measure luminescence of LNCaP cell lysates the Firefly Luciferase Assay System (Promega) was employed, according to manufacturer's protocol.

Statistical analyses were performed using GraphPad Prism (Version 6.01 for Windows; La Jolla, CA, USA). Comparisons between treatment and control groups were compared using Two-Way ANOVA with post-hoc Dunnett's and Tukey's tests. Differences were considered statistically significant at P values less than 0.05. Densitometric quantification of relative AR levels was determined by Image.

Table 1 shows the IC$_{50}$ of representative Compounds from Tables A-B from androgen-induced PSA luciferase assay. EPI-002 has the following structure:

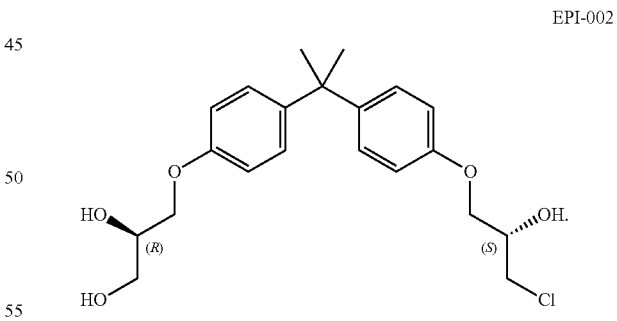

EPI-002

TABLE 1

IC$_{50}$ of Representative Compounds on Androgen-Induced PSA Luciferase Activity

| Compound ID | Androgen-induced PSA-luciferase IC$_{50}$ (nM) | n |
|---|---|---|
| AA31 | 51 | 5 |
| AA33 | 38 | 6 |

TABLE 1-continued

IC$_{50}$ of Representative Compounds on Androgen-Induced PSA Luciferase Activity

| Compound ID | Androgen-induced PSA-luciferase IC$_{50}$ (nM) | n |
|---|---|---|
| AA52 | 74 | 3 |
| AA56 | 344 | 3 |
| AA85 | 368 | 1 |
| 1a | 1410 | 11 |
| 5a | 1030 | 6 |
| 9a | 3120 | 11 |
| 11a | 1050 | 10 |
| 12a | 2260 | 4 |
| 13a | 1054 | 3 |
| 14a | 950 | 11 |
| EPI-002 | 9580 | 2 |
| Enzalutamide | 189 | 8 |
| Bicalutamide | 306 | 2 |

Material and Methods for Examples 30-33

Western Blot Analysis: Cell lysates (20 µg) were run on 8% SDS-PAGE and transferred to nitrocellulose membrane for Western blot with anti-AR antibody (N20 from Santa Cruz) and anti-b-actin antibody.

Cell Proliferation and Viability Assay: Each breast cancer cell line was plated at 5,000 cells per well in a 96-well plate in culture medium containing 5% or 10% fetal bovine serum. LNCaP and LNCaP95 (resistance to enzalutamide) prostate cancer cell lines were included as controls. The next day, cells were treated with vehicle control, enzalutamide, EPI-002 or Compound 13a at indicated concentrations with or without Palbociclib. For proliferation assay, cells were treated for 4 days and labeled with BrdU for 2 hours. Incorporation of BrdU was measured by enzyme-linked immunosorbent assay (ELISA; Cell Proliferation ELISA, BrdU (colorimetric) from Roche). For cell viability assays, alamarBlue was used for assess cell viability after 2 or 3 days of treatment.

Cell Cycle Analysis: Breast cancer or prostate cancer cell lines were plated at 150,000-300,000 cells per 60-mm culture dish in medium containing 5% or 10% fetal bovine serum (5% charcoal-stripped serum for LNCaP95). Next day cells were treated with vehicle control, Enzalutamide or an androgen receptor N-terminal domain inhibitor with or without Palbociclib. At indicated time points, cells were labeled with BrdU for 2 hours and harvested for cell cycle analysis. Collected cells were stained with anti-BrdU-FTIC antibody and 7-aminoactinomycin D, and analyzed by flow cytometry using FACSCalibur.

Colony Forming Assay: Cell lines were plated at 400 (SUM-159PT) or 500 (LNCaP95) cells per well of 24-well plates in medium containing 5% fetal bovine serum (or charcoal-stripped serum for LNCaP95). Next day cells were treated with vehicle control, Enzalutamide, an androgen receptor N-terminal domain inhibitor or Palbociclib at indicated concentrations. After 7 days (SUM-159PT) or 15 days (LNCaP95) of treatments, cells were fixed and stained with crystal violet.

Example 30. Cell Proliferation and Cell Viability Assays

Breast cancer cell lines and a prostate cancer cell line LNCaP were treated with vehicle control, enzalutamide (ENZA; 10 µM) or EPI-002 (35 µM) for 4 days. BrdU incorporation was used to assess cell proliferation. Data from each treatments were normalized to vehicle control as shown in FIG. 1. Results are presented as mean±SEM (n≥3 except n=2 for MDA-MB-468).

Breast cancer and prostate cancer cell lines were treated with vehicle control, various concentrations of Compound 13a or Enzalutamide (ENZA), with or without 0.25 mM Palbociclib (Palbo) for 2 or 3 days. AlamarBlue was used to assess cell viability. Data from each treatments were normalized to vehicle control as shown in FIGS. 2A-2D. Results are presented as mean±SEM (n=3 except n=6 for LNCaP).

These assays demonstrated that cell proliferation and viability of AR-positive breast cancer cell lines were significantly inhibited by treatment with EPI-002 or Compound 13a. Anti-androgen such as enzalutamide had no or negligible effects.

Example 31. Cell Cycle Analysis

Figure 3:
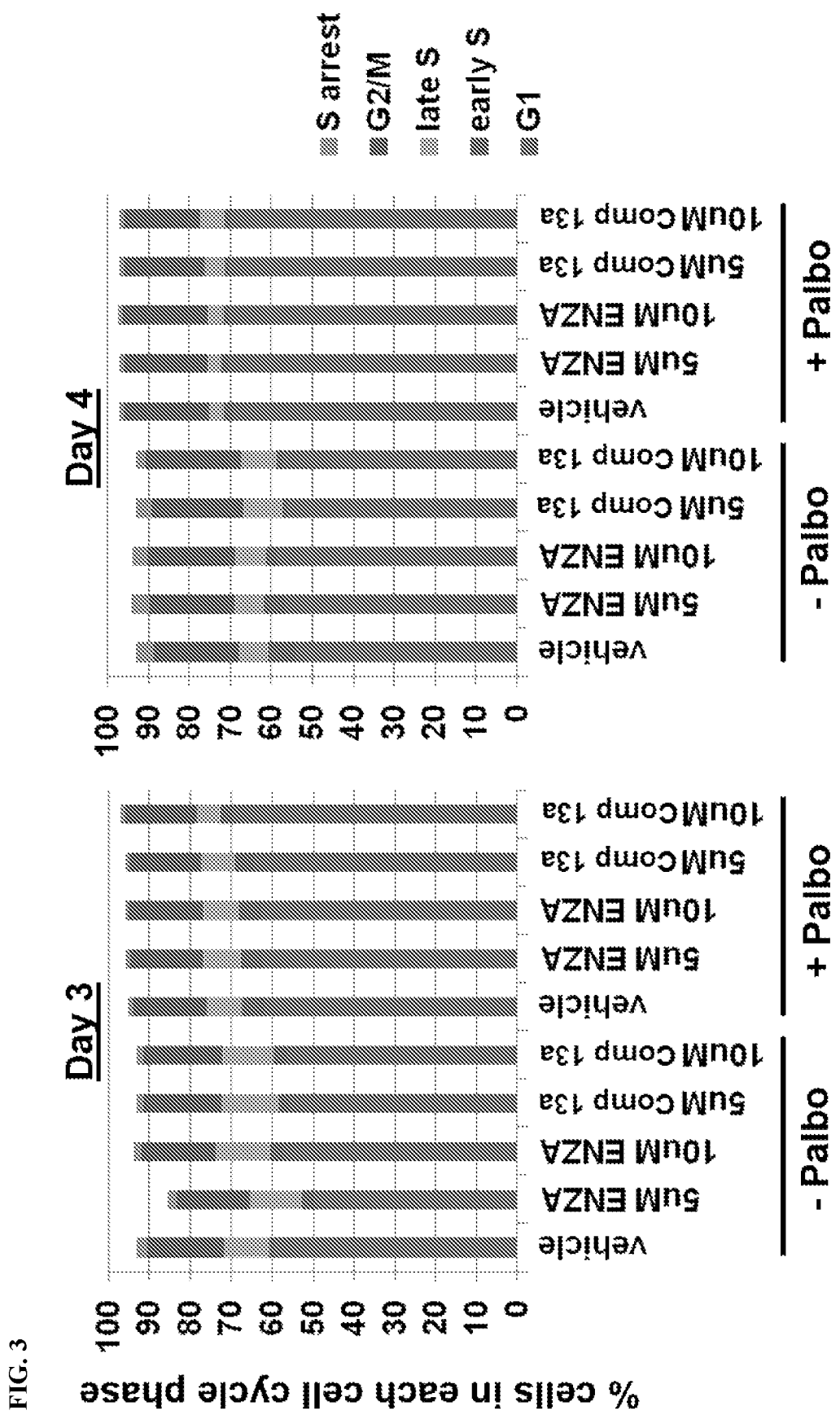
FIG. 3 shows % cells in each cell cycle phase for AR-positive SUM-159PT cells in a cell cycle study.
Figure 4:
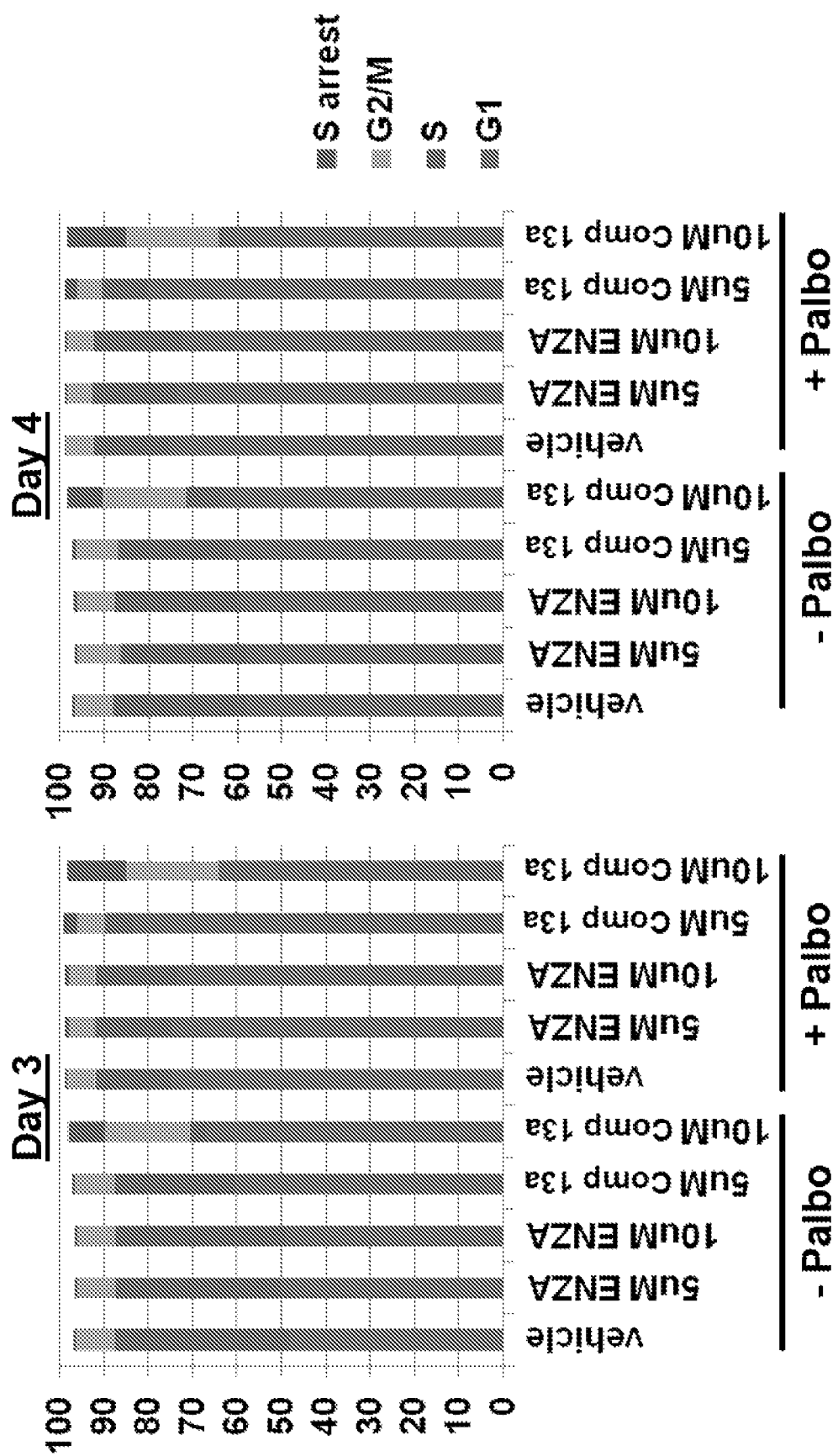
FIG. 4 shows % cells in each cell cycle phase for LNCaP95 cells in a cell cycle study.

Breast cancer and prostate cancer cell lines were treated with vehicle control, 5 µM or 10 µM of Compound 13a or Enzalutamide (ENZA), with or without 0.25 µM Palbociclib (Palbo) for 2, 3 or 4 days. Representative data are shown. n≥3. Stacked columns show average results from 3-4 experiments. FIG. 3 shows % cells in each cell cycle phase for AR-positive SUM-159PT cells and FIG. 4 shows % cells in each cell cycle phase for LNCaP95 prostate cancer cells.

Results demonstrated that Compound 13a caused cell cycle disruption. Combination with palbociclib resulted in cell accumulation in G1 phase and cell reduction in early S phase for AR-positive SUM-159PT cells, while the combination resulted in cell accumulation in G1 and G2/M phases and almost complete elimination in S phase for LNCaP95 prostate cancer cells.

Figure 5:
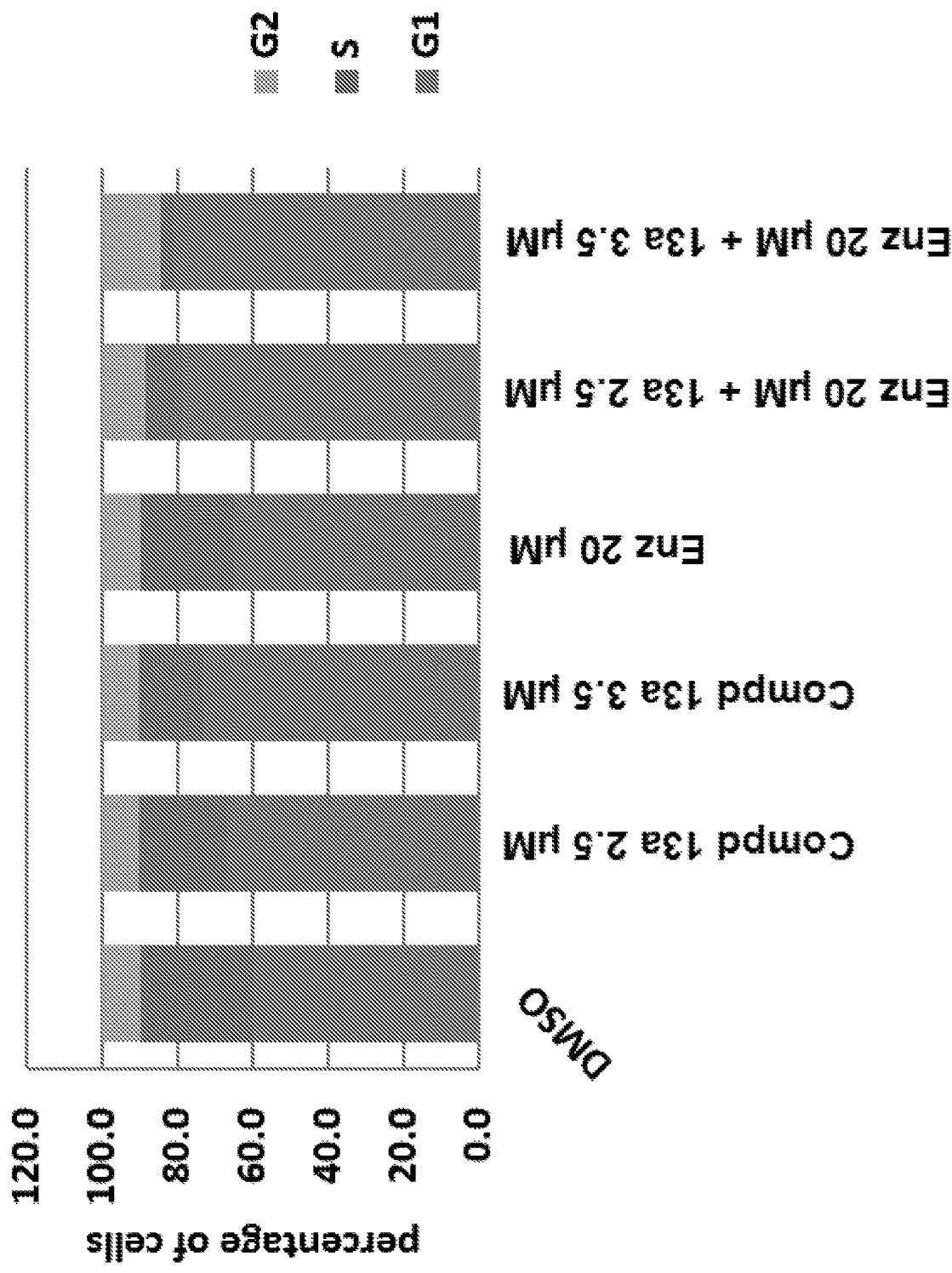
FIG. 5 shows % cells in each cell cycle phase for C4-2B-MDVR cells in a cell cycle study.

Enzalutamide resistant human prostate cancer cell line C4-2B-MDVR was treated with vehicle control (DMSO), 2.5 µM or 3.5 µM of Compound 13a with or without Enzalutamide (ENZA). Stacked columns, FIG. 5 shows % cells in each cell cycle phase for C4-2B-MDVR.

Results demonstrated that Compound 13a in combination with enzalutamide lead to G1 arrest in C4-2B-MDVR.

Example 32. Colony Formation

Breast cancer and prostate cancer cell lines were treated with vehicle control, various concentrations of Compound 13a, Enzalutamide (ENZA), or Palbociclib (Palbo) for 7 days (SUM-159PT) or for 15 days (LNCaP95). Representative data are shown. n≥3.

Combination of Compound 13a and palbociclib reduced colony formation in AR-positive SUM159-PT breast and LNCaP95 prostate cancer cells. This inhibitory effect is reversible.

Figure 6:
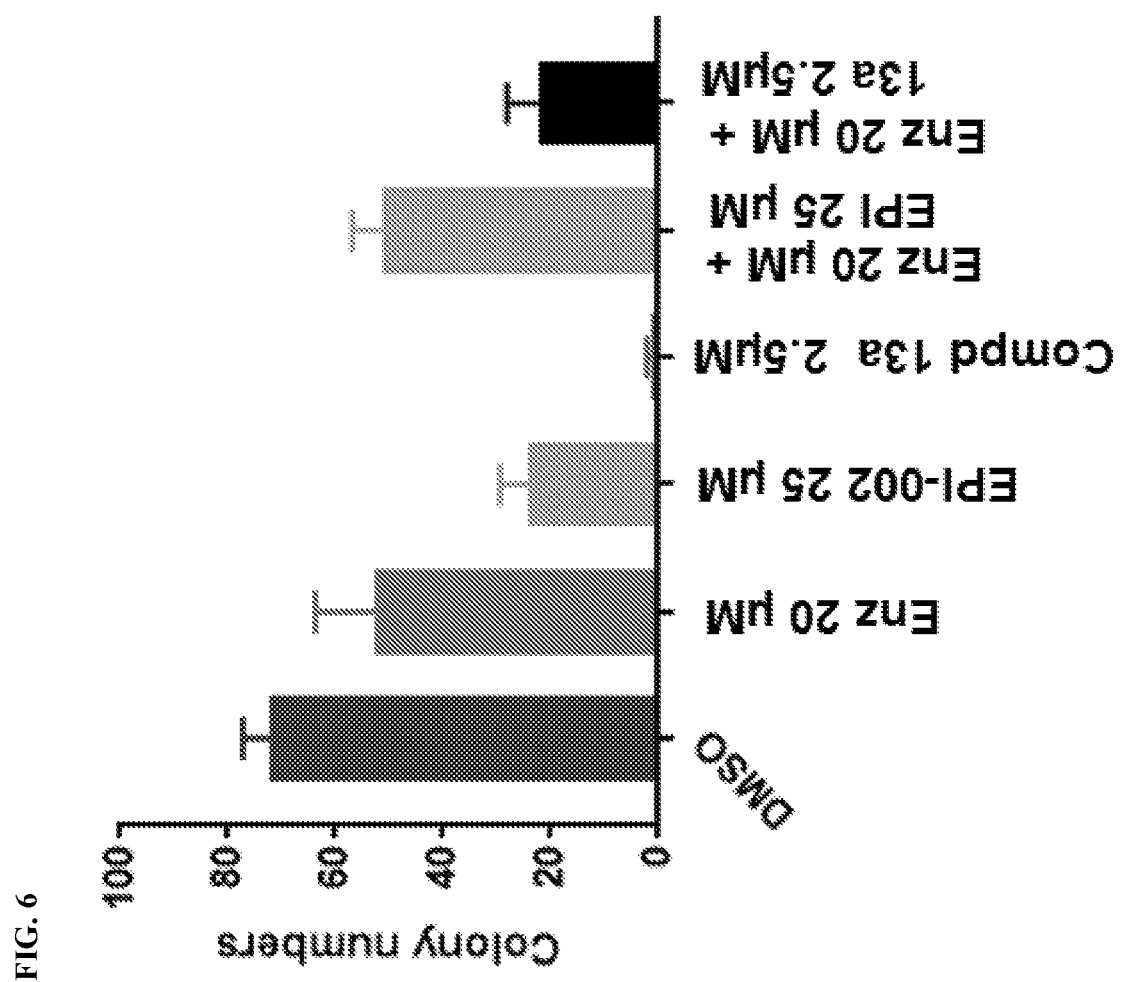
FIG. 6 shows colony numbers in C4-2B-MDVR cells treated with EPI-002 or Compound 13a, alone or in combination with enzalutamide.

Enzalutamide resistant human prostate cancer cell line C4-2B-MDVR was treated with vehicle control (DMSO), various concentration of EPI-002, Compound 13a, Enzalutamide (ENZA), or combination of EPI-002 or Compound 13a with Enzalutamide. The combination reduced colony formation (FIG. 6).

Results from Examples 30-32 demonstrate targeting AR NTD with androgen receptor N-terminal domain inhibitor, such as Compound 13a, may benefit patients with breast cancer that express AR. Without bound to any theory, a targeted, combination therapeutic approach could allow more specific and effective treatments for breast cancer patients and prostate cancer patients.

Figure 7C:
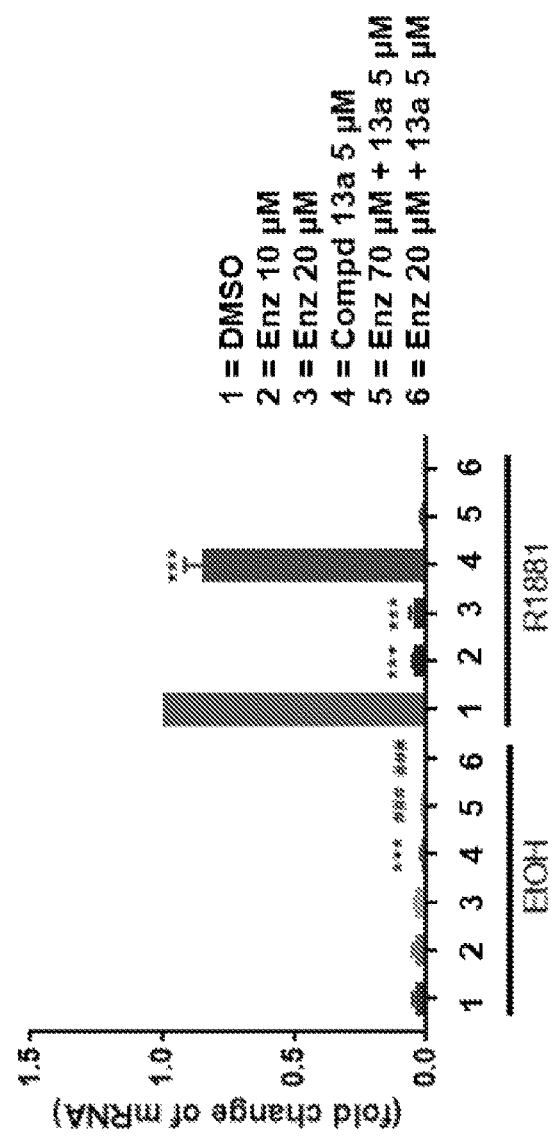
FIG. 7A shows Compound 13a and/or enzalutamide effects on levels of PSA mRNA in C4-2B-MDVR.
FIG. 7B shows Compound 13a and/or enzalutamide effects on levels of UBE2C mRNA in C4-2B-MDVR.
FIG. 7 C shows Compound 13a and/or enzalutamide effects on levels of FKBP5 mRNA in C4-2B-MDVR.
FIG. 7D shows Compound 13a and/or enzalutamide effects on levels of Cyclin A2 mRNA in C4-2B-MDVR.
FIG. 7E shows Compound 13a and/or enzalutamide effects on levels of TMPRSS2 mRNA in C4-2B-MDVR.
FIG. 7F shows Compound 13a and/or enzalutamide effects on levels of CDC20 mRNA in C4-2B-MDVR.
Figure 7D:
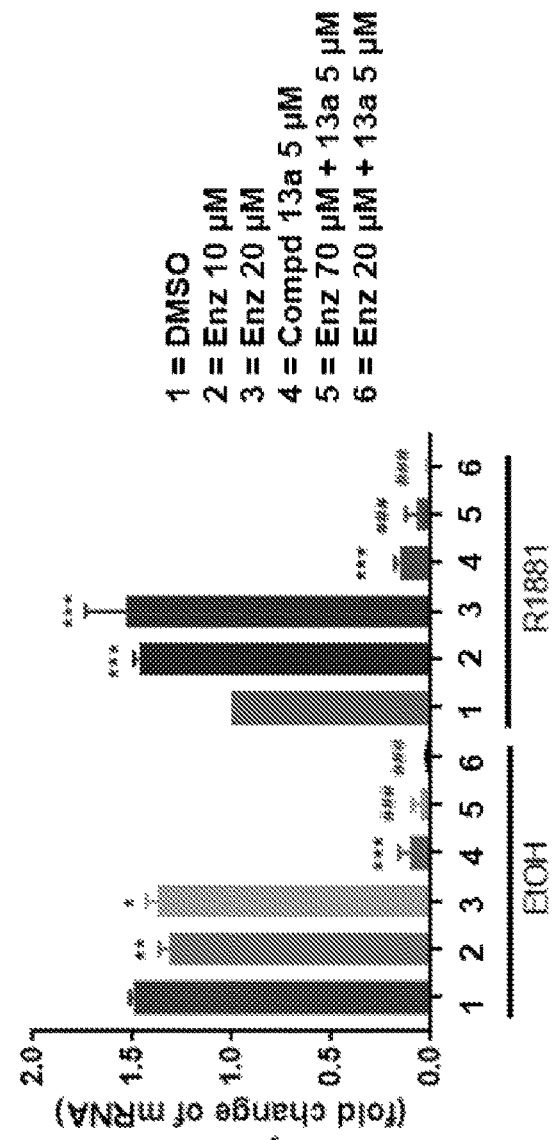
Figure 7E:
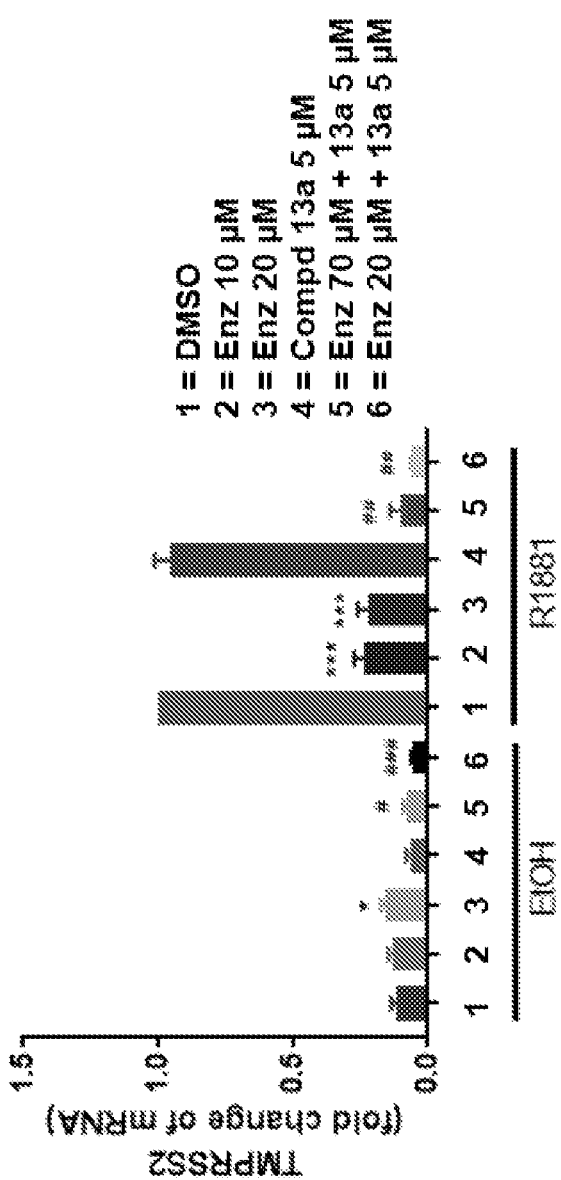
Figure 7F:
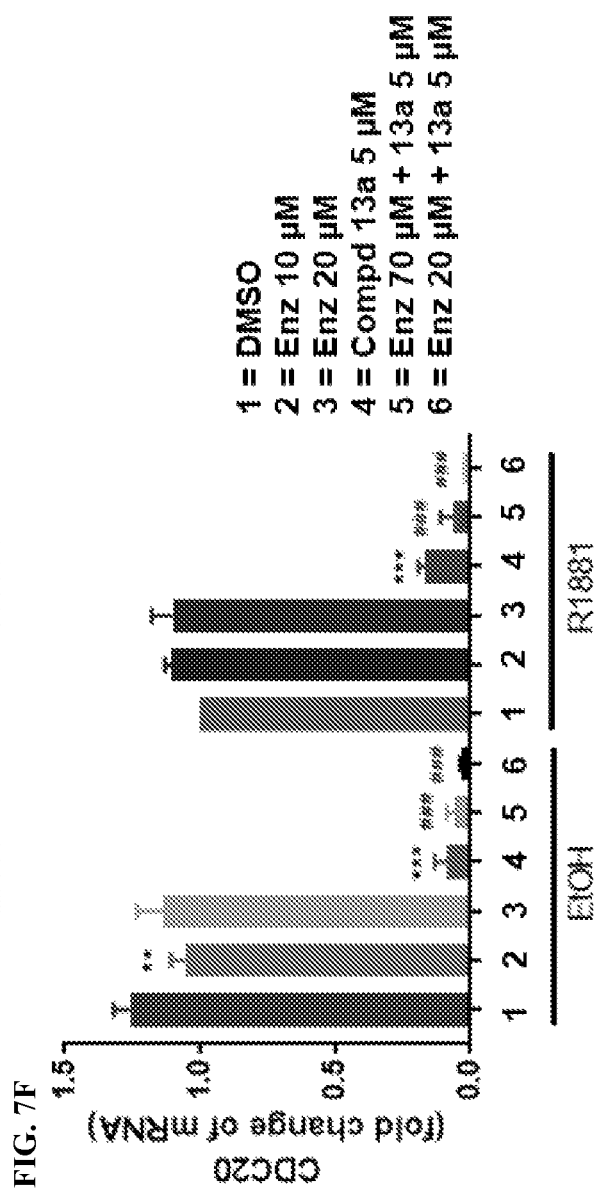
Figure 8:
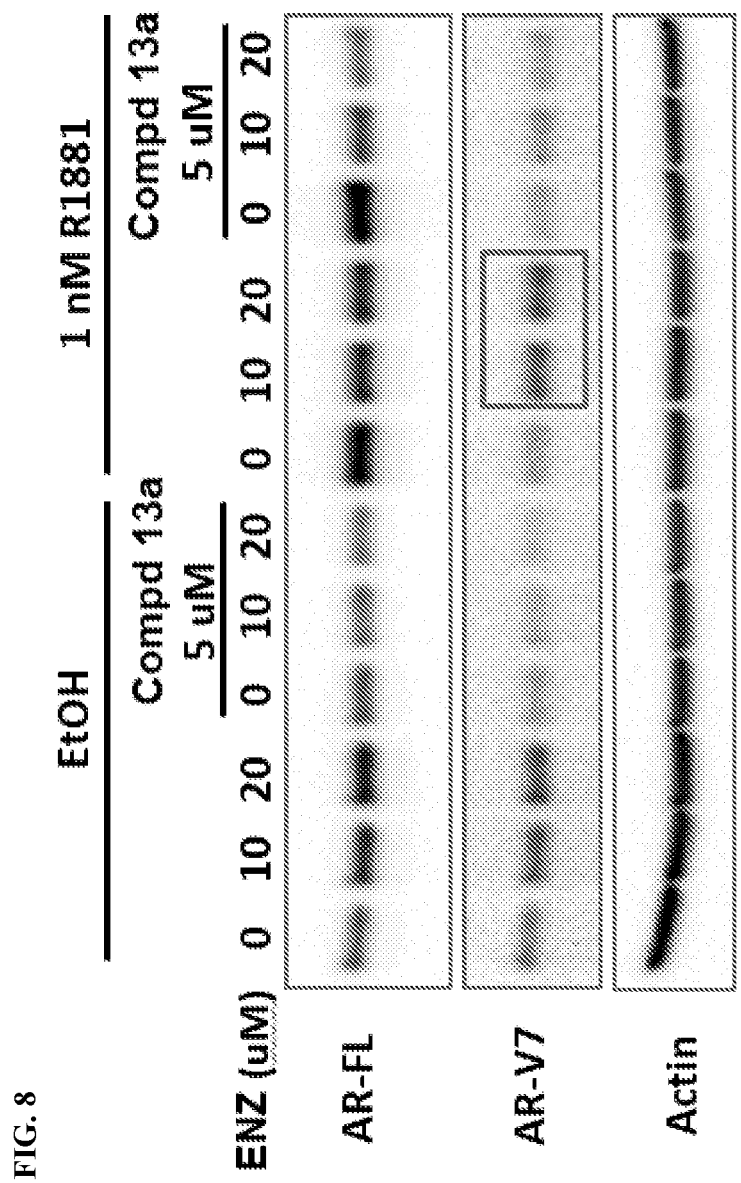
FIG. 8 shows protein levels of AR-FL and AR-V7 from C4-2B-MDVR cells treated with Compound 13a alone or in combination with enzalutamide, normalized to β-actin

Example 33. Effect of Compound 13a and Enzalutamide on F1-AR and AR-V7 Regulated Genes Transcript levels of PSA, UBE2C, FKBP5, CYCLIN A2, TMPRSS2, and CDC20, were measured in enzalutamide resistant human prostate cancer cell line C4-2B-MDVR. Enzalutamide increased the expression of UBE2C and cyclin A2 in the presence of androgen (FIG. 7B, FIG. 7D) and had no effect on $CDCl_2O$ (FIG. 7F). Compound 13a decreased transcript expression of the M-phase cell cycle genes UBE2C, CYCLIN A2, CDC20 and PSA, FKBP5, and CDC20 (FIGS. 7B, 7D, and 7F). While Compound 13a alone did not decrease transcript expression in PSA, FKBP5, and CDC20 but not TMPRSS23 (FIGS. 7A-7F), in R1881 treated cells, Compound 13a in combination with enzalutamide decreased the transcript expression more than monotherapies. FIG. 8 shows protein levels of AR-FL and AR-V7 from C4-2B-MDVR cells treated with Compound 13a alone or in combination with enzalutamide, normalized to β-actin.

As shown in FIGS. 9B-9D, Compound 13a inhibited transcriptional activities of ectopic AR-V7.

Without bound to any theory, targeting AR-NTD in addition to AR-LBD to block both FL-AR and AR-Vs could be a potential treatment option for CRPC.

Example 34. Effect of Compound 13a and Enzalutamide on Cell Proliferation

Figure 10:
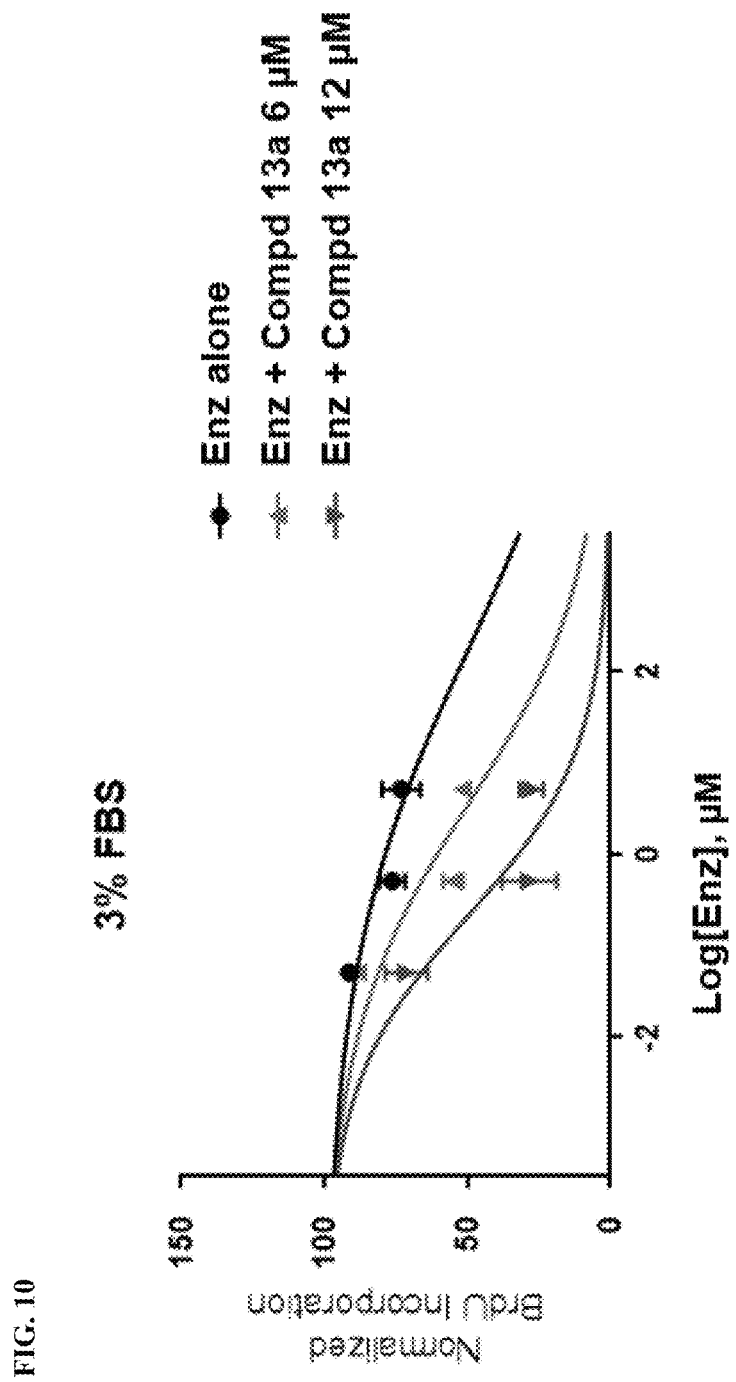

Prostate cancer cell line VCaP were treated with vehicle control, Enzalutamide (ENZA; 0.05, 0.5, or 5 µM) with or without Compound 13a (6 or 12 µM). BrdU incorporation was used to assess cell proliferation. Data from each treatments were normalized to vehicle control as shown in FIG. 10. $IC_{50}$ was determined as shown in Table 2.

TABLE 2

| $IC_{50}$ for blocking proliferation of VCaP cells | |
| --- | --- |
| Compound ID | $IC_{50}$ (µM) |
| Enzalutamide | 163.6 |
| Enzalutamide + 13a (6 µM) | 3.350 |
| Enzalutamide + 13a (6 µM) | 0.2060 |

Figure 11A:
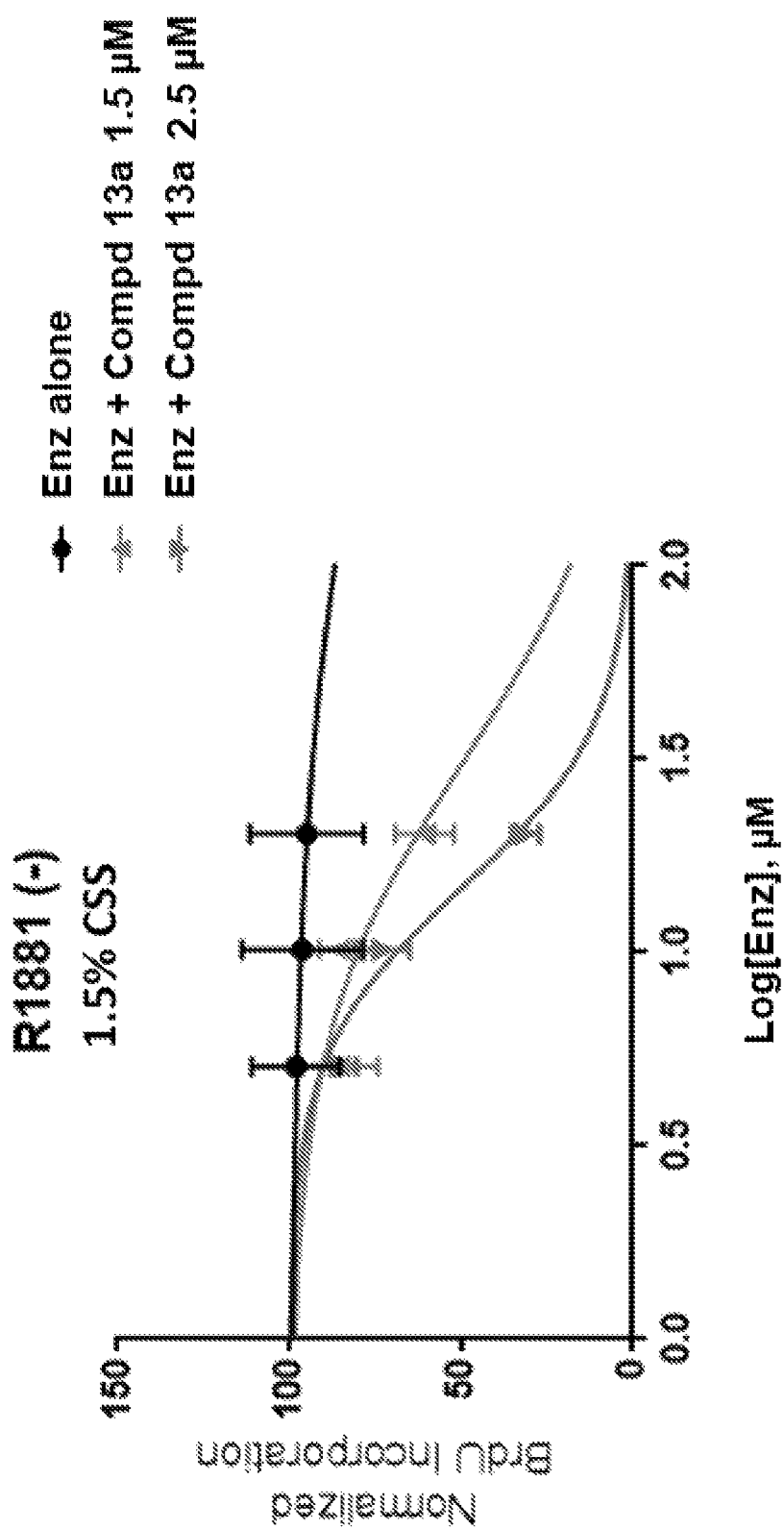
FIG. 11 A shows cell proliferation assay results for C4-2B-MDVR cell lines treated enzalutamide (ENZ) alone or in combination with Compound 13a in the absence of R1881.
Figure 11B:
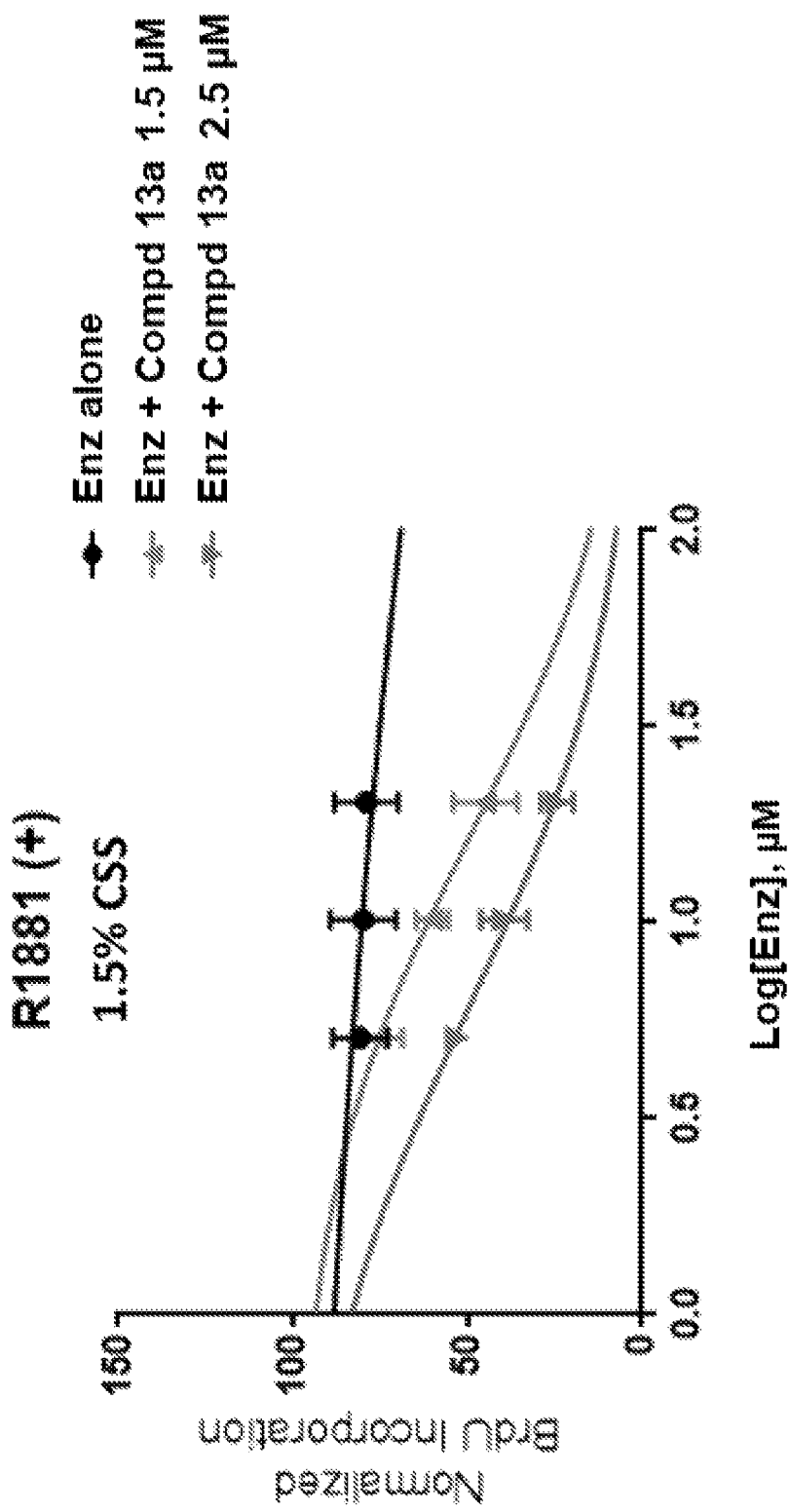

Enzalutamide resistant human prostate cancer cell line C4-2B-MDVR were treated with vehicle control, Enzalutamide (ENZA; 0.75, 1.5, or 1.25 µM) with or without Compound 13a (1.5 or 2.5 µM) in cells treated with R1881 and in cells not treated with R1881. BrdU incorporation was used to assess cell proliferation. Data from each treatments were normalized to vehicle control as shown in FIGS. 11A and 11B. $IC_{50}$ was determined as shown in Table 3.

As shown in FIGS. 10, 11A and 11B and Tables 3-4, synergistic effect of Compound 13a and enzalutamide was observed in cell proliferation assay.

TABLE 3

| $IC_{50}$ in C4-2B-MDVR 1.5% CSS cell proliferation assay | | |
| --- | --- | --- |
| Compound ID | $IC_{50}$ (µM) +R1881 | $IC_{50}$ (µM) −R1881 |
| Enzalutamide + 13a (1.5 µM) | 15.98 | 30.16 |
| Enzalutamide + 13a (2.5 µM) | 5.91 | 15.98 |

Example 35. Combination of Compound 13a and Radiation

Figure 12A:
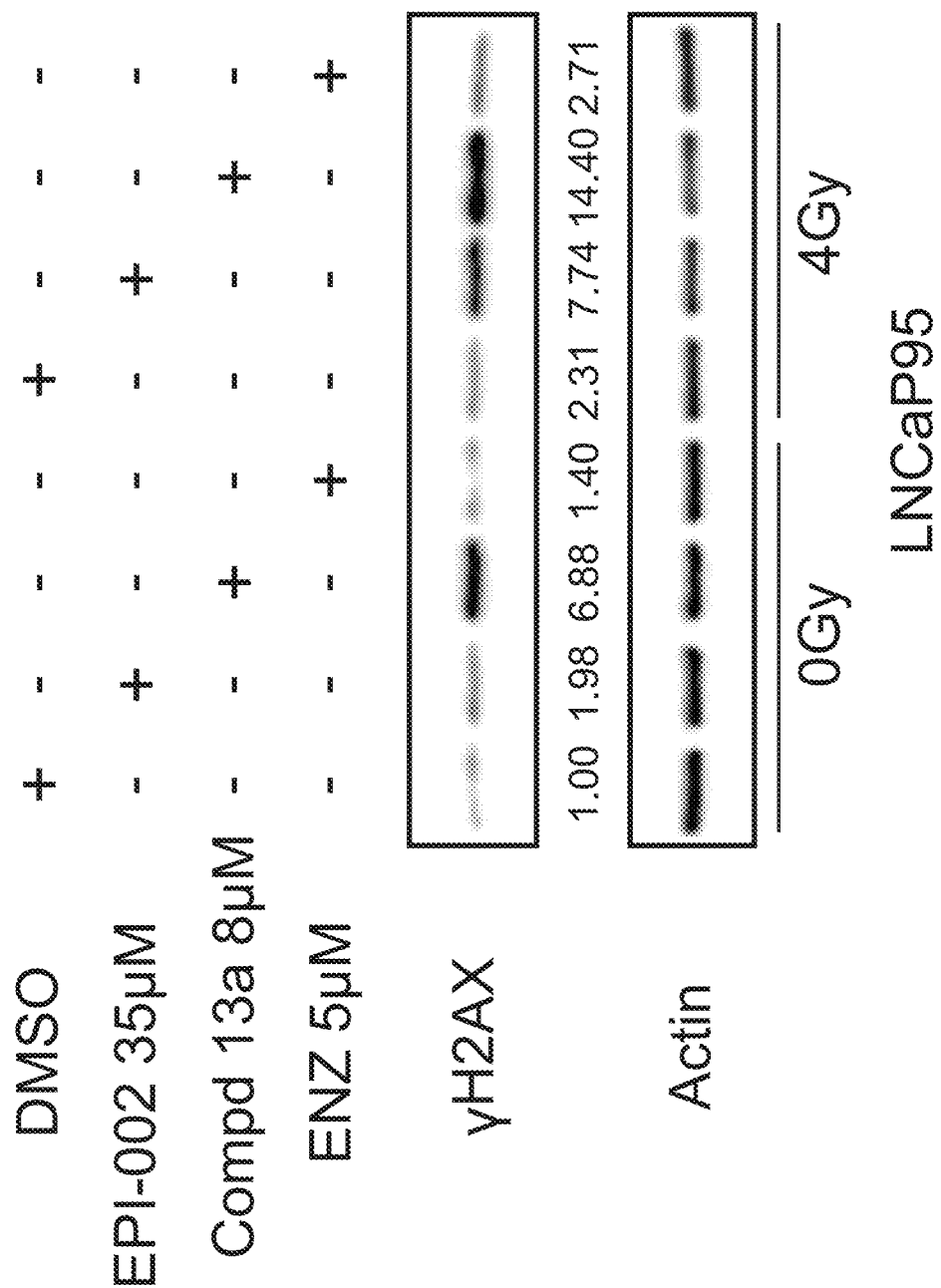
FIG. 12A shows Western blot analyses for γH2AX in protein lysates from LNCaP95 cells treated with DMSO (control), EPI-002 (35 μM), Compound 13a (8 μM), or enzalutamide (ENZ, 5 μM) with or without irradiation (4Gy) harvested after 48 h incubation.

LNCaP95 cells treated with DMSO (control), EPI-002 (35 µM), Compound 13a (8 µM), or enzalutamide (ENZ, 5 µM) with or without irradiation (4Gy) and harvested after 48 h incubation. Western blot analyses measuring γH2AX protein is shown in FIG. 12A.

Figure 12B:
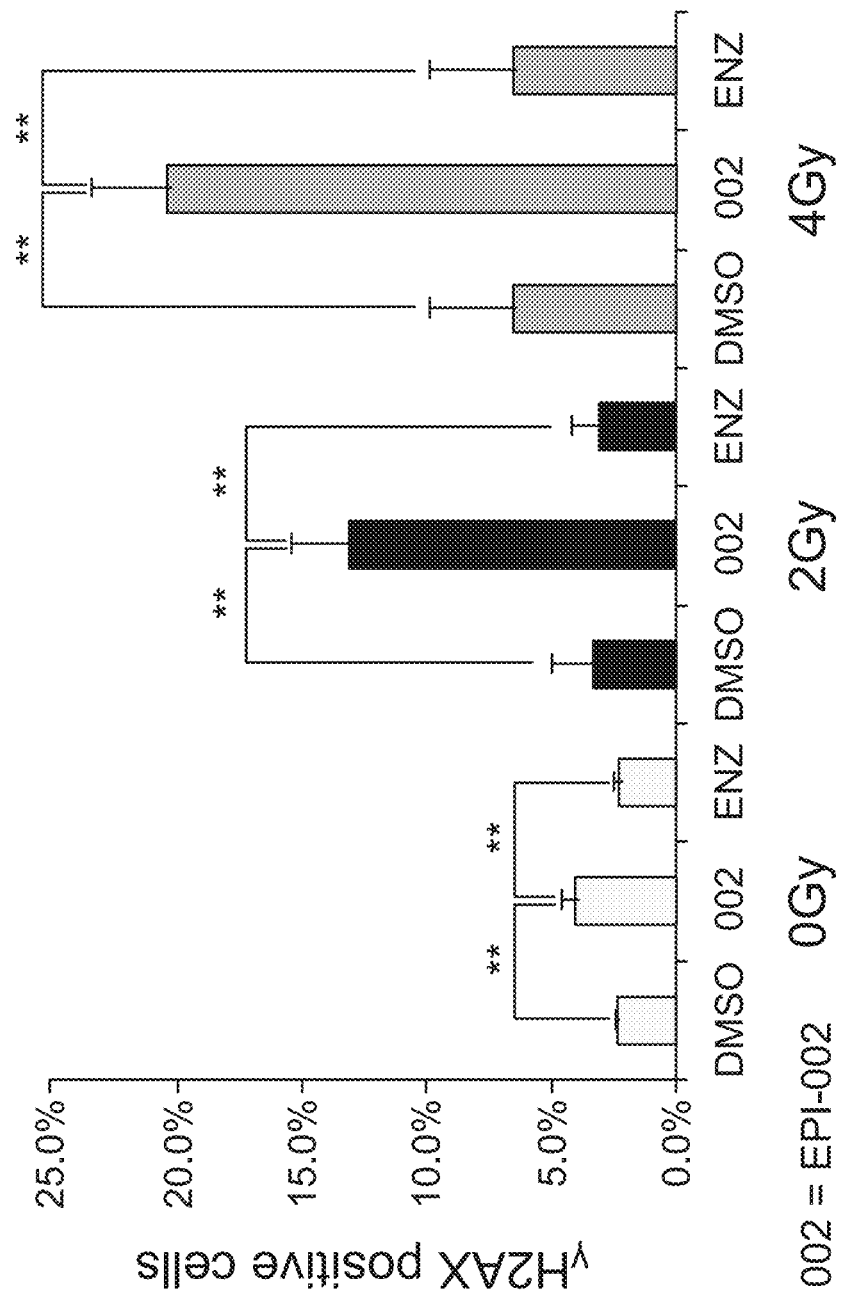
FIG. 12B shows percent of LNCaP95 cells positive for γH2AX after treatment with DMSO (control), EPI-002, or enzalutamide (ENZ) with or without irradiation (2 Gy or 4Gy).
Figure 12C:
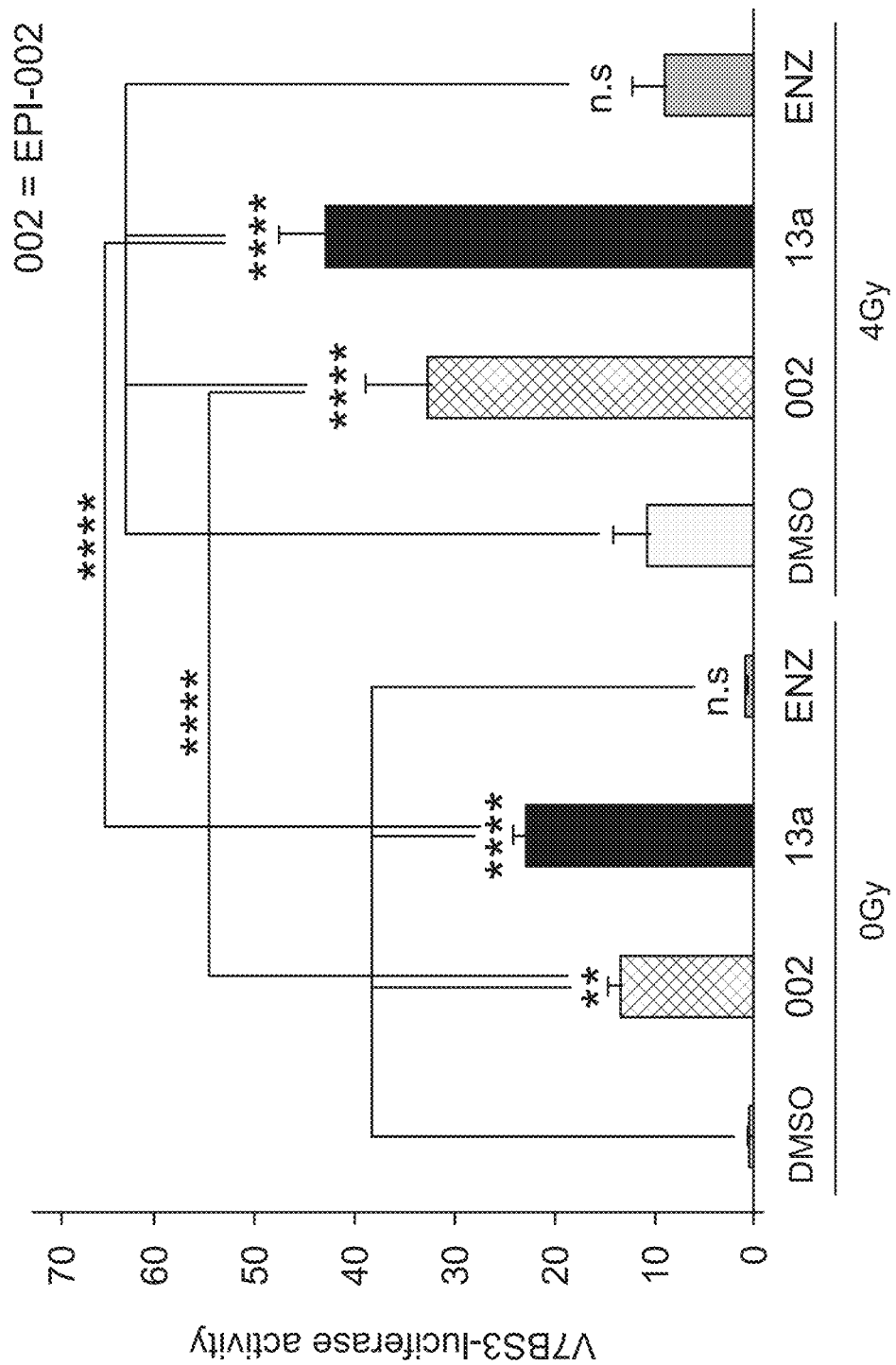
FIG. 12C shows percent of γH2AX foci in LNCaP95 cells treated with DMSO (control), EPI-002, Compound 13a, or enzalutamide (ENZ) with or without irradiation (4Gy).

Further, cells were labelled for γH2AX and 7AAD and analyzed by flow cytometry (FIG. 12B). The percent of cells positive for γH2AX are shown in FIG. 12B. The percentage of cells containing above 10 γH2AX foci (mean±SD from three independent experiments) are represented in FIG. 12C. Enzalutamide had no effect whereas Compound 13a did.

Figure 12D:
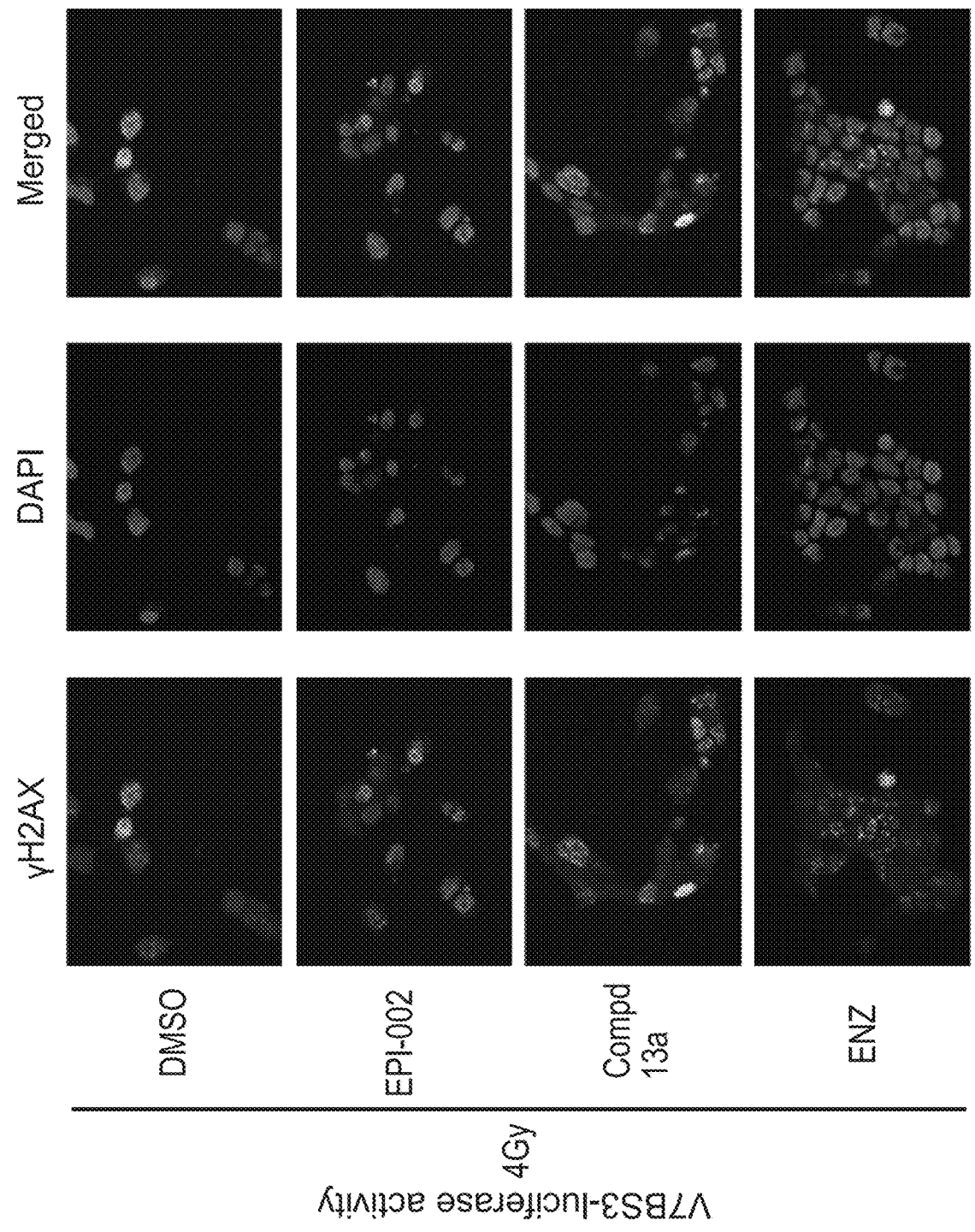
FIG. 12D shows representative images of γH2AX foci in LNCaP95 cells treated with DMSO (control), EPI-002, Compound 13a, or enzalutamide (ENZ) with irradiation (4Gy).

FIG. 12D shows representative images of foci of DNA damage.

Flow Cytometry: Cell cycle analysis was conducted by flow cytometry using BrdU-FITC and 7AAD. DNA damage was analyzed using γH2AX antibody (CST) and 7AAD. Cells were analyzed on FACScalibur flow cytometer.

Immunofluorescence staining: γH2AX antibody (Millipore mouse), Alexa488 anti-mouse antibody were used for staining. Cells were analyzed on Axio observer (×20 magnification) equipped with epitome 2.

Statistical analysis: Graphs represent the means±SEM from three independent experiments performed with three technical replicates. Statistical significance was determined using GraphPad Prism software with a one-way ANOVA; *P<0.05, P<0.01, *P<0.001, ****P<0.0001.

Without bound to any theory, this experiment shows combination of Compound 13a and radiation therapy increases accumulation of DNA damage in vitro.

Material and Methods for Examples 36-38

Compounds: Juglone and all-trans retinoic acid (ATRA) were purchased from Sigma-Aldrich. EPI-002 was provided by NAEJA, Compound 13a was prepared in house, and enzalutamide (ENZ) was purchased from OmegaChem.

Pint activity assay: Pin1 PPIase activity assay was measured using the Fluorimetric Green Pin1 Assay kit (AnaSpec) using 500 ng of recombinant human Pin1 protein (Abcam) incubated at 37° C. for 60 min.

Transfections and luciferase assays: Plasmids and transfections have been previously described elsewhere in Andersen et al., Cancer Cell. 2010, and Myung et al., J Clin Invest. 2013.

Flow cytometry: Fixed cells were probed with anti-BrdU-FITC antibody (BD Biosciences) and stained with 7AAD (Sigma). Data was acquired on a FACSCalibur flow cytometer (BD Biosciences) with CellQUEST Pro and later analyzed using FlowJo V10 software.

β-galactosidase staining: Cells grown in chamber slides and treated with compounds were fixed at room temperature with 2% formaldehyde/0.2% glutaraldehyde, and then incubated at 37° C. with fresh β-gal staining solution (Cell Signaling) titrated to pH 6.0. Staining was optimal after incubating the slides overnight for 16-18 hours.

Statistical analyses: Statistical significance was determined with GraphPad Prism 8 software using two-way ANOVA with Dunnett's multiple comparisons test unless indicated otherwise; *P<0.05, P<0.01, *P<0.001; ns, not significant.

Example 36. Effect of Pin1 Inhibitors on Transcriptional Activity of AR

Figure 13:
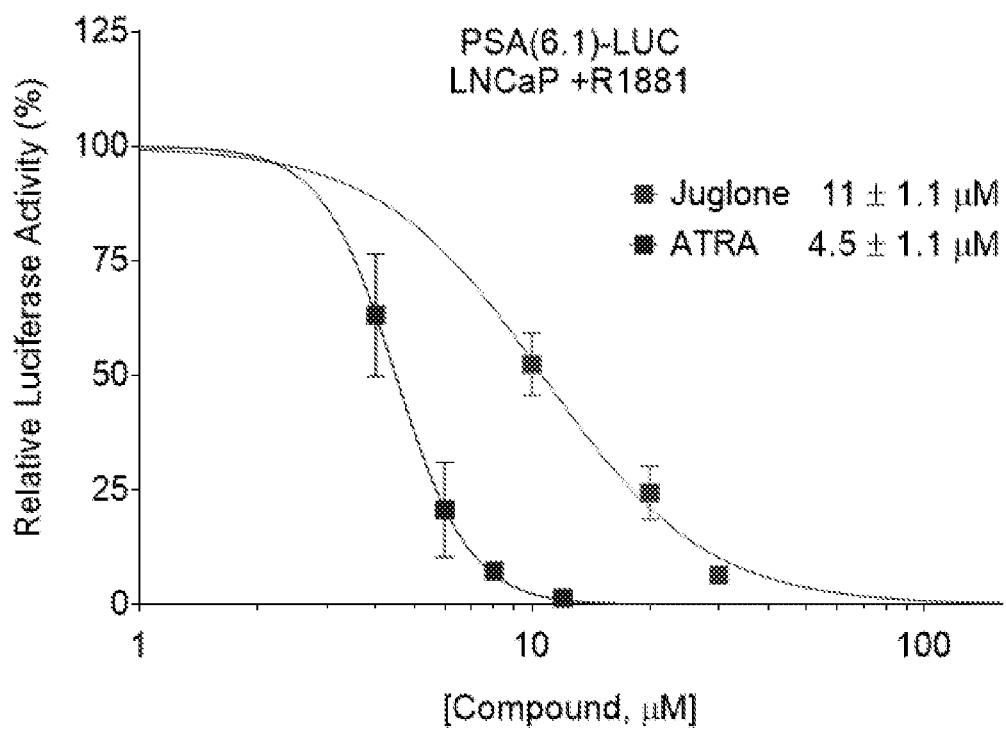
FIG. 13 shows inhibitory dose-response curve for juglone and ATRA in PSA (6.1 kb)-luciferase assay.
Figure 14:
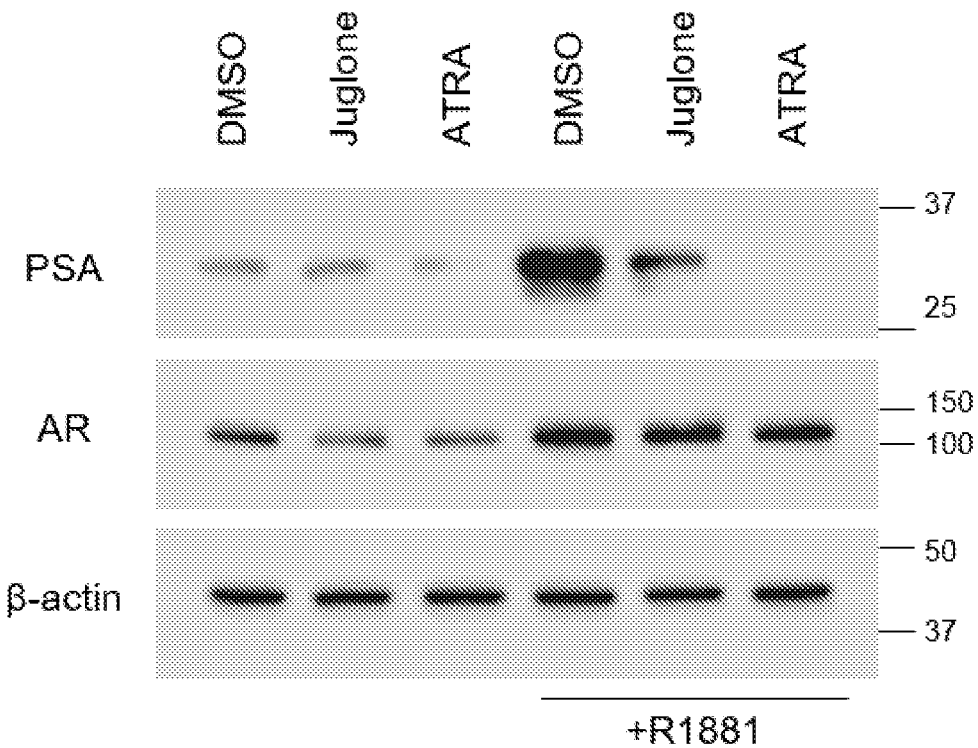
FIG. 14 is a Western blot showing the levels PSA and AR protein in lysates prepared from LNCaP cells treated with juglone (20 μM) or ATRA (10 μM), and R1881 (1 nM) or vehicle for 24 h.

LNCaP cells were transfected with the PSA (6.1 kb)-luciferase reporter for 24 h, and then treated with indicated concentration of juglone, ATRA, or 13CisRA (inactive conformation) with synthetic androgen, R1881 (1 nM) for 24 h as described in Example 35. After 24 h of incubation with R1881, the cells were harvested, and relative luciferase activities were determined. FIG. 13 shows inhibitory dose-response curve for juglone and ATRA on PSA (6.1 kb)-luciferase activity. FIG. 14 is a Western blot showing the levels PSA and AR protein in lysates prepared from LNCaP cells treated with juglone (20 μM) or ATRA (10 μM), and R1881 (1 nM) or vehicle for 24 h. Data shown in Figures are the means±SE from 4 independent experiments.

No inhibitory effects were observed for reporter constructs regulated by CMV promoter or AP-1 binding sites with juglone, ATRA, or 13CisRA.

Figure 15:
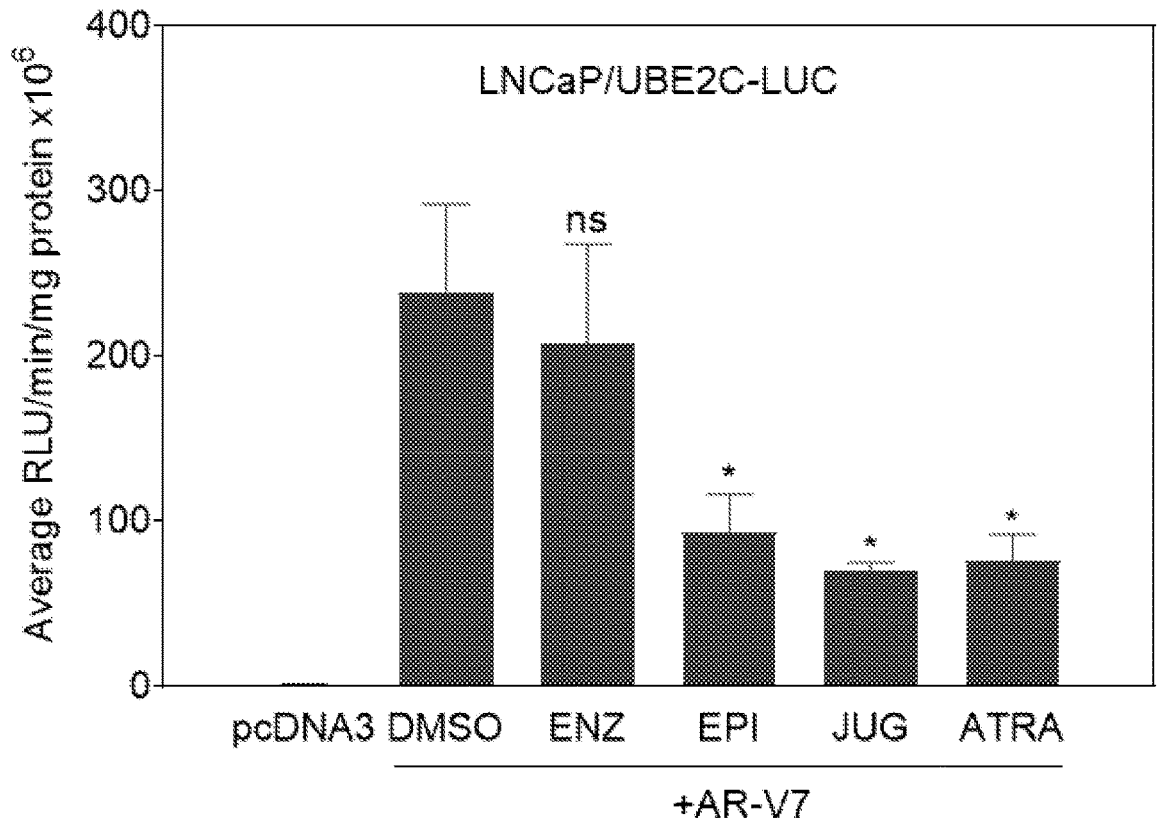
FIG. 15 shows transcription activity of AR-V7 in LNCaP cells measured with luciferase reporter gene regulated by UBE2C promoter.
Figure 16:
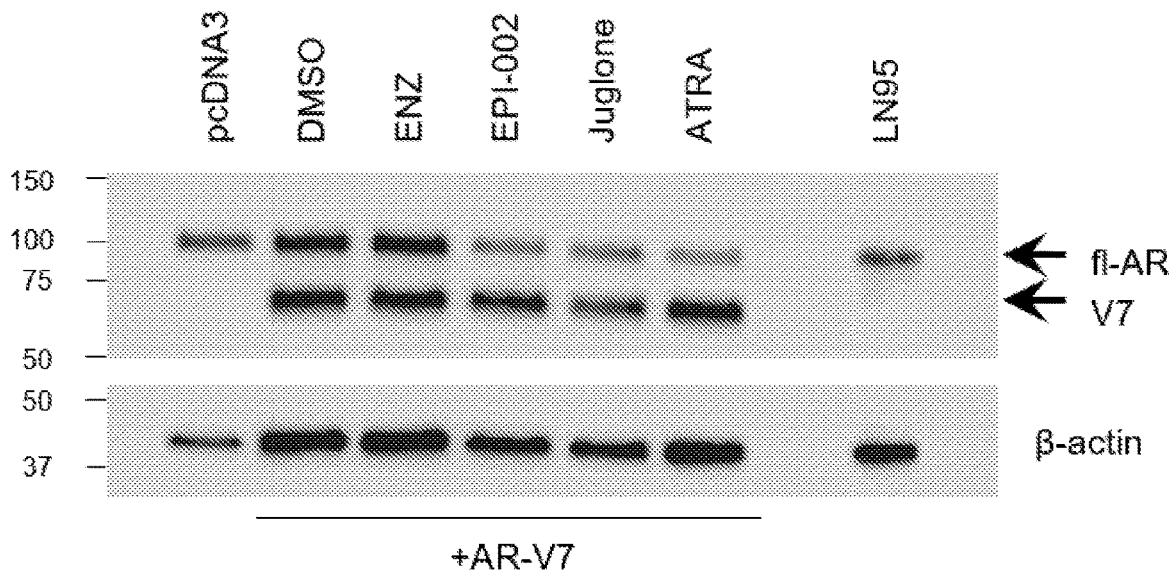
FIG. 16 is a Western blot showing the levels AR-V7 expression in lysates prepared from LNCaP cells.

Transcriptional activity of AR-V7 was measured using a luciferase reporter gene regulated by UBE2C promoter (FIG. 15). In LNCaP cells, UBE2C is selectively activated by ectopic AR-V7 expression. Cells transfected with V7 and UBE2C luciferase were incubated with enzalutamide (ENZ, 10 μM), EPI-002 (25 μM), juglone (JUG, 20 μM), or ATRA (10 μM) for 24 h. FIG. 16 is a Western blot showing equal levels of V7 expression between treatment groups. Results shown in FIGS. 15 and 16 are the means±SE from 3 independent experiments.

The above-described assays demonstrated that inhibiting Pin1 with ATRA decreased the transcriptional activity of AR and androgen-induced expression of PSA protein. Further, the assays demonstrated that ATRA also reduced the transcriptional activity of AR-V7 and androgen-independent growth of LN95 cells expressing both full-length AR and V7.

Figure 17:
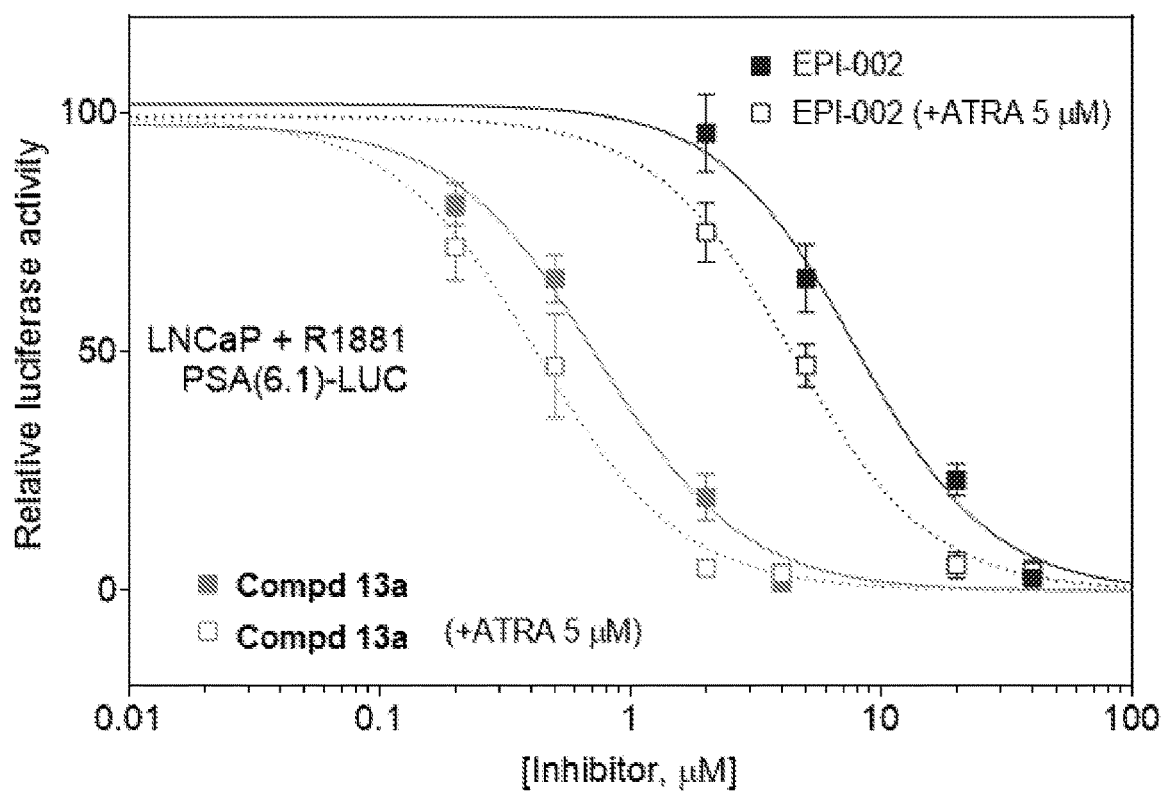
FIG. 17 shows inhibitory dose-response curve for EPI-002 and Compound 13a with or without ATRA in PSA (6.1 kb)-luciferase assay.

Example 37. Effect of Compound 13a and ATRA on Transcriptional Activity of AR LNCaP cells were transfected with the PSA (6.1 kb)-luciferase reporter for 24 h, and then treated with indicated concentration of ATRA and EPI-002 or ATRA and Compound 13a with synthetic androgen, R1881 (1 nM) for 24 h as described in Example 35. After 24 h of incubation with R1881, the cells were harvested, and relative luciferase activities were determined. FIG. 17 shows inhibitory dose-response curve on PSA (6.1 kb)-luciferase activity. Table 4 shows the calculated $IC_{50}$ in the above-described luciferase assay.

ATRA and EPI-002 or Compound 13a demonstrated a synergistic effect on inhibiting AR transcriptional activity. In the presence of ATRA, the dose-response curves for EPI-002 and Compound 13a shifted to the left, resulting in a 2-fold decrease in their $IC_{50}$ values.

TABLE 4

| | $IC_{50}$ in Luciferase Assay | |
| --- | --- | --- |
| | $IC_{50}$ ± SE (μM) | $R^2$ |
| EPI-002 | 7.9 ± 1.2 | .94 |
| EPI-002 (+ATRA) | 4.4 ± 1.1 | .97 |
| Compound 13a | 0.74 ± 1.2 | .96 |
| Compound 13a (+ATRA) | 0.42 ± 1.2 | .93 |

This experiment demonstrated that ATRA enhanced the potency of androgen receptor inhibitors/modulators. Pharmaceutical combination of Pin1 and androgen receptor modulators can be a new therapeutic strategy for the treatment of prostate cancer, including CRPC.

Example 38. Cell Cycle Analysis and Cellular Senescence

Figure 19A:
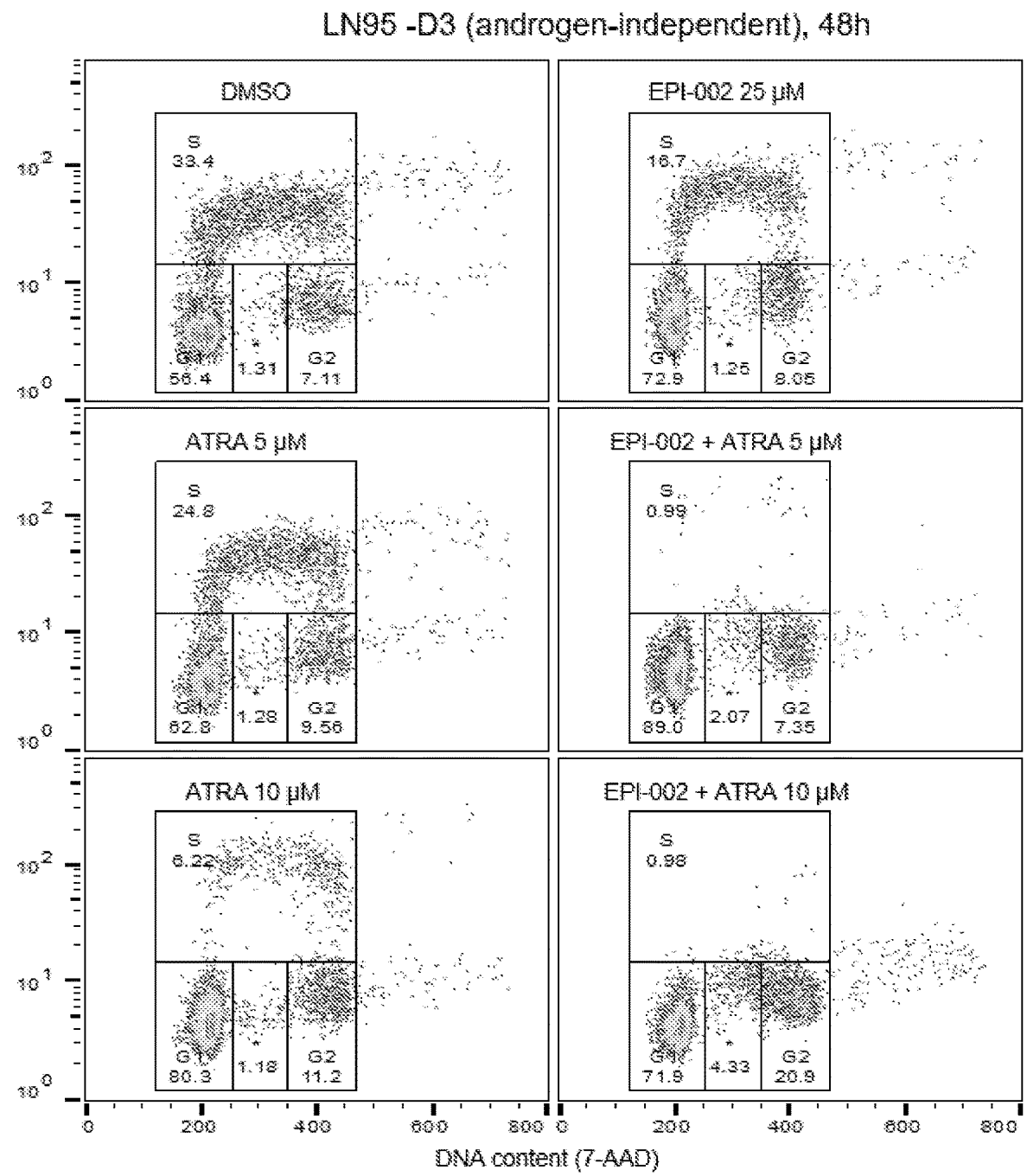
FIGS. 19A and 19B shows cell cycle analysis of LN95-D3 cells after treating with combination of ATRA and EPI-002 or Compound 13a or Enzalutamide (EnZ), in 1.5% charcoal-tripped serum.
Figure 19B:
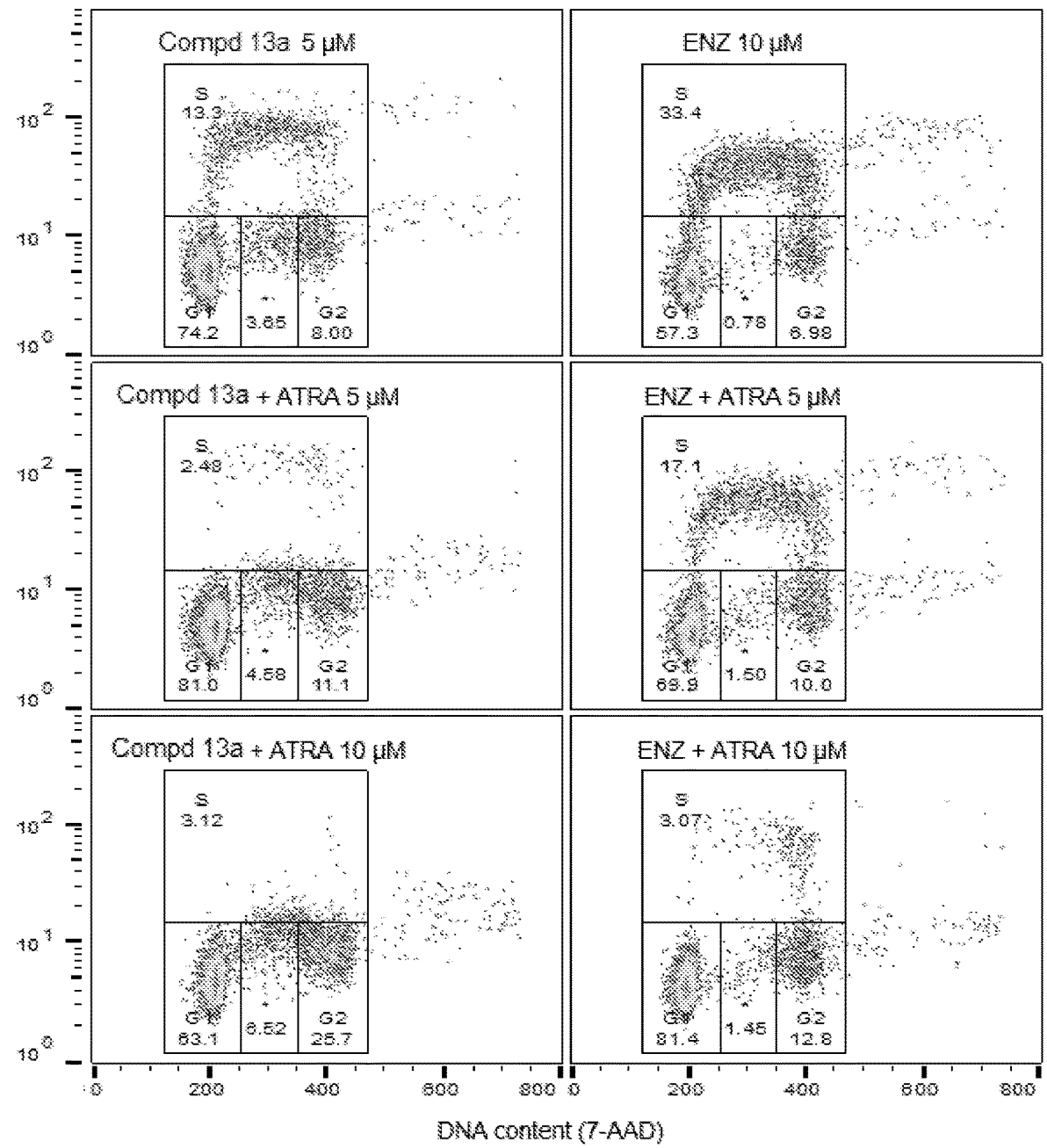
Figure 20:
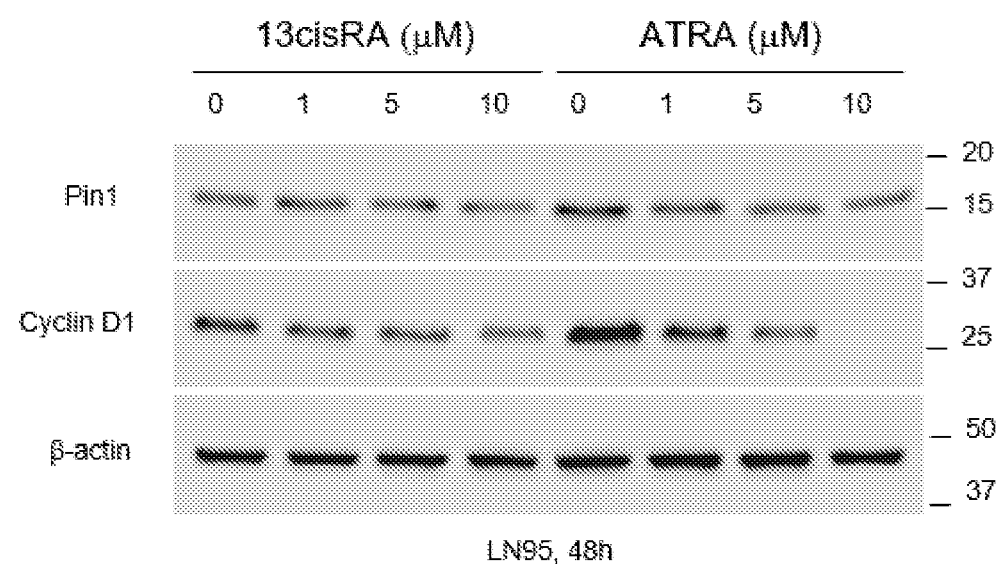
FIG. 20 shows Western blots showing stability of Cylin D1 and Pin 1 with the treatment with ATRA or 13CisRA.

Cell cycle analysis of LN95-D3 cells after treating with combinations of ATRA and ARNTD modulators (EPI-002, Compound 13a) or antiandrogen (ENZ, enzalutamide), in 1.5% charcoal-stripped serum. After incubating with the compounds, cells were labelled with BrdU for 2 h and then processed for flow cytometry. ATRA arrested cells in G1 and decreased the S phase population in a dose-dependent manner. These effects were synergistic with EPI-002 and with Compound 13a, but not with ENZ (FIGS. 19A and 19B). Further, Western blot analysis shows that ATRA inhibits Pin1 and leads to its degradation, which in turn affects the stability of Cyclin D1, a Pin1 substrate (FIG. 20).

Figure 18A:
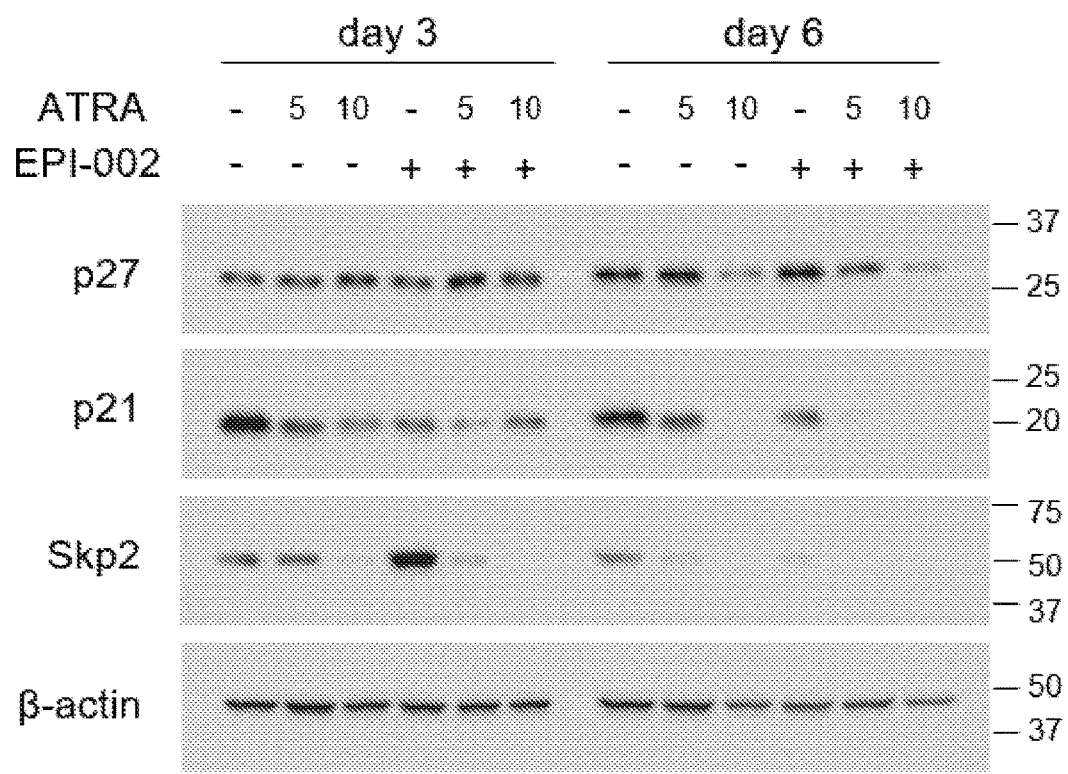
FIGS. 18A and 18 B are Western blots showing the levels altered expression of proteins regulating senescence in lysates prepared from the cells after 3 or 6 days of treatment with ATRA, EPI-002, or the combination thereof.
Figure 18B:
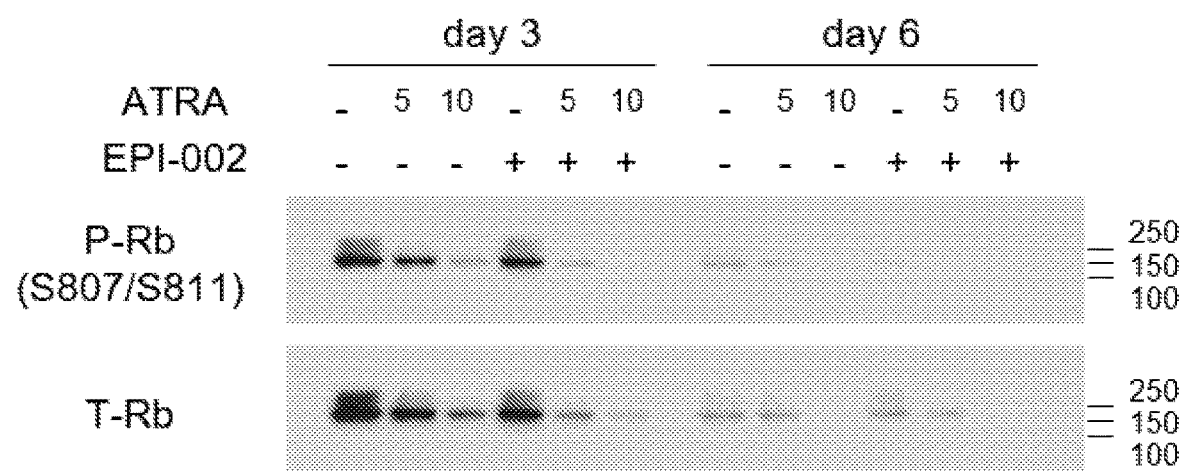

Senescence-associated β-gal staining of LN95 cells were observed after incubating in 1.5% charcoal-stripped serum with EPI-002, ATRA, or combination for 3 days. Combining EPI-002 and ATRA showed synergy for increasing the percentage of β-gal-positive cells. FIGS. 18A and 18B are Western blots of lysates prepared from the cells after 3 or 6 days of treatment showed altered expression of proteins regulating senescence. Results shown are representative of 3 independent experiments. Without bound to any theory, a more potent androgen receptor modulators of the present disclosure in combination with Pin1 inhibitors, e.g., ATRA, would also demonstrate synergy for increasing the percentage of 3-gal-positive cells.

NUMBERED EMBODIMENTS

Embodiment 1. A pharmaceutical composition comprising an androgen receptor N-terminal domain inhibitor and a second therapeutically active agent.

Embodiment 2. A pharmaceutical composition comprising a Pin1 inhibitor and an androgen receptor N-terminal domain inhibitor, wherein the androgen receptor N-terminal domain inhibitor is not 3-(4-(2-(4-(3-chloro-2-hydroxypropoxy)phenyl)propan-2-yl)phenoxy)propane-1,2-diol, 3-(4-(2-(4-(2-acetoxy-3-chloropropoxy)phenyl)propan-2-yl)phenoxy)propane-1,2-diyl diacetate, or stereoisomers thereof.

Embodiment 3. The pharmaceutical composition of Embodiment 1 or 2, wherein the androgen receptor N-terminal domain inhibitor is a compound of formula (i):

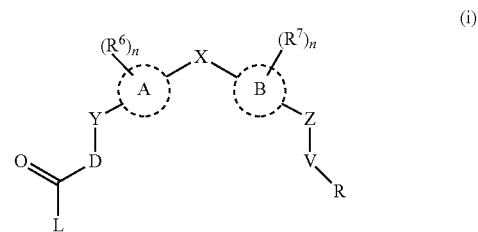

or a pharmaceutically acceptable salt, tautomer, stereoisomer or prodrug thereof, wherein:
A and B are each independently aryl or heteroaryl;
X is a bond, —$(CR^8R^9)_t$—, —O—, —C(=O)—, —S(O)$_n$—, —$NR^1$—, —$CONR^{10}$—, —$NR^{10}CO$—, —$SO_2NR^{10}$—, or —$NR^{10}SO_2$—;
Y and Z are each independently a bond, —$(CR^8R^9)_t$—, —O—, —S(O)$_n$—, —$NR_{10}$—, —$CONR^{10}$—, —$NR^{10}CO$—, —$SO_2NR^{10}$—, or —$NR^{10}SO_2$—;

V is a bond, optionally substituted —$(CR^{11}R^{12})_m$—, —C(=O)—, —N($R^{10}$)CO—, —$CONR^{10}$—, or —$NSO_2R^{10}$—;

R is —$(CR^{4a}R^{4b})$—$(CR^{5a}R^{5b})$—W or W;

W is hydrogen, halogen, —$CF_3$, —$CF_2R^{10}$, —CN, —$OR^{13}$, —$NR^{13}R^{14}$, optionally substituted —$CONR^{13}R^{14}$, optionally substituted carbocyclyl, optionally substituted heterocyclyl, optionally substituted aryl, or optionally substituted heteroaryl;

D is —$(CR^{1a}R^{1b})_q$—, —O—, or —$NR^{10}$—;

L is —$(CR^{2a}R^{2b})$—$R^3$ or -E-$R^3$;

E is —$(CR^{2a}R^{2b})_g$—, —O—, —$NR^{10}$—, or —$NR^{10}$—$(CR^{2a}R^{2b})_g$—;

$R^{1a}$, $R^{1b}$, $R^{2a}$, and $R^{2b}$ are each independently hydrogen, halogen, hydroxy, optionally substituted $C_{1-6}$ alkyl, optionally substituted $C_2$-$C_6$ alkenyl, optionally substituted $C_2$-$C_6$ alkynyl, optionally substituted $C_{1-6}$ alkoxy, optionally substituted —OCO($C_1$-$C_6$ alkyl), —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, optionally substituted carbocyclyl, optionally substituted heterocyclyl, optionally substituted aryl, or optionally substituted heteroaryl;

or alternatively, $R^{1a}$ and $R^{1b}$ taken together form an optionally substituted carbocyclyl, optionally substituted heterocyclyl, optionally substituted aryl, or optionally substituted heteroaryl;

or alternatively, $R^{2a}$ and $R^{2b}$ taken together form a CO, optionally substituted carbocyclyl, optionally substituted heterocyclyl, optionally substituted aryl, or optionally substituted heteroaryl;

or alternatively, $R^{1a}$, $R^{1b}$, $R^{2a}$ and $R^{2b}$ taken together form an optionally substituted carbocyclyl, optionally substituted heterocyclyl, optionally substituted aryl, or optionally substituted heteroaryl;

$R^{4a}$, $R^{4b}$, $R^{5a}$, and $R^{5b}$ are each independently hydrogen, halogen, hydroxy, optionally substituted $C_{1-6}$ alkyl, optionally substituted $C_2$-$C_6$ alkenyl, optionally substituted $C_2$-$C_6$ alkynyl, optionally substituted $C_{1-6}$ alkoxy, optionally substituted —OCO($C_1$-$C_6$ alkyl), —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, optionally substituted carbocyclyl, optionally substituted heterocyclyl, optionally substituted aryl, or optionally substituted heteroaryl;

or alternatively, $R^{4a}$ and $R^{4b}$ taken together form a CO, optionally substituted carbocyclyl, optionally substituted heterocyclyl, optionally substituted aryl, or optionally substituted heteroaryl;

or alternatively, $R^{4a}$, $R^{4b}$, $R^{5a}$ and $R^{5b}$ taken together form an optionally substituted carbocyclyl, optionally substituted heterocyclyl, optionally substituted aryl, or optionally substituted heteroaryl;

$R^3$ is absent, hydrogen, —CN, —$CF_3$, —OH, optionally substituted $C_1$-$C_6$ alkyl, optionally substituted $C_2$-$C_6$ alkenyl, optionally substituted $C_2$-$C_6$ alkynyl, optionally substituted —$OR^{15}$, optionally substituted $C_1$-$C_6$ alkoxy, —$NH_2$, —$NR^{16}R^{17}$, —$NR^{16}COR^{18}$, —$NR^{16}S(O)_pR^{18}$, —$CONR^{14}R^{15}$, —$SONR^{14}R^{15}$, —$SO_2NR^{14}R^{15}$, optionally substituted —$S(O)_pR^{18}$, —$N_3$, optionally substituted carbocyclyl, optionally substituted heterocyclyl, optionally substituted aryl, or optionally substituted heteroaryl;

or alternatively, $R^{2a}$, $R^{2b}$ and $R^3$ taken together form an optionally substituted carbocyclyl, optionally substituted heterocyclyl, optionally substituted aryl, or optionally substituted heteroaryl;

or alternatively, $R^{2a}$ and $R^{10}$ taken together form an optionally substituted heterocyclyl;

$R^6$ and $R^7$ are each independently H, methyl, methoxy, —CN, F, Cl, Br, I, $^{123}$I, —$CF_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —$NR^{13}R^{14}$, optionally substituted —($C_1$-$C_6$ alkyl)-$NR^{13}R^{14}$, —$NR^{14}SO_2R^{16}$, optionally substituted —($C_1$-$C_6$ alkyl)$NR^{14}SO_2R^{16}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, —$SO_2NR^{14}R^{15}$, optionally substituted —($C_1$-$C_6$ alkyl)-$SO_2NR^{14}R^{15}$, optionally substituted —$SO_2R^{16}$, or optionally substituted —($C_1$-$C_6$ alkyl)-$SO_2R^{16}$, optionally substituted carbocyclyl, optionally substituted heterocyclyl, optionally substituted aryl, or optionally substituted heteroaryl;

$R^8$, $R^9$, $R^{11}$ and $R^{12}$ are each independently hydrogen, —OH, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ alkylamino, optionally substituted —OCO($C_1$-$C_6$ alkyl), —$NR^{13}R^{14}$, optionally substituted —($C_1$-$C_6$ alkyl)-$NR^{13}R^{14}$, —$NR^{14}COR^{16}$, optionally substituted —($C_1$-$C_6$ alkyl)-$NR^{14}COR^{16}$, —$CONR^{14}R^{15}$, optionally substituted —($C_1$-$C_6$ alkyl)-$CONR^{14}R^{15}$, optionally substituted carbocyclyl, optionally substituted heterocyclyl, optionally substituted aryl, or optionally substituted heteroaryl;

or alternatively, $R^8$ and $R^9$ taken together form an optionally substituted carbocyclyl or optionally substituted heterocyclyl;

or alternatively, $R^{11}$ and $R^{12}$, on a same carbon atom or a different carbon atom, taken together form an optionally substituted carbocyclyl, optionally substituted heterocyclyl, optionally substituted aryl, or optionally substituted heteroaryl;

$R^{10}$ is hydrogen, halogen, optionally substituted $C_1$-$C_6$ alkyl, optionally substituted $C_1$-$C_6$ alkoxy, —CO($C_1$-$C_6$ alkyl), optionally substituted $C_1$-$C_6$ alkylamino, optionally substituted carbocyclyl, optionally substituted heterocyclyl, optionally substituted aryl, or optionally substituted heteroaryl;

$R^{13}$, $R^{14}$, $R^{15}$, $R^{16}$, $R^{17}$ and $R^{18}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl;

or alternatively, $R^{14}$ and $R^{15}$ are taken together to form an optionally substituted heterocyclyl, or optionally substituted heteroaryl;

or alternatively, $R^{16}$ and $R^{17}$ are taken together to form an optionally substituted heterocyclyl, or optionally substituted heteroaryl;

m is 0, 1, 2, 3, or 4;
each n is independently 0, 1 or 2;
each p is independently 0, 1 or 2;
q is 0, 1 or 2;
each g is independently 0, 1, 2, 3, or 4; and
each t is independently 1 or 2.

Embodiment 4. The pharmaceutical composition of Embodiment 3, wherein R is W.

Embodiment 5. The pharmaceutical composition of Embodiment 3 or 4, wherein W is hydrogen, halogen, —$CF_3$, or —$NR^{13}R^{14}$.

Embodiment 6. The pharmaceutical composition of any one of Embodiments 3-5, wherein L is -E-$R^3$.

Embodiment 7. The pharmaceutical composition of any one of Embodiments 3-6, wherein $R^3$ is selected from hydrogen, —$C_1$-$C_3$ alkyl, —$NR^{16}SO(C_1$-$C_3$ alkyl), —$NR^{16}SO_2(C_1$-$C_3$ alkyl), —$SONR^{14}R^{15}$, —$SO_2NR^{14}R^{15}$, —$SOR^{18}$, or —$SO_2R^{18}$.

Embodiment 8. The compound of any one of Embodiments 3-7, wherein $R^3$ is selected from —$NHSO_2(C_1$-$C_3$ alkyl), —$NCH_3SO_2(C_1$-$C_3$ alkyl), or —$SO_2(C_1$-$C_3$ alkyl).

Embodiment 9. The pharmaceutical composition of Embodiment 3, wherein the androgen receptor N-terminal domain inhibitor is a compound of formula (ii):

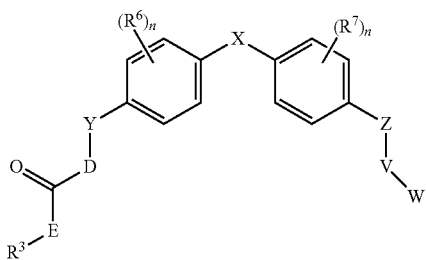

(ii)

or a pharmaceutically acceptable salt, tautomer, stereoisomer or prodrug thereof, wherein:
X is a bond, —$NR^{10}$—, or —$(CR^{8a}R^{9a})_t$—;
Y and Z are each independently a bond, —$CH_2$—, —$C(CH_3)H$—, —O—, —S—, —NH—, —$NCH_3$—, or —$N(COCH_3)$—;
V is —$CH_2$—, —$CH_2CH_2$—, —$CH_2CH_2CH_2$—, —$CH_2CH(CH_3)CH_2$—, —$CH_2CH(OH)CH_2$—, or —$CH_2C(OH)(CH_3)CH_2$—;
W is halogen, —$NH_2$, or —$CF_3$.
D is —$NR^{10}$— and E is —$(CR^{2a}R^{2b})_g$—, —$NR^{10}$—, or —$NR^{10}$—$(CR^{2a}R^{2b})_g$—;
or alternatively, E is —$NR^{10}$— or —$NR^{10}$—$(CR^{2a}R^{2b})_g$—, and D is —$(CR^{1a}R^{1b})_q$— or —$NR^{10}$—;
$R^{1a}$, $R^{1b}$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —$OCO(C_1$-$C_3$ alkyl), —$NR^{13}R^{14}$, —$(C_1$-$C_3$ alkyl)-$NR^{13}R^{14}$, —$NR^{14}COR^{16}$, —$(C_1$-$C_3$ alkyl)-$NR^{14}COR^{16}$, —$CONR^{14}R^{15}$ or —$(C_1$-$C_6$ alkyl)-$CONR^{14}R^{15}$; or ($R^{1a}$ and $R^{1b}$) or ($R^{2a}$ and $R^{2b}$) taken together form an oxo (=O), an optionally substituted carbocyclyl, or an optionally substituted heterocyclyl;
$R^3$ is selected from hydrogen, —$C_1$-$C_6$ alkyl, —$OR^{15}$, —$SR^{18}$, —$C_1$-$C_6$ alkoxy, —$NR^{16}R^{17}$, —$NR^{16}SR^{18}$, —$NR^{16}SOR^{18}$, —$NR^{16}SO_2R^{18}$, —$NR^{16}COR^{18}$, —$CONR^{14}R^{15}$, —$SONR^{14}R^{15}$, —$SO_2NR^{14}R^{15}$, —$SOR^{18}$, or —$SO_2R^{18}$;
$R^6$ and $R^7$ are each independently H, halogen, —CN, —$CF_3$, —OH, or $C_1$-$C_3$ alkyl;
$R^{8a}$ and $R^{9a}$ are each independently hydrogen, halogen, —OH, or $C_1$-$C_3$ alkyl; or $R^{8a}$ and $R^{9a}$ taken together form an 3- to 6-membered carbocyclyl or heterocyclyl;
$R^{10}$ is each independently hydrogen, $C_1$-$C_3$ alkyl, $C_2$-$C_3$ alkenyl, $C_2$-$C_3$ alkynyl, or —$CO(C_1$-$C_3$ alkyl);
$R^{13}$, $R^{14}$, $R^{15}$, $R^{16}$, $R^{17}$ and $R^{18}$ are each independently hydrogen, $C_1$-$C_3$ alkyl, $C_2$-$C_3$ alkenyl, or $C_2$-$C_3$ alkynyl; or $R^{14}$ and $R^{15}$ taken together form an optionally substituted 5- or 6-membered heterocyclyl;
each n is independently 0, 1 or 2;
q is 0, 1 or 2;
each g is independently 0, 1, 2, 3, or 4; and
each t is independently 1 or 2.

Embodiment 10. The pharmaceutical composition of Embodiment 3, wherein the androgen receptor N-terminal domain inhibitor is a compound of formula (iii):

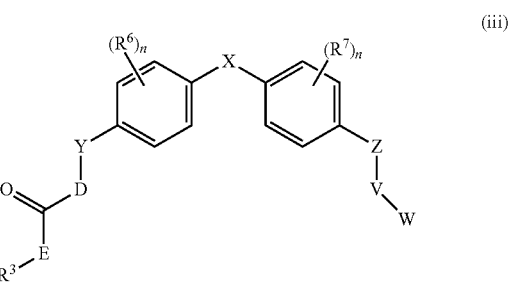

(iii)

or a pharmaceutically acceptable salt, tautomer, stereoisomer or prodrug thereof, wherein:
X is a bond, —$NR^{10}$—, or —$(CR^{8a}R^{9a})_t$—;
Y and Z are each independently a bond, —$CH_2$—, —$C(CH_3)H$—, —O—, —S—, —NH—, —$NCH_3$—, or —$N(COCH_3)$—;
V is —$CH_2$—, —$CH_2CH_2$—, —$CH_2CH_2CH_2$—, —$CH_2CH(CH_3)CH_2$—, —$CH_2CH(OH)CH_2$—, or —$CH_2C(OH)(CH_3)CH_2$—;
W is halogen, —$NH_2$ or —$CF_3$;
D is —O— or —$NR^{10}$— and E is —$(CR^{2a}R^{2b})_{gg}$—;
or alternatively, E is —O—, —$NR^{10}$— or —$NR^{10}$—$(CR^{2a}R^{2b})_g$—, and D is —$(CR^{1a}R^{1b})_q$—;
$R^{1a}$, $R^{1b}$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —$OCO(C_1$-$C_3$ alkyl), —$NR^{13}R^{14}$, —$(C_1$-$C_3$ alkyl)-$NR^{13}R^{14}$, —$NR^{14}COR^{16}$, —$(C_1$-$C_3$ alkyl)-$NR^{14}COR^{16}$, —$CONR^{14}R^{15}$, or —$(C_1$-$C_6$ alkyl)-$CONR^{14}R^{15}$; or ($R^{1a}$ and $R^{1b}$) or ($R^{2a}$ and $R^{2b}$) taken together form an oxo (=O), an optionally substituted carbocyclyl, or an optionally substituted heterocyclyl;
$R^3$ is selected from hydrogen, —$C_1$-$C_6$ alkyl, —$OR^{15}$, —$SR^{18}$, —$C_1$-$C_6$ alkoxy, —$NR^{16}R^{17}$, —$NR^{16}SR^{18}$, —$NR^{16}SOR^{18}$, —$NR^{16}SO_2R^{18}$, —$NR^{16}COR^{18}$, —$CONR^{14}R^{15}$, —$SONR^{14}R^{15}$, —$SO_2NR^{14}R^{15}$, —$SOR^{18}$, or —$SO_2R^{18}$;
$R^6$ and $R^7$ are each independently H, halogen, —CN, —$CF_3$, —OH, or $C_1$-$C_3$ alkyl;
$R^{8a}$ and $R^{9a}$ are each independently hydrogen, halogen, —OH, or $C_1$-$C_3$ alkyl; or $R^{8a}$ and $R^{9a}$ taken together form an 3- to 6-membered carbocyclyl or heterocyclyl;
$R^{10}$ is each independently hydrogen, $C_1$-$C_3$ alkyl, $C_2$-$C_3$ alkenyl, $C_2$-$C_3$ alkynyl, or —$CO(C_1$-$C_3$ alkyl);
$R^{13}$, $R^{14}$, $R^{15}$, $R^{16}$, $R^{17}$ and $R^{18}$ are each independently hydrogen, $C_1$-$C_3$ alkyl, $C_2$-$C_3$ alkenyl, or $C_2$-$C_3$ alkynyl; or $R^{14}$ and $R^{15}$ taken together form an optionally substituted 5- or 6-membered heterocyclyl;
m is 0, 1, 2, 3, or 4;
each n is independently 0, 1 or 2;
q is 1 or 2;
g is 0, 1, 2, 3, or 4;

gg is 1, 2, 3, or 4; and t is 1 or 2.

Embodiment 11. The pharmaceutical composition of Embodiment 9 or 10, wherein W is Cl, Br, I, or F.

Embodiment 12. The pharmaceutical composition of any one of Embodiments 9-11, wherein D is —CH$_2$—, —CH(CH$_3$)—, —C(CH$_3$)$_2$—, or —CH$_2$CH$_2$—.

Embodiment 13. The pharmaceutical composition of Embodiment 9, wherein q is 0.

Embodiment 14. The pharmaceutical composition of any one of Embodiments 9-13, wherein E is —CH$_2$—, —CH(CH$_3$)—, —C(CH$_3$)$_2$—, —CH$_2$CH$_2$—, or —CH$_2$CH$_2$CH$_2$—.

Embodiment 15. The pharmaceutical composition of any one of Embodiments 9-14, wherein g is 0.

Embodiment 16. The pharmaceutical composition of any one of Embodiments 9-15, wherein $R^3$ is selected from —NHSO$_2$(C$_1$-C$_3$ alkyl), —NCH$_3$SO$_2$(C$_1$-C$_3$ alkyl), or —SO$_2$(C$_1$-C$_3$ alkyl).

Embodiment 17. The pharmaceutical composition of any one of Embodiments 9-16, wherein $R^6$ and $R^7$ are each independently H, halogen, —CN, or methyl.

Embodiment 18. The pharmaceutical composition of any one of Embodiments 9-17, wherein X is a bond, —CH$_2$—, —C(CH$_3$)$_2$—, —CH$_2$CH$_2$—, —NH—, —N(CH$_3$)—, —N(iPr)—, or —N(COCH$_3$)—.

Embodiment 19. The pharmaceutical composition of any one of Embodiments 9-18, Z is —CH$_2$—, —O—, —NH—, —NCH$_3$—, or —N(COCH$_3$)—.

Embodiment 20. The pharmaceutical composition of any one of Embodiments 9-19, Y is —CH$_2$—, —O—, —NH—, or —NCH$_3$—.

Embodiment 21. The pharmaceutical composition of any one of Embodiments 9-20, wherein at least one of Z and Y is —O—.

Embodiment 22. The pharmaceutical composition of Embodiment 3, wherein the androgen receptor N-terminal domain inhibitor is a compound of formula (iv):

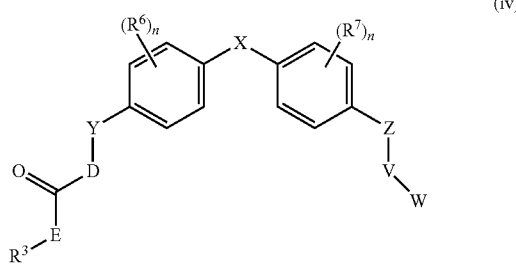

(iv)

or a pharmaceutically acceptable salt, tautomer, stereoisomer or prodrug thereof, wherein:

X is a bond, —NR$^{10}$—, or —(CR$^{8a}$R$^{9a}$)$_t$—;

Y and Z are each independently a bond, —CH$_2$—, —C(CH$_3$)H—, —O—, —S—, —NH—, —NCH$_3$—, or —N(COCH$_3$)—;

V is —CH$_2$—, —CH$_2$CH$_2$—, —CH$_2$CH$_2$CH$_2$—, —CH$_2$CH(CH$_3$)CH$_2$—, —CH$_2$CH(OH)CH$_2$—, or —CH$_2$C(OH)(CH$_3$)CH$_2$—;

W is halogen, —CF$_2$R$^{10}$, —NR$^{13}$R$^{14}$, optionally substituted carbocyclyl, optionally substituted heterocyclyl, optionally substituted aryl, or optionally substituted heteroaryl;

D is —(CR$^{1a}$R$^{1b}$)$_q$—;

E is —(CR$^{2a}$R$^{2b}$)$_g$—;

R$^{1a}$, R$^{1b}$, R$^{2a}$, and R$^{2b}$ are each independently hydrogen, halogen, —OH, C$_1$-C$_3$ alkyl, C$_2$-C$_3$ alkenyl, C$_2$-C$_3$ alkynyl, C$_1$-C$_3$ alkoxy, —OCO(C$_1$-C$_3$ alkyl), —NR$^{13}$R$^{14}$, —(C$_1$-C$_3$ alkyl)-NR$^{13}$R$^{14}$, —NR$^{14}$COR$^{16}$, —(C$_1$-C$_3$ alkyl)-NR$^{14}$COR$^{16}$, —CONR$^{14}$R$^{15}$, or —(C$_1$-C$_6$ alkyl)-CONR$^{14}$R$^{15}$; or (R$^{1a}$ and R$^{1b}$) or (R$^{2a}$ and R$^{2b}$) taken together form an oxo (═O), an optionally substituted carbocyclyl, or an optionally substituted heterocyclyl;

R$^3$ is selected from hydrogen, —C$_1$-C$_6$ alkyl, —OR$^{15}$, —SR$^{18}$, —C$_1$-C$_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, —SOR$^{18}$, or —SO$_2$R$^{18}$;

R$^6$ and R$^7$ are each independently H, halogen, —CN, —CF$_3$, —OH, or C$_1$-C$_3$ alkyl;

R$^{8a}$ and R$^{9a}$ are each independently hydrogen, halogen, —OH, or C$_1$-C$_3$ alkyl; or R$^{8a}$ and R$^{9a}$ taken together form an optionally substituted carbocyclyl or optionally substituted heterocyclyl;

R$^{10}$ is each independently hydrogen, C$_1$-C$_3$ alkyl, C$_2$-C$_3$ alkenyl, C$_2$-C$_3$ alkynyl, or —CO(C$_1$-C$_3$ alkyl);

R$^{13}$, R$^{14}$, R$^{15}$, R$^{16}$, R$^{17}$ and R$^{18}$ are each independently hydrogen, C$_1$-C$_3$ alkyl, C$_2$-C$_3$ alkenyl, or C$_2$-C$_3$ alkynyl; or R$^{14}$ and R$^{15}$ taken together form an optionally substituted 5- or 6-membered heterocyclyl;

m is 0, 1, 2, 3, or 4;

each n is independently 0, 1 or 2;

q is 0, 1 or 2;

g is 0, 1, 2, 3, or 4; and t is 1 or 2.

Embodiment 23. The pharmaceutical composition of Embodiment 1 or 2, wherein the androgen receptor N-terminal domain inhibitor is selected from Table A.

Embodiment 24. The pharmaceutical composition of Embodiment 1 or 2, wherein the androgen receptor N-terminal domain inhibitor is a compound of formula (a):

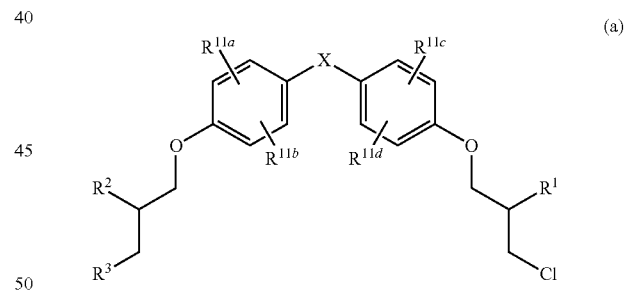

(a)

or a pharmaceutically acceptable salt, tautomer, stereoisomer or prodrug thereof, wherein:

X is —S(O)$_n$— or —C(R$^8$R$^9$)—;

R$^1$ is H, hydroxyl or —OC(═O)R$^{13}$;

R$^2$ is hydroxyl or —OC(═O)R$^{13}$;

R$^3$ is halo, —OH, —OR$^4$; —OC(═O)R$^{13}$, —NH$_2$, —NHC(═O)R$^{13}$, —N(C(═O)R$^{13}$)$_2$, —NHS(O)$_n$R$^5$, —N(C(═O)R$^{13}$)(S(O)$_n$R$^5$), —N(C$_1$-C$_6$ alkyl)(S(O)$_n$R$^5$), —S(O)$_n$R$^5$, —N$_3$, aryl, carbocyclyl, heteroaryl or heterocyclyl which are optionally substituted with one or more R$^6$;

R$^4$ is C$_1$-C$_6$ alkyl, C$_2$-C$_6$ alkenyl, C$_2$-C$_6$ alkynyl, aryl, carbocyclyl, heteroaryl or heterocyclyl which are optionally substituted with one or more R$^6$;

R$^5$ is each independently C$_1$-C$_6$ alkyl or aryl which are optionally substituted with one or more R$^6$ R$^6$ is each independently selected from the group consisting of H, F, Cl, Br, I, $^{123}$I, hydroxyl, oxo, C$_1$-C$_6$ alkyl, C$_2$-C$_6$ alkenyl, C$_2$-C$_6$ alkynyl, C$_1$-C$_6$ alkoxy, C$_6$-C$_{12}$ aryl, wherein each R$^6$ is optionally substituted with one or more of halogen, $^{123}$I, $^{18}$F, hydroxyl, —OS(O)$_2$-aryl, C$_1$-C$_6$ alkyl, C$_2$-C$_6$ alkenyl, or C$_2$-C$_6$ alkynyl;

R$^8$ and R$^9$ are each independently H, or C$_1$-C$_6$ alkyl;

R$^{11a}$, R$^{11b}$, R$^{11c}$ and R$^{11d}$ are each independently H, methyl, —CN, F, Cl, Br, I, or $^{123}$I;

R$^{13}$ is C$_1$-C$_6$ alkyl; and n is 0, 1, or 2;

wherein at least one of R$^{11a}$, R$^{11b}$, R$^{11c}$ and R$^{11d}$ is methyl, —CN, F, Cl, Br, I, or $^{123}$I.

Embodiment 25. The pharmaceutical composition of Embodiment 24, wherein at least two of R$^{11a}$, R$^{11b}$, R$^{11c}$ and R$^{11d}$ are methyl, —CN, F, Cl, Br, I, or $^{123}$I.

Embodiment 26. The pharmaceutical composition of Embodiment 24, wherein R$^{11c}$ and R$^{11d}$ are each independently methyl, —CN, Cl, or Br.

Embodiment 27. The pharmaceutical composition of Embodiment 24, wherein R$^{11c}$ and R$^{11d}$ are each Cl or —CN.

Embodiment 28. The pharmaceutical composition of any one of Embodiments 24-27, wherein X is —C(R$^8$R$^9$)— and R$^8$ and R$^9$ are each independently C$_1$-C$_3$ alkyl.

Embodiment 29. The pharmaceutical composition of Embodiment 28, wherein R$^8$ an R$^9$ are each methyl.

Embodiment 30. The pharmaceutical composition of any one of Embodiments 24-29, wherein R$^1$ and R$^2$ are both hydroxyl.

Embodiment 31. The pharmaceutical composition of any one of Embodiments 24-30, wherein R$^3$ is an optionally substituted 5 or 6 membered heteroaryl or an optionally substituted 3 to 7 membered heterocyclyl, wherein said heteroaryl or said heterocyclyl respectively comprise at least one N atom.

Embodiment 32. The pharmaceutical composition of any one of Embodiments 24-30, wherein R$^3$ is selected from a group consisting of pyrrole, furan, thiophene, pyrazole, pyridine, pyridazine, pyrimidine, imidazole, thiazole, isoxazole, oxadiazole, thiadiazole, oxazole, triazole, isothiazole, oxazine, triazine, azepine, pyrrolidine, pyrroline, imidazoline, imidazolidine, pyrazoline, pyrazolidine, piperidine, dioxane, morpholine, dithiane, thiomorpholine, piperazine, and tetrazine.

Embodiment 33. The pharmaceutical composition of any one of Embodiments 24-30, wherein R$^3$ is —NH$_2$, —NHC(=O)R$^{13}$, —N(C(=O)R$^{13}$)$_2$, —NHS(O)$_n$R$^5$, —N(C(=O)R$^{13}$)(S(O)$_n$R$^5$), —N(C$_1$-C$_6$ alkyl)(S(O)$_n$R$^5$) or —S(O)$_n$R$^5$.

Embodiment 34. The pharmaceutical composition of any one of Embodiments 24-30, wherein R$^3$ is —NH$_2$, —NHC(=O)(C$_1$-C$_4$ alkyl), —N[(C(=O)(C$_1$-C$_4$ alkyl)]$_2$, —NHS(O)$_n$(C$_1$-C$_3$ alkyl), —N[C(=O)(C$_1$-C$_4$ alkyl)][S(O)$_n$(C$_1$-C$_3$ alkyl)], —N[C$_1$-C$_6$ alkyl][S(O)$_n$(C$_1$-C$_3$ alkyl)], or —S(O)$_n$(C$_1$-C$_3$ alkyl).

Embodiment 35. The pharmaceutical composition of Embodiment 1 or 2, wherein the androgen receptor N-terminal domain inhibitor is selected from Table B.

Embodiment 36. The pharmaceutical composition of any one of Embodiments 1 and 3-35, wherein the second therapeutically active agent is selected from a poly (ADP-ribose) polymerase (PARP) inhibitor, an androgen receptor ligand-binding domain inhibitor, an inhibitor of CYP17, a microtubule inhibitor, a modulator of PD-1 or PD-L1, a gonadotropin releasing hormone agonist, a 5-alpha reductase inhibitor, a vascular endothelial growth factor inhibitor, a histone deacetylase inhibitor, an integrin alpha-v-beta-3 inhibitor, a receptor tyrosine kinase, a phosphoinositide 3-kinase inhibitor, an anaplastic lymphoma kinase (ALK) inhibitor, an endothelin receptor A antagonist, an anti-CTLA4 inhibitor, an heat shock protein 27 (HSP27) inhibitor, an androgen receptor degrader, a androgen receptor DNA-binding domain inhibitor, a bromodomain and extra-terminal motif (BET) inhibitor, an androgen receptor N-terminal domain inhibitor, an alpha-particle emitting radioactive therapeutic agent, niclosamide, a selective estrogen receptor modulator (SERM), a selective estrogen receptor degrader (SERD), an aromatase inhibitor, selective progesterone receptor modulator (SPRM), a glucocorticoid receptor inhibitor, a CDK4/6 inhibitor, a HER2 receptor antagonist, a mammalian target of rapamycin (mTOR) inhibitor, an AKT inhibitor, a B-cell lymphoma-2 (Bcl-2) inhibitor, an aurora kinase inhibitor, a Wnt-targeting antagonist, a CYP11a inhibitor, a selective androgen receptor N-terminal domain inhibitor, or enhancer of zeste homolog 2 (EZH2) inhibitor.

Embodiment 37. The pharmaceutical composition of any one of Embodiments 1 and 3-35, wherein the CDK4/6 inhibitor is selected from palbociclib, ribociclib, trilaciclib or abemaciclib.

Embodiment 38. The pharmaceutical composition of any one of Embodiments 1 and 3-35, wherein the CDK4/6 inhibitor is palbociclib.

Embodiment 39. The pharmaceutical composition of any one of Embodiments 1 and 3-35, wherein the androgen receptor ligand-binding domain inhibitor is enzalutamide, apalutamide, darolutamide, bicalutamide, nilutamide, flutamide, ODM-204, or TAS3681.

Embodiment 40. The pharmaceutical composition of any one of Embodiments 1 and 3-35, wherein the androgen receptor ligand-binding domain inhibitor is enzalutamide.

Embodiment 41. The pharmaceutical composition of any one of Embodiments 2-35, wherein the Pin1 inhibitor is selected from juglone, plumbagin, PiB, PiJ, epigallocatechin gallate (EGCG), all-trans retinoic acid (ATRA), dipentamethylene thiauram monosulfide, TME-001 (2-(3-chloro-4-fluoro-phenyl)-isothiazol-3-one), KPT-6566, API-1, buparvaquone, or a pharmaceutically acceptable salt thereof.

Embodiment 42. The pharmaceutical composition of any one of Embodiments 2-35, wherein the Pin1 inhibitor is selected from Table C or a pharmaceutically acceptable salt thereof.

Embodiment 43. The pharmaceutical composition of any one of Embodiments 2-35, wherein the Pin1 inhibitor is selected from Table D or a pharmaceutically acceptable salt thereof.

Embodiment 44. The pharmaceutical composition of any one of Embodiments 2-35, wherein the Pin1 inhibitor is CRYPEVEIC, wherein the cysteine residues of said peptide are cyclized by a disulfide bond (SEQ ID NO: 1); Ac-Lys(N-biotinoyl)-Ala-Ala-Bth-D-Thr(PO$_3$H$_2$)-Pip-Nal-Gln-NH$_2$ (SEQ ID NO: 2); Ac-Phe-D-Thr(PO$_3$H$_2$)-Pip-Nal-Gln-NH$_2$ (SEQ ID NO: 3); and Ac-Phe-Phe-pSer-Ψ[(Z)CHdC-Pro-Arg-NH$_2$ (SEQ ID NO: 4).

Embodiment 45. The pharmaceutical composition of any one of Embodiments 2-35, wherein the Pin1 inhibitor is selected from 5-hydroxy-1,4-naphthalenedione, (1-piperidinecarbodithioic acid, anhydrosulfide), or diethyl-1,3,6,8-tetrahydro-1,3,6,8tetraoxobenzo[1mn] phenanthroline-2,7-diacetate, or a pharmaceutically acceptable salt thereof.

Embodiment 46. The pharmaceutical composition of any one of Embodiments 2-35, wherein the Pin1 inhibitor is ATRA.

Embodiment 47. The pharmaceutical composition of any one of Embodiments 1-46, further comprising a pharmaceutically acceptable carrier.

Embodiment 48. A method for inhibiting androgen receptor activity, comprising administering a pharmaceutical composition of any one of Embodiments 1-47, to a subject in need thereof.

Embodiment 49. The method of Embodiment 48, wherein the inhibiting androgen receptor activity is for treating a condition or disease selected from prostate cancer, breast cancer, ovarian cancer, bladder cancer, pancreatic cancer, hepatocellular cancer, endometrial cancer, salivary gland carcinoma, hair loss, acne, hirsutism, ovarian cysts, polycystic ovary disease, precocious puberty, spinal and bulbar muscular atrophy, or age-related macular degeneration.

Embodiment 50. A method for treating cancer, comprising administering the pharmaceutical composition of any one of Embodiments 1-47, to a subject in need thereof.

Embodiment 51. The method of Embodiment 50, wherein the cancer is breast cancer.

Embodiment 52. The method of Embodiment 51, wherein the breast cancer is triple negative breast cancer.

Embodiment 53. The method of Embodiment 50, wherein the cancer is selected from prostate cancer, breast cancer, ovarian cancer, bladder cancer, pancreatic cancer, hepatocellular cancer, endometrial cancer, or salivary gland carcinoma.

Embodiment 54. The method of Embodiment 50, wherein the cancer is prostate cancer.

Embodiment 55. The method of Embodiment 54, wherein the prostate cancer is primary or localized prostate cancer, locally advanced prostate cancer, recurrent prostate cancer, advanced prostate cancer, metastatic prostate cancer, metastatic castration-resistant prostate cancer, and hormone-sensitive prostate cancer.

Embodiment 56. The method of Embodiment 54, wherein the prostate cancer is metastatic castration-resistant prostate cancer.

Embodiment 57. The method of Embodiment 54, wherein the prostate cancer expresses full-length androgen receptor or truncated androgen receptor splice variant.

Embodiment 58. The method of any one of Embodiments 50-54, further comprising administering radiation therapy the subject.

Embodiment 59. The method of Embodiment 58, wherein the radiation therapy is ionizing radiation therapy.

Embodiment 60. The method of Embodiment 58 or 59, wherein the administering the pharmaceutical composition and the administering radiation therapy occurs during same treatment period or during different treatment period.

Embodiment 61. The method of any one of Embodiments 58-60, wherein the subject has prostate cancer.

Embodiment 62. The method of any one of Embodiments 50-61, wherein the prostate cancer is resistant to enzalutamide monotherapy.

Embodiment 63. A method of treating cancer, comprising administering a therapeutically effective amount of an androgen receptor modulator and a radiation therapy to a subject in need thereof.

Embodiment 64. The method of Embodiment 63, wherein the androgen receptor N-terminal domain inhibitor is a compound of formula (i):

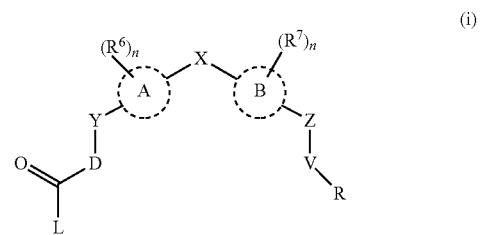

or a pharmaceutically acceptable salt, tautomer, stereoisomer or prodrug thereof, wherein:

A and B are each independently aryl or heteroaryl;

X is a bond, $-(CR^8R^9)_t-$, $-O-$, $-C(=O)-$, $-S(O)_n-$, $-NR^{10}-$, $-CONR^{10}-$, $-NR^{10}CO-$, $-SO_2NR^{10}-$, or $-NR^{10}SO_2-$;

Y and Z are each independently a bond, $-(CR^8R^9)_t-$, $-O-$, $-S(O)_n-$, $-NR^{10}-$, $-CONR^{10}-$, $-NR^{10}CO-$, $-SO_2NR^{10}-$, or $-NR^{10}SO_2-$;

V is a bond, optionally substituted $-(CR^{11}R^{12})_m-$, $-C(=O)-$, $-N(R^{10})CO-$, $-CONR^{10}-$, or $-NSO_2R^{10}-$;

R is $-(CR^{4a}R^{4b})-(CR^{5a}R^{5b})-W$ or $W$;

W is hydrogen, halogen, $-CF_3$, $-CF_2R^{10}$, $-CN$, $-OR^{13}$, $-NR^{13}R^{14}$, optionally substituted $-CONR^{13}R^{14}$, optionally substituted carbocyclyl, optionally substituted heterocyclyl, optionally substituted aryl, or optionally substituted heteroaryl;

D is $-(CR^{1a}R^{1b})_q-$, $-O-$, or $-NR^{10}-$;

L is $-(CR^{2a}R^{2b})-R^3$ or -E-$R^3$;

E is $-(CR^{2a}R^{2b})_g-$, $-O-$, $-NR^{10}-$, or $-NR^{10}-(CR^{2a}R^{2b})_g-$;

$R^{1a}$, $R^{1b}$, $R^{2a}$, and $R^{2b}$ are each independently hydrogen, halogen, hydroxy, optionally substituted $C_{1-6}$ alkyl, optionally substituted $C_2$-$C_6$ alkenyl, optionally substituted $C_2$-$C_6$ alkynyl, optionally substituted $C_{1-6}$ alkoxy, optionally substituted $-OCO(C_1$-$C_6$ alkyl), $-NR^{13}R^{14}$, optionally substituted $-(C_1$-$C_6$ alkyl)-$NR^{13}R^{14}$, $-NR^{14}COR^{16}$, optionally substituted $-(C_1$-$C_6$ alkyl)-$NR^{14}COR^{16}$, $-CONR^{14}R^{15}$, optionally substituted $-(C_1$-$C_6$ alkyl)-$CONR^{14}R^{15}$, optionally substituted carbocyclyl, optionally substituted heterocyclyl, optionally substituted aryl, or optionally substituted heteroaryl;

or alternatively, $R^{1a}$ and $R^{1b}$ taken together form an optionally substituted carbocyclyl, optionally substituted heterocyclyl, optionally substituted aryl, or optionally substituted heteroaryl;

or alternatively, $R^{2a}$ and $R^{2b}$ taken together form a CO, optionally substituted carbocyclyl, optionally substituted heterocyclyl, optionally substituted aryl, or optionally substituted heteroaryl;

or alternatively, $R^{1a}$, $R^{1b}$, $R^{2a}$ and $R^{2b}$ taken together form an optionally substituted carbocyclyl, optionally substituted heterocyclyl, optionally substituted aryl, or optionally substituted heteroaryl;

$R^{4a}$, $R^{4b}$, $R^{5a}$, and $R^{5b}$ are each independently hydrogen, halogen, hydroxy, optionally substituted $C_{1-6}$ alkyl, optionally substituted $C_2$-$C_6$ alkenyl, optionally substituted $C_2$-$C_6$ alkynyl, optionally substituted $C_{1-6}$ alkoxy, optionally substituted $-OCO(C_1$-$C_6$ alkyl), $-NR^{13}R^{14}$, optionally substituted $-(C_1$-$C_6$ alkyl)-$NR^{13}R^{14}$, $-NR^{14}COR^{16}$, optionally substituted $-(C_1$-$C_6$ alkyl)-$NR^{14}COR^{16}$, $-CONR^{14}R^{15}$, optionally substituted $-(C_1$-$C_6$ alkyl)-$CONR^{14}R^{15}$, optionally substituted carbocyclyl, optionally substituted heterocyclyl, optionally substituted aryl, or optionally substituted heteroaryl;

or alternatively, $R^{4a}$ and $R^{4b}$ taken together form a CO, optionally substituted carbocyclyl, optionally substituted heterocyclyl, optionally substituted aryl, or optionally substituted heteroaryl;

or alternatively, $R^{4a}$, $R^{4b}$, $R^{5a}$ and $R^{5b}$ taken together form an optionally substituted carbocyclyl, optionally substituted heterocyclyl, optionally substituted aryl, or optionally substituted heteroaryl;

$R^3$ is absent, hydrogen, —CN, —CF$_3$, —OH, optionally substituted $C_1$-$C_6$ alkyl, optionally substituted $C_2$-$C_6$ alkenyl, optionally substituted $C_2$-$C_6$ alkynyl, optionally substituted —OR$^{15}$, optionally substituted $C_1$-$C_6$ alkoxy, —NH$_2$, —NR$^{16}$R$^7$, —NR$^{16}$COR$^{18}$, —NR$^{16}$S(O)$_p$R$^{18}$, —CONR$^{14}$R$^{15}$, —SONR$^{14}$R$^{15}$, —SO$_2$NR$^{14}$R$^{15}$, optionally substituted —S(O)$_p$R$^{18}$, —N$_3$, optionally substituted carbocyclyl, optionally substituted heterocyclyl, optionally substituted aryl, or optionally substituted heteroaryl;

or alternatively, $R^{2a}$, $R^{2b}$ and $R^3$ taken together form an optionally substituted carbocyclyl, optionally substituted heterocyclyl, optionally substituted aryl, or optionally substituted heteroaryl;

or alternatively, $R^{2a}$ and $R^{10}$ taken together form an optionally substituted heterocyclyl;

$R^6$ and $R^7$ are each independently H, methyl, methoxy, —CN, F, Cl, Br, I, $^{123}$I, —CF$_3$, —OH, optionally substituted $C_1$-$C_6$ alkyl, optionally substituted $C_1$-$C_6$ alkoxy, optionally substituted —($C_1$-$C_6$ alkyl)-($C_1$-$C_6$ alkoxy), optionally substituted —($C_1$-$C_6$ alkyl)-OH, —NR$^{13}$R$^{14}$, optionally substituted —($C_1$-$C_6$ alkyl)-NR$^{13}$R$^{14}$, —NR$^{14}$SO$_2$R$^{16}$, optionally substituted —($C_1$-$C_6$ alkyl)NR$^{14}$SO$_2$R$^{16}$, —NR$^{14}$COR$^{16}$, optionally substituted —($C_1$-$C_6$ alkyl)-NR$^{14}$COR$^{16}$, —CONR$^{14}$R$^{15}$, optionally substituted —($C_1$-$C_6$ alkyl)-CONR$^{14}$R$^{15}$, —SO$_2$NR$^{14}$R$^{15}$, optionally substituted —($C_1$-$C_6$ alkyl)-SO$_2$NR$^{14}$R$^{15}$, optionally substituted —SO$_2$R$^{16}$, or optionally substituted —($C_1$-$C_6$ alkyl)-SO$_2$R$^{16}$, optionally substituted carbocyclyl, optionally substituted heterocyclyl, optionally substituted aryl, or optionally substituted heteroaryl;

$R^8$, $R^9$, $R^{11}$ and $R^{12}$ are each independently hydrogen, —OH, halogen, optionally substituted $C_1$-$C_6$ alkyl, optionally substituted $C_2$-$C_6$ alkenyl, optionally substituted $C_2$-$C_6$ alkynyl, optionally substituted $C_1$-$C_6$ alkoxy, optionally substituted $C_1$-$C_6$ alkylamino, optionally substituted —OCO($C_1$-$C_6$ alkyl), —NR$^{13}$R$^{14}$, optionally substituted —($C_1$-$C_6$ alkyl)-NR$^{13}$R$^{14}$, —NR$^{14}$COR$^{16}$, optionally substituted —($C_1$-$C_6$ alkyl)-NR$^{14}$COR$^{16}$, —CONR$^{14}$R$^{15}$, optionally substituted —($C_1$-$C_6$ alkyl)-CONR$^{14}$R$^{15}$, optionally substituted carbocyclyl, optionally substituted heterocyclyl, optionally substituted aryl, or optionally substituted heteroaryl;

or alternatively, $R^8$ and $R^9$ taken together form an optionally substituted carbocyclyl or optionally substituted heterocyclyl;

or alternatively, $R^{11}$ and $R^{12}$, on a same carbon atom or a different carbon atom, taken together form an optionally substituted carbocyclyl, optionally substituted heterocyclyl, optionally substituted aryl, or optionally substituted heteroaryl;

$R^{10}$ is hydrogen, halogen, optionally substituted $C_1$-$C_6$ alkyl, optionally substituted $C_1$-$C_6$ alkoxy, —CO($C_1$-$C_6$ alkyl), optionally substituted $C_1$-$C_6$ alkylamino, optionally substituted carbocyclyl, optionally substituted heterocyclyl, optionally substituted aryl, or optionally substituted heteroaryl;

$R^{13}$, $R^{14}$, $R^{15}$, $R^{16}$, $R^{17}$ and $R^{18}$ are each independently hydrogen, optionally substituted $C_1$-$C_6$ alkyl, optionally substituted $C_2$-$C_6$ alkenyl, optionally substituted $C_2$-$C_6$ alkynyl, optionally substituted carbocyclyl, optionally substituted heterocyclyl, optionally substituted aryl, or optionally substituted heteroaryl;

or alternatively, $R^{14}$ and $R^{15}$ are taken together to form an optionally substituted heterocyclyl, or optionally substituted heteroaryl;

or alternatively, $R^{16}$ and $R^{17}$ are taken together to form an optionally substituted heterocyclyl, or optionally substituted heteroaryl;

m is 0, 1, 2, 3, or 4;

each n is independently 0, 1 or 2;

each p is independently 0, 1 or 2;

q is 0, 1 or 2;

each g is independently 0, 1, 2, 3, or 4; and each t is independently 1 or 2.

Embodiment 64. The method of Embodiment 63, wherein R is W.

Embodiment 65. The method of Embodiment 63 or 64, W is hydrogen, halogen, —CF$_3$, or —NR$^{13}$R$^{14}$.

Embodiment 66. The method of any one of Embodiments 63-65, wherein L is -E-R$^3$.

Embodiment 67. The method of any one of Embodiments 63-66, wherein R$^3$ is selected from hydrogen, —C$_1$-C$_3$ alkyl, —NR$^{16}$SO($C_1$-$C_3$ alkyl), —NR$^{16}$SO$_2$($C_1$-$C_3$ alkyl), —SONR$^{14}$R$^{15}$, —SO$_2$NR$^{14}$R$^{15}$, —SOR$^{18}$, or —SO$_2$R$^{18}$.

Embodiment 68. The method of any one of Embodiments 63-67, wherein R$^3$ is selected from —NHSO$_2$($C_1$-$C_3$ alkyl), —NCH$_3$SO$_2$($C_1$-$C_3$ alkyl), or —SO$_2$($C_1$-$C_3$ alkyl).

Embodiment 69. The method of Embodiment 63, wherein the androgen receptor N-terminal domain inhibitor is a compound of formula (ii):

(ii)

or a pharmaceutically acceptable salt, tautomer, stereoisomer or prodrug thereof, wherein:

X is a bond, —NR$^{10}$—, or —(CR$^{8a}$R$^{9a}$)$_t$—;

Y and Z are each independently a bond, —CH$_2$—, —C(CH$_3$)H—, —O—, —S—, —NH—, —NCH$_3$—, or —N(COCH$_3$)—;

V is —CH$_2$—, —CH$_2$CH$_2$—, —CH$_2$CH$_2$CH$_2$—, —CH$_2$CH(CH$_3$)CH$_2$—, —CH$_2$CH(OH)CH$_2$—, or —CH$_2$C(OH)(CH$_3$)CH$_2$—;

W is halogen, —NH$_2$, or —CF$_3$.

D is —NR$^{10}$— and E is —(CR$^{2a}$R$^{2b}$)$_g$—, —NR$^{10}$—, or —NR$^{10}$—(CR$^{2a}$R$^{2b}$).

or alternatively, E is —NR$^{10}$— or —NR$^{10}$—(CR$^{2a}$R$^{2b}$)$_g$—, and D is —(CR$^{1a}$R$^{1b}$)$_q$— or —NR$^{10}$—;

$R^{1a}$, $R^{1b}$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —NR$^{13}$R$^{14}$, —($C_1$-$C_3$ alkyl)-NR$^{13}$R$^{14}$, —NR$^{14}$COR$^{16}$, —($C_1$-$C_3$ alkyl)-NR$^{14}$COR$^{16}$, —CONR$^{14}$R$^{15}$, or —($C_1$-$C_6$ alkyl)-CONR$^{14}$R$^{15}$; or (R$^{1a}$ and R$^{1b}$) or (R$^{2a}$ and R$^{2b}$) taken together form an oxo (=O), an optionally substituted carbocyclyl, or an optionally substituted heterocyclyl;

R$^3$ is selected from hydrogen, —$C_1$-$C_6$ alkyl, —OR$^{15}$, —SR$^{18}$, —$C_1$-$C_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, —SOR$^{18}$, or —SO$_2$R$^{18}$;

R$^6$ and R$^7$ are each independently H, halogen, —CN, —CF$_3$, —OH, or $C_1$-$C_3$ alkyl;

R$^{8a}$ and R$^{9a}$ are each independently hydrogen, halogen, —OH, or $C_1$-$C_3$ alkyl; or R$^{8a}$ and R$^{9a}$ taken together form an 3- to 6-membered carbocyclyl or heterocyclyl;

R$^{10}$ is each independently hydrogen, $C_1$-$C_3$ alkyl, $C_2$-$C_3$ alkenyl, $C_2$-$C_3$ alkynyl, or —CO($C_1$-$C_3$ alkyl);

R$^{13}$, R$^{14}$, R$^{15}$, R$^{16}$, R$^{17}$ and R$^{18}$ are each independently hydrogen, $C_1$-$C_3$ alkyl, $C_2$-$C_3$ alkenyl, or $C_2$-$C_3$ alkynyl; or R$^{14}$ and R$^{15}$ taken together form an optionally substituted 5- or 6-membered heterocyclyl;

each n is independently 0, 1 or 2;

q is 0, 1 or 2;

each g is independently 0, 1, 2, 3, or 4; and each t is independently 1 or 2.

Embodiment 70. The method of Embodiment 63, wherein the androgen receptor N-terminal domain inhibitor is a compound of formula (iii):

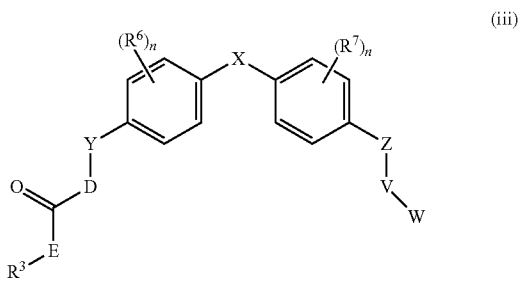

or a pharmaceutically acceptable salt, tautomer, stereoisomer or prodrug thereof, wherein:

X is a bond, —NR$^{10}$—, or —(CR$^{8a}$R$^{9a}$)$_t$—;

Y and Z are each independently a bond, —CH$_2$—, —C(CH$_3$)H—, —O—, —S—, —NH—, —NCH$_3$—, or —N(COCH$_3$)—;

V is —CH$_2$—, —CH$_2$CH$_2$—, —CH$_2$CH$_2$CH$_2$—, —CH$_2$CH(CH$_3$)CH$_2$—, —CH$_2$CH(OH)CH$_2$—, or —CH$_2$C(OH)(CH$_3$)CH$_2$—;

W is halogen, —NH$_2$ or —CF$_3$;

D is —O— or —NR$^{10}$— and E is —(CR$^{2a}$R$^{2b}$)$_{gg}$—; or alternatively, E is —O—, —NR$^{10}$— or —NR$^{10}$—(CR$^{2a}$R$^{2b}$)$_g$—, and D is —(CR$^{1a}$R$^{1b}$)$_q$—;

R$^{1a}$, R$^{1b}$, R$^{2a}$, and R$^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —OCO($C_1$-$C_3$ alkyl), —NR$^{13}$R$^{14}$, —($C_1$-$C_3$ alkyl)-NR$^{13}$R$^{14}$, —NR$^{14}$COR$^{16}$, —($C_1$-$C_3$ alkyl)-NR$^{14}$COR$^{16}$, —CONR$^{14}$R$^{15}$, or —($C_1$-$C_6$ alkyl)-CONR$^{14}$R$^{15}$; or (R$^{1a}$ and R$^{1b}$) or (R$^{2a}$ and R$^{2b}$) taken together form an oxo (=O), an optionally substituted carbocyclyl, or an optionally substituted heterocyclyl;

R$^3$ is selected from hydrogen, —$C_1$-$C_6$ alkyl, —OR$^{15}$, —SR$^{18}$, —$C_1$-$C_6$ alkoxy, —NR$^{16}$R$^{17}$, —NR$^{16}$SR$^{18}$, —NR$^{16}$SOR$^{18}$, —NR$^{16}$SO$_2$R$^{18}$, —NR$^{16}$COR$^{18}$, —CONR$^{14}$R$^{15}$, —SONR$^{14}$R$^{15}$, —SO$_2$NR$^{14}$R$^{15}$, —SOR$^{18}$, or —SO$_2$R$^{18}$;

R$^6$ and R$^7$ are each independently H, halogen, —CN, —CF$_3$, —OH, or $C_1$-$C_3$ alkyl;

R$^{8a}$ and R$^{9a}$ are each independently hydrogen, halogen, —OH, or $C_1$-$C_3$ alkyl; or R$^{8a}$ and R$^{9a}$ taken together form an 3- to 6-membered carbocyclyl or heterocyclyl;

R$^{10}$ is each independently hydrogen, $C_1$-$C_3$ alkyl, $C_2$-$C_3$ alkenyl, $C_2$-$C_3$ alkynyl, or —CO($C_1$-$C_3$ alkyl);

R$^{13}$, R$^{14}$, R$^{15}$, R$^{16}$, R$^{17}$ and R$^{18}$ are each independently hydrogen, $C_1$-$C_3$ alkyl, $C_2$-$C_3$ alkenyl, or $C_2$-$C_3$ alkynyl; or R$^{14}$ and R$^{15}$ taken together form an optionally substituted 5- or 6-membered heterocyclyl;

m is 0, 1, 2, 3, or 4;

each n is independently 0, 1 or 2;

q is 1 or 2;

g is 0, 1, 2, 3, or 4;

gg is 1, 2, 3, or 4; and t is 1 or 2.

Embodiment 71. The method of Embodiment 69 or 70, wherein W is Cl, Br, I, or F.

Embodiment 72. The method of any one of Embodiments 134-136, wherein D is —CH$_2$—, —CH(CH$_3$)—, —C(CH$_3$)$_2$—, or —CH$_2$CH$_2$—.

Embodiment 73. The method of Embodiment 69, wherein q is 0.

Embodiment 74. The method of any one of Embodiments 69-73, wherein E is —CH$_2$—, —CH(CH$_3$)—, —C(CH$_3$)$_2$—, —CH$_2$CH$_2$—, or —CH$_2$CH$_2$CH$_2$—.

Embodiment 75. The method of any one of Embodiments 69-74, wherein g is 0.

Embodiment 76. The method of any one of Embodiments 69-75, wherein R$^3$ is selected from —NHSO$_2$($C_1$-$C_3$ alkyl), —NCH$_3$SO$_2$($C_1$-$C_3$ alkyl), or —SO$_2$($C_1$-$C_3$ alkyl).

Embodiment 77. The method of any one of Embodiments 69-76, wherein R$^6$ and R$^7$ are each independently H, halogen, —CN, or methyl.

Embodiment 78. The method of any one of Embodiments 69-77, wherein X is a bond, —CH$_2$—, —C(CH$_3$)$_2$—, —CH$_2$CH$_2$—, —NH—, —N(CH$_3$)—, —N(iPr)—, or —N(COCH$_3$)—.

Embodiment 79. The method of any one of Embodiments 69-78, Z is —CH$_2$—, —O—, —NH—, —NCH$_3$—, or —N(COCH$_3$)—.

Embodiment 80. The method of any one of Embodiments 69-79, Y is —CH$_2$—, —O—, —NH—, or —NCH$_3$—.

Embodiment 81. The method of any one of Embodiments 69-80, wherein at least one of Z and Y is —O—.

Embodiment 82. The method of Embodiment 63, wherein the androgen receptor N-terminal domain inhibitor is a compound of formula (iv):

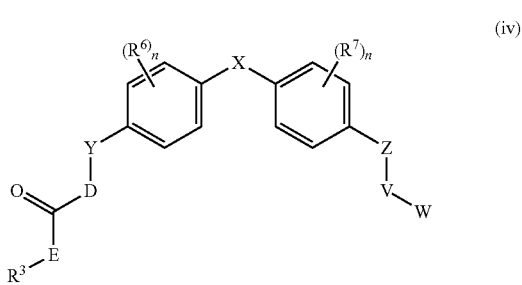

or a pharmaceutically acceptable salt, tautomer, stereoisomer or prodrug thereof, wherein:

X is a bond, —$NR^{10}$—, or —$(CR^{8a}R^{9a})_t$—;

Y and Z are each independently a bond, —$CH_2$—, —$C(CH_3)H$—, —O—, —S—, —NH—, —$NCH_3$—, or —$N(COCH_3)$—;

V is —$CH_2$—, —$CH_2CH_2$—, —$CH_2CH_2CH_2$—, —$CH_2CH(CH_3)CH_2$—, —$CH_2CH(OH)CH_2$—, or —$CH_2C(OH)(CH_3)CH_2$—;

W is halogen, —$CF_2R^{10}$, —$NR^{13}R^{14}$, optionally substituted carbocyclyl, optionally substituted heterocyclyl, optionally substituted aryl, or optionally substituted heteroaryl;

D is —$(CR^{1a}R^{1b})_q$—;

E is —$(CR^{2a}R^{2b})_g$—;

$R^{1a}$, $R^{1b}$, $R^{2a}$, and $R^{2b}$ are each independently hydrogen, halogen, —OH, $C_1$-$C_3$ alkyl, $C_2$-$C_3$ alkenyl, $C_2$-$C_3$ alkynyl, $C_1$-$C_3$ alkoxy, —$OCO(C_1$-$C_3$ alkyl), —$NR^{13}R^{14}$, —$(C_1$-$C_3$ alkyl)-$NR^{13}R^{14}$, —$NR^{14}COR^{16}$, —$(C_1$-$C_3$ alkyl)-$NR^{14}COR^{16}$, —$CONR^{14}R^{15}$, or —$(C_1$-$C_6$ alkyl)-$CONR^{14}R^{15}$; or ($R^{1a}$ and $R^{1b}$) or ($R^{2a}$ and $R^{2b}$) taken together form an oxo (=O), an optionally substituted carbocyclyl, or an optionally substituted heterocyclyl;

$R^3$ is selected from hydrogen, —$C_1$-$C_6$ alkyl, —$OR^{15}$, —$SR^{18}$, —$C_1$-$C_6$ alkoxy, —$NR^{16}R^{17}$, —$NR^{16}SR^{18}$, —$NR^{16}SOR^{18}$, —$NR^{16}SO_2R^{18}$, —$NR^{16}COR^{18}$, —$CONR^{14}R^{15}$, —$SONR^{14}R^{15}$, —$SO_2NR^{14}R^{15}$, —$SOR^{18}$, or —$SO_2R^{18}$;

$R^6$ and $R^7$ are each independently H, halogen, —CN, —$CF_3$, —OH, or $C_1$-$C_3$ alkyl;

$R^{8a}$ and $R^{9a}$ are each independently hydrogen, halogen, —OH, or $C_1$-$C_3$ alkyl; or $R^{8a}$ and $R^{9a}$ taken together form an optionally substituted carbocyclyl or optionally substituted heterocyclyl;

$R^{10}$ is each independently hydrogen, $C_1$-$C_3$ alkyl, $C_2$-$C_3$ alkenyl, $C_2$-$C_3$ alkynyl, or —$CO(C_1$-$C_3$ alkyl);

$R^{13}$, $R^{14}$, $R^{15}$, $R^{16}$, $R^{17}$ and $R^{18}$ are each independently hydrogen, $C_1$-$C_3$ alkyl, $C_2$-$C_3$ alkenyl, or $C_2$-$C_3$ alkynyl; or $R^{14}$ and $R^{15}$ taken together form an optionally substituted 5- or 6-membered heterocyclyl;

m is 0, 1, 2, 3, or 4;

each n is independently 0, 1 or 2;

q is 0, 1 or 2;

g is 0, 1, 2, 3, or 4; and t is 1 or 2.

Embodiment 83. The method of Embodiment 63 wherein the androgen receptor N-terminal domain inhibitor is selected from Table A.

Embodiment 84. The method of Embodiment 63, wherein the androgen receptor N-terminal domain inhibitor is a compound of formula (a):

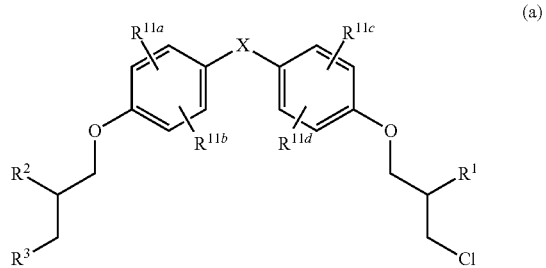

or a pharmaceutically acceptable salt, tautomer, stereoisomer or prodrug thereof, wherein:

X is —$S(O)_n$— or —$C(R^8R^9)$—;

$R^1$ is H, hydroxyl or —$OC(=O)R^{13}$;

$R^2$ is hydroxyl or —$OC(=O)R^{13}$;

$R^3$ is halo, —OH, —$OR^4$, —$OC(=O)R^{13}$, —$NH_2$, —$NHC(=O)R^{13}$, —$N(C(=O)R^{13})_2$, —$NHS(O)_nR^5$, —$N(C(=O)R^{13})(S(O)_nR^5)$, —$N(C_1$-$C_6$ alkyl)$(S(O)_nR^5)$, —$S(O)_nR^5$, —$N_3$, aryl, carbocyclyl, heteroaryl or heterocyclyl which are optionally substituted with one or more $R^6$ $R^4$ is $C_1$-$C_6$ alkyl, $C_2$-$C_6$ alkenyl, $C_2$-$C_6$ alkynyl, aryl, carbocyclyl, heteroaryl or heterocyclyl which are optionally substituted with one or more $R^6$ $R^5$ is each independently $C_1$-$C_6$ alkyl or aryl which are optionally substituted with one or more $R^6$;

$R^6$ is each independently selected from the group consisting of H, F, Cl, Br, I, $^{123}$I, hydroxyl, oxo, $C_1$-$C_6$ alkyl, $C_2$-$C_6$ alkenyl, $C_2$-$C_6$ alkynyl, $C_1$-$C_6$ alkoxy, $C_6$-$C_{12}$ aryl, wherein each $R^6$ is optionally substituted with one or more of halogen, $^{123}$I, $^{18}$F, hydroxyl, —$OS(O)_2$-aryl, $C_1$-$C_6$ alkyl, $C_2$-$C_6$ alkenyl, or $C_2$-$C_6$ alkynyl;

$R^8$ and $R^9$ are each independently H, or $C_1$-$C_6$ alkyl;

$R^{11a}$, $R^{11b}$, $R^{11c}$ and $R^{11d}$ are each independently H, methyl, —CN, F, Cl, Br, I, or $^{123}$I;

$R^{13}$ is $C_1$-$C_6$ alkyl; and n is 0, 1, or 2;

wherein at least one of $R^{11a}$, $R^{11b}$, $R^{11c}$ and $R^{11d}$ is methyl, —CN, F, Cl, Br, I, or $^{123}$I.

Embodiment 85. The method of Embodiment 84, wherein at least two of $R^{11a}$, $R^{11b}$, $R^{11c}$ and $R^{11d}$ are methyl, —CN, F, Cl, Br, I, or $^{123}$I.

Embodiment 86. The method of Embodiment 84, wherein $R^{11c}$ and $R^{11d}$ are each independently methyl, —CN, Cl, or Br.

Embodiment 87. The method of Embodiment 84, wherein $R^{11c}$ and $R^{11d}$ are each Cl or —CN.

Embodiment 88. The method of any one of Embodiments 84-87, wherein X is —$C(R^8R^9)$— and $R^8$ and $R^9$ are each independently $C_1$-$C_3$ alkyl.

Embodiment 89. The method of Embodiment 88, wherein $R^8$ an $R^9$ are each methyl.

Embodiment 90. The method of any one of Embodiments 84-89, wherein $R^1$ and $R^2$ are both hydroxyl.

Embodiment 91. The method of any one of Embodiments 84-90, wherein $R^3$ is an optionally substituted 5 or 6 membered heteroaryl or an optionally substituted 3 to 7 membered heterocyclyl, wherein said heteroaryl or said heterocyclyl respectively comprise at least one N atom.

Embodiment 92. The method of any one of Embodiments 84-91, wherein $R^3$ is selected from a group consisting of pyrrole, furan, thiophene, pyrazole, pyridine, pyridazine, pyrimidine, imidazole, thiazole, isoxazole, oxadiazole, thiadiazole, oxazole, triazole, isothiazole, oxazine, triazine, azepine, pyrrolidine, pyrroline, imidazoline, imidazolidine, pyrazoline, pyrazolidine, piperidine, dioxane, morpholine, dithiane, thiomorpholine, piperazine, and tetrazine.

Embodiment 93. The method of any one of Embodiments 84-92, wherein $R^3$ is —$NH_2$, —$NHC(=O)R^{13}$, —$N(C(=O)R^{13})_2$, —$NHS(O)_nR^5$, —$N(C(=O)R^{13})(S(O)_nR^5)$, —$N(C_1$-$C_6$ alkyl)$(S(O)_nR^5)$ or —$S(O)_nR^5$.

Embodiment 94. The method of any one of Embodiments 84-93, wherein $R^3$ is —$NH_2$, —$NHC(=O)(C_1$-$C_4$ alkyl), —$N[(C(=O)(C_1$-$C_4$ alkyl)]_2$, —$NHS(O)_n(C_1$-$C_3$ alkyl), —$N[C(=O)(C_1$-$C_4$ alkyl)][(S(O)_n(C_1$-$C_3$ alkyl)]$, —$N[C_1$-$C_6$ alkyl]$[S(O)_n(C_1$-$C_3$ alkyl)]$, or —$S(O)_n(C_1$-$C_3$ alkyl)$.

Embodiment 95. The method of Embodiment 63, wherein the androgen receptor N-terminal domain inhibitor is selected from Table B.

Embodiment 96. The method of any one of Embodiments 48-95, further comprising administering a second therapeutically active agent.

Embodiment 97. The method of Embodiment 96, wherein the second therapeutically active agent is selected from a poly (ADP-ribose) polymerase (PARP) inhibitor, an androgen receptor ligand-binding domain inhibitor, an inhibitor of CYP17, a microtubule inhibitor, a modulator of PD-1 or PD-L1, a gonadotropin releasing hormone agonist, a 5-alpha reductase inhibitor, a vascular endothelial growth factor inhibitor, a histone deacetylase inhibitor, an integrin alpha-v-beta-3 inhibitor, a receptor tyrosine kinase, a phosphoinositide 3-kinase inhibitor, an anaplastic lymphoma kinase (ALK) inhibitor, an endothelin receptor A antagonist, an anti-CTLA4 inhibitor, an heat shock protein 27 (HSP27) inhibitor, an androgen receptor degrader, a androgen receptor DNA-binding domain inhibitor, a bromodomain and extra-terminal motif (BET) inhibitor, an androgen receptor N-terminal domain inhibitor, an alpha-particle emitting radioactive therapeutic agent, niclosamide, a selective estrogen receptor modulator (SERM), a selective estrogen receptor degrader (SERD), an aromatase inhibitor, selective progesterone receptor modulator (SPRM), a glucocorticoid receptor inhibitor, a CDK4/6 inhibitor, a HER2 receptor antagonist, a mammalian target of rapamycin (mTOR) inhibitor, an AKT inhibitor, a B-cell lymphoma-2 (Bcl-2) inhibitor, an aurora kinase inhibitor, a Wnt-targeting antagonist, a CYP11a inhibitor, a selective androgen receptor N-terminal domain inhibitor, or enhancer of zeste homolog 2 (EZH2) inhibitor.

Embodiment 98. The method of Embodiment 97, wherein the CDK4/6 inhibitor is selected from palbociclib, ribociclib, trilaciclib or abemaciclib.

Embodiment 99. The method of Embodiment 97, wherein the CDK4/6 inhibitor is palbociclib.

Embodiment 100. The method of Embodiment 97, wherein the androgen receptor ligand-binding domain inhibitor is enzalutamide, apalutamide, darolutamide, bicalutamide, nilutamide, flutamide, ODM-204, or TAS3681.

Embodiment 101. The method of Embodiment 97, wherein the androgen receptor ligand-binding domain inhibitor is enzalutamide.

Embodiment 102. The method of Embodiment 97, wherein the PSMA antibody contains lutetium-177.

Embodiment 103. The method of any one of Embodiments 98-102, wherein the cancer is selected from prostate cancer, breast cancer, ovarian cancer, bladder cancer, pancreatic cancer, hepatocellular cancer, endometrial cancer, or salivary gland carcinoma.

Embodiment 104. The method of Embodiment 103, wherein the cancer is prostate cancer.

Embodiment 105. The method of Embodiment 103, wherein the prostate cancer is primary or localized prostate cancer, locally advanced prostate cancer, recurrent prostate cancer, advanced prostate cancer, metastatic prostate cancer, metastatic castration-resistant prostate cancer, and hormone-sensitive prostate cancer.

Embodiment 106. The method of Embodiment 103, wherein the prostate cancer is metastatic castration-resistant prostate cancer.

Embodiment 107. The method of Embodiment 103, wherein the prostate cancer expresses full-length androgen receptor or truncated androgen receptor splice variant.

Embodiment 108. The method of any one of Embodiments 103-107, wherein the prostate cancer is resistant to enzalutamide used with LHRH (luteinizing hormone-releasing hormone) analogues.

Embodiment A. The method of Embodiment 103, wherein the cancer is breast cancer.

Embodiment 110. The method of Embodiment 109, wherein the breast cancer is triple negative breast cancer.

Embodiment 111. The method of any one of Embodiments 63-110, wherein the radiation therapy is ionizing radiation therapy.

Embodiment 112. The method of any one of Embodiments 63-110, wherein the administering the androgen receptor N-terminal domain inhibitor and the administering radiation therapy occurs during same treatment period or during different treatment period.

The publications discussed herein are provided solely for their disclosure prior to the filing date of the present application. Nothing herein is to be construed as an admission that the present invention is not entitled to antedate such publication by virtue of prior invention.

While the invention has been described in connection with proposed specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method of treating cancer comprising administering to a subject in need thereof, a compound having the structure

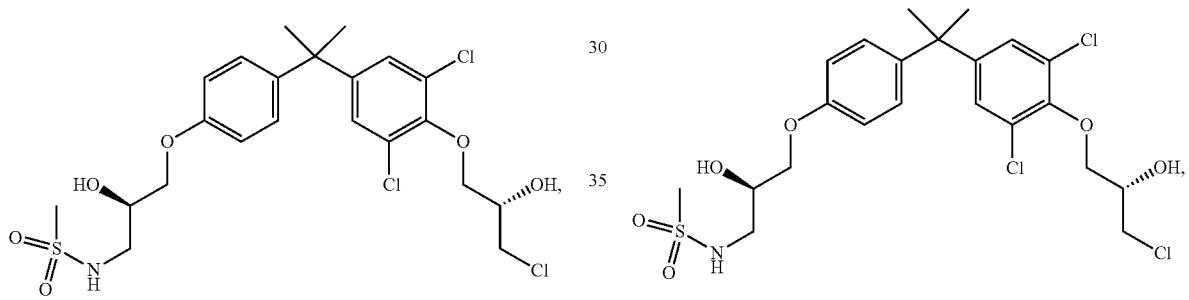

or a pharmaceutically acceptable salt thereof, and all-trans retinoic acid (ATRA).

2. The method of claim 1, wherein the cancer is selected from prostate cancer, breast cancer, ovarian cancer, bladder cancer, pancreatic cancer, hepatocellular cancer, endometrial cancer, or salivary gland carcinoma.

3. The method of claim 1, wherein the cancer is prostate cancer.

4. The method of claim 3, wherein the prostate cancer is primary or localized prostate cancer, locally advanced prostate cancer, recurrent prostate cancer, advanced prostate cancer, metastatic prostate cancer, metastatic castration-resistant prostate cancer, and hormone-sensitive prostate cancer.

5. The method of claim 1, comprising administering the second therapeutic agent and a radiation therapy to the subject.

6. The method of claim 5, wherein the radiation therapy is administered concurrently with lutetium-177 or other alpha emitters.

7. The method of claim 5, wherein the radiation therapy is ionizing radiation therapy.

8. The method of claim 5, wherein the administering the compound, or a pharmaceutically acceptable salt thereof, and the administering the radiation therapy occurs during same treatment period or during different treatment period.

9. A method of treating cancer comprising administering to a subject in need thereof, a compound having the structure

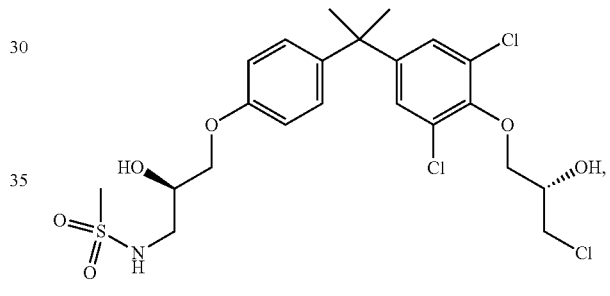

or a pharmaceutically acceptable salt thereof, and enzalutamide;

wherein the cancer is prostate cancer that is resistant to enzalutamide monotherapy.

10. The method of claim 9, wherein the prostate cancer is primary or localized prostate cancer, locally advanced prostate cancer, recurrent prostate cancer, advanced prostate cancer, metastatic prostate cancer, metastatic castration-resistant prostate cancer, and hormone-sensitive prostate cancer.

11. The method of claim 9, comprising administering a radiation therapy to the subject.

12. The method of claim 11, wherein the radiation therapy is administered concurrently with lutetium-177 or other alpha emitters.

13. The method of claim 11, wherein the radiation therapy is ionizing radiation therapy.

14. The method of claim 11, wherein the administering the compound, or a pharmaceutically acceptable salt thereof, and the administering the radiation therapy occurs during same treatment period or during different treatment period.

15. A method of treating cancer comprising administering to a subject in need thereof, a compound having the structure

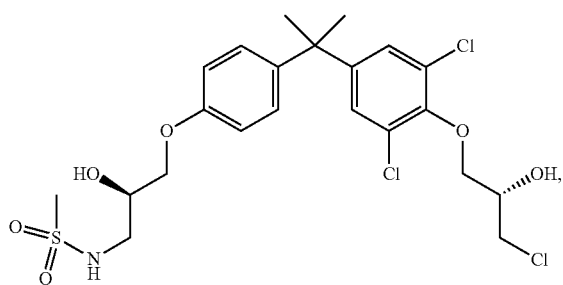 [SMILES: CC(C)(c1ccc(OC[C@H](O)CNS(C)(=O)=O)cc1)c1cc(Cl)c(OC[C@H](O)CCl)c(Cl)c1]

or a pharmaceutically acceptable salt thereof, a second therapeutically active agent, and a radiation therapy to the subject; wherein:
   the second therapeutically active agent is palbociclib, ribociclib, trilaciclib, abemaciclib, juglone, plumbagin, PiB, PiJ, epigallocatechin gallate (EGCG), all-trans retinoic acid (ATRA), dipentamethylene thiauram monosulfide, TME-001 (2-(3-chloro-4-fluoro-phenyl)-isothiazol-3-one), KPT-6566, API-1, or buparvaquone; and
   the radiation therapy is administered concurrently with lutetium-177 or other alpha emitters.

16. The method of claim 15, wherein the second therapeutically active agent is palbociclib, ribociclib, trilaciclib or abemaciclib.

17. The method of claim 15, wherein the second therapeutically active agent is ATRA.

18. The method of claim 15, wherein the second therapeutically active agent is palbociclib or ATRA.

19. The method of claim 15, wherein the cancer is selected from prostate cancer, breast cancer, ovarian cancer, bladder cancer, pancreatic cancer, hepatocellular cancer, endometrial cancer, or salivary gland carcinoma.

20. The method of claim 15, wherein the cancer is prostate cancer.

21. The method of claim 19, wherein the prostate cancer is primary or localized prostate cancer, locally advanced prostate cancer, recurrent prostate cancer, advanced prostate cancer, metastatic prostate cancer, metastatic castration-resistant prostate cancer, and hormone-sensitive prostate cancer.

22. The method of claim 15, wherein the radiation therapy is ionizing radiation therapy.

23. The method of claim 15, wherein the administering the compound, or a pharmaceutically acceptable salt thereof, and the administering the radiation therapy occurs during same treatment period or during different treatment period.

* * * * *

UNITED STATES PATENT AND TRADEMARK OFFICE
CERTIFICATE OF CORRECTION

| | | |
|---|---|---|
| PATENT NO. | : 12,109,179 B2 | Page 1 of 1 |
| APPLICATION NO. | : 17/599329 | |
| DATED | : October 8, 2024 | |
| INVENTOR(S) | : Peter Virsik et al. | |

It is certified that error appears in the above-identified patent and that said Letters Patent is hereby corrected as shown below:

In the Specification

At Column 1, Line 19, please insert:
-- STATEMENT REGARDING FEDERALLY SPONSORED RESEARCH OR DEVELOPMENT
This invention was made with government support under R01 CA105304 awarded by the National Institutes of Health. The government has certain rights in the invention. --

Signed and Sealed this
Tenth Day of December, 2024

Katherine Kelly Vidal
*Director of the United States Patent and Trademark Office*

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: PIN1 inhibitor peptide
<220> FEATURE:
<221> NAME/KEY: DISULFID
<222> LOCATION: (1)..(9)

<400> SEQUENCE: 1

Cys Arg Tyr Pro Glu Val Glu Ile Cys
1               5
```

```
<210> SEQ ID NO 2
<211> LENGTH: 8
<212> TYPE: PRT
<213> ORGANISM: Artificial Sequence
<220> FEATURE:
<223> OTHER INFORMATION: PIN1 inhibitor peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Lys is Lys(N-biotinoyl)
<220> FEATURE:
<221> NAME/KEY: MOD_RES
<222> LOCATION: (4)..(4)
<223> OTHER INFORMATION: Ala is Bth : beta-(3-benzothienyl)alanine
<220> FEATURE:
<221> NAME/KEY: MOD_RES
<222> LOCATION: (5)..(5)
<223> OTHER INFORMATION: Thr is D-Thr(PO3H2)
<220> FEATURE:
<221> NAME/KEY: MOD_RES
<222> LOCATION: (6)..(6)
<223> OTHER INFORMATION: Xaa is Pip : piperidine-2-carboxylic acid
<220> FEATURE:
<221> NAME/KEY: MOD_RES
<222> LOCATION: (7)..(7)
<223> OTHER INFORMATION: Ala is Nal : beta-(2-naphthyl)alanine
<220> FEATURE:
<221> NAME/KEY: MOD_RES
<222> LOCATION: (8)..(8)
<223> OTHER INFORMATION: AMIDATION

<400> SEQUENCE: 2

Lys Ala Ala Ala Thr Xaa Ala Gln
1               5

<210> SEQ ID NO 3
<211> LENGTH: 5
<212> TYPE: PRT
<213> ORGANISM: Artificial Sequence
<220> FEATURE:
<223> OTHER INFORMATION: PIN1 inhibitor peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Thr is D-Thr(PO3H2)
<220> FEATURE:
<221> NAME/KEY: MOD_RES
<222> LOCATION: (3)..(3)
<223> OTHER INFORMATION: Xaa is Pip : piperidine-2-carboxylic acid
<220> FEATURE:
<221> NAME/KEY: MOD_RES
<222> LOCATION: (4)..(4)
<223> OTHER INFORMATION: Ala is Nal : beta-(2-naphthyl)alanine
<220> FEATURE:
<221> NAME/KEY: MOD_RES
<222> LOCATION: (5)..(5)
<223> OTHER INFORMATION: AMIDATION

<400> SEQUENCE: 3

Phe Thr Xaa Ala Gln
1               5

<210> SEQ ID NO 4
<211> LENGTH: 5
<212> TYPE: PRT
```

```
<213> ORGANISM: Artificial Sequence
<220> FEATURE:
<223> OTHER INFORMATION: PIN1 inhibitor peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: Ser is pSer
<220> FEATURE:
<221> NAME/KEY: BINDING
<222> LOCATION: (3)..(4)
<223> OTHER INFORMATION: Pseudopeptidic binding Phy[(Z)CHdC]
<220> FEATURE:
<221> NAME/KEY: MOD_RES
<222> LOCATION: (5)..(5)
<223> OTHER INFORMATION: AMIDATION

<400> SEQUENCE: 4

Phe Phe Ser Pro Arg
1               5
```